United States Patent
Thurston et al.

(10) Patent No.: US 9,371,379 B2
(45) Date of Patent: Jun. 21, 2016

(54) METHODS FOR TREATING MALARIA BY ADMINISTERING AN ANTIBODY THAT SPECIFICALLY BINDS ANGIOPOIETIN-2 (ANG-2)

(71) Applicant: Regeneron Pharmaceuticals, Inc., Tarrytown, NY (US)

(72) Inventors: Gavin Thurston, White Plains, NY (US); Christopher Daly, New York, NY (US); Lisa Purcell Ngambo, Garnerville, NY (US)

( * ) Notice: Subject to any disclaimer, the term of this patent is extended or adjusted under 35 U.S.C. 154(b) by 146 days.

(21) Appl. No.: 14/134,880

(22) Filed: Dec. 19, 2013

(65) Prior Publication Data

US 2014/0112930 A1     Apr. 24, 2014

Related U.S. Application Data

(63) Continuation of application No. 13/417,372, filed on Mar. 12, 2012, now abandoned, which is a continuation-in-part of application No. 12/843,905, filed on Jul. 27, 2010, now Pat. No. 8,987,420.

(60) Provisional application No. 61/229,418, filed on Jul. 29, 2009, provisional application No. 61/295,194, filed on Jan. 15, 2010.

(51) Int. Cl.
| | |
|---|---|
| *A61K 39/395* | (2006.01) |
| *C07K 16/22* | (2006.01) |
| *A61K 31/513* | (2006.01) |
| *A61K 45/06* | (2006.01) |
| *A61K 39/00* | (2006.01) |

(52) U.S. Cl.
CPC .............. *C07K 16/22* (2013.01); *A61K 31/513* (2013.01); *A61K 39/3955* (2013.01); *A61K 45/06* (2013.01); *A61K 2039/505* (2013.01); *C07K 2317/21* (2013.01); *C07K 2317/24* (2013.01); *C07K 2317/33* (2013.01); *C07K 2317/34* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,521,073 A | 5/1996 | Davis et al. | |
| 5,643,755 A | 7/1997 | Davis et al. | |
| 6,166,185 A | 12/2000 | Davis et al. | |
| 7,138,370 B2 | 11/2006 | Oliner et al. | |
| 7,205,275 B2 | 4/2007 | Oliner et al. | |
| 7,309,483 B2 | 12/2007 | Wiegand et al. | |
| 7,354,578 B2 | 4/2008 | Kandel et al. | |
| 7,521,053 B2 | 4/2009 | Oliner et al. | |
| 7,521,425 B2 | 4/2009 | Bradshaw et al. | |
| 7,658,924 B2 | 2/2010 | Oliner et al. | |
| 7,666,831 B2 | 2/2010 | Oliner et al. | |
| 7,666,832 B2 | 2/2010 | Oliner et al. | |
| 7,666,839 B2 | 2/2010 | Oliner et al. | |
| 7,723,499 B2 | 5/2010 | Oliner et al. | |
| 7,973,140 B2 | 7/2011 | Green et al. | |
| 2006/0018909 A1 | 1/2006 | Oliner et al. | |
| 2006/0246071 A1 | 11/2006 | Green et al. | |
| 2007/0154482 A1 | 7/2007 | Sukhatme et al. | |
| 2007/0225221 A1 | 9/2007 | Oliner et al. | |
| 2008/0267971 A1 | 10/2008 | Green et al. | |
| 2009/0054323 A1 | 2/2009 | Oliner et al. | |
| 2009/0123474 A1 | 5/2009 | Blakey et al. | |
| 2009/0191212 A1 | 7/2009 | Oliner et al. | |
| 2009/0304694 A1 | 12/2009 | Oliner et al. | |
| 2010/0159587 A1 | 6/2010 | Brinkmann et al. | |
| 2011/0027286 A1 | 2/2011 | Thurston et al. | |
| 2012/0189635 A1 | 7/2012 | Thurston et al. | |
| 2013/0129722 A1 | 5/2013 | Lowy et al. | |

FOREIGN PATENT DOCUMENTS

| | | |
|---|---|---|
| WO | WO 2006/045049 A1 | 4/2006 |
| WO | WO 2006/068953 A2 | 6/2006 |
| WO | WO 2009/097325 A1 | 8/2009 |
| WO | WO 2010/069532 A1 | 6/2010 |
| WO | WO 2011/014469 A1 | 2/2011 |

OTHER PUBLICATIONS

Dechkum et al., Monocyte cheomattractant protein 1 (MCP-1) gene polymorphism is not associated with severe cerbral malaria in Thailand, Jpn. J. Infect. Dis. 59:239-244, 2006.*

Holash et al., "Vessel Cooption, Regression, and Growth in Tumors Mediated by Angiopoietins and VEGF," Science, 284:1994-1998, (1998).

Rudikoff et al., "Single amino acid substitution altering antigen-binding specificity," PNAS USA, Immunology, 79:1979-1983, (1982).

U.S. Appl. No. 12/843,905, Notice of Allowance mailed Sep. 18, 2014.

U.S. Appl. No. 12/843,905, Notice of Allowance mailed Nov. 13, 2014.

U.S. Appl. No. 13/747,728, Non-Final Office Action mailed Jul. 7, 2014.

U.S. Appl. No. 13/747,728, Notice of Allowance mailed Nov. 7, 2014.

Barton et al., "Crystal structures of the Tie2 receptor ectodomain and the angiopoitein-2-Tie2 complex," Nat. Struct. Mol. Biol., 13:524-532, (2006).

(Continued)

*Primary Examiner* — Claire Kaufman
(74) *Attorney, Agent, or Firm* — Alston & Bird LLP; Aparna G. Patankar

(57) ABSTRACT

The present invention provides methods for treating malaria by administering to a patient in need thereof a pharmaceutical composition comprising an antibody that specifically binds human angiopoietin-2 (Ang-2).

8 Claims, 3 Drawing Sheets

(56) References Cited

OTHER PUBLICATIONS

Barton et al., "Structure of the angiopoietin-2 receptor binding domain and identification of surfaces involved in Tie2 recognition," Structure, 13:825-832, (2005).
Brown et al., "A Human Monoclonal Anti-ANG2 Antibody Leads to Broad Antitumor Activity in Combination . . . ," Mol. Cancer Ther., 9:145-56, (2010).
Cai et al., "Single chain Fv antibody angainst angiopoietin-2 inhibits VEGF-induced endotheli . . . ," Biochem. Biophys. Res. Commun., 309:946-51, (2003).
Conroy et al., "Endothelium-based biomarkers are associated with cerebal malaria in Malawian children: a retrospective case-control study," PLos One, 5(12):e15291, (2010).
Conroy et al., "Whole blood angiopoietin-1 and -2 levels discriminate cerebral and severe (non-cerebral) malaria from uncomplicated malaria," Malaria Journal, 8:295, (2009).
Coxon et al., "Combined treatment of angiopoietin and VEGF pathway antagonists enhances antitumor activity in preclinical models of colon carcinoma," Am Assoc Cancer Res, Ann Mtg, Abstract 1113, 49:262-263, (2006).
Falcon et al., "Complementary and opposing effects of angiopoietin-1 and angiopoietin-2 inhibitors on tumor blood vessels and normalization," Proceedings of the American Association for Cancer Research Annual Meeting, Abstract#1996, 50:483-483, (2009).
Hu et al., "Angiopoietin-2: Development of inhibitors for cancer therapy," Current Oncology Reports, 11:111-116, (2009).
Imanishi et al., "Angiopoietin-2 Stimulates Breast Cancer Metastasis through the alpha5beta1 Integrin . . . ," Cancer Res., 67:4254-63, (2007).
Jendreyko et al., "Simultaneous, phenotypic knockout of VEGF-R2 and Tie-2 with an intradiabody enhances antiangiogenic effects in vivo,"Klintsche Paediatrie, 218(3):143-151, (2006).
Ladner, "Mapping the epitopes of antibodies," Biotechnol. Genet. Eng. Rev., 24:1-30, (2007).
Leow et al., "MEDI3617, a fully human anti-angiopoietin 2 monoclonal antibody . . . ," Am Assoc Cancer Res, Ann Mtg, Denver CO, Abstract 2793, (2009).
Leow et al., "MEDI3617, a human anti-Angiopoietin 2 monoclonal antibody, inhibits angiogenesis and tumor growth in human tumor xenograft models," Int J Oncol, 40(5):1321-1330, (2012).
Lovegrove at al., "Serum angiopoietin-1 and -2 levels discriminate cerebral malaria from uncomplicated malaria and predict clinical outcome in African children," PLos One, 4(3):e4912, (2009).
Maisonpierre et al., "Angiopoietin-2, a Natural Antagonist for Tie2 That Disrupts in vivo Angiogenesis," Science, 277:55-60, (1997).
Nasarre et al., "Host-Derived Angiopoietin-2 Affects Early Stages of Tumor Develpoment and Vessel Maturation but is Dispensable for Later Stages of Tumor Growth," Cancer Research, 69(4)1324-1333, (2009).
Neal et al., "AMG-386, a Selective Angiopoietin-1/-2-Neutralizing Peptibody for the Potential Treatment of Cancer," Curr. Opin. Mol. Therapeutics, 12:487-495, (2010).
Oliner et al., "Suppression of angiogenesis and tumor growth by selective inhibition of angiopoietin-2," Cancer Cell, Cell Press, 6(5):507-516, (2004).
Oshima et al., "Different effects of angiopoietin-2 in different vascular beds in the eye . . . ," FASEB J., 19:963-965, (2005).
PCT International Preliminary Report on Patetability for application PCT/US2010/043295 mailed Jul. 29, 2009.
PCT International Search Report for application PCT/US2010/043295 mailed Nov. 2, 2010.
Penn et al., "Vascular endothelial growth factor in eye disease," Progress in Retinal Eye Research, 27:331-71, (2008).
Seegar et al., "Tie1-Tie2 interactions mediate functional differences between angiopoietin ligands," Mol. Cell, 37:643-655, (2010).
Thurston et al., "Angiopoietin-1 protects the adult vasculature against plasma leakage," Nature Medicine, 6:460-463. (2000).
Thurston et al., "Leakage-Resistant Blood Vessels in Mice Transgenically Overexpressing Angiopoietin-1," Science, 286:2511-2514, (1999).
U.S. Appl. No. 12/843,905, Final Office Action mailed Jul. 25, 2012.
U.S. Appl. No. 12/843,905, Non-Final Office Action mailed Mar. 5, 2012.
U.S. Appl. No. 12/843,905, Requirement for Restriction/Election mailed Dec. 13, 2011.
U.S. Appl. No. 13/417,372, Non-Final Office Action mailed Jun. 28, 2013.
Yeo at al., "Antiopoietin-2 is associated with decreased endothelial nitric oxide and poor clinical outcome in severe falciparum malaria" PNAS USA, 105(44):17097-17102, (2008).

* cited by examiner hAng2  TAGKISSTSQPGNDFSTKDGDNDKCTCKCSQMLTGGWFDACGPSNLNGMYYPQRQNTNKFNGIKWYYWKGSGYSLKATTMMIRPADF
hAng1  TAGKQSSLILHGADFSTKDADNDNCMCKCALMLTGGWFDACGPSNLNGMFYTAGQNHGKLNGIKWHYFKGPSYSLRSTTMMIRPLDF \* = hAng-2 amino acids that were shown to interact with Tie-2 by crystal structure analysis.

▲ = Amino acids that differ between hAng-2 and hAng-1 and that correspond to Tie-2-interacting amino acid residues.

SEQUENCE LISTING

<160> NUMBER OF SEQ ID NOS: 531

<210> SEQ ID NO 1
<211> LENGTH: 366
<212> TYPE: DNA
<213> ORGANISM: Artificial Sequence
<220> FEATURE:
<223> OTHER INFORMATION: synthetic

<400> SEQUENCE: 1
caggtgcagc tggtgcagtc tgggggaggc ttggtacagc cggggggtc cctgagactc      60 tcctgtgcag cctctggatt caccttcagt agctacgaca tacactgggt ccgtcaagct    120
acaggaaaag gtctggagtg ggtctcagct attggtcctg ctggtgacac atactatcca    180
ggctccgtga agggccgatt caccatctcc agagaaaatg ccaagaactc cttgtatctt    240
caaatgaaca gcctgagagc cggggacacg gctgtgtatt actgtgcaag aggtttgatt    300
acgtttgggg gcttatcgc cccgtttgac tactggggcc agggaaccct ggtcaccgtc    360
tcctca                                                               366

<210> SEQ ID NO 2
<211> LENGTH: 122
<212> TYPE: PRT
<213> ORGANISM: Artificial Sequence
<220> FEATURE:
<223> OTHER INFORMATION: synthetic

<400> SEQUENCE: 2

Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Ile His Trp Val Arg Gln Ala Thr Gly Lys Gly Leu Glu Trp Val
        35                  40                  45

Ser Ala Ile Gly Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Leu Ile Thr Phe Gly Gly Leu Ile Ala Pro Phe Asp Tyr Trp
            100                 105                 110

Gly Gln Gly Thr Leu Val Thr Val Ser Ser
        115                 120

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggattcacct tcagtagcta cgac                                             24

<210> SEQ ID NO 4
<211> LENGTH: 8
<212> TYPE: PRT
<213> ORGANISM: Artificial Sequence
<220> FEATURE:
<223> OTHER INFORMATION: synthetic -continued

<400> SEQUENCE: 4

Gly Phe Thr Phe Ser Ser Tyr Asp
 1               5

<210> SEQ ID NO 5
<211> LENGTH: 21
<212> TYPE: DNA
<213> ORGANISM: Artificial Sequence
<220> FEATURE:
<223> OTHER INFORMATION: synthetic

<400> SEQUENCE: 5
attggtcctg ctggtgacac a                                           21

<210> SEQ ID NO 6
<211> LENGTH: 7
<212> TYPE: PRT
<213> ORGANISM: Artificial Sequence
<220> FEATURE:
<223> OTHER INFORMATION: synthetic

<400> SEQUENCE: 6

Ile Gly Pro Ala Gly Asp Thr
 1               5

<210> SEQ ID NO 7
<211> LENGTH: 48
<212> TYPE: DNA
<213> ORGANISM: Artificial Sequence
<220> FEATURE:
<223> OTHER INFORMATION: synthetic

<400> SEQUENCE: 7
gcaagaggtt tgattacgtt tgggggcgtt atcgccccgt ttgactac              48

<210> SEQ ID NO 8
<211> LENGTH: 16
<212> TYPE: PRT
<213> ORGANISM: Artificial Sequence
<220> FEATURE:
<223> OTHER INFORMATION: synthetic

<400> SEQUENCE: 8

Ala Arg Gly Leu Ile Thr Phe Gly Gly Leu Ile Ala Pro Phe Asp Tyr
 1               5                  10                  15

<210> SEQ ID NO 9
<211> LENGTH: 324
<212> TYPE: DNA
<213> ORGANISM: Artificial Sequence
<220> FEATURE:
<223> OTHER INFORMATION: synthetic

<400> SEQUENCE: 9
gacatccagt tgacccagtc tccaggcacc ctgtctttgt ctccagggga aagagccacc     60
ctctcctgca gggccagtca gagtgttagc agcacctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cattatgata actcacaaac gttcggccaa    300
gggaccaagg tggaaatcaa acga                                           324

-continued

<210> SEQ ID NO 10
<211> LENGTH: 108
<212> TYPE: PRT
<213> ORGANISM: Artificial Sequence
<220> FEATURE:
<223> OTHER INFORMATION: synthetic

<400> SEQUENCE: 10

```
Asp Ile Gln Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asp Asn Ser Gln
                85                  90                  95

Thr Phe Gly Gln Gly Thr Lys Val Glu Ile Lys Arg
            100                 105
```

<210> SEQ ID NO 11
<211> LENGTH: 21
<212> TYPE: DNA
<213> ORGANISM: Artificial Sequence
<220> FEATURE:
<223> OTHER INFORMATION: synthetic

<400> SEQUENCE: 11
cagagtgtta gcagcaccta c                                              21

<210> SEQ ID NO 12
<211> LENGTH: 7
<212> TYPE: PRT
<213> ORGANISM: Artificial Sequence
<220> FEATURE:
<223> OTHER INFORMATION: synthetic

<400> SEQUENCE: 12

```
Gln Ser Val Ser Ser Thr Tyr
 1               5
```

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 ggtgcatcc                                                             9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

```
Gly Ala Ser
 1
```

<210> SEQ ID NO 15
<211> LENGTH: 24
<212> TYPE: DNA
<213> ORGANISM: Artificial Sequence
<220> FEATURE:
<223> OTHER INFORMATION: synthetic

<400> SEQUENCE: 15
cagcattatg ataactcaca aacg                                            24

<210> SEQ ID NO 16
<211> LENGTH: 8
<212> TYPE: PRT
<213> ORGANISM: Artificial Sequence
<220> FEATURE:
<223> OTHER INFORMATION: synthetic

<400> SEQUENCE: 16

Gln His Tyr Asp Asn Ser Gln Thr
 1               5

<210> SEQ ID NO 17
<211> LENGTH: 366
<212> TYPE: DNA
<213> ORGANISM: Artificial Sequence
<220> FEATURE:
<223> OTHER INFORMATION: synthetic

<400> SEQUENCE: 17
gaggtgcagc tggtggagtc tgggggaggc ttggtacagc cggggggggtc cctgagactc     60 tcctgtgcag cctctggatt caccttcagt agctacgaca tacactgggt ccgtcaagct    120
acaggaaaag gtctggagtg gtctcagct attggtcctg ctggtgacac atactatcca    180
ggctccgtga agggccgatt caccatctcc agagaaaatg ccaagaactc cttgtatctt    240
caaatgaaca gcctgagagc cggggacacg gctgtgtatt actgtgcaag aggttttgatt    300 acgtttgggg ggcttatcgc cccgtttgac tactggggcc agggaaccct ggtcaccgtc    360
tcctca                                                               366

<210> SEQ ID NO 18
<211> LENGTH: 122
<212> TYPE: PRT
<213> ORGANISM: Artificial Sequence
<220> FEATURE:
<223> OTHER INFORMATION: synthetic

<400> SEQUENCE: 18

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Ile His Trp Val Arg Gln Ala Thr Gly Lys Gly Leu Glu Trp Val
        35                  40                  45

Ser Ala Ile Gly Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Leu Ile Thr Phe Gly Gly Leu Ile Ala Pro Phe Asp Tyr Trp

```
                100                 105                 110
Gly Gln Gly Thr Leu Val Thr Val Ser Ser
        115                 120
```

<210> SEQ ID NO 19
<211> LENGTH: 321
<212> TYPE: DNA
<213> ORGANISM: Artificial Sequence
<220> FEATURE:
<223> OTHER INFORMATION: synthetic

<400> SEQUENCE: 19

```
gaaattgtgt tgacgcagtc tccaggcacc ctgtctttgt ctccagggga aagagccacc    60
ctctcctgca gggccagtca gagtgttagc agcacctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cattatgata actcacaaac gttcggccaa   300
gggaccaagg tggaaatcaa a                                             321
```

<210> SEQ ID NO 20
<211> LENGTH: 107
<212> TYPE: PRT
<213> ORGANISM: Artificial Sequence
<220> FEATURE:
<223> OTHER INFORMATION: synthetic

<400> SEQUENCE: 20

```
Glu Ile Val Leu Thr Gln Ser Pro Gly Thr Leu Ser Leu Ser Pro Gly
  1               5                  10                  15
Glu Arg Ala Thr Leu Ser Cys Arg Ala Ser Gln Ser Val Ser Ser Thr
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln His Tyr Asp Asn Ser Gln
                85                  90                  95
Thr Phe Gly Gln Gly Thr Lys Val Glu Ile Lys
            100                 105
```

<210> SEQ ID NO 21
<211> LENGTH: 366
<212> TYPE: DNA
<213> ORGANISM: Artificial Sequence
<220> FEATURE:
<223> OTHER INFORMATION: synthetic

<400> SEQUENCE: 21

```
gaggtgcagc tggtggagtc tgggggaggc ttggtacagc ctggggggtc cctgagactc    60
tcctgtgcag cctctggatt caccttcagt agctacgaca tgcactgggt ccgccaagct   120
acaggaaaag gtctggagtg ggtctcagct attggtcctg ctggtgacac atactatcca   180
ggctccgtga agggccgatt caccatctcc agagaaaatg ccaagaactc cttgtatctt   240
caaatgaaca gcctgagagc cggggacacg gctgtgtatt actgtgcaag aggtttgatt   300
acgtttgggg ggcttatcgc cccgtttgac tactggggcc agggaaccct ggtcaccgtc   360
```

-continued tcctca                                                                  366

<210> SEQ ID NO 22
<211> LENGTH: 122
<212> TYPE: PRT
<213> ORGANISM: Artificial Sequence
<220> FEATURE:
<223> OTHER INFORMATION: synthetic

<400> SEQUENCE: 22

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Leu Ile Thr Phe Gly Gly Leu Ile Ala Pro Phe Asp Tyr Trp
            100                 105                 110

Gly Gln Gly Thr Leu Val Thr Val Ser Ser
        115                 120

<210> SEQ ID NO 23
<211> LENGTH: 322
<212> TYPE: DNA
<213> ORGANISM: Artificial Sequence
<220> FEATURE:
<223> OTHER INFORMATION: synthetic

<400> SEQUENCE: 23
gaaattgtgt tgacgcagtc tccaggcacc ctgtctttgt ctccagggga aagagccacc        60
ctctcctgca gggccagtca gagtgttagc agcacctact tagcctggta ccagcagaaa       120
cctggccagg ctcccaggct cctcatctat ggtgcatcca gcagggccac tggcatccca       180
gacaggttca gtggcagtgg gtctgggaca gacttcactc tcaccatcag cagactggag       240
cctgaagatt ttgcagtgta ttactgtcag cattatgata actcacaaac gttcggccaa       300
gggaccaagg tggaaatcaa ac                                                322

<210> SEQ ID NO 24
<211> LENGTH: 107
<212> TYPE: PRT
<213> ORGANISM: Artificial Sequence
<220> FEATURE:
<223> OTHER INFORMATION: synthetic

<400> SEQUENCE: 24

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser

```
                50                   55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln His Tyr Asp Asn Ser Gln
                 85                  90                  95

Thr Phe Gly Gln Gly Thr Lys Val Glu Ile Lys
            100                 105

<210> SEQ ID NO 25
<211> LENGTH: 366
<212> TYPE: DNA
<213> ORGANISM: Artificial Sequence
<220> FEATURE:
<223> OTHER INFORMATION: synthetic

<400> SEQUENCE: 25
gaggtgcagc tggtgcagtc tgggggaggc ttggttcagc ctggggagtc cctgagactc      60
tcctgtgcag cctctggatt cacctttagc agctatgcca tgagctgggt ccgccagggt     120
ccagggaagg gcctggagtg ggtctcaagt attactggga gtggtgatac acatactac     180 gcagactccg tgaagggccg gttcaccatc tccagagaca attccaagaa cacgctgtat    240
ctgcacatga acagcctgag agccgaggac acggccgtat attactgtgc gaaagatttt    300
cttgactaca gtacctacct tgcttttgat ctctggggcc aagggacaat ggtcaccgtc    360
tcttca                                                              366

<210> SEQ ID NO 26
<211> LENGTH: 122
<212> TYPE: PRT
<213> ORGANISM: Artificial Sequence
<220> FEATURE:
<223> OTHER INFORMATION: synthetic

<400> SEQUENCE: 26

Glu Val Gln Leu Val Gln Ser Gly Gly Gly Leu Val Gln Pro Gly Glu
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Gly Pro Gly Lys Gly Leu Glu Trp Val
         35                  40                  45

Ser Ser Ile Thr Gly Ser Gly Asp Thr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu His Met Asn Ser Leu Arg Ala Glu Asp Thr Ala Val Tyr Tyr Cys
                 85                  90                  95

Ala Lys Asp Phe Leu Asp Tyr Ser Thr Tyr Leu Ala Phe Asp Leu Trp
            100                 105                 110

Gly Gln Gly Thr Met Val Thr Val Ser Ser
        115                 120

<210> SEQ ID NO 27
<211> LENGTH: 24
<212> TYPE: DNA
<213> ORGANISM: Artificial Sequence
<220> FEATURE:
<223> OTHER INFORMATION: synthetic

<400> SEQUENCE: 27
```

```
ggattcacct ttagcagcta tgcc                                          24
```

<210> SEQ ID NO 28
<211> LENGTH: 8
<212> TYPE: PRT
<213> ORGANISM: Artificial Sequence
<220> FEATURE:
<223> OTHER INFORMATION: synthetic

<400> SEQUENCE: 28

Gly Phe Thr Phe Ser Ser Tyr Ala
 1               5

<210> SEQ ID NO 29
<211> LENGTH: 24
<212> TYPE: DNA
<213> ORGANISM: Artificial Sequence
<220> FEATURE:
<223> OTHER INFORMATION: synthetic

<400> SEQUENCE: 29

```
attactggga gtggtgatac caca                                          24
```

<210> SEQ ID NO 30
<211> LENGTH: 8
<212> TYPE: PRT
<213> ORGANISM: Artificial Sequence
<220> FEATURE:
<223> OTHER INFORMATION: synthetic

<400> SEQUENCE: 30

Ile Thr Gly Ser Gly Asp Thr Thr
 1               5

<210> SEQ ID NO 31
<211> LENGTH: 45
<212> TYPE: DNA
<213> ORGANISM: Artificial Sequence
<220> FEATURE:
<223> OTHER INFORMATION: synthetic

<400> SEQUENCE: 31

```
gcgaaagatt tcttgacta cagtacctac cttgcttttg atctc                    45
```

<210> SEQ ID NO 32
<211> LENGTH: 15
<212> TYPE: PRT
<213> ORGANISM: Artificial Sequence
<220> FEATURE:
<223> OTHER INFORMATION: synthetic

<400> SEQUENCE: 32

Ala Lys Asp Phe Leu Asp Tyr Ser Thr Tyr Leu Ala Phe Asp Leu
 1               5                  10                  15

<210> SEQ ID NO 33
<211> LENGTH: 324
<212> TYPE: DNA
<213> ORGANISM: Artificial Sequence
<220> FEATURE:
<223> OTHER INFORMATION: synthetic

<400> SEQUENCE: 33

```
gacatccaga tgacccagtc tccagccacc ctgtctttgt ctccagggga aagagccacc    60
ctctcctgca gggccagtca gagtgttagc agctacttaa cctggtacca gcagaaacct   120
```

```
ggccaggctc ccaggctcct cagctatgat gcatctaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggccgctcac tttcggcgga    300
gggaccaagg tggaaatcaa acga                                            324
```

```
<210> SEQ ID NO 34
<211> LENGTH: 108
<212> TYPE: PRT
<213> ORGANISM: Artificial Sequence
<220> FEATURE:
<223> OTHER INFORMATION: synthetic

<400> SEQUENCE: 34
```

```
Asp Ile Gln Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Thr Trp Tyr Gln Gln Lys Pro Gly Gln Ala Pro Arg Leu Leu Ser
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
             85                  90                  95

Thr Phe Gly Gly Gly Thr Lys Val Glu Ile Lys Arg
            100                 105
```

```
<210> SEQ ID NO 35
<211> LENGTH: 18
<212> TYPE: DNA
<213> ORGANISM: Artificial Sequence
<220> FEATURE:
<223> OTHER INFORMATION: synthetic

<400> SEQUENCE: 35
cagagtgtta gcagctac                                                    18
```

```
<210> SEQ ID NO 36
<211> LENGTH: 6
<212> TYPE: PRT
<213> ORGANISM: Artificial Sequence
<220> FEATURE:
<223> OTHER INFORMATION: synthetic

<400> SEQUENCE: 36
```

```
Gln Ser Val Ser Ser Tyr
 1               5
```

```
<210> SEQ ID NO 37
<211> LENGTH: 9
<212> TYPE: DNA
<213> ORGANISM: Artificial Sequence
<220> FEATURE:
<223> OTHER INFORMATION: synthetic

<400> SEQUENCE: 37 gatgcatct                                                              9
```

```
<210> SEQ ID NO 38
<211> LENGTH: 3
```

<210> SEQ ID NO 38
<211> LENGTH: 3
<212> TYPE: PRT
<213> ORGANISM: Artificial Sequence
<220> FEATURE:
<223> OTHER INFORMATION: synthetic

<400> SEQUENCE: 38

Asp Ala Ser
 1

<210> SEQ ID NO 39
<211> LENGTH: 27
<212> TYPE: DNA
<213> ORGANISM: Artificial Sequence
<220> FEATURE:
<223> OTHER INFORMATION: synthetic

<400> SEQUENCE: 39
cagcagcgta gcaactggcc gctcact                                           27

<210> SEQ ID NO 40
<211> LENGTH: 9
<212> TYPE: PRT
<213> ORGANISM: Artificial Sequence
<220> FEATURE:
<223> OTHER INFORMATION: synthetic

<400> SEQUENCE: 40

Gln Gln Arg Ser Asn Trp Pro Leu Thr
 1               5

<210> SEQ ID NO 41
<211> LENGTH: 366
<212> TYPE: DNA
<213> ORGANISM: Artificial Sequence
<220> FEATURE:
<223> OTHER INFORMATION: synthetic

<400> SEQUENCE: 41
gaggtgcagc tggtggagtc tgggggaggc ttggttcagc ctggggagtc cctgagactc        60
tcctgtgcag cctctggatt cacctttagc agctatgcca tgagctgggt ccgccagggt       120
ccagggaagg gcctggagtg gtctcaagt attactggga gtggtgatac cacatactac       180
gcagactccg tgaagggccg gttcaccatc tccagagaca attccaagaa cacgctgtat       240
ctgcacatga acagcctgag agccgaggac acggccgtat attactgtgc gaaagatttt       300
cttgactaca gtacctacct tgcttttgat ctctggggcc aagggacaat ggtcaccgtc       360
tcttca                                                                 366

<210> SEQ ID NO 42
<211> LENGTH: 122
<212> TYPE: PRT
<213> ORGANISM: Artificial Sequence
<220> FEATURE:
<223> OTHER INFORMATION: synthetic

<400> SEQUENCE: 42

Glu Val Gln Leu Val Glu Ser Gly Gly Gly Leu Val Gln Pro Gly Glu
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Gly Pro Gly Lys Gly Leu Glu Trp Val
            35                  40                  45

Ser Ser Ile Thr Gly Ser Gly Asp Thr Thr Tyr Tyr Ala Asp Ser Val

```
                    50                  55                  60
Lys Gly Arg Phe Thr Ile Ser Arg Asp Asn Ser Lys Asn Thr Leu Tyr
 65                  70                  75                  80

Leu His Met Asn Ser Leu Arg Ala Glu Asp Thr Ala Val Tyr Tyr Cys
                 85                  90                  95

Ala Lys Asp Phe Leu Asp Tyr Ser Thr Tyr Leu Ala Phe Asp Leu Trp
            100                 105                 110

Gly Gln Gly Thr Met Val Thr Val Ser Ser
        115                 120
```

```
<210> SEQ ID NO 43
<211> LENGTH: 321
<212> TYPE: DNA
<213> ORGANISM: Artificial Sequence
<220> FEATURE:
<223> OTHER INFORMATION: synthetic

<400> SEQUENCE: 43
gaaattgtgt tgacacagtc tccagccacc ctgtctttgt ctccagggga aagagccacc      60
ctctcctgca gggccagtca gagtgttagc agctacttaa cctggtacca gcagaaacct     120
ggccaggctc ccaggctcct cagctatgat gcatctaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggccgctcac tttcggcgga     300
gggaccaagg tggagatcaa a                                              321
```

```
<210> SEQ ID NO 44
<211> LENGTH: 107
<212> TYPE: PRT
<213> ORGANISM: Artificial Sequence
<220> FEATURE:
<223> OTHER INFORMATION: synthetic

<400> SEQUENCE: 44

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Thr Trp Tyr Gln Gln Lys Pro Gly Gln Ala Pro Arg Leu Leu Ser
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
            100                 105
```

```
<210> SEQ ID NO 45
<211> LENGTH: 366
<212> TYPE: DNA
<213> ORGANISM: Artificial Sequence
<220> FEATURE:
<223> OTHER INFORMATION: synthetic

<400> SEQUENCE: 45
gaggtgcagc tggtggagtc tgggggaggc ttggtacagc ctggggggtc cctgagactc      60
```

```
tcctgtgcag cctctggatt cacctttagc agctatgcca tgagctgggt ccgccaggct      120
ccagggaagg ggctggagtg ggtctcagct attactggga gtggtgatac cacatactac      180
gcagactccg tgaagggccg gttcaccatc tccagagaca attccaagaa cacgctgtat      240
ctgcaaatga acagcctgag agccgaggac acggccgtat attactgtgc gaaagatttt      300
cttgactaca gtacctacct tgctttttgat ctctggggcc aagggacaat ggtcaccgtc      360
tcttca                                                                 366
```

```
<210> SEQ ID NO 46
<211> LENGTH: 122
<212> TYPE: PRT
<213> ORGANISM: Artificial Sequence
<220> FEATURE:
<223> OTHER INFORMATION: synthetic

<400> SEQUENCE: 46

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Thr Gly Ser Gly Asp Thr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Phe Leu Asp Tyr Ser Thr Tyr Leu Ala Phe Asp Leu Trp
            100                 105                 110

Gly Gln Gly Thr Met Val Thr Val Ser Ser
        115                 120
```

```
<210> SEQ ID NO 47
<211> LENGTH: 322
<212> TYPE: DNA
<213> ORGANISM: Artificial Sequence
<220> FEATURE:
<223> OTHER INFORMATION: synthetic

<400> SEQUENCE: 47
gaaattgtgt tgacacagtc tccagccacc ctgtctttgt ctccagggga aagagccacc       60
ctctcctgca gggccagtca gagtgttagc agctacttag cctggtacca acagaaacct      120
ggccaggctc ccaggctcct catctatgat gcatctaaca gggccactgg catcccagcc      180
aggttcagtg gcagtgggtc tgggagagac ttcactctca ccatcagcag cctagagcct      240
gaagattttg cagtttatta ctgtcagcag cgtagcaact ggccgctcac tttcggcgga      300
gggaccaagg tggagatcaa ac                                               322
```

```
<210> SEQ ID NO 48
<211> LENGTH: 107
<212> TYPE: PRT
<213> ORGANISM: Artificial Sequence
<220> FEATURE:
<223> OTHER INFORMATION: synthetic

<400> SEQUENCE: 48

Glu Ile Val Leu Thr Gln Ser Pro Ala Thr Leu Ser Leu Ser Pro Gly
```

```
                1               5                  10                 15
Glu Arg Ala Thr Leu Ser Cys Arg Ala Ser Gln Ser Val Ser Ser Tyr
                    20                  25                 30

Leu Ala Trp Tyr Gln Gln Lys Pro Gly Gln Ala Pro Arg Leu Leu Ile
                    35                  40                 45

Tyr Asp Ala Ser Asn Arg Ala Thr Gly Ile Pro Ala Arg Phe Ser Gly
                    50                  55                 60

Ser Gly Ser Gly Arg Asp Phe Thr Leu Thr Ile Ser Ser Leu Glu Pro
 65                 70                  75                 80

Glu Asp Phe Ala Val Tyr Tyr Cys Gln Gln Arg Ser Asn Trp Pro Leu
                    85                  90                 95

Thr Phe Gly Gly Gly Thr Lys Val Glu Ile Lys
                   100                 105
```

<210> SEQ ID NO 49
<211> LENGTH: 366
<212> TYPE: DNA
<213> ORGANISM: Artificial Sequence
<220> FEATURE:
<223> OTHER INFORMATION: synthetic

<400> SEQUENCE: 49

```
caggtgcagc tggtggagtc tgggggaggc ttggtgcagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtga cataggctat     180
gcggactctg tgaagggccg attcaccatc tccagagaca cgccaagaa ctccctgtat      240
ctgcaaatga acagtctgag agctcaggac acggccttgt attactgtgc aaaagcttac     300
ggtgactact actacttta cggtatggac gtctggggcc aagggaccac ggtcaccgtc      360
tcctca                                                                366
```

<210> SEQ ID NO 50
<211> LENGTH: 122
<212> TYPE: PRT
<213> ORGANISM: Artificial Sequence
<220> FEATURE:
<223> OTHER INFORMATION: synthetic

<400> SEQUENCE: 50

```
Gln Val Gln Leu Val Glu Ser Gly Gly Gly Leu Val Gln Pro Gly Arg
 1               5                  10                 15

Ser Leu Arg Leu Ser Cys Ala Ala Ser Gly Phe Thr Phe Asp Asp Tyr
                    20                  25                 30

Ala Met His Trp Val Arg Gln Ala Pro Gly Lys Gly Leu Glu Trp Val
                    35                  40                 45

Ser Gly Ile Ser Trp Asn Ser Gly Asp Ile Gly Tyr Ala Asp Ser Val
                    50                  55                 60

Lys Gly Arg Phe Thr Ile Ser Arg Asp Asn Ala Lys Asn Ser Leu Tyr
 65                 70                  75                 80

Leu Gln Met Asn Ser Leu Arg Ala Gln Asp Thr Ala Leu Tyr Tyr Cys
                    85                  90                 95

Ala Lys Ala Tyr Gly Asp Tyr Tyr Tyr Phe Tyr Gly Met Asp Val Trp
                   100                 105                110

Gly Gln Gly Thr Thr Val Thr Val Ser Ser
                   115                 120
```

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51
ggattcacct ttgatgatta tgcc                                          24

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

Gly Phe Thr Phe Asp Asp Tyr Ala
 1               5

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
attagttgga atagtggtga cata                                          24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Ile Ser Trp Asn Ser Gly Asp Ile
 1               5

<210> SEQ ID NO 55
<211> LENGTH: 45
<212> TYPE: DNA
<213> ORGANISM: Artificial Sequence
<220> FEATURE:
<223> OTHER INFORMATION: synthetic

<400> SEQUENCE: 55
gcaaaagctt acggtgacta ctactacttt tacggtatgg acgtc                   45

<210> SEQ ID NO 56
<211> LENGTH: 15
<212> TYPE: PRT
<213> ORGANISM: Artificial Sequence
<220> FEATURE:
<223> OTHER INFORMATION: synthetic

<400> SEQUENCE: 56

Ala Lys Ala Tyr Gly Asp Tyr Tyr Tyr Phe Tyr Gly Met Asp Val
 1               5                  10                  15

<210> SEQ ID NO 57
<211> LENGTH: 324
<212> TYPE: DNA
<213> ORGANISM: Artificial Sequence
<220> FEATURE:
<223> OTHER INFORMATION: synthetic

<400> SEQUENCE: 57

```
gacatcgtga tgacccagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatcttt agtgcatcca gcagggccac tggcatccca    180
gacaggttca gtggcagtgg gtctgggaca gacttcactc tcaccatcag cagactggag    240
cctgaagatt ttgcagtgta ttactgtcag cagtatgata actcactcac tttcggcgga    300
gggaccaaag tggatatcaa acga                                           324
```

<210> SEQ ID NO 58
<211> LENGTH: 108
<212> TYPE: PRT
<213> ORGANISM: Artificial Sequence
<220> FEATURE:
<223> OTHER INFORMATION: synthetic

<400> SEQUENCE: 58

```
Asp Ile Val Met Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Phe Ser Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Asn Ser Leu
                85                  90                  95

Thr Phe Gly Gly Gly Thr Lys Val Asp Ile Lys Arg
            100                 105
```

<210> SEQ ID NO 59
<211> LENGTH: 21
<212> TYPE: DNA
<213> ORGANISM: Artificial Sequence
<220> FEATURE:
<223> OTHER INFORMATION: synthetic

<400> SEQUENCE: 59

```
cagagtgtta gcagcagcta c                                               21
```

<210> SEQ ID NO 60
<211> LENGTH: 7
<212> TYPE: PRT
<213> ORGANISM: Artificial Sequence
<220> FEATURE:
<223> OTHER INFORMATION: synthetic

<400> SEQUENCE: 60

```
Gln Ser Val Ser Ser Ser Tyr
 1               5
```

<210> SEQ ID NO 61
<211> LENGTH: 9
<212> TYPE: DNA
<213> ORGANISM: Artificial Sequence
<220> FEATURE:

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

Ser Ala Ser
 1

<210> SEQ ID NO 63
<211> LENGTH: 24
<212> TYPE: DNA
<213> ORGANISM: Artificial Sequence
<220> FEATURE:
<223> OTHER INFORMATION: synthetic

<400> SEQUENCE: 63
cagcagtatg ataactcact cact                                          24

<210> SEQ ID NO 64
<211> LENGTH: 8
<212> TYPE: PRT
<213> ORGANISM: Artificial Sequence
<220> FEATURE:
<223> OTHER INFORMATION: synthetic

<400> SEQUENCE: 64

Gln Gln Tyr Asp Asn Ser Leu Thr
 1               5

<210> SEQ ID NO 65
<211> LENGTH: 363
<212> TYPE: DNA
<213> ORGANISM: Artificial Sequence
<220> FEATURE:
<223> OTHER INFORMATION: synthetic

<400> SEQUENCE: 65
gaagtgcagc tggtggagtc tgggggaggc ttggtgcagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtga cataggctat     180
gcggactctg tgaagggccg attcaccatc tccagagaca cgccaagaa ctccctgtat      240 ctgcaaatga acagtctgag agctcaggac acggccttgt attactgtgc aaaagcttac    300
ggtgactact actactttta cggtatggac gtctggggcc aagggaccac ggtcaccgtc    360
tcc                                                                 363

<210> SEQ ID NO 66
<211> LENGTH: 121
<212> TYPE: PRT
<213> ORGANISM: Artificial Sequence
<220> FEATURE:
<223> OTHER INFORMATION: synthetic

<400> SEQUENCE: 66

Glu Val Gln Leu Val Glu Ser Gly Gly Gly Leu Val Gln Pro Gly Arg

```
                1               5                   10                  15
Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Asp Ile Gly Tyr Ala Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Gln Asp Thr Ala Leu Tyr Tyr Cys
                85                  90                  95

Ala Lys Ala Tyr Gly Asp Tyr Tyr Phe Tyr Gly Met Asp Val Trp
            100                 105                 110

Gly Gln Gly Thr Thr Val Thr Val Ser
            115                 120
```

<210> SEQ ID NO 67
<211> LENGTH: 321
<212> TYPE: DNA
<213> ORGANISM: Artificial Sequence
<220> FEATURE:
<223> OTHER INFORMATION: synthetic

<400> SEQUENCE: 67

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatcttt agtgcatcca gcagggccac tggcatccca     180
gacaggttca gtggcagtgg gtctgggaca gacttcactc tcaccatcag cagactggag     240
cctgaagatt ttgcagtgta ttactgtcag cagtatgata actcactcac tttcggcgga     300
gggaccaagg tggagatcaa a                                                321
```

<210> SEQ ID NO 68
<211> LENGTH: 107
<212> TYPE: PRT
<213> ORGANISM: Artificial Sequence
<220> FEATURE:
<223> OTHER INFORMATION: synthetic

<400> SEQUENCE: 68

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Phe Ser Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Asn Ser Leu
                85                  90                  95

Thr Phe Gly Gly Gly Thr Lys Val Glu Ile Lys
            100                 105
```

<210> SEQ ID NO 69
<211> LENGTH: 364

<212> TYPE: DNA
<213> ORGANISM: Artificial Sequence
<220> FEATURE:
<223> OTHER INFORMATION: synthetic

<400> SEQUENCE: 69

```
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtga cataggctat     180
gcggactctg tgaagggccg attcaccatc tccagagaca acgccaagaa ctccctgtat     240
ctgcaaatga acagtctgag agctgaggac acggccttgt attactgtgc aaaagcttac     300
ggtgactact actacttta cggtatggac gtctggggcc aagggaccac ggtcaccgtc     360
tcct                                                                  364
```

<210> SEQ ID NO 70
<211> LENGTH: 121
<212> TYPE: PRT
<213> ORGANISM: Artificial Sequence
<220> FEATURE:
<223> OTHER INFORMATION: synthetic

<400> SEQUENCE: 70

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Ile Ser Trp Asn Ser Gly Asp Ile Gly Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Ala Tyr Gly Asp Tyr Tyr Tyr Phe Tyr Gly Met Asp Val Trp
            100                 105                 110

Gly Gln Gly Thr Thr Val Thr Val Ser
        115                 120
```

<210> SEQ ID NO 71
<211> LENGTH: 322
<212> TYPE: DNA
<213> ORGANISM: Artificial Sequence
<220> FEATURE:
<223> OTHER INFORMATION: synthetic

<400> SEQUENCE: 71

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat agtgcatcca gcagggccac tggcatccca     180
gacaggttca gtggcagtgg gtctgggaca gacttcactc tcaccatcag cagactggag     240
cctgaagatt ttgcagtgta ttactgtcag cagtatgata actcactcac tttcggcgga     300
gggaccaagg tggagatcaa ac                                              322
```

<210> SEQ ID NO 72

```
<211> LENGTH: 107
<212> TYPE: PRT
<213> ORGANISM: Artificial Sequence
<220> FEATURE:
<223> OTHER INFORMATION: synthetic

<400> SEQUENCE: 72

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Ser Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Asn Ser Leu
                85                  90                  95

Thr Phe Gly Gly Gly Thr Lys Val Glu Ile Lys
            100                 105

<210> SEQ ID NO 73
<211> LENGTH: 366
<212> TYPE: DNA
<213> ORGANISM: Artificial Sequence
<220> FEATURE:
<223> OTHER INFORMATION: synthetic

<400> SEQUENCE: 73
caggtgcagc tggtggagtc tgggggaggc ttggttcagc ctggggagtc cctgagactc      60
tcctgtgcag cctctggatt cacctttagc agctatgcca tgagctgggt ccgccagggt     120
ccagggaagg gcctggagtg gtctcaagt attagtggga gtggtggtac acttactac       180 gcagactccg tggagggccg gttcaccatc tccagagaca attccaagaa cacgctgtat     240
ctgcacatga acagcctgag agccgaggac acggccgtat attactgtgc gaaagatttt     300
cttgactaca gtacctacct tgcttttgat ctctggggcc aaggacaat ggtcaccgtc      360 tcttca                                                                366

<210> SEQ ID NO 74
<211> LENGTH: 122
<212> TYPE: PRT
<213> ORGANISM: Artificial Sequence
<220> FEATURE:
<223> OTHER INFORMATION: synthetic

<400> SEQUENCE: 74

Gln Val Gln Leu Val Glu Ser Gly Gly Gly Leu Val Gln Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Gly Pro Gly Lys Gly Leu Glu Trp Val
        35                  40                  45

Ser Ser Ile Ser Gly Ser Gly Gly Thr Thr Tyr Tyr Ala Asp Ser Val
50                  55                  60

Glu Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
```

```
                    85                  90                  95
Ala Lys Asp Phe Leu Asp Tyr Ser Thr Tyr Leu Ala Phe Asp Leu Trp
        100                 105                 110

Gly Gln Gly Thr Met Val Thr Val Ser Ser
        115                 120
```

<210> SEQ ID NO 75
<211> LENGTH: 24
<212> TYPE: DNA
<213> ORGANISM: Artificial Sequence
<220> FEATURE:
<223> OTHER INFORMATION: synthetic

<400> SEQUENCE: 75
ggattcacct ttagcagcta tgcc                                          24

<210> SEQ ID NO 76
<211> LENGTH: 8
<212> TYPE: PRT
<213> ORGANISM: Artificial Sequence
<220> FEATURE:
<223> OTHER INFORMATION: synthetic

<400> SEQUENCE: 76

Gly Phe Thr Phe Ser Ser Tyr Ala
1               5

<210> SEQ ID NO 77
<211> LENGTH: 24
<212> TYPE: DNA
<213> ORGANISM: Artificial Sequence
<220> FEATURE:
<223> OTHER INFORMATION: synthetic

<400> SEQUENCE: 77
attagtggga gtggtggtac cact                                          24

<210> SEQ ID NO 78
<211> LENGTH: 8
<212> TYPE: PRT
<213> ORGANISM: Artificial Sequence
<220> FEATURE:
<223> OTHER INFORMATION: synthetic

<400> SEQUENCE: 78

Ile Ser Gly Ser Gly Gly Thr Thr
1               5

<210> SEQ ID NO 79
<211> LENGTH: 45
<212> TYPE: DNA
<213> ORGANISM: Artificial Sequence
<220> FEATURE:
<223> OTHER INFORMATION: synthetic

<400> SEQUENCE: 79
gcgaaagatt tccttgacta cagtacctac cttgcttttg atctc                   45

<210> SEQ ID NO 80
<211> LENGTH: 15
<212> TYPE: PRT
<213> ORGANISM: Artificial Sequence
<220> FEATURE:
<223> OTHER INFORMATION: synthetic

<400> SEQUENCE: 80

Ala Lys Asp Phe Leu Asp Tyr Ser Thr Tyr Leu Ala Phe Asp Leu
1               5                   10                  15

<210> SEQ ID NO 81
<211> LENGTH: 324
<212> TYPE: DNA
<213> ORGANISM: Artificial Sequence
<220> FEATURE:
<223> OTHER INFORMATION: synthetic

<400> SEQUENCE: 81

```
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttacta ttgtcaacag gctaacagtt ccctcggac gttcggccaa      300 gggaccaagg tggagatcaa acga                                             324
```

<210> SEQ ID NO 82
<211> LENGTH: 108
<212> TYPE: PRT
<213> ORGANISM: Artificial Sequence
<220> FEATURE:
<223> OTHER INFORMATION: synthetic

<400> SEQUENCE: 82

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys Arg
            100                 105

<210> SEQ ID NO 83
<211> LENGTH: 18
<212> TYPE: DNA
<213> ORGANISM: Artificial Sequence
<220> FEATURE:
<223> OTHER INFORMATION: synthetic

<400> SEQUENCE: 83

```
cagggtatta gcagctgg                                                    18
```

<210> SEQ ID NO 84
<211> LENGTH: 6
<212> TYPE: PRT
<213> ORGANISM: Artificial Sequence
<220> FEATURE:
<223> OTHER INFORMATION: synthetic

<400> SEQUENCE: 84

-continued

Gln Gly Ile Ser Ser Trp
1               5

<210> SEQ ID NO 85
<211> LENGTH: 9
<212> TYPE: DNA
<213> ORGANISM: Artificial Sequence
<220> FEATURE:
<223> OTHER INFORMATION: synthetic

<400> SEQUENCE: 85 gctgcatcc                                                                 9

<210> SEQ ID NO 86
<211> LENGTH: 3
<212> TYPE: PRT
<213> ORGANISM: Artificial Sequence
<220> FEATURE:
<223> OTHER INFORMATION: synthetic

<400> SEQUENCE: 86

Ala Ala Ser
1

<210> SEQ ID NO 87
<211> LENGTH: 27
<212> TYPE: DNA
<213> ORGANISM: Artificial Sequence
<220> FEATURE:
<223> OTHER INFORMATION: synthetic

<400> SEQUENCE: 87
caacaggcta acagtttccc tcggacg                                            27

<210> SEQ ID NO 88
<211> LENGTH: 9
<212> TYPE: PRT
<213> ORGANISM: Artificial Sequence
<220> FEATURE:
<223> OTHER INFORMATION: synthetic

<400> SEQUENCE: 88

Gln Gln Ala Asn Ser Phe Pro Arg Thr
1               5

<210> SEQ ID NO 89
<211> LENGTH: 366
<212> TYPE: DNA
<213> ORGANISM: Artificial Sequence
<220> FEATURE:
<223> OTHER INFORMATION: synthetic

<400> SEQUENCE: 89
gaggtgcagc tggtggagtc tgggggaggc ttggttcagc ctggggagtc cctgagactc         60
tcctgtgcag cctctggatt cacctttagc agctatgcca tgagctgggt ccgccagggt        120
ccagggaagg gcctggagtg ggtctcaagt attagtggga gtggtggtac cacttactac        180
gcagactccg tgagggccg gttcaccatc tccagagaca attccaagaa cacgctgtat         240
ctgcacatga acagcctgag agccgaggac acggccgtat attactgtgc gaaagatttt        300
cttgactaca gtacctacct tgcttttgat ctctggggcc aagggacaat ggtcaccgtc        360
tcttca                                                                  366

<210> SEQ ID NO 90

<211> LENGTH: 122
<212> TYPE: PRT
<213> ORGANISM: Artificial Sequence
<220> FEATURE:
<223> OTHER INFORMATION: synthetic

<400> SEQUENCE: 90

```
Glu Val Gln Leu Val Glu Ser Gly Gly Gly Leu Val Gln Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Gly Pro Gly Lys Gly Leu Glu Trp Val
        35                  40                  45

Ser Ser Ile Ser Gly Ser Gly Gly Thr Thr Tyr Tyr Ala Asp Ser Val
50                  55                  60

Glu Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Lys Asp Phe Leu Asp Tyr Ser Thr Tyr Leu Ala Phe Asp Leu Trp
            100                 105                 110

Gly Gln Gly Thr Met Val Thr Val Ser Ser
        115                 120
```

<210> SEQ ID NO 91
<211> LENGTH: 321
<212> TYPE: DNA
<213> ORGANISM: Artificial Sequence
<220> FEATURE:
<223> OTHER INFORMATION: synthetic

<400> SEQUENCE: 91

```
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt tccctcggac gttcggccaa   300
gggaccaagg tggaaatcaa a                                              321
```

<210> SEQ ID NO 92
<211> LENGTH: 107
<212> TYPE: PRT
<213> ORGANISM: Artificial Sequence
<220> FEATURE:
<223> OTHER INFORMATION: synthetic

<400> SEQUENCE: 92

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys
            100                 105
```

<210> SEQ ID NO 93
<211> LENGTH: 366
<212> TYPE: DNA
<213> ORGANISM: Artificial Sequence
<220> FEATURE:
<223> OTHER INFORMATION: synthetic

<400> SEQUENCE: 93

```
gaggtgcagc tggtggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggga gtggtggtac cacttactac   180
gcagactccg tgaagggccg gttcaccatc tccagagaca attccaagaa cacgctgtat   240
ctgcaaatga acagcctgag agccgaggac acggccgtat attactgtgc gaaagatttt   300
cttgactaca gtacctacct tgcttttgat ctctggggcc aagggacaat ggtcaccgtc   360
tcttca                                                              366
```

<210> SEQ ID NO 94
<211> LENGTH: 122
<212> TYPE: PRT
<213> ORGANISM: Artificial Sequence
<220> FEATURE:
<223> OTHER INFORMATION: synthetic

<400> SEQUENCE: 94

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Phe Leu Asp Tyr Ser Thr Tyr Leu Ala Phe Asp Leu Trp
            100                 105                 110

Gly Gln Gly Thr Met Val Thr Val Ser Ser
        115                 120
```

<210> SEQ ID NO 95
<211> LENGTH: 322
<212> TYPE: DNA
<213> ORGANISM: Artificial Sequence
<220> FEATURE:
<223> OTHER INFORMATION: synthetic

<400> SEQUENCE: 95

```
gacatccaga tgacccagtc tccatcttct gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccagtt tgcaaagtgg ggtcccatca   180
```

```
aggttcagcg gcagtggatc tgggacagat ttcactctca ctatcagcag cctgcagcct    240
gaagattttg caacttacta ttgtcaacag gctaacagtt tccctcggac gttcggccaa    300
gggaccaagg tggaaatcaa ac                                             322
```

<210> SEQ ID NO 96
<211> LENGTH: 107
<212> TYPE: PRT
<213> ORGANISM: Artificial Sequence
<220> FEATURE:
<223> OTHER INFORMATION: synthetic

<400> SEQUENCE: 96

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys
            100                 105
```

<210> SEQ ID NO 97
<211> LENGTH: 363
<212> TYPE: DNA
<213> ORGANISM: Artificial Sequence
<220> FEATURE:
<223> OTHER INFORMATION: synthetic

<400> SEQUENCE: 97

```
caggtgcagc tggtggagtc tgggggaggc ttggtaaagc ctggggggtc ccttagactc     60
tcctgtgcag cctctggatt cactttcagt aacgcctgga tgagctgggt ccgccaggct    120
ccagggaagg ggctggagtg ggttggccgt attaaaagca aaactgatgg tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
gatggcgtag cagctcgtta ctttgactac tggggccagg gaaccctggt caccgtctcc    360
tca                                                                  363
```

<210> SEQ ID NO 98
<211> LENGTH: 121
<212> TYPE: PRT
<213> ORGANISM: Artificial Sequence
<220> FEATURE:
<223> OTHER INFORMATION: synthetic

<400> SEQUENCE: 98

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
```

```
                35                  40                  45
Gly Arg Ile Lys Ser Lys Thr Asp Gly Gly Thr Thr Asp Tyr Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Gly Val Ala Ala Arg Tyr Phe Thr Tyr Trp Gly
            100                 105                 110

Gln Gly Thr Leu Val Thr Val Ser Ser
        115                 120
```

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99
ggattcactt tcagtaacgc ctgg            24

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

```
Gly Phe Thr Phe Ser Asn Ala Trp
1               5
```

<210> SEQ ID NO 101
<211> LENGTH: 30
<212> TYPE: DNA
<213> ORGANISM: Artificial Sequence
<220> FEATURE:
<223> OTHER INFORMATION: synthetic

<400> SEQUENCE: 101
attaaaagca aaactgatgg tgggacaaca            30

<210> SEQ ID NO 102
<211> LENGTH: 10
<212> TYPE: PRT
<213> ORGANISM: Artificial Sequence
<220> FEATURE:
<223> OTHER INFORMATION: synthetic

<400> SEQUENCE: 102

```
Ile Lys Ser Lys Thr Asp Gly Gly Thr Thr
1               5                   10
```

<210> SEQ ID NO 103
<211> LENGTH: 36
<212> TYPE: DNA
<213> ORGANISM: Artificial Sequence
<220> FEATURE:
<223> OTHER INFORMATION: synthetic

<400> SEQUENCE: 103
accacagatg gcgtagcagc tcgttacttt gactac            36

<210> SEQ ID NO 104
<211> LENGTH: 12
<212> TYPE: PRT
<213> ORGANISM: Artificial Sequence
<220> FEATURE:
<223> OTHER INFORMATION: synthetic

<400> SEQUENCE: 104

```
Thr Thr Asp Gly Val Ala Ala Arg Tyr Phe Asp Tyr
 1               5                  10
```

<210> SEQ ID NO 105
<211> LENGTH: 324
<212> TYPE: DNA
<213> ORGANISM: Artificial Sequence
<220> FEATURE:
<223> OTHER INFORMATION: synthetic

<400> SEQUENCE: 105

```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attctcggac gttcggccaa   300
gggaccaagg tggagatcaa acga                                          324
```

<210> SEQ ID NO 106
<211> LENGTH: 108
<212> TYPE: PRT
<213> ORGANISM: Artificial Sequence
<220> FEATURE:
<223> OTHER INFORMATION: synthetic

<400> SEQUENCE: 106

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys Arg
            100                 105
```

<210> SEQ ID NO 107
<211> LENGTH: 18
<212> TYPE: DNA
<213> ORGANISM: Artificial Sequence
<220> FEATURE:
<223> OTHER INFORMATION: synthetic

<400> SEQUENCE: 107

```
cagagtatta gtagctgg                                                  18
```

```
<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

Gln Ser Ile Ser Ser Trp
 1               5

<210> SEQ ID NO 109
<211> LENGTH: 9
<212> TYPE: DNA
<213> ORGANISM: Artificial Sequence
<220> FEATURE:
<223> OTHER INFORMATION: synthetic

<400> SEQUENCE: 109 aaggcgtct                                                                  9

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

Lys Ala Ser
 1

<210> SEQ ID NO 111
<211> LENGTH: 27
<212> TYPE: DNA
<213> ORGANISM: Artificial Sequence
<220> FEATURE:
<223> OTHER INFORMATION: synthetic

<400> SEQUENCE: 111
caacagtata atagttattc tcggacg                                             27

<210> SEQ ID NO 112
<211> LENGTH: 9
<212> TYPE: PRT
<213> ORGANISM: Artificial Sequence
<220> FEATURE:
<223> OTHER INFORMATION: synthetic

<400> SEQUENCE: 112

Gln Gln Tyr Asn Ser Tyr Ser Arg Thr
 1               5

<210> SEQ ID NO 113
<211> LENGTH: 363
<212> TYPE: DNA
<213> ORGANISM: Artificial Sequence
<220> FEATURE:
<223> OTHER INFORMATION: synthetic

<400> SEQUENCE: 113
gaggtgcagc tggtggagtc tgggggaggc ttggtaaagc ctggggggtc ccttagactc        60
tcctgtgcag cctctggatt cactttcagt aacgcctgga tgagctgggt ccgccaggct      120
ccagggaagg ggctggagtg ggttggccgt attaaaagca aaactgatgg tgggacaaca      180
gactacgctg cacccgtgaa aggcagattc accatctcaa gagatgattc aaaaaacacg      240
```

```
ctgtatctgc aaatgaacag cctgaaaacc gaggacacag ccgtgtatta ctgtaccaca      300
gatggcgtag cagctcgtta ctttgactac tggggccagg gaaccctggt caccgtctcc      360
tca                                                                    363
```

<210> SEQ ID NO 114
<211> LENGTH: 121
<212> TYPE: PRT
<213> ORGANISM: Artificial Sequence
<220> FEATURE:
<223> OTHER INFORMATION: synthetic

<400> SEQUENCE: 114

| Glu | Val | Gln | Leu | Val | Glu | Ser | Gly | Gly | Gly | Leu | Val | Lys | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Asn | Ala |
|---|---|---|---|---|---|---|---|---|---|---|---|---|---|---|---|
| | | | 20 | | | | | 25 | | | | | 30 | | |

| Trp | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Gly | Arg | Ile | Lys | Ser | Lys | Thr | Asp | Gly | Gly | Thr | Thr | Asp | Tyr | Ala | Ala |
|---|---|---|---|---|---|---|---|---|---|---|---|---|---|---|---|
| 50 | | | | | 55 | | | | | 60 | | | | | |

| Pro | Val | Lys | Gly | Arg | Phe | Thr | Ile | Ser | Arg | Asp | Asp | Ser | Lys | Asn | Thr |
|---|---|---|---|---|---|---|---|---|---|---|---|---|---|---|---|
| 65 | | | | | 70 | | | | | 75 | | | | | 80 |

| Leu | Tyr | Leu | Gln | Met | Asn | Ser | Leu | Lys | Thr | Glu | Asp | Thr | Ala | Val | Tyr |
|---|---|---|---|---|---|---|---|---|---|---|---|---|---|---|---|
| | | | | 85 | | | | | 90 | | | | | 95 | |

| Tyr | Cys | Thr | Thr | Asp | Gly | Val | Ala | Ala | Arg | Tyr | Phe | Asp | Tyr | Trp | Gly |
|---|---|---|---|---|---|---|---|---|---|---|---|---|---|---|---|
| | | | 100 | | | | | 105 | | | | | 110 | | |

| Gln | Gly | Thr | Leu | Val | Thr | Val | Ser | Ser |
|---|---|---|---|---|---|---|---|---|
| | | | 115 | | | | | 120 |

<210> SEQ ID NO 115
<211> LENGTH: 321
<212> TYPE: DNA
<213> ORGANISM: Artificial Sequence
<220> FEATURE:
<223> OTHER INFORMATION: synthetic

<400> SEQUENCE: 115

```
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatagtt attctcggac gttcggccaa     300
gggaccaagg tggaaatcaa a                                               321
```

<210> SEQ ID NO 116
<211> LENGTH: 107
<212> TYPE: PRT
<213> ORGANISM: Artificial Sequence
<220> FEATURE:
<223> OTHER INFORMATION: synthetic

<400> SEQUENCE: 116

| Asp | Ile | Gln | Met | Thr | Gln | Ser | Pro | Ser | Thr | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Gln | Ser | Ile | Ser | Ser | Trp |
|---|---|---|---|---|---|---|---|---|---|---|---|---|---|---|---|
| | | | 20 | | | | | 25 | | | | | 30 | | |

```
Leu Ala Trp Tyr Gln Gln Lys Pro Gly Lys Ala Pro Lys Leu Leu Ile
             35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Arg
                 85                  90                  95

Thr Phe Gly Gln Gly Thr Lys Val Glu Ile Lys
                100                 105
```

<210> SEQ ID NO 117
<211> LENGTH: 363
<212> TYPE: DNA
<213> ORGANISM: Artificial Sequence
<220> FEATURE:
<223> OTHER INFORMATION: synthetic

<400> SEQUENCE: 117

```
gaggtgcagc tggtggagtc tgggggaggc ttggtaaagc ctggggggtc ccttagactc    60
tcctgtgcag cctctggatt cactttcagt aacgcctgga tgagctgggt ccgccaggct   120
ccagggaagg ggctggagtg ggttggccgt attaaaagca aaactgatgg tgggacaaca   180
gactacgctg cacccgtgaa aggcagattc accatctcaa gagatgattc aaaaaacacg   240
ctgtatctgc aaatgaacag cctgaaaacc gaggacacag ccgtgtatta ctgtaccaca   300
gatggcgtag cagctcgtta ctttgactac tggggccagg gaaccctggt caccgtctcc   360
tca                                                                363
```

<210> SEQ ID NO 118
<211> LENGTH: 121
<212> TYPE: PRT
<213> ORGANISM: Artificial Sequence
<220> FEATURE:
<223> OTHER INFORMATION: synthetic

<400> SEQUENCE: 118

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Lys Ser Lys Thr Asp Gly Gly Thr Thr Asp Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Asp Gly Val Ala Ala Arg Tyr Phe Asp Tyr Trp Gly
                100                 105                 110

Gln Gly Thr Leu Val Thr Val Ser Ser
        115                 120
```

<210> SEQ ID NO 119
<211> LENGTH: 322
<212> TYPE: DNA
<213> ORGANISM: Artificial Sequence
<220> FEATURE:

<223> OTHER INFORMATION: synthetic

<400> SEQUENCE: 119

```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attctcggac gttcggccaa   300
gggaccaagg tggaaatcaa ac                                            322
```

<210> SEQ ID NO 120
<211> LENGTH: 107
<212> TYPE: PRT
<213> ORGANISM: Artificial Sequence
<220> FEATURE:
<223> OTHER INFORMATION: synthetic

<400> SEQUENCE: 120

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105
```

<210> SEQ ID NO 121
<211> LENGTH: 366
<212> TYPE: DNA
<213> ORGANISM: Artificial Sequence
<220> FEATURE:
<223> OTHER INFORMATION: synthetic

<400> SEQUENCE: 121

```
gaggtgcagc tggtgcagtc tgggggaggc gtggtccagc ctggggaggtc cctgagactc    60
tcctgtgcag cgtctggatt caccttcagt agctatggca tgcactgggt ccgccaggct   120
ccaggcaagg ggctggagtg ggtggcagtt atgtggtatg atgaaactaa taaatactat   180
gcagactccg tgaagggccg attcaccatc tccagagaca attccaagaa cacgctgtat   240
ctgcaaatga acagcctgag agccgaggac acggctgtgt attactgtgc gagatatagt   300
ggctacgagg actactacca cggtatggac gtctggggcc aagggaccac ggtcaccgtc   360
tcctca                                                              366
```

<210> SEQ ID NO 122
<211> LENGTH: 122
<212> TYPE: PRT
<213> ORGANISM: Artificial Sequence
<220> FEATURE:
<223> OTHER INFORMATION: synthetic

<400> SEQUENCE: 122

Glu Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Trp Tyr Asp Glu Thr Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Gly Tyr Glu Asp Tyr Tyr His Gly Met Asp Val Trp
            100                 105                 110

Gly Gln Gly Thr Thr Val Thr Val Ser Ser
        115                 120

<210> SEQ ID NO 123
<211> LENGTH: 24
<212> TYPE: DNA
<213> ORGANISM: Artificial Sequence
<220> FEATURE:
<223> OTHER INFORMATION: synthetic

<400> SEQUENCE: 123
ggattcacct tcagtagcta tggc                                          24

<210> SEQ ID NO 124
<211> LENGTH: 8
<212> TYPE: PRT
<213> ORGANISM: Artificial Sequence
<220> FEATURE:
<223> OTHER INFORMATION: synthetic

<400> SEQUENCE: 124

Gly Phe Thr Phe Ser Ser Tyr Gly
1               5

<210> SEQ ID NO 125
<211> LENGTH: 24
<212> TYPE: DNA
<213> ORGANISM: Artificial Sequence
<220> FEATURE:
<223> OTHER INFORMATION: synthetic

<400> SEQUENCE: 125
atgtggtatg atgaaactaa taaa                                          24

<210> SEQ ID NO 126
<211> LENGTH: 8
<212> TYPE: PRT
<213> ORGANISM: Artificial Sequence
<220> FEATURE:
<223> OTHER INFORMATION: synthetic

<400> SEQUENCE: 126

Met Trp Tyr Asp Glu Thr Asn Lys
1               5

<210> SEQ ID NO 127
<211> LENGTH: 45

<212> TYPE: DNA
<213> ORGANISM: Artificial Sequence
<220> FEATURE:
<223> OTHER INFORMATION: synthetic

<400> SEQUENCE: 127
gcgagatata gtggctacga ggactactac cacggtatgg acgtc    45

<210> SEQ ID NO 128
<211> LENGTH: 15
<212> TYPE: PRT
<213> ORGANISM: Artificial Sequence
<220> FEATURE:
<223> OTHER INFORMATION: synthetic

<400> SEQUENCE: 128

Ala Arg Tyr Ser Gly Tyr Glu Asp Tyr Tyr His Gly Met Asp Val
 1               5                  10                  15

<210> SEQ ID NO 129
<211> LENGTH: 321
<212> TYPE: DNA
<213> ORGANISM: Artificial Sequence
<220> FEATURE:
<223> OTHER INFORMATION: synthetic

<400> SEQUENCE: 129
gccatccaga tgacccagtc tccagccacc ccgtctgtgt ctccagggga aagagccacc    60
ctctcctgca gggccagtca gagtattagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcac tataataact ggatcacctt cggccaaggg   300
acacgactgg agattaaacg a                                              321

<210> SEQ ID NO 130
<211> LENGTH: 107
<212> TYPE: PRT
<213> ORGANISM: Artificial Sequence
<220> FEATURE:
<223> OTHER INFORMATION: synthetic

<400> SEQUENCE: 130

Ala Ile Gln Met Thr Gln Ser Pro Ala Thr Pro Ser Val Ser Pro Gly
 1               5                  10                  15

Glu Arg Ala Thr Leu Ser Cys Arg Ala Ser Gln Ser Ile Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln His Tyr Asn Asn Trp Ile Thr
                85                  90                  95

Phe Gly Gln Gly Thr Arg Leu Glu Ile Lys Arg
            100                 105

<210> SEQ ID NO 131
<211> LENGTH: 18
<212> TYPE: DNA

<213> ORGANISM: Artificial Sequence
<220> FEATURE:
<223> OTHER INFORMATION: synthetic

<400> SEQUENCE: 131
cagagtatta gcagcaac                                                   18

<210> SEQ ID NO 132
<211> LENGTH: 6
<212> TYPE: PRT
<213> ORGANISM: Artificial Sequence
<220> FEATURE:
<223> OTHER INFORMATION: synthetic

<400> SEQUENCE: 132

Gln Ser Ile Ser Ser Asn
 1               5

<210> SEQ ID NO 133
<211> LENGTH: 9
<212> TYPE: DNA
<213> ORGANISM: Artificial Sequence
<220> FEATURE:
<223> OTHER INFORMATION: synthetic

<400> SEQUENCE: 133 ggtgcatcc                                                              9

<210> SEQ ID NO 134
<211> LENGTH: 3
<212> TYPE: PRT
<213> ORGANISM: Artificial Sequence
<220> FEATURE:
<223> OTHER INFORMATION: synthetic

<400> SEQUENCE: 134

Gly Ala Ser
 1

<210> SEQ ID NO 135
<211> LENGTH: 24
<212> TYPE: DNA
<213> ORGANISM: Artificial Sequence
<220> FEATURE:
<223> OTHER INFORMATION: synthetic

<400> SEQUENCE: 135
cagcactata ataactggat cacc                                             24

<210> SEQ ID NO 136
<211> LENGTH: 8
<212> TYPE: PRT
<213> ORGANISM: Artificial Sequence
<220> FEATURE:
<223> OTHER INFORMATION: synthetic

<400> SEQUENCE: 136

Gln His Tyr Asn Asn Trp Ile Thr
 1               5

<210> SEQ ID NO 137
<211> LENGTH: 363
<212> TYPE: DNA
<213> ORGANISM: Artificial Sequence
<220> FEATURE:
<223> OTHER INFORMATION: synthetic

<400> SEQUENCE: 137

```
caggtgcagc tggtggagtc tgggggaggc gtggtccagc ctggggaggtc cctgagactc    60
tcctgtgcag cgtctggatt caccttcagt agctatggca tgcactgggt ccgccaggct   120
ccaggcaagg gctggagtg gtggcagtt atgtggtatg atgaaactaa taaatactat   180
gcagactccg tgaagggccg attcaccatc tccagagaca attccaagaa cacgctgtat   240
ctgcaaatga acagcctgag agccgaggac acggctgtgt attactgtgc gagatatagt   300
ggctacgagg actactacca cggtatggac gtctggggcc aagggaccac ggtcaccgtc   360
tcc                                                                  363
```

<210> SEQ ID NO 138
<211> LENGTH: 121
<212> TYPE: PRT
<213> ORGANISM: Artificial Sequence
<220> FEATURE:
<223> OTHER INFORMATION: synthetic

<400> SEQUENCE: 138

```
Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Met Trp Tyr Asp Glu Thr Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Tyr Ser Gly Tyr Glu Asp Tyr Tyr His Gly Met Asp Val Trp
            100                 105                 110
Gly Gln Gly Thr Thr Val Thr Val Ser
        115                 120
```

<210> SEQ ID NO 139
<211> LENGTH: 318
<212> TYPE: DNA
<213> ORGANISM: Artificial Sequence
<220> FEATURE:
<223> OTHER INFORMATION: synthetic

<400> SEQUENCE: 139

```
gaaatagtga tgacgcagtc tccagccacc ccgtctgtgt ctccagggga aagagccacc    60
ctctcctgca gggccagtca gagtattagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagttttatta ctgtcagcac tataataact ggatcacctt cggccaaggg   300
acacgactgg agattaaa                                                  318
```

<210> SEQ ID NO 140
<211> LENGTH: 106
<212> TYPE: PRT
<213> ORGANISM: Artificial Sequence
<220> FEATURE:
<223> OTHER INFORMATION: synthetic

<400> SEQUENCE: 140

Glu Ile Val Met Thr Gln Ser Pro Ala Thr Pro Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Asn Asn Trp Ile Thr
                85                  90                  95

Phe Gly Gln Gly Thr Arg Leu Glu Ile Lys
            100                 105

<210> SEQ ID NO 141
<211> LENGTH: 364
<212> TYPE: DNA
<213> ORGANISM: Artificial Sequence
<220> FEATURE:
<223> OTHER INFORMATION: synthetic

<400> SEQUENCE: 141
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atgtggtatg atgaaactaa taatactat     180 gcagactccg tgaagggccg attcaccatc tccagagaca actccaagaa cacgctgtat     240
ctgcaaatga acagcctgag agccgaggac acggctgtgt attactgtgc gagatatagt     300
ggctacgagg actactacca cggtatggac gtctggggcc aagggaccac ggtcaccgtc     360
tcct                                                                  364

<210> SEQ ID NO 142
<211> LENGTH: 121
<212> TYPE: PRT
<213> ORGANISM: Artificial Sequence
<220> FEATURE:
<223> OTHER INFORMATION: synthetic

<400> SEQUENCE: 142

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Trp Tyr Asp Glu Thr Asn Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Gly Tyr Glu Asp Tyr Tyr His Gly Met Asp Val Trp
            100                 105                 110

```
Gly Gln Gly Thr Thr Val Thr Val Ser
        115                 120
```

<210> SEQ ID NO 143
<211> LENGTH: 319
<212> TYPE: DNA
<213> ORGANISM: Artificial Sequence
<220> FEATURE:
<223> OTHER INFORMATION: synthetic

<400> SEQUENCE: 143

```
gaaatagtga tgacgcagtc tccagccacc ctgtctgtgt ctccagggga aagagccacc    60
ctctcctgca gggccagtca gagtattagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcac tataataact ggatcacctt cggccaaggg   300
acacgactgg agattaaac                                                319
```

<210> SEQ ID NO 144
<211> LENGTH: 106
<212> TYPE: PRT
<213> ORGANISM: Artificial Sequence
<220> FEATURE:
<223> OTHER INFORMATION: synthetic

<400> SEQUENCE: 144

```
Glu Ile Val Met Thr Gln Ser Pro Ala Thr Leu Ser Val Ser Pro Gly
  1               5                  10                  15
Glu Arg Ala Thr Leu Ser Cys Arg Ala Ser Gln Ser Ile Ser Ser Asn
             20                  25                  30
Leu Ala Trp Tyr Gln Gln Lys Pro Gly Gln Ala Pro Arg Leu Leu Ile
         35                  40                  45
Tyr Gly Ala Ser Thr Arg Ala Thr Gly Ile Pro Ala Arg Phe Ser Gly
     50                  55                  60
Ser Gly Ser Gly Thr Glu Phe Thr Leu Thr Ile Ser Ser Leu Gln Ser
 65                  70                  75                  80
Glu Asp Phe Ala Val Tyr Tyr Cys Gln His Tyr Asn Asn Trp Ile Thr
                 85                  90                  95
Phe Gly Gln Gly Thr Arg Leu Glu Ile Lys
            100                 105
```

<210> SEQ ID NO 145
<211> LENGTH: 357
<212> TYPE: DNA
<213> ORGANISM: Artificial Sequence
<220> FEATURE:
<223> OTHER INFORMATION: synthetic

<400> SEQUENCE: 145

```
caggtgcagc tggtgcagtc tggggggaggc ttggtcaagc ctggagggtc cctgagactc    60
tcctgtgcag cctctggatt caccttcagt gactactaca tgagctggat ccgccaggct   120
ccagggaagg ggctggagtg ggtttcatac attagttata ctggtaggac catatactac   180
gcggactctg tgaagggccg attcaccatc tccagggaca acgccaagaa ctcactgtat   240
ctgcaaatga acagcctgag agccgaggac acggccgtgt attactgtgc gagagatacg   300
gactacggtg acttctttga ctactggggc cagggaaccc tggtcaccgt ctcctca      357
```

<210> SEQ ID NO 146
<211> LENGTH: 119
<212> TYPE: PRT
<213> ORGANISM: Artificial Sequence
<220> FEATURE:
<223> OTHER INFORMATION: synthetic

<400> SEQUENCE: 146

```
Gln Val Gln Leu Val Gln Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Tyr Thr Gly Arg Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
            85                  90                  95

Ala Arg Asp Thr Asp Tyr Gly Asp Phe Phe Asp Tyr Trp Gly Gln Gly
           100                 105                 110

Thr Leu Val Thr Val Ser Ser
        115
```

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147
ggattcacct tcagtgacta ctac                                        24

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

```
Gly Phe Thr Phe Ser Asp Tyr Tyr
 1               5
```

<210> SEQ ID NO 149
<211> LENGTH: 24
<212> TYPE: DNA
<213> ORGANISM: Artificial Sequence
<220> FEATURE:
<223> OTHER INFORMATION: synthetic

<400> SEQUENCE: 149
attagttata ctggtaggac cata                                        24

<210> SEQ ID NO 150
<211> LENGTH: 8
<212> TYPE: PRT
<213> ORGANISM: Artificial Sequence
<220> FEATURE:
<223> OTHER INFORMATION: synthetic

<400> SEQUENCE: 150

```
Ile Ser Tyr Thr Gly Arg Thr Ile
 1               5
```

<210> SEQ ID NO 151
<211> LENGTH: 36
<212> TYPE: DNA
<213> ORGANISM: Artificial Sequence
<220> FEATURE:
<223> OTHER INFORMATION: synthetic

<400> SEQUENCE: 151
gcgagagata cggactacgg tgacttcttt gactac                                    36

<210> SEQ ID NO 152
<211> LENGTH: 12
<212> TYPE: PRT
<213> ORGANISM: Artificial Sequence
<220> FEATURE:
<223> OTHER INFORMATION: synthetic

<400> SEQUENCE: 152

```
Ala Arg Asp Thr Asp Tyr Gly Asp Phe Phe Asp Tyr
 1               5                  10
```

<210> SEQ ID NO 153
<211> LENGTH: 324
<212> TYPE: DNA
<213> ORGANISM: Artificial Sequence
<220> FEATURE:
<223> OTHER INFORMATION: synthetic

<400> SEQUENCE: 153
gccatccaga tgacccagtc tccatcctca ctgtctgcat ctgtaggaga cagagtcacc          60
atcacttgtc gggcgagtca gggcattagc aattatttag cctggtttca gcagaaacca        120
gggaaagccc ctaagtccct gatctatgct gcatccagtt tgcaaagtgg ggtcccatca        180
aagttcagcg gcagtggatc tgggacagat ttcactctca ccatcagcag cctgcagcct        240
gaagattttg caacttatta ctgccaacag tataatagtt acccgctcac tttcggcgga        300
gggaccaagg tggagatcaa acga                                              324

<210> SEQ ID NO 154
<211> LENGTH: 108
<212> TYPE: PRT
<213> ORGANISM: Artificial Sequence
<220> FEATURE:
<223> OTHER INFORMATION: synthetic

<400> SEQUENCE: 154

```
Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
             20                  25                  30

Leu Ala Trp Phe Gln Gln Lys Pro Gly Lys Ala Pro Lys Ser Leu Ile
         35                  40                  45

Tyr Ala Ala Ser Ser Leu Gln Ser Gly Val Pro Ser Lys Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95
```

Thr Phe Gly Gly Gly Thr Lys Val Glu Ile Lys Arg
            100                 105

<210> SEQ ID NO 155
<211> LENGTH: 18
<212> TYPE: DNA
<213> ORGANISM: Artificial Sequence
<220> FEATURE:
<223> OTHER INFORMATION: synthetic

<400> SEQUENCE: 155
cagggcatta gcaattat                                          18

<210> SEQ ID NO 156
<211> LENGTH: 6
<212> TYPE: PRT
<213> ORGANISM: Artificial Sequence
<220> FEATURE:
<223> OTHER INFORMATION: synthetic

<400> SEQUENCE: 156

Gln Gly Ile Ser Asn Tyr
1               5

<210> SEQ ID NO 157
<211> LENGTH: 9
<212> TYPE: DNA
<213> ORGANISM: Artificial Sequence
<220> FEATURE:
<223> OTHER INFORMATION: synthetic

<400> SEQUENCE: 157 gctgcatcc                                                     9

<210> SEQ ID NO 158
<211> LENGTH: 3
<212> TYPE: PRT
<213> ORGANISM: Artificial Sequence
<220> FEATURE:
<223> OTHER INFORMATION: synthetic

<400> SEQUENCE: 158

Ala Ala Ser
1

<210> SEQ ID NO 159
<211> LENGTH: 27
<212> TYPE: DNA
<213> ORGANISM: Artificial Sequence
<220> FEATURE:
<223> OTHER INFORMATION: synthetic

<400> SEQUENCE: 159
caacagtata atagttaccc gctcact                                27

<210> SEQ ID NO 160
<211> LENGTH: 9
<212> TYPE: PRT
<213> ORGANISM: Artificial Sequence
<220> FEATURE:
<223> OTHER INFORMATION: synthetic

<400> SEQUENCE: 160

Gln Gln Tyr Asn Ser Tyr Pro Leu Thr
1               5

<210> SEQ ID NO 161
<211> LENGTH: 357
<212> TYPE: DNA
<213> ORGANISM: Artificial Sequence
<220> FEATURE:
<223> OTHER INFORMATION: synthetic

<400> SEQUENCE: 161

```
caggtgcagc tggtggagtc tgggggaggc ttggtcaagc ctggagggtc cctgagactc    60
tcctgtgcag cctctggatt caccttcagt gactactaca tgagctggat ccgccaggct   120
ccagggaagg gctggagtg gtttcatac attagttata ctggtaggac catatactac     180
gcggactctg tgaagggccg attcaccatc tccaggaca acgccaagaa ctcactgtat    240
ctgcaaatga acagcctgag agccgaggac acggccgtgt attactgtgc gagagatacg   300
gactacggtg acttctttga ctactggggc cagggaaccc tggtcaccgt ctcctca      357
```

<210> SEQ ID NO 162
<211> LENGTH: 119
<212> TYPE: PRT
<213> ORGANISM: Artificial Sequence
<220> FEATURE:
<223> OTHER INFORMATION: synthetic

<400> SEQUENCE: 162

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Tyr Thr Gly Arg Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Asp Tyr Gly Asp Phe Phe Asp Tyr Trp Gly Gln Gly
            100                 105                 110

Thr Leu Val Thr Val Ser Ser
        115
```

<210> SEQ ID NO 163
<211> LENGTH: 321
<212> TYPE: DNA
<213> ORGANISM: Artificial Sequence
<220> FEATURE:
<223> OTHER INFORMATION: synthetic

<400> SEQUENCE: 163

```
gacatccaga tgacccagtc tccatcctca ctgtctgcat ctgtaggaga cagagtcacc    60
atcacttgtc gggcgagtca gggcattagc aattatttag cctggtttca gcagaaacca   120
gggaaagccc ctaagtccct gatctatgct gcatccagtt tgcaaagtgg ggtcccatca   180
aagttcagcg gcagtggatc tgggacagat ttcactctca ccatcagcag cctgcagcct   240
gaagattttg caacttatta ctgccaacag tataatagtt acccgctcac tttcggcgga   300
gggaccaagg tggagatcaa a                                             321
```

<210> SEQ ID NO 164

<211> LENGTH: 107
<212> TYPE: PRT
<213> ORGANISM: Artificial Sequence
<220> FEATURE:
<223> OTHER INFORMATION: synthetic

<400> SEQUENCE: 164

```
Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Gly Ile Ser Asn Tyr
             20                  25                  30
Leu Ala Trp Phe Gln Gln Lys Pro Gly Lys Ala Pro Lys Ser Leu Ile
         35                  40                  45
Tyr Ala Ala Ser Ser Leu Gln Ser Gly Val Pro Ser Lys Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Tyr Asn Ser Tyr Pro Leu
                 85                  90                  95
Thr Phe Gly Gly Gly Thr Lys Val Glu Ile Lys
            100                 105
```

<210> SEQ ID NO 165
<211> LENGTH: 357
<212> TYPE: DNA
<213> ORGANISM: Artificial Sequence
<220> FEATURE:
<223> OTHER INFORMATION: synthetic

<400> SEQUENCE: 165

```
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagttata ctggtaggac catatactac     180
gcagactctg tgaagggccg attcaccatc tccagggaca acgccaagaa ctcactgtat     240
ctgcaaatga acagcctgag agccgaggac acggccgtgt attactgtgc gagagatacg     300
gactacggtg acttctttga ctactggggc cagggaaccc tggtcaccgt ctcctca       357
```

<210> SEQ ID NO 166
<211> LENGTH: 119
<212> TYPE: PRT
<213> ORGANISM: Artificial Sequence
<220> FEATURE:
<223> OTHER INFORMATION: synthetic

<400> SEQUENCE: 166

```
Gln Val Gln Leu Val Glu Ser Gly Gly Gly Leu Val Lys Pro Gly Gly
  1               5                  10                  15
Ser Leu Arg Leu Ser Cys Ala Ala Ser Gly Phe Thr Phe Ser Asp Tyr
             20                  25                  30
Tyr Met Ser Trp Ile Arg Gln Ala Pro Gly Lys Gly Leu Glu Trp Val
         35                  40                  45
Ser Tyr Ile Ser Tyr Thr Gly Arg Thr Ile Tyr Tyr Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
```

Ala Arg Asp Thr Asp Tyr Gly Asp Phe Phe Asp Tyr Trp Gly Gln Gly
            100                 105                 110

Thr Leu Val Thr Val Ser Ser
        115

<210> SEQ ID NO 167
<211> LENGTH: 322
<212> TYPE: DNA
<213> ORGANISM: Artificial Sequence
<220> FEATURE:
<223> OTHER INFORMATION: synthetic

<400> SEQUENCE: 167
gacatccaga tgacccagtc tccatcctca ctgtctgcat ctgtaggaga cagagtcacc    60
atcacttgtc gggcgagtca gggcattagc aattatttag cctggtttca gcagaaacca   120
gggaaagccc ctaagtccct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgccaacag tataatagtt acccgctcac tttcggcgga   300
gggaccaagg tggagatcaa ac                                            322

<210> SEQ ID NO 168
<211> LENGTH: 107
<212> TYPE: PRT
<213> ORGANISM: Artificial Sequence
<220> FEATURE:
<223> OTHER INFORMATION: synthetic

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 169
<211> LENGTH: 360
<212> TYPE: DNA
<213> ORGANISM: Artificial Sequence
<220> FEATURE:
<223> OTHER INFORMATION: synthetic

<400> SEQUENCE: 169
caggtgcagc tggtgcagtc ggggggagac gtggtccagc ctgggaggtc cctgagactc    60
tcctgtgcag cgtctggatt caccttcagt agttatggca tgcactgggt ccgccaggct   120
ccaggcaagg gactggagtg ggtggcaatt atatggtatg atggaagtaa taaatattat   180
gcagactccg tgaagggccg attcaccatc tccagagaca attccaagaa cacgctttat   240
ctccaaatga acagcctgag agtcgaggac acggctgtgt actcctgtgc gagagatttt   300

```
agtatatcat ctcgccactt tgactattgg ggccagggaa ccctggtcac cgtctcctca    360
```

<210> SEQ ID NO 170
<211> LENGTH: 120
<212> TYPE: PRT
<213> ORGANISM: Artificial Sequence
<220> FEATURE:
<223> OTHER INFORMATION: synthetic

<400> SEQUENCE: 170

```
Gln Val Gln Leu Val Gln Ser Gly Gly Asp Val Val Gln Pro Gly Arg
  1               5                  10                  15
Ser Leu Arg Leu Ser Cys Ala Ala Ser Gly Phe Thr Phe Ser Ser Tyr
             20                  25                  30
Gly Met His Trp Val Arg Gln Ala Pro Gly Lys Gly Leu Glu Trp Val
         35                  40                  45
Ala Ile Ile Trp Tyr Asp Gly Ser Asn Lys Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Val Glu Asp Thr Ala Val Tyr Ser Cys
                 85                  90                  95
Ala Arg Asp Phe Ser Ile Ser Ser Arg His Phe Asp Tyr Trp Gly Gln
            100                 105                 110
Gly Thr Leu Val Thr Val Ser Ser
        115                 120
```

<210> SEQ ID NO 171
<211> LENGTH: 24
<212> TYPE: DNA
<213> ORGANISM: Artificial Sequence
<220> FEATURE:
<223> OTHER INFORMATION: synthetic

<400> SEQUENCE: 171

```
ggattcacct tcagtagtta tggc                                            24
```

<210> SEQ ID NO 172
<211> LENGTH: 8
<212> TYPE: PRT
<213> ORGANISM: Artificial Sequence
<220> FEATURE:
<223> OTHER INFORMATION: synthetic

<400> SEQUENCE: 172

```
Gly Phe Thr Phe Ser Ser Tyr Gly
  1               5
```

<210> SEQ ID NO 173
<211> LENGTH: 24
<212> TYPE: DNA
<213> ORGANISM: Artificial Sequence
<220> FEATURE:
<223> OTHER INFORMATION: synthetic

<400> SEQUENCE: 173

```
atatggtatg atggaagtaa taaa                                            24
```

<210> SEQ ID NO 174
<211> LENGTH: 8
<212> TYPE: PRT
<213> ORGANISM: Artificial Sequence
<220> FEATURE:

<223> OTHER INFORMATION: synthetic

<400> SEQUENCE: 174

Ile Trp Tyr Asp Gly Ser Asn Lys
1               5

<210> SEQ ID NO 175
<211> LENGTH: 39
<212> TYPE: DNA
<213> ORGANISM: Artificial Sequence
<220> FEATURE:
<223> OTHER INFORMATION: synthetic

<400> SEQUENCE: 175
gcgagagatt ttagtatatc atctcgccac tttgactat                        39

<210> SEQ ID NO 176
<211> LENGTH: 13
<212> TYPE: PRT
<213> ORGANISM: Artificial Sequence
<220> FEATURE:
<223> OTHER INFORMATION: synthetic

<400> SEQUENCE: 176

Ala Arg Asp Phe Ser Ile Ser Ser Arg His Phe Asp Tyr
1               5                   10

<210> SEQ ID NO 177
<211> LENGTH: 324
<212> TYPE: DNA
<213> ORGANISM: Artificial Sequence
<220> FEATURE:
<223> OTHER INFORMATION: synthetic

<400> SEQUENCE: 177
gacatccaga tgacccagtc tccatcctct ctgtctgcat ctgtaggaga cagagtcacc    60
atcacttgtc gggcgagtca ggccattaac aattatttag cctggtttca gcagaaacca   120
gggaaagccc ctaagtccct gatctatgct acatccaatt tgcaaagtgg ggtcccttca   180
cagttcagcg gcagtggatc tgggacagat tacactctca ccatcagcag cctgcagcct   240
gaagattttg caacttatta ctgccaacag tattatattt acccgatcac cttcggccaa   300
gggacacgac tggagattaa acga                                          324

<210> SEQ ID NO 178
<211> LENGTH: 108
<212> TYPE: PRT
<213> ORGANISM: Artificial Sequence
<220> FEATURE:
<223> OTHER INFORMATION: synthetic

<400> SEQUENCE: 178

Asp Ile Gln Met Thr Gln Ser Pro Ser Leu Ser Ala Ser Val Gly
1               5                   10                  15

Asp Arg Val Thr Ile Thr Cys Arg Ala Ser Gln Ala Ile Asn Asn Tyr
                20                  25                  30

Leu Ala Trp Phe Gln Gln Lys Pro Gly Lys Ala Pro Lys Ser Leu Ile
            35                  40                  45

Tyr Ala Thr Ser Asn Leu Gln Ser Gly Val Pro Ser Gln Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Ile
            85                  90                  95

Thr Phe Gly Gln Gly Thr Arg Leu Glu Ile Lys Arg
            100                 105

<210> SEQ ID NO 179
<211> LENGTH: 18
<212> TYPE: DNA
<213> ORGANISM: Artificial Sequence
<220> FEATURE:
<223> OTHER INFORMATION: synthetic

<400> SEQUENCE: 179
caggccatta acaattat                                                 18

<210> SEQ ID NO 180
<211> LENGTH: 6
<212> TYPE: PRT
<213> ORGANISM: Artificial Sequence
<220> FEATURE:
<223> OTHER INFORMATION: synthetic

<400> SEQUENCE: 180

Gln Ala Ile Asn Asn Tyr
 1               5

<210> SEQ ID NO 181
<211> LENGTH: 9
<212> TYPE: DNA
<213> ORGANISM: Artificial Sequence
<220> FEATURE:
<223> OTHER INFORMATION: synthetic

<400> SEQUENCE: 181 gctacatcc                                                            9

<210> SEQ ID NO 182
<211> LENGTH: 3
<212> TYPE: PRT
<213> ORGANISM: Artificial Sequence
<220> FEATURE:
<223> OTHER INFORMATION: synthetic

<400> SEQUENCE: 182

Ala Thr Ser
 1

<210> SEQ ID NO 183
<211> LENGTH: 27
<212> TYPE: DNA
<213> ORGANISM: Artificial Sequence
<220> FEATURE:
<223> OTHER INFORMATION: synthetic

<400> SEQUENCE: 183
caacagtatt atatttaccc gatcacc                                       27

<210> SEQ ID NO 184
<211> LENGTH: 9
<212> TYPE: PRT
<213> ORGANISM: Artificial Sequence
<220> FEATURE:
<223> OTHER INFORMATION: synthetic

<400> SEQUENCE: 184

Gln Gln Tyr Tyr Ile Tyr Pro Ile Thr

<210> SEQ ID NO 185
<211> LENGTH: 360
<212> TYPE: DNA
<213> ORGANISM: Artificial Sequence
<220> FEATURE:
<223> OTHER INFORMATION: synthetic

<400> SEQUENCE: 185

```
caggtgcagc tggtggagtc tgggggagac gtggtccagc ctggggaggtc cctgagactc    60
tcctgtgcag cgtctggatt caccttcagt agttatggca tgcactgggt ccgccaggct   120
ccaggcaagg gactggagtg ggtggcaatt atatggtatg atggaagtaa taaatattat   180
gcagactccg tgaagggccg attcaccatc tccagagaca attccaagaa cacgctttat   240
ctccaaatga acagcctgag agtcgaggac acggctgtgt actcctgtgc gagagatttt   300
agtatatcat ctcgccactt tgactattgg ggccagggaa ccctggtcac cgtctcctca   360
```

<210> SEQ ID NO 186
<211> LENGTH: 120
<212> TYPE: PRT
<213> ORGANISM: Artificial Sequence
<220> FEATURE:
<223> OTHER INFORMATION: synthetic

<400> SEQUENCE: 186

Gln Val Gln Leu Val Glu Ser Gly Gly Asp Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Ile Ile Trp Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Val Glu Asp Thr Ala Val Tyr Ser Cys
                85                  90                  95
Ala Arg Asp Phe Ser Ile Ser Ser Arg His Phe Asp Tyr Trp Gly Gln
            100                 105                 110
Gly Thr Leu Val Thr Val Ser Ser
        115                 120

<210> SEQ ID NO 187
<211> LENGTH: 321
<212> TYPE: DNA
<213> ORGANISM: Artificial Sequence
<220> FEATURE:
<223> OTHER INFORMATION: synthetic

<400> SEQUENCE: 187

```
gacatccaga tgacccagtc tccatcctct ctgtctgcat ctgtaggaga cagagtcacc    60
atcacttgtc gggcgagtca ggccattaac aattatttag cctggtttca gcagaaacca   120
gggaaagccc ctaagtccct gatctatgct acatccaatt tgcaaagtgg ggtcccttca   180
cagttcagcg gcagtggatc tgggacagat tacactctca ccatcagcag cctgcagcct   240
gaagattttg caacttatta ctgccaacag tattatattt acccgatcac cttcggccaa   300
gggacacgac tggagattaa a                                             321
```

<210> SEQ ID NO 188
<211> LENGTH: 107
<212> TYPE: PRT
<213> ORGANISM: Artificial Sequence
<220> FEATURE:
<223> OTHER INFORMATION: synthetic

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Asn Asn Tyr
            20                  25                  30

Leu Ala Trp Phe Gln Gln Lys Pro Gly Lys Ala Pro Lys Ser Leu Ile
        35                  40                  45

Tyr Ala Thr Ser Asn Leu Gln Ser Gly Val Pro Ser Gln Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Ile
                85                  90                  95

Thr Phe Gly Gln Gly Thr Arg Leu Glu Ile Lys
            100                 105

<210> SEQ ID NO 189
<211> LENGTH: 360
<212> TYPE: DNA
<213> ORGANISM: Artificial Sequence
<220> FEATURE:
<223> OTHER INFORMATION: synthetic

<400> SEQUENCE: 189
caggtgcagc tggtggagtc tgggggaggc gtggtccagc ctggagggtc cctgagactc      60
tcctgtgcag cgtctggatt caccttcagt agttatggca tgcactgggt ccgccaggct     120
ccaggcaagg ggctagagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagatttt     300
agtatatcat ctcgccactt tgactattgg ggccagggaa ccctggtcac cgtctcctca     360

<210> SEQ ID NO 190
<211> LENGTH: 120
<212> TYPE: PRT
<213> ORGANISM: Artificial Sequence
<220> FEATURE:
<223> OTHER INFORMATION: synthetic

<400> SEQUENCE: 190

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Asp Phe Ser Ile Ser Ser Arg His Phe Asp Tyr Trp Gly Gln
            100                 105                 110

Gly Thr Leu Val Thr Val Ser Ser
        115                 120

<210> SEQ ID NO 191
<211> LENGTH: 322
<212> TYPE: DNA
<213> ORGANISM: Artificial Sequence
<220> FEATURE:
<223> OTHER INFORMATION: synthetic

<400> SEQUENCE: 191
gacatccaga tgacccagtc tccatcctca ctgtctgcat ctgtaggaga cagagtcacc      60
atcacttgtc gggcgagtca ggccattaac aattatttag cctggtttca gcagaaacca     120
gggaaagccc ctaagtccct gatctatgct acatccagtt tgcaaagtgg ggtcccatca     180
aggttcagcg gcagtggatc tgggacagat ttcactctca ccatcagcag cctgcagcct     240
gaagattttg caacttatta ctgccaacag tattatattt acccgatcac cttcggccaa     300
gggacacgac tggagattaa ac                                              322

<210> SEQ ID NO 192
<211> LENGTH: 107
<212> TYPE: PRT
<213> ORGANISM: Artificial Sequence
<220> FEATURE:
<223> OTHER INFORMATION: synthetic

<400> SEQUENCE: 192

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ala Ile Asn Asn Tyr
             20                  25                  30

Leu Ala Trp Phe Gln Gln Lys Pro Gly Lys Ala Pro Lys Ser Leu Ile
         35                  40                  45

Tyr Ala Thr Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Ile
                 85                  90                  95

Thr Phe Gly Gln Gly Thr Arg Leu Glu Ile Lys
            100                 105

<210> SEQ ID NO 193
<211> LENGTH: 372
<212> TYPE: DNA
<213> ORGANISM: Artificial Sequence
<220> FEATURE:
<223> OTHER INFORMATION: synthetic

<400> SEQUENCE: 193
gaggtgcagc tggtggagtc tgggggaggc gtggtccagc ctggggggtc cctgagactc      60
tcctgtgcag cgtctggatt caccttcagt agctatggca tgcactgggt ccgccaggct     120
ccagacaagg ggctggagtg ggtggcagtt aaatgggatg atggaagtaa taaatattat     180
gcagactccg tgaagggccg attcaccatc tccagagaca attccaagaa cacgctgtat     240
```

```
ctgcaaatga acagcctgag agccgaggac acggctgtgt attactgtgc gagagaaggc    300
ccttacgatt tttacagtgg ttatggagct tttgatatct ggggccaagg gacaatggtc    360
accgtctctt ca                                                       372
```

<210> SEQ ID NO 194
<211> LENGTH: 124
<212> TYPE: PRT
<213> ORGANISM: Artificial Sequence
<220> FEATURE:
<223> OTHER INFORMATION: synthetic

<400> SEQUENCE: 194

```
Glu Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Asp Lys Gly Leu Glu Trp Val
         35                  40                  45

Ala Val Lys Trp Asp Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Pro Tyr Asp Phe Tyr Ser Gly Tyr Gly Ala Phe Asp
            100                 105                 110

Ile Trp Gly Gln Gly Thr Met Val Thr Val Ser Ser
        115                 120
```

<210> SEQ ID NO 195
<211> LENGTH: 24
<212> TYPE: DNA
<213> ORGANISM: Artificial Sequence
<220> FEATURE:
<223> OTHER INFORMATION: synthetic

<400> SEQUENCE: 195

```
ggattcacct tcagtagcta tggc                                           24
```

<210> SEQ ID NO 196
<211> LENGTH: 8
<212> TYPE: PRT
<213> ORGANISM: Artificial Sequence
<220> FEATURE:
<223> OTHER INFORMATION: synthetic

<400> SEQUENCE: 196

```
Gly Phe Thr Phe Ser Ser Tyr Gly
  1               5
```

<210> SEQ ID NO 197
<211> LENGTH: 24
<212> TYPE: DNA
<213> ORGANISM: Artificial Sequence
<220> FEATURE:
<223> OTHER INFORMATION: synthetic

<400> SEQUENCE: 197

```
aaatgggatg atggaagtaa taaa                                           24
```

```
<210> SEQ ID NO 198
<211> LENGTH: 8
<212> TYPE: PRT
<213> ORGANISM: Artificial Sequence
<220> FEATURE:
<223> OTHER INFORMATION: synthetic

<400> SEQUENCE: 198

Lys Trp Asp Asp Gly Ser Asn Lys
 1               5

<210> SEQ ID NO 199
<211> LENGTH: 51
<212> TYPE: DNA
<213> ORGANISM: Artificial Sequence
<220> FEATURE:
<223> OTHER INFORMATION: synthetic

<400> SEQUENCE: 199
gcgagagaag gcccttacga tttttacagt ggttatggag cttttgatat c          51

<210> SEQ ID NO 200
<211> LENGTH: 17
<212> TYPE: PRT
<213> ORGANISM: Artificial Sequence
<220> FEATURE:
<223> OTHER INFORMATION: synthetic

<400> SEQUENCE: 200

Ala Arg Glu Gly Pro Tyr Asp Phe Tyr Ser Gly Tyr Gly Ala Phe Asp
 1               5                  10                  15

Ile

<210> SEQ ID NO 201
<211> LENGTH: 324
<212> TYPE: DNA
<213> ORGANISM: Artificial Sequence
<220> FEATURE:
<223> OTHER INFORMATION: synthetic

<400> SEQUENCE: 201
gacatccaga tgacccagtc tccatcctca ctgtctgcat ctgtaggaga cagagtcacc     60
atcacttgtc gggcgagtca gggcattagc aattatttag cctggtttca gcagaaacca    120
gggaaagccc ctaagtccct gatctatgct gcatccagtt tgcaaagtgg ggtcccatca    180
aagttcagcg gcagtggatc tgggacagat ttcactctca ccatcagcag cctgcagcct    240
gaagattttg caacttatta ctgccaacag tataatagtt accctcggac gttcggccaa    300
gggaccaagg tggagatcaa acga                                          324

<210> SEQ ID NO 202
<211> LENGTH: 108
<212> TYPE: PRT
<213> ORGANISM: Artificial Sequence
<220> FEATURE:
<223> OTHER INFORMATION: synthetic

<400> SEQUENCE: 202

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
                20                  25                  30

Leu Ala Trp Phe Gln Gln Lys Pro Gly Lys Ala Pro Lys Ser Leu Ile
            35                  40                  45
```

Tyr Ala Ala Ser Ser Leu Gln Ser Gly Val Pro Ser Lys Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                 85                  90                  95

Thr Phe Gly Gln Gly Thr Lys Val Glu Ile Lys Arg
            100                 105

<210> SEQ ID NO 203
<211> LENGTH: 18
<212> TYPE: DNA
<213> ORGANISM: Artificial Sequence
<220> FEATURE:
<223> OTHER INFORMATION: synthetic

<400> SEQUENCE: 203
cagggcatta gcaattat                                              18

<210> SEQ ID NO 204
<211> LENGTH: 6
<212> TYPE: PRT
<213> ORGANISM: Artificial Sequence
<220> FEATURE:
<223> OTHER INFORMATION: synthetic

<400> SEQUENCE: 204

Gln Gly Ile Ser Asn Tyr
 1               5

<210> SEQ ID NO 205
<211> LENGTH: 9
<212> TYPE: DNA
<213> ORGANISM: Artificial Sequence
<220> FEATURE:
<223> OTHER INFORMATION: synthetic

<400> SEQUENCE: 205 gctgcatcc                                                         9

<210> SEQ ID NO 206
<211> LENGTH: 3
<212> TYPE: PRT
<213> ORGANISM: Artificial Sequence
<220> FEATURE:
<223> OTHER INFORMATION: synthetic

<400> SEQUENCE: 206

Ala Ala Ser
 1

<210> SEQ ID NO 207
<211> LENGTH: 27
<212> TYPE: DNA
<213> ORGANISM: Artificial Sequence
<220> FEATURE:
<223> OTHER INFORMATION: synthetic

<400> SEQUENCE: 207
caacagtata atagttaccc tcggacg                                    27

<210> SEQ ID NO 208
<211> LENGTH: 9
<212> TYPE: PRT

<213> ORGANISM: Artificial Sequence
<220> FEATURE:
<223> OTHER INFORMATION: synthetic

<400> SEQUENCE: 208

Gln Gln Tyr Asn Ser Tyr Pro Arg Thr
1               5

<210> SEQ ID NO 209
<211> LENGTH: 372
<212> TYPE: DNA
<213> ORGANISM: Artificial Sequence
<220> FEATURE:
<223> OTHER INFORMATION: synthetic

<400> SEQUENCE: 209

```
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccagacaagg ggctggagtg ggtggcagtt aaatgggatg atggaagtaa taaatattat     180
gcagactccg tgaagggccg attcaccatc tccagagaca attccaagaa cacgctgtat     240
ctgcaaatga acagcctgag agccgaggac acggctgtgt attactgtgc gagagaaggc     300
ccttacgatt tttacagtgg ttatggagct tttgatatct ggggccaagg gacaatggtc     360
accgtctctt ca                                                         372
```

<210> SEQ ID NO 210
<211> LENGTH: 124
<212> TYPE: PRT
<213> ORGANISM: Artificial Sequence
<220> FEATURE:
<223> OTHER INFORMATION: synthetic

<400> SEQUENCE: 210

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Asp Lys Gly Leu Glu Trp Val
        35                  40                  45

Ala Val Lys Trp Asp Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Pro Tyr Asp Phe Tyr Ser Gly Tyr Gly Ala Phe Asp
            100                 105                 110

Ile Trp Gly Gln Gly Thr Met Val Thr Val Ser Ser
        115                 120

<210> SEQ ID NO 211
<211> LENGTH: 321
<212> TYPE: DNA
<213> ORGANISM: Artificial Sequence
<220> FEATURE:
<223> OTHER INFORMATION: synthetic

<400> SEQUENCE: 211

```
gacatccaga tgacccagtc tccatcctca ctgtctgcat ctgtaggaga cagagtcacc      60
```

```
atcacttgtc gggcgagtca gggcattagc aattatttag cctggtttca gcagaaacca    120
gggaaagccc ctaagtccct gatctatgct gcatccagtt tgcaaagtgg ggtcccatca    180
aagttcagcg gcagtggatc tgggacagat ttcactctca ccatcagcag cctgcagcct    240
gaagattttg caacttatta ctgccaacag tataatagtt accctcggac gttcggccaa    300
gggaccaagg tggaaatcaa a                                              321
```

<210> SEQ ID NO 212
<211> LENGTH: 107
<212> TYPE: PRT
<213> ORGANISM: Artificial Sequence
<220> FEATURE:
<223> OTHER INFORMATION: synthetic

<400> SEQUENCE: 212

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Asn Tyr
             20                  25                  30

Leu Ala Trp Phe Gln Gln Lys Pro Gly Lys Ala Pro Lys Ser Leu Ile
         35                  40                  45

Tyr Ala Ala Ser Ser Leu Gln Ser Gly Val Pro Ser Lys Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                 85                  90                  95

Thr Phe Gly Gln Gly Thr Lys Val Glu Ile Lys
            100                 105
```

<210> SEQ ID NO 213
<211> LENGTH: 372
<212> TYPE: DNA
<213> ORGANISM: Artificial Sequence
<220> FEATURE:
<223> OTHER INFORMATION: synthetic

<400> SEQUENCE: 213

```
caggtgcagc tggtggagtc tgggggaggc gtggtccagc ctgggaggtc cctgagactc    60
tcctgtgcag cgtctggatt caccttcagt agctatggca tgcactgggt ccgccaggct    120
ccaggcaagg gctagagtg gtggcagtt aaatgggatg atggaagtaa taaatactat    180
gcagactccg tgaagggccg attcaccatc tccagagaca attccaagaa cacgctgtat    240
ctgcaaatga acagcctgag agccgaggac acggctgtgt attactgtgc gagagaaggc    300
ccttacgatt tttacagtgg ttatggagct tttgatatct ggggccaagg gacaatggtc    360
accgtctctt ca                                                        372
```

<210> SEQ ID NO 214
<211> LENGTH: 124
<212> TYPE: PRT
<213> ORGANISM: Artificial Sequence
<220> FEATURE:
<223> OTHER INFORMATION: synthetic

<400> SEQUENCE: 214

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
```

```
                    20                  25                  30
Gly Met His Trp Val Arg Gln Ala Pro Gly Lys Gly Leu Glu Trp Val
                35                  40                  45

Ala Val Lys Trp Asp Asp Gly Ser Asn Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Pro Tyr Asp Phe Tyr Ser Gly Tyr Gly Ala Phe Asp
                100                 105                 110

Ile Trp Gly Gln Gly Thr Met Val Thr Val Ser Ser
                115                 120

<210> SEQ ID NO 215
<211> LENGTH: 322
<212> TYPE: DNA
<213> ORGANISM: Artificial Sequence
<220> FEATURE:
<223> OTHER INFORMATION: synthetic

<400> SEQUENCE: 215
gacatccaga tgacccagtc tccatcctca ctgtctgcat ctgtaggaga cagagtcacc      60
atcacttgtc gggcgagtca gggcattagc aattatttag cctggtttca gcagaaacca    120
gggaaagccc ctaagtccct gatctatgct gcatccagtt tgcaaagtgg ggtcccatca    180
aggttcagcg gcagtggatc tgggacagat ttcactctca ccatcagcag cctgcagcct    240
gaagattttg caacttatta ctgccaacag tataatagtt accctcggac gttcggccaa    300
gggaccaagg tggaaatcaa ac                                             322

<210> SEQ ID NO 216
<211> LENGTH: 107
<212> TYPE: PRT
<213> ORGANISM: Artificial Sequence
<220> FEATURE:
<223> OTHER INFORMATION: synthetic

<400> SEQUENCE: 216

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Phe Gln Gln Lys Pro Gly Lys Ala Pro Lys Ser Leu Ile
                35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
                100                 105

<210> SEQ ID NO 217
<211> LENGTH: 372
<212> TYPE: DNA
<213> ORGANISM: Artificial Sequence
<220> FEATURE:
```

<223> OTHER INFORMATION: synthetic

<400> SEQUENCE: 217

```
gaggtgcagc tggtgcagtc tgggggaggc gtggtccagc ctgggaggtc cctgagactc    60
tcctgtgcag cgtctggatt caccttcagt agctatggca tgcactgggt ccgccaggct   120
ccagacaagg ggctggagtg ggtggcagtt aaatgggatg atggaagtaa taaatattat   180
gcagactccg tgaagggccg attcaccatc tccagagaca attccaagaa cacgctgtat   240
ctgcaaatga acagcctgag agccgaggac acggctgtgt attactgtgc gagagaaggc   300
ccttacgatt tttacagtgg ttatggagct tttgatatct ggggccaagg gacaatggtc   360
accgtctctt ca                                                      372
```

<210> SEQ ID NO 218
<211> LENGTH: 124
<212> TYPE: PRT
<213> ORGANISM: Artificial Sequence
<220> FEATURE:
<223> OTHER INFORMATION: synthetic

<400> SEQUENCE: 218

```
Glu Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Asp Lys Gly Leu Glu Trp Val
        35                  40                  45

Ala Val Lys Trp Asp Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Pro Tyr Asp Phe Tyr Ser Gly Tyr Gly Ala Phe Asp
            100                 105                 110

Ile Trp Gly Gln Gly Thr Met Val Thr Val Ser Ser
        115                 120
```

<210> SEQ ID NO 219
<211> LENGTH: 24
<212> TYPE: DNA
<213> ORGANISM: Artificial Sequence
<220> FEATURE:
<223> OTHER INFORMATION: synthetic

<400> SEQUENCE: 219

```
ggattcacct tcagtagcta tggc                                          24
```

<210> SEQ ID NO 220
<211> LENGTH: 8
<212> TYPE: PRT
<213> ORGANISM: Artificial Sequence
<220> FEATURE:
<223> OTHER INFORMATION: synthetic

<400> SEQUENCE: 220

```
Gly Phe Thr Phe Ser Ser Tyr Gly
 1               5
```

<210> SEQ ID NO 221

<210> SEQ ID NO 221
<211> LENGTH: 24
<212> TYPE: DNA
<213> ORGANISM: Artificial Sequence
<220> FEATURE:
<223> OTHER INFORMATION: synthetic

<400> SEQUENCE: 221
aaatgggatg atggaagtaa taaa                                           24

<210> SEQ ID NO 222
<211> LENGTH: 8
<212> TYPE: PRT
<213> ORGANISM: Artificial Sequence
<220> FEATURE:
<223> OTHER INFORMATION: synthetic

<400> SEQUENCE: 222

Lys Trp Asp Asp Gly Ser Asn Lys
 1               5

<210> SEQ ID NO 223
<211> LENGTH: 51
<212> TYPE: DNA
<213> ORGANISM: Artificial Sequence
<220> FEATURE:
<223> OTHER INFORMATION: synthetic

<400> SEQUENCE: 223
gcgagagaag gcccttacga tttttacagt ggttatggag cttttgatat c             51

<210> SEQ ID NO 224
<211> LENGTH: 17
<212> TYPE: PRT
<213> ORGANISM: Artificial Sequence
<220> FEATURE:
<223> OTHER INFORMATION: synthetic

<400> SEQUENCE: 224

Ala Arg Glu Gly Pro Tyr Asp Phe Tyr Ser Gly Tyr Gly Ala Phe Asp
 1               5                  10                  15

Ile

<210> SEQ ID NO 225
<211> LENGTH: 324
<212> TYPE: DNA
<213> ORGANISM: Artificial Sequence
<220> FEATURE:
<223> OTHER INFORMATION: synthetic

<400> SEQUENCE: 225
gacatccagt tgacccagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcactcac tttcggcgga   300
gggaccaagc tggagatcaa acga                                          324

<210> SEQ ID NO 226
<211> LENGTH: 108
<212> TYPE: PRT
<213> ORGANISM: Artificial Sequence
<220> FEATURE:
<223> OTHER INFORMATION: synthetic

<400> SEQUENCE: 226

Asp Ile Gln Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Leu Glu Ile Lys Arg
            100                 105

<210> SEQ ID NO 227
<211> LENGTH: 21
<212> TYPE: DNA
<213> ORGANISM: Artificial Sequence
<220> FEATURE:
<223> OTHER INFORMATION: synthetic

<400> SEQUENCE: 227
cagagtgtta gcagcagcta c                                          21

<210> SEQ ID NO 228
<211> LENGTH: 7
<212> TYPE: PRT
<213> ORGANISM: Artificial Sequence
<220> FEATURE:
<223> OTHER INFORMATION: synthetic

<400> SEQUENCE: 228

Gln Ser Val Ser Ser Ser Tyr
1               5

<210> SEQ ID NO 229
<211> LENGTH: 9
<212> TYPE: DNA
<213> ORGANISM: Artificial Sequence
<220> FEATURE:
<223> OTHER INFORMATION: synthetic

<400> SEQUENCE: 229 ggtgcatcc                                                         9

<210> SEQ ID NO 230
<211> LENGTH: 3
<212> TYPE: PRT
<213> ORGANISM: Artificial Sequence
<220> FEATURE:
<223> OTHER INFORMATION: synthetic

<400> SEQUENCE: 230

Gly Ala Ser
1

<210> SEQ ID NO 231
<211> LENGTH: 24
<212> TYPE: DNA
<213> ORGANISM: Artificial Sequence
<220> FEATURE:
<223> OTHER INFORMATION: synthetic

<400> SEQUENCE: 231
cagcagtatg gtagctcact cact                                              24

<210> SEQ ID NO 232
<211> LENGTH: 8
<212> TYPE: PRT
<213> ORGANISM: Artificial Sequence
<220> FEATURE:
<223> OTHER INFORMATION: synthetic

<400> SEQUENCE: 232

Gln Gln Tyr Gly Ser Ser Leu Thr
 1               5

<210> SEQ ID NO 233
<211> LENGTH: 372
<212> TYPE: DNA
<213> ORGANISM: Artificial Sequence
<220> FEATURE:
<223> OTHER INFORMATION: synthetic

<400> SEQUENCE: 233
caggtgcagc tggtggagtc tgggggaggc gtggtccagc ctggaggtc cctgagactc          60 tcctgtgcag cgtctggatt caccttcagt agctatggca tgcactgggt ccgccaggct        120
ccagacaagg ggctggagtg ggtggcagtt aaatgggatg atggaagtaa taaatattat        180
gcagactccg tgaagggccg attcaccatc tccagagaca attccaagaa cacgctgtat        240
ctgcaaatga acagcctgag agccgaggac acggctgtgt attactgtgc gagagaaggc        300
ccttacgatt tttacagtgg ttatggagct tttgatatct ggggccaagg gacaatggtc        360
accgtctctt ca                                                           372

<210> SEQ ID NO 234
<211> LENGTH: 124
<212> TYPE: PRT
<213> ORGANISM: Artificial Sequence
<220> FEATURE:
<223> OTHER INFORMATION: synthetic

<400> SEQUENCE: 234

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Asp Lys Gly Leu Glu Trp Val
            35                  40                  45

Ala Val Lys Trp Asp Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Gly Pro Tyr Asp Phe Tyr Ser Gly Tyr Gly Ala Phe Asp
                100                 105                 110

Ile Trp Gly Gln Gly Thr Met Val Thr Val Ser Ser
            115                 120

<210> SEQ ID NO 235
<211> LENGTH: 321
<212> TYPE: DNA
<213> ORGANISM: Artificial Sequence
<220> FEATURE:
<223> OTHER INFORMATION: synthetic

<400> SEQUENCE: 235

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcactcac tttcggcgga     300
gggaccaagg tggagatcaa a                                                321
```

<210> SEQ ID NO 236
<211> LENGTH: 107
<212> TYPE: PRT
<213> ORGANISM: Artificial Sequence
<220> FEATURE:
<223> OTHER INFORMATION: synthetic

<400> SEQUENCE: 236

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105
```

<210> SEQ ID NO 237
<211> LENGTH: 372
<212> TYPE: DNA
<213> ORGANISM: Artificial Sequence
<220> FEATURE:
<223> OTHER INFORMATION: synthetic

<400> SEQUENCE: 237

```
caggtgcagc tggtggagtc tgggggaggc gtggtccagc ctggggaggtc cctgagactc      60
tcctgtgcag cgtctggatt caccttcagt agctatggca tgcactgggt ccgccaggct     120
ccaggcaagg ggctagagtg ggtggcagtt aaatgggatg atggaagtaa taatactat      180
gcagactccg tgaagggccg attcaccatc tccagagaca attccaagaa cacgctgtat     240
ctgcaaatga acagcctgag agccgaggac acggctgtgt attactgtgc gagagaaggc     300
ccttacgatt tttacagtgg ttatggagct tttgatatct ggggccaagg gacaatggtc     360
accgtctctt ca                                                          372
```

<210> SEQ ID NO 238
<211> LENGTH: 124

```
<212> TYPE: PRT
<213> ORGANISM: Artificial Sequence
<220> FEATURE:
<223> OTHER INFORMATION: synthetic

<400> SEQUENCE: 238

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
                35                  40                  45

Ala Val Lys Trp Asp Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Pro Tyr Asp Phe Tyr Ser Gly Tyr Gly Ala Phe Asp
            100                 105                 110

Ile Trp Gly Gln Gly Thr Met Val Thr Val Ser Ser
        115                 120

<210> SEQ ID NO 239
<211> LENGTH: 322
<212> TYPE: DNA
<213> ORGANISM: Artificial Sequence
<220> FEATURE:
<223> OTHER INFORMATION: synthetic

<400> SEQUENCE: 239
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcactcac tttcggcgga   300
gggaccaagg tggagatcaa ac                                            322

<210> SEQ ID NO 240
<211> LENGTH: 107
<212> TYPE: PRT
<213> ORGANISM: Artificial Sequence
<220> FEATURE:
<223> OTHER INFORMATION: synthetic

<400> SEQUENCE: 240

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
```

```
                        85                  90                  95

Thr Phe Gly Gly Gly Thr Lys Val Glu Ile Lys
            100                 105

<210> SEQ ID NO 241
<211> LENGTH: 360
<212> TYPE: DNA
<213> ORGANISM: Artificial Sequence
<220> FEATURE:
<223> OTHER INFORMATION: synthetic

<400> SEQUENCE: 241
gaggtgcaat tggtggagtc gggggggaggc ttggtaaggc cggggggggtc ccttagactc      60 tcctgtgcag cctctggatt cactttcact aacgcctgga tgagctgggt ccgccaggct     120
ccagggaagg ggctggagtg gattggccag attaaaagca aaactgatgg tgggacaata     180
gactacgctg cacccgtgaa aggcagattc accgtctcaa gagatgattc agaaaatacg     240
ctgtttctgc aaatgaacag cctgaaaacc gaggacacag ccgtgtatta ctgtgcgggg     300
aactggaact acgtggactt tgactactgg ggccagggaa ccctggtcac cgtctcctca     360

<210> SEQ ID NO 242
<211> LENGTH: 120
<212> TYPE: PRT
<213> ORGANISM: Artificial Sequence
<220> FEATURE:
<223> OTHER INFORMATION: synthetic

<400> SEQUENCE: 242

Glu Val Gln Leu Val Glu Ser Gly Gly Gly Leu Val Arg Pro Gly Gly
 1               5                  10                  15

Ser Leu Arg Leu Ser Cys Ala Ala Ser Gly Phe Thr Phe Thr Asn Ala
            20                  25                  30

Trp Met Ser Trp Val Arg Gln Ala Pro Gly Lys Gly Leu Glu Trp Ile
        35                  40                  45

Gly Gln Ile Lys Ser Lys Thr Asp Gly Gly Thr Ile Asp Tyr Ala Ala
    50                  55                  60

Pro Val Lys Gly Arg Phe Thr Val Ser Arg Asp Asp Ser Glu Asn Thr
65                  70                  75                  80

Leu Phe Leu Gln Met Asn Ser Leu Lys Thr Glu Asp Thr Ala Val Tyr
                85                  90                  95

Tyr Cys Ala Gly Asn Trp Asn Tyr Val Asp Phe Asp Tyr Trp Gly Gln
            100                 105                 110

Gly Thr Leu Val Thr Val Ser Ser
        115                 120

<210> SEQ ID NO 243
<211> LENGTH: 24
<212> TYPE: DNA
<213> ORGANISM: Artificial Sequence
<220> FEATURE:
<223> OTHER INFORMATION: synthetic

<400> SEQUENCE: 243
ggattcactt tcactaacgc ctgg                                              24

<210> SEQ ID NO 244
<211> LENGTH: 8
<212> TYPE: PRT
<213> ORGANISM: Artificial Sequence
<220> FEATURE:
```

<223> OTHER INFORMATION: synthetic

<400> SEQUENCE: 244

Gly Phe Thr Phe Thr Asn Ala Trp
1               5

<210> SEQ ID NO 245
<211> LENGTH: 30
<212> TYPE: DNA
<213> ORGANISM: Artificial Sequence
<220> FEATURE:
<223> OTHER INFORMATION: synthetic

<400> SEQUENCE: 245
attaaaagca aaactgatgg tgggacaata                                        30

<210> SEQ ID NO 246
<211> LENGTH: 10
<212> TYPE: PRT
<213> ORGANISM: Artificial Sequence
<220> FEATURE:
<223> OTHER INFORMATION: synthetic

<400> SEQUENCE: 246

Ile Lys Ser Lys Thr Asp Gly Gly Thr Ile
1               5                   10

<210> SEQ ID NO 247
<211> LENGTH: 33
<212> TYPE: DNA
<213> ORGANISM: Artificial Sequence
<220> FEATURE:
<223> OTHER INFORMATION: synthetic

<400> SEQUENCE: 247
gcggggaact ggaactacgt ggactttgac tac                                    33

<210> SEQ ID NO 248
<211> LENGTH: 11
<212> TYPE: PRT
<213> ORGANISM: Artificial Sequence
<220> FEATURE:
<223> OTHER INFORMATION: synthetic

<400> SEQUENCE: 248

Ala Gly Asn Trp Asn Tyr Val Asp Phe Asp Tyr
1               5                   10

<210> SEQ ID NO 249
<211> LENGTH: 321
<212> TYPE: DNA
<213> ORGANISM: Artificial Sequence
<220> FEATURE:
<223> OTHER INFORMATION: synthetic

<400> SEQUENCE: 249
gacatccaga tgacccagtc tccatcctcc ctgtctgcat ctgtaggaga cagagtcacc        60
atcacttgcc gggcaagtca ggacattaga aatgatttag ctggtatca gcagaaacca       120 gggaaagccc ctaagcgcct gatctatgct gcatccagtt tgcaaggtgg ggtcccatca      180
aggttcagcg gcagtggatc tgggacagaa ttcactctca caatcagcag cctgcagcct      240
gaagattttg caacttatta ctgtctacag cataatagtt acccttcac tttcggccct      300 gggaccaaag tggatatcaa a                                                321

<210> SEQ ID NO 250
<211> LENGTH: 107
<212> TYPE: PRT
<213> ORGANISM: Artificial Sequence
<220> FEATURE:
<223> OTHER INFORMATION: synthetic

<400> SEQUENCE: 250

```
Asp Ile Gln Met Thr Gln Ser Pro Ser Leu Ser Ala Ser Val Gly
 1               5                  10                  15

Asp Arg Val Thr Ile Thr Cys Arg Ala Ser Gln Asp Ile Arg Asn Asp
                20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Gly Gly Val Pro Ser Arg Phe Ser Gly
     50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Phe
                85                  90                  95

Thr Phe Gly Pro Gly Thr Lys Val Asp Ile Lys
            100                 105
```

<210> SEQ ID NO 251
<211> LENGTH: 18
<212> TYPE: DNA
<213> ORGANISM: Artificial Sequence
<220> FEATURE:
<223> OTHER INFORMATION: synthetic

<400> SEQUENCE: 251
caggacatta gaaatgat                                                    18

<210> SEQ ID NO 252
<211> LENGTH: 6
<212> TYPE: PRT
<213> ORGANISM: Artificial Sequence
<220> FEATURE:
<223> OTHER INFORMATION: synthetic

<400> SEQUENCE: 252

```
Gln Asp Ile Arg Asn Asp
 1               5
```

<210> SEQ ID NO 253
<211> LENGTH: 9
<212> TYPE: DNA
<213> ORGANISM: Artificial Sequence
<220> FEATURE:
<223> OTHER INFORMATION: synthetic

<400> SEQUENCE: 253 gctgcatcc                                                               9

<210> SEQ ID NO 254
<211> LENGTH: 3
<212> TYPE: PRT
<213> ORGANISM: Artificial Sequence
<220> FEATURE:
<223> OTHER INFORMATION: synthetic

<400> SEQUENCE: 254

Ala Ala Ser

<210> SEQ ID NO 255
<211> LENGTH: 27
<212> TYPE: DNA
<213> ORGANISM: Artificial Sequence
<220> FEATURE:
<223> OTHER INFORMATION: synthetic

<400> SEQUENCE: 255
ctacagcata atagttaccc tttcact                                         27

<210> SEQ ID NO 256
<211> LENGTH: 9
<212> TYPE: PRT
<213> ORGANISM: Artificial Sequence
<220> FEATURE:
<223> OTHER INFORMATION: synthetic

<400> SEQUENCE: 256

Leu Gln His Asn Ser Tyr Pro Phe Thr
 1               5

<210> SEQ ID NO 257
<211> LENGTH: 360
<212> TYPE: DNA
<213> ORGANISM: Artificial Sequence
<220> FEATURE:
<223> OTHER INFORMATION: synthetic

<400> SEQUENCE: 257
gaggtgcagc tggtggagtc tgggggaggc ttggtaaggc cggggggggtc ccttagactc     60 tcctgtgcag cctctggatt cactttcact aacgcctgga tgagctgggt ccgccaggct    120
ccagggaagg ggctggagtg gattggccag attaaaagca aaactgatgg tgggacaata    180
gactacgctg cacccgtgaa aggcagattc accgtctcaa gagatgattc agaaaatacg    240
ctgtttctgc aaatgaacag cctgaaaacc gaggacacag ccgtgtatta ctgtgcgggg    300
aactggaact acgtggactt tgactactgg ggccagggaa ccctggtcac cgtctcctca    360

<210> SEQ ID NO 258
<211> LENGTH: 120
<212> TYPE: PRT
<213> ORGANISM: Artificial Sequence
<220> FEATURE:
<223> OTHER INFORMATION: synthetic

<400> SEQUENCE: 258

Glu Val Gln Leu Val Glu Ser Gly Gly Gly Leu Val Arg Pro Gly Gly
 1               5                  10                  15

Ser Leu Arg Leu Ser Cys Ala Ala Ser Gly Phe Thr Phe Thr Asn Ala
             20                  25                  30

Trp Met Ser Trp Val Arg Gln Ala Pro Gly Lys Gly Leu Glu Trp Ile
         35                  40                  45

Gly Gln Ile Lys Ser Lys Thr Asp Gly Gly Thr Ile Asp Tyr Ala Ala
     50                  55                  60

Pro Val Lys Gly Arg Phe Thr Val Ser Arg Asp Asp Ser Glu Asn Thr
65                  70                  75                  80

Leu Phe Leu Gln Met Asn Ser Leu Lys Thr Glu Asp Thr Ala Val Tyr
                 85                  90                  95

Tyr Cys Ala Gly Asn Trp Asn Tyr Val Asp Phe Asp Tyr Trp Gly Gln
            100                 105                 110

```
Gly Thr Leu Val Thr Val Ser Ser
        115                 120

<210> SEQ ID NO 259
<211> LENGTH: 321
<212> TYPE: DNA
<213> ORGANISM: Artificial Sequence
<220> FEATURE:
<223> OTHER INFORMATION: synthetic

<400> SEQUENCE: 259
gacatccaga tgacccagtc tccatcctcc ctgtctgcat ctgtaggaga cagagtcacc      60
atcacttgcc gggcaagtca ggacattaga aatgatttag ctggtatca gcagaaacca     120 gggaaagccc ctaagcgcct gatctatgct gcatccagtt tgcaaggtgg ggtcccatca    180
aggttcagcg gcagtggatc tgggacagaa ttcactctca caatcagcag cctgcagcct    240
gaagattttg caacttatta ctgtctacag cataatagtt acccctttac tttcggccct    300
gggaccaaag tggatatcaa a                                              321

<210> SEQ ID NO 260
<211> LENGTH: 107
<212> TYPE: PRT
<213> ORGANISM: Artificial Sequence
<220> FEATURE:
<223> OTHER INFORMATION: synthetic

<400> SEQUENCE: 260

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Gly Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Phe
                85                  90                  95

Thr Phe Gly Pro Gly Thr Lys Val Asp Ile Lys
            100                 105

<210> SEQ ID NO 261
<211> LENGTH: 360
<212> TYPE: DNA
<213> ORGANISM: Artificial Sequence
<220> FEATURE:
<223> OTHER INFORMATION: synthetic

<400> SEQUENCE: 261
gaggtgcagc tggtggagtc tgggggaggc ttggtaaagc ctggggggtc ccttagactc      60
tcctgtgcag cctctggatt cactttcact aacgcctgga tgagctgggt ccgccaggct    120
ccagggaagg ggctggagtg ggttggccgt attaaaagca aaactgatgg tggacaata     180 gactacgctg cacccgtgaa aggcagattc accatctcaa gagatgattc aaaaaacacg    240
ctgtatctgc aaatgaacag cctgaaaacc gaggacacag ccgtgtatta ctgtgcgggg    300
aactggaact acgtggactt tgactactgg ggccagggaa ccctggtcac cgtctcctca    360
```

<210> SEQ ID NO 262
<211> LENGTH: 120
<212> TYPE: PRT
<213> ORGANISM: Artificial Sequence
<220> FEATURE:
<223> OTHER INFORMATION: synthetic

<400> SEQUENCE: 262

```
Glu Val Gln Leu Val Glu Ser Gly Gly Leu Val Lys Pro Gly Gly
 1               5                  10                  15

Ser Leu Arg Leu Ser Cys Ala Ala Ser Gly Phe Thr Phe Thr Asn Ala
                20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Ile Asp Tyr Ala Ala
        50                  55                  60

Pro Val Lys Gly Arg Phe Thr Ile Ser Arg Asp Asp Ser Lys Asn Thr
 65                 70                  75                  80

Leu Tyr Leu Gln Met Asn Ser Leu Lys Thr Glu Asp Thr Ala Val Tyr
                85                  90                  95

Tyr Cys Ala Gly Asn Trp Asn Tyr Val Asp Phe Asp Tyr Trp Gly Gln
            100                 105                 110

Gly Thr Leu Val Thr Val Ser Ser
        115                 120
```

<210> SEQ ID NO 263
<211> LENGTH: 322
<212> TYPE: DNA
<213> ORGANISM: Artificial Sequence
<220> FEATURE:
<223> OTHER INFORMATION: synthetic

<400> SEQUENCE: 263

```
gacatccaga tgacccagtc tccatcctcc ctgtctgcat ctgtaggaga cagagtcacc    60
atcacttgcc gggcaagtca ggacattaga aatgatttag ctggtatca gcagaaacca   120 gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caactatta ctgtctacag cataatagtt acccttcac tttcggccct    300 gggaccaaag tggatatcaa ac                                           322
```

<210> SEQ ID NO 264
<211> LENGTH: 107
<212> TYPE: PRT
<213> ORGANISM: Artificial Sequence
<220> FEATURE:
<223> OTHER INFORMATION: synthetic

<400> SEQUENCE: 264

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
```

```
                    65                  70                  75                  80
Glu Asp Phe Ala Thr Tyr Tyr Cys Leu Gln His Asn Ser Tyr Pro Phe
                85                  90                  95
Thr Phe Gly Pro Gly Thr Lys Val Asp Ile Lys
            100                 105
```

<210> SEQ ID NO 265
<211> LENGTH: 375
<212> TYPE: DNA
<213> ORGANISM: Artificial Sequence
<220> FEATURE:
<223> OTHER INFORMATION: synthetic

<400> SEQUENCE: 265

```
caggtgcagc tggtggagtc tgggggaggc gtggtccagc ctggagggtc cctgagactc     60
tcctgtgcag cgtctggatt caccctcagt aactatggca tgcactgggt ccgccaggct    120
ccaggcaagg ggctggagtg ggtggcagtt atatggcatg atggaagtaa tacatactat    180
gcagactccg tgaagggccg attcaccatc tccagagaca attctaagaa cacgctgtat    240
ctgcaaatga acagcctgag agccgaagac acggctgtgt attactgtac gagagagggg    300
ctcgattttt ggagtggtta ttaccctaac tggttcgacc cctggggcca gggaaccctg    360
gtcaccgtct cctca                                                     375
```

<210> SEQ ID NO 266
<211> LENGTH: 125
<212> TYPE: PRT
<213> ORGANISM: Artificial Sequence
<220> FEATURE:
<223> OTHER INFORMATION: synthetic

<400> SEQUENCE: 266

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Leu Ser Asn Tyr
             20                  25                  30

Gly Met His Trp Val Arg Gln Ala Pro Gly Lys Gly Leu Glu Trp Val
         35                  40                  45

Ala Val Ile Trp His Asp Gly Ser Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Glu Gly Leu Asp Phe Trp Ser Gly Tyr Tyr Pro Asn Trp Phe
            100                 105                 110

Asp Pro Trp Gly Gln Gly Thr Leu Val Thr Val Ser Ser
        115                 120                 125
```

<210> SEQ ID NO 267
<211> LENGTH: 24
<212> TYPE: DNA
<213> ORGANISM: Artificial Sequence
<220> FEATURE:
<223> OTHER INFORMATION: synthetic

<400> SEQUENCE: 267

```
ggattcaccc tcagtaacta tggc                                            24
```

```
<210> SEQ ID NO 268
<211> LENGTH: 8
<212> TYPE: PRT
<213> ORGANISM: Artificial Sequence
<220> FEATURE:
<223> OTHER INFORMATION: synthetic

<400> SEQUENCE: 268

Gly Phe Thr Leu Ser Asn Tyr Gly
1               5

<210> SEQ ID NO 269
<211> LENGTH: 24
<212> TYPE: DNA
<213> ORGANISM: Artificial Sequence
<220> FEATURE:
<223> OTHER INFORMATION: synthetic

<400> SEQUENCE: 269
atatggcatg atggaagtaa taca                                              24

<210> SEQ ID NO 270
<211> LENGTH: 8
<212> TYPE: PRT
<213> ORGANISM: Artificial Sequence
<220> FEATURE:
<223> OTHER INFORMATION: synthetic

<400> SEQUENCE: 270

Ile Trp His Asp Gly Ser Asn Thr
1               5

<210> SEQ ID NO 271
<211> LENGTH: 54
<212> TYPE: DNA
<213> ORGANISM: Artificial Sequence
<220> FEATURE:
<223> OTHER INFORMATION: synthetic

<400> SEQUENCE: 271
acgagagagg ggctcgattt ttggagtggt tattacccta actggttcga cccc            54

<210> SEQ ID NO 272
<211> LENGTH: 18
<212> TYPE: PRT
<213> ORGANISM: Artificial Sequence
<220> FEATURE:
<223> OTHER INFORMATION: synthetic

<400> SEQUENCE: 272

Thr Arg Glu Gly Leu Asp Phe Trp Ser Gly Tyr Tyr Pro Asn Trp Phe
1               5                   10                  15

Asp Pro

<210> SEQ ID NO 273
<211> LENGTH: 321
<212> TYPE: DNA
<213> ORGANISM: Artificial Sequence
<220> FEATURE:
<223> OTHER INFORMATION: synthetic

<400> SEQUENCE: 273
gacatccaga tgacccagtc tccatcctcc ctgtctgcat ctgtaggaga cagagtcacc       60
atcacttgcc gggcaagtca gggcattaga aatgatttag ctggtatca gcagaaacca      120 gggaaagccc ctaagcgcct gatctatgct gcatccaatt tgcaaggtgg ggtcccatca      180
```

```
aggttcagcg gcagtggatc tgggacagaa ttcactctca caatcagcag cctgcagcct    240
gaagattttg cagcttatta ctgtctacag cataatattt acccgctcac tttcggcgga    300
gggaccaagg tggagatcaa a                                              321
```

<210> SEQ ID NO 274
<211> LENGTH: 107
<212> TYPE: PRT
<213> ORGANISM: Artificial Sequence
<220> FEATURE:
<223> OTHER INFORMATION: synthetic

<400> SEQUENCE: 274

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Asn Leu Gln Gly Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Ala Tyr Tyr Cys Leu Gln His Asn Ile Tyr Pro Leu
                 85                  90                  95

Thr Phe Gly Gly Gly Thr Lys Val Glu Ile Lys
            100                 105
```

<210> SEQ ID NO 275
<211> LENGTH: 18
<212> TYPE: DNA
<213> ORGANISM: Artificial Sequence
<220> FEATURE:
<223> OTHER INFORMATION: synthetic

<400> SEQUENCE: 275

```
cagggcatta gaaatgat                                                   18
```

<210> SEQ ID NO 276
<211> LENGTH: 6
<212> TYPE: PRT
<213> ORGANISM: Artificial Sequence
<220> FEATURE:
<223> OTHER INFORMATION: synthetic

<400> SEQUENCE: 276

```
Gln Gly Ile Arg Asn Asp
  1               5
```

<210> SEQ ID NO 277
<211> LENGTH: 9
<212> TYPE: DNA
<213> ORGANISM: Artificial Sequence
<220> FEATURE:
<223> OTHER INFORMATION: synthetic

<400> SEQUENCE: 277

```
gctgcatcc                                                              9
```

<210> SEQ ID NO 278
<211> LENGTH: 3
<212> TYPE: PRT

<210> SEQ ID NO 279
<211> LENGTH: 27
<212> TYPE: DNA
<213> ORGANISM: Artificial Sequence
<220> FEATURE:
<223> OTHER INFORMATION: synthetic

<400> SEQUENCE: 278

Ala Ala Ser
 1

<210> SEQ ID NO 279
<211> LENGTH: 27
<212> TYPE: DNA
<213> ORGANISM: Artificial Sequence
<220> FEATURE:
<223> OTHER INFORMATION: synthetic

<400> SEQUENCE: 279
ctacagcata atatttaccc gctcact                                         27

<210> SEQ ID NO 280
<211> LENGTH: 9
<212> TYPE: PRT
<213> ORGANISM: Artificial Sequence
<220> FEATURE:
<223> OTHER INFORMATION: synthetic

<400> SEQUENCE: 280

Leu Gln His Asn Ile Tyr Pro Leu Thr
 1               5

<210> SEQ ID NO 281
<211> LENGTH: 375
<212> TYPE: DNA
<213> ORGANISM: Artificial Sequence
<220> FEATURE:
<223> OTHER INFORMATION: synthetic

<400> SEQUENCE: 281
caggtgcagc tggtggagtc tgggggaggc gtggtccagc ctggggaggtc cctgagactc     60 tcctgtgcag cgtctggatt caccctcagt aactatggca tgcactgggt ccgccaggct    120
ccaggcaagg gctggagtg gtggcagtt atatggcatg atggaagtaa tacatactat    180
gcagactccg tgaagggccg attcaccatc tccagagaca attctaagaa cacgctgtat    240
ctgcaaatga acagcctgag agccgaagac acggctgtgt attactgtac gagagagggg    300
ctcgattttt ggagtggtta ttaccctaac tggttcgacc cctggggcca gggaaccctg    360
gtcaccgtct cctca                                                     375

<210> SEQ ID NO 282
<211> LENGTH: 125
<212> TYPE: PRT
<213> ORGANISM: Artificial Sequence
<220> FEATURE:
<223> OTHER INFORMATION: synthetic

<400> SEQUENCE: 282

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Leu Ser Asn Tyr
             20                  25                  30

Gly Met His Trp Val Arg Gln Ala Pro Gly Lys Gly Leu Glu Trp Val
         35                  40                  45

Ala Val Ile Trp His Asp Gly Ser Asn Thr Tyr Tyr Ala Asp Ser Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Glu Gly Leu Asp Phe Trp Ser Gly Tyr Tyr Pro Asn Trp Phe
            100                 105                 110

Asp Pro Trp Gly Gln Gly Thr Leu Val Thr Val Ser Ser
        115                 120                 125

<210> SEQ ID NO 283
<211> LENGTH: 321
<212> TYPE: DNA
<213> ORGANISM: Artificial Sequence
<220> FEATURE:
<223> OTHER INFORMATION: synthetic

<400> SEQUENCE: 283
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccaatt tgcaaggtgg ggtcccatca   180
aggttcagcg gcagtggatc tgggacagaa ttcactctca caatcagcag cctgcagcct   240
gaagattttg cagcttatta ctgtctacag cataatattt acccgctcac tttcggcgga   300
gggaccaagg tggagatcaa a                                             321

<210> SEQ ID NO 284
<211> LENGTH: 107
<212> TYPE: PRT
<213> ORGANISM: Artificial Sequence
<220> FEATURE:
<223> OTHER INFORMATION: synthetic

<400> SEQUENCE: 284

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Asn Leu Gln Gly Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Ala Tyr Tyr Cys Leu Gln His Asn Ile Tyr Pro Leu
                85                  90                  95

Thr Phe Gly Gly Gly Thr Lys Val Glu Ile Lys
            100                 105

<210> SEQ ID NO 285
<211> LENGTH: 375
<212> TYPE: DNA
<213> ORGANISM: Artificial Sequence
<220> FEATURE:
<223> OTHER INFORMATION: synthetic

<400> SEQUENCE: 285
caggtgcagc tggtggagtc tgggggaggc gtggtccagc ctgggaggtc cctgagactc    60
tcctgtgcag cgtctggatt caccctcagt aactatggca tgcactgggt ccgccaggct   120

```
ccaggcaagg ggctagagtg ggtggcagtt atatggcatg atggaagtaa tacatactat    180
gcagactccg tgaagggccg attcaccatc tccagagaca attccaagaa cacgctgtat    240
ctgcaaatga acagcctgag agccgaggac acggctgtgt attactgtac gagagagggg    300
ctcgattttt ggagtggtta ttaccctaac tggttcgacc cctggggcca gggaaccctg    360
gtcaccgtct cctca                                                     375
```

```
<210> SEQ ID NO 286
<211> LENGTH: 125
<212> TYPE: PRT
<213> ORGANISM: Artificial Sequence
<220> FEATURE:
<223> OTHER INFORMATION: synthetic

<400> SEQUENCE: 286
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Asn Tyr
            20                  25                  30

Gly Met His Trp Val Arg Gln Ala Pro Gly Lys Gly Leu Glu Trp Val
        35                  40                  45

Ala Val Ile Trp His Asp Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Glu Gly Leu Asp Phe Trp Ser Gly Tyr Tyr Pro Asn Trp Phe
            100                 105                 110

Asp Pro Trp Gly Gln Gly Thr Leu Val Thr Val Ser Ser
        115                 120                 125

```
<210> SEQ ID NO 287
<211> LENGTH: 322
<212> TYPE: DNA
<213> ORGANISM: Artificial Sequence
<220> FEATURE:
<223> OTHER INFORMATION: synthetic

<400> SEQUENCE: 287
gacatccaga tgacccagtc tccatcctcc ctgtctgcat ctgtaggaga cagagtcacc     60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatattt acccgctcac tttcggcgga    300
gggaccaagg tggagatcaa ac                                             322
```

```
<210> SEQ ID NO 288
<211> LENGTH: 107
<212> TYPE: PRT
<213> ORGANISM: Artificial Sequence
<220> FEATURE:
<223> OTHER INFORMATION: synthetic

<400> SEQUENCE: 288
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ile Tyr Pro Leu
                85                  90                  95

Thr Phe Gly Gly Gly Thr Lys Val Glu Ile Lys
            100                 105

<210> SEQ ID NO 289
<211> LENGTH: 363
<212> TYPE: DNA
<213> ORGANISM: Artificial Sequence
<220> FEATURE:
<223> OTHER INFORMATION: synthetic

<400> SEQUENCE: 289
gaggtgcagc tggtggagtc tgggggagac ttggtccagc ctggggggtc cctgagactc      60
tcctgtacag cctctggatt cacctttagt aaatattgga tgacctgggt ccgccaggct     120
ccagggaggg gctggagtg gtggccaac ataaaggaag atggaaatga aaatactt       180 ctggactctg tgaagggccg cttcaccatt tccagagaca acgccaagga tttattgttt     240
ctgcaaatga acagcctgag aggcgaggac acggctgtgt attactgtgt gagagatcga     300
ggtatagaag tggctggccc ctttgactac tggggccagg gaaccctggt caccgtctcc     360
tca                                                                   363

<210> SEQ ID NO 290
<211> LENGTH: 121
<212> TYPE: PRT
<213> ORGANISM: Artificial Sequence
<220> FEATURE:
<223> OTHER INFORMATION: synthetic

<400> SEQUENCE: 290

Glu Val Gln Leu Val Glu Ser Gly Gly Asp Leu Val Gln Pro Gly Gly
1               5                   10                  15

Ser Leu Arg Leu Ser Cys Thr Ala Ser Gly Phe Thr Phe Ser Lys Tyr
            20                  25                  30

Trp Met Thr Trp Val Arg Gln Ala Pro Gly Arg Gly Leu Glu Trp Val
        35                  40                  45

Ala Asn Ile Lys Glu Asp Gly Asn Glu Lys Tyr Phe Leu Asp Ser Val
    50                  55                  60

Lys Gly Arg Phe Thr Ile Ser Arg Asp Asn Ala Lys Asp Leu Leu Phe
65                  70                  75                  80

Leu Gln Met Asn Ser Leu Arg Gly Glu Asp Thr Ala Val Tyr Tyr Cys
                85                  90                  95

Val Arg Asp Arg Gly Ile Glu Val Ala Gly Pro Phe Asp Tyr Trp Gly
            100                 105                 110

Gln Gly Thr Leu Val Thr Val Ser Ser
        115                 120

<210> SEQ ID NO 291

```
<211> LENGTH: 24
<212> TYPE: DNA
<213> ORGANISM: Artificial Sequence
<220> FEATURE:
<223> OTHER INFORMATION: synthetic

<400> SEQUENCE: 291
ggattcacct ttagtaaata ttgg                                          24

<210> SEQ ID NO 292
<211> LENGTH: 8
<212> TYPE: PRT
<213> ORGANISM: Artificial Sequence
<220> FEATURE:
<223> OTHER INFORMATION: synthetic

<400> SEQUENCE: 292

Gly Phe Thr Phe Ser Lys Tyr Trp
1               5

<210> SEQ ID NO 293
<211> LENGTH: 24
<212> TYPE: DNA
<213> ORGANISM: Artificial Sequence
<220> FEATURE:
<223> OTHER INFORMATION: synthetic

<400> SEQUENCE: 293
ataaaggaag atggaaatga aaaa                                          24

<210> SEQ ID NO 294
<211> LENGTH: 8
<212> TYPE: PRT
<213> ORGANISM: Artificial Sequence
<220> FEATURE:
<223> OTHER INFORMATION: synthetic

<400> SEQUENCE: 294

Ile Lys Glu Asp Gly Asn Glu Lys
1               5

<210> SEQ ID NO 295
<211> LENGTH: 42
<212> TYPE: DNA
<213> ORGANISM: Artificial Sequence
<220> FEATURE:
<223> OTHER INFORMATION: synthetic

<400> SEQUENCE: 295
gtgagagatc gaggtataga agtggctggc ccctttgact ac                      42

<210> SEQ ID NO 296
<211> LENGTH: 14
<212> TYPE: PRT
<213> ORGANISM: Artificial Sequence
<220> FEATURE:
<223> OTHER INFORMATION: synthetic

<400> SEQUENCE: 296

Val Arg Asp Arg Gly Ile Glu Val Ala Gly Pro Phe Asp Tyr
1               5                   10

<210> SEQ ID NO 297
<211> LENGTH: 318
<212> TYPE: DNA
<213> ORGANISM: Artificial Sequence
<220> FEATURE:
```

<223> OTHER INFORMATION: synthetic

<400> SEQUENCE: 297

| | | | | |
|---|---|---|---|---|
| gacatccaga tgacccagtc tccttccacc ctgtctgcat ctgttgggga cagagtcacc | | | | 60 |
| gtcacttgcc gggccagtca gactattatt aattggttgg cctggtatca gcagaaacca | | | | 120 |
| gggaaagccc ctaaactcct gatctctaag gcgtctagtt tagaaagtgg ggtcccatca | | | | 180 |
| aggttcagcg gcagtggatc tgggacagaa ttcactctca ccattagcag cctgcagcct | | | | 240 |
| gatgattttg caacttatta ctgccaacag tataataggt attggacgtt cggccaaggg | | | | 300 |
| accatggtgg aaatcaaa | | | | 318 |

<210> SEQ ID NO 298
<211> LENGTH: 106
<212> TYPE: PRT
<213> ORGANISM: Artificial Sequence
<220> FEATURE:
<223> OTHER INFORMATION: synthetic

<400> SEQUENCE: 298

Asp Ile Gln Met Thr Gln Ser Pro Ser Thr Leu Ser Ala Ser Val Gly
1               5                   10                  15
Asp Arg Val Thr Val Thr Cys Arg Ala Ser Gln Thr Ile Ile Asn Trp
            20                  25                  30
Leu Ala Trp Tyr Gln Gln Lys Pro Gly Lys Ala Pro Lys Leu Leu Ile
        35                  40                  45
Ser Lys Ala Ser Ser Leu Glu Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Tyr Asn Arg Tyr Trp Thr
                85                  90                  95
Phe Gly Gln Gly Thr Met Val Glu Ile Lys
            100                 105

<210> SEQ ID NO 299
<211> LENGTH: 18
<212> TYPE: DNA
<213> ORGANISM: Artificial Sequence
<220> FEATURE:
<223> OTHER INFORMATION: synthetic

<400> SEQUENCE: 299

| | |
|---|---|
| cagactatta ttaattgg | 18 |

<210> SEQ ID NO 300
<211> LENGTH: 6
<212> TYPE: PRT
<213> ORGANISM: Artificial Sequence
<220> FEATURE:
<223> OTHER INFORMATION: synthetic

<400> SEQUENCE: 300

Gln Thr Ile Ile Asn Trp
1               5

<210> SEQ ID NO 301
<211> LENGTH: 9
<212> TYPE: DNA
<213> ORGANISM: Artificial Sequence
<220> FEATURE:
<223> OTHER INFORMATION: synthetic

<400> SEQUENCE: 301 aaggcgtct                                                                                    9

<210> SEQ ID NO 302
<211> LENGTH: 3
<212> TYPE: PRT
<213> ORGANISM: Artificial Sequence
<220> FEATURE:
<223> OTHER INFORMATION: synthetic

<400> SEQUENCE: 302

Lys Ala Ser
 1

<210> SEQ ID NO 303
<211> LENGTH: 24
<212> TYPE: DNA
<213> ORGANISM: Artificial Sequence
<220> FEATURE:
<223> OTHER INFORMATION: synthetic

<400> SEQUENCE: 303
caacagtata ataggtattg gacg                                                                  24

<210> SEQ ID NO 304
<211> LENGTH: 8
<212> TYPE: PRT
<213> ORGANISM: Artificial Sequence
<220> FEATURE:
<223> OTHER INFORMATION: synthetic

<400> SEQUENCE: 304

Gln Gln Tyr Asn Arg Tyr Trp Thr
 1               5

<210> SEQ ID NO 305
<211> LENGTH: 363
<212> TYPE: DNA
<213> ORGANISM: Artificial Sequence
<220> FEATURE:
<223> OTHER INFORMATION: synthetic

<400> SEQUENCE: 305
gaggtgcagc tggtggagtc tgggggagac ttggtccagc ctgggggtc cctgagactc          60 tcctgtacag cctctggatt cacctttagt aaatattgga tgacctgggt ccgccaggct        120
ccagggaggg ggctggagtg ggtggccaac ataaaggaag atggaaatga aaaatacttt        180
ctggactctg tgaagggccg cttcaccatt tccagagaca acgccaagga tttattgttt        240
ctgcaaatga acagcctgag aggcgaggac acggctgtgt attactgtgt gagagatcga        300
ggtatagaag tggctggccc ctttgactac tggggccagg gaaccctggt caccgtctcc        360
tca                                                                                        363

<210> SEQ ID NO 306
<211> LENGTH: 121
<212> TYPE: PRT
<213> ORGANISM: Artificial Sequence
<220> FEATURE:
<223> OTHER INFORMATION: synthetic

<400> SEQUENCE: 306

Glu Val Gln Leu Val Glu Ser Gly Gly Asp Leu Val Gln Pro Gly Gly
 1               5                  10                  15

Ser Leu Arg Leu Ser Cys Thr Ala Ser Gly Phe Thr Phe Ser Lys Tyr
            20                  25                  30

Trp Met Thr Trp Val Arg Gln Ala Pro Gly Arg Gly Leu Glu Trp Val
        35                  40                  45

Ala Asn Ile Lys Glu Asp Gly Asn Glu Lys Tyr Phe Leu Asp Ser Val
50                  55                  60

Lys Gly Arg Phe Thr Ile Ser Arg Asp Asn Ala Lys Asp Leu Leu Phe
65                  70                  75                  80

Leu Gln Met Asn Ser Leu Arg Gly Glu Asp Thr Ala Val Tyr Tyr Cys
                85                  90                  95

Val Arg Asp Arg Gly Ile Glu Val Ala Gly Pro Phe Tyr Trp Gly
            100                 105                 110

Gln Gly Thr Leu Val Thr Val Ser Ser
        115                 120

<210> SEQ ID NO 307
<211> LENGTH: 318
<212> TYPE: DNA
<213> ORGANISM: Artificial Sequence
<220> FEATURE:
<223> OTHER INFORMATION: synthetic

<400> SEQUENCE: 307
gacatccaga tgacccagtc tccttccacc ctgtctgcat ctgttgggga cagagtcacc      60
gtcacttgcc gggccagtca gactattatt aattggttgg cctggtatca gcagaaacca     120
gggaaagccc ctaaactcct gatctctaag gcgtctagtt tagaaagtgg ggtcccatca     180
aggttcagcg gcagtggatc tgggacagaa ttcactctca ccattagcag cctgcagcct     240
gatgattttg caacttatta ctgccaacag tataataggt attggacgtt cggccaaggg     300
accaaggtgg aaatcaaa                                                   318

<210> SEQ ID NO 308
<211> LENGTH: 106
<212> TYPE: PRT
<213> ORGANISM: Artificial Sequence
<220> FEATURE:
<223> OTHER INFORMATION: synthetic

<400> SEQUENCE: 308

Asp Ile Gln Met Thr Gln Ser Pro Ser Thr Leu Ser Ala Ser Val Gly
1               5                   10                  15

Asp Arg Val Thr Val Thr Cys Arg Ala Ser Gln Thr Ile Ile Asn Trp
            20                  25                  30

Leu Ala Trp Tyr Gln Gln Lys Pro Gly Lys Ala Pro Lys Leu Leu Ile
        35                  40                  45

Ser Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Arg Tyr Trp Thr
                85                  90                  95

Phe Gly Gln Gly Thr Lys Val Glu Ile Lys
            100                 105

<210> SEQ ID NO 309
<211> LENGTH: 363
<212> TYPE: DNA

<213> ORGANISM: Artificial Sequence
<220> FEATURE:
<223> OTHER INFORMATION: synthetic

<400> SEQUENCE: 309

```
gaggtgcagc tggtggagtc tgggggaggc ttggtccagc ctgggggtc  cctgagactc      60
tcctgtgcag cctctggatt cacctttagt aaatattgga tgagctgggt ccgccaggct     120
ccagggaagg ggctggagtg ggtggccaac ataaaggaag atggaaatga aaaatactat     180
gtggactctg tgaagggccg attcaccatc tccagagaca cgccaagaa  ctcactgtat     240
ctgcaaatga acagcctgag agccgaggac acggctgtgt attactgtgt gagagatcga     300
ggtatagaag tggctggccc ctttgactac tggggccagg gaaccctggt caccgtctcc     360
tca                                                                   363
```

<210> SEQ ID NO 310
<211> LENGTH: 121
<212> TYPE: PRT
<213> ORGANISM: Artificial Sequence
<220> FEATURE:
<223> OTHER INFORMATION: synthetic

<400> SEQUENCE: 310

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Lys Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Asn Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Arg Gly Ile Glu Val Ala Gly Pro Phe Asp Tyr Trp Gly
            100                 105                 110

Gln Gly Thr Leu Val Thr Val Ser Ser
        115                 120
```

<210> SEQ ID NO 311
<211> LENGTH: 319
<212> TYPE: DNA
<213> ORGANISM: Artificial Sequence
<220> FEATURE:
<223> OTHER INFORMATION: synthetic

<400> SEQUENCE: 311

```
gacatccaga tgacccagtc tccttccacc ctgtctgcat ctgtaggaga cagagtcacc      60
atcacttgcc gggccagtca gactattatt aattggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataataggt attggacgtt cggccaaggg     300
accaaggtgg aaatcaaac                                                  319
```

<210> SEQ ID NO 312
<211> LENGTH: 106

```
<212> TYPE: PRT
<213> ORGANISM: Artificial Sequence
<220> FEATURE:
<223> OTHER INFORMATION: synthetic

<400> SEQUENCE: 312

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Thr Ile Ile Asn Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Arg Tyr Trp Thr
                85                  90                  95

Phe Gly Gln Gly Thr Lys Val Glu Ile Lys
            100                 105

<210> SEQ ID NO 313
<211> LENGTH: 363
<212> TYPE: DNA
<213> ORGANISM: Artificial Sequence
<220> FEATURE:
<223> OTHER INFORMATION: synthetic

<400> SEQUENCE: 313
caggtgcagc tggtggagtc tgggggaggc gtggtccagc ctggagggtc cctgagactc        60
tcctgtgcag cgtctggatt caccttcagt agctatggca tgcactgggt ccgccaggct       120
ccaggcaagg ggctggagtg ggtggcagtt atatggtatg atgaatttaa taaatactat       180
gcagactccg tgaagggccg attcaccatc tccagagaca attccaagaa cacgctgtat       240
ctgcaaatga acagcctgag agccgaggac acggctgtgt attactgtgc gagagagaga       300
gagagtggat acagttatgg ttttgactac tggggccagg gaaccctggt caccgtctcc       360
tca                                                                     363

<210> SEQ ID NO 314
<211> LENGTH: 121
<212> TYPE: PRT
<213> ORGANISM: Artificial Sequence
<220> FEATURE:
<223> OTHER INFORMATION: synthetic

<400> SEQUENCE: 314

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Glu Phe Asn Lys Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Glu Arg Glu Ser Gly Tyr Ser Tyr Gly Phe Asp Tyr Trp Gly
            100                 105                 110

Gln Gly Thr Leu Val Thr Val Ser Ser
        115                 120

<210> SEQ ID NO 315
<211> LENGTH: 24
<212> TYPE: DNA
<213> ORGANISM: Artificial Sequence
<220> FEATURE:
<223> OTHER INFORMATION: synthetic

<400> SEQUENCE: 315
ggattcacct tcagtagcta tggc                                          24

<210> SEQ ID NO 316
<211> LENGTH: 8
<212> TYPE: PRT
<213> ORGANISM: Artificial Sequence
<220> FEATURE:
<223> OTHER INFORMATION: synthetic

<400> SEQUENCE: 316

Gly Phe Thr Phe Ser Ser Tyr Gly
1               5

<210> SEQ ID NO 317
<211> LENGTH: 24
<212> TYPE: DNA
<213> ORGANISM: Artificial Sequence
<220> FEATURE:
<223> OTHER INFORMATION: synthetic

<400> SEQUENCE: 317
atatggtatg atgaatttaa taaa                                          24

<210> SEQ ID NO 318
<211> LENGTH: 8
<212> TYPE: PRT
<213> ORGANISM: Artificial Sequence
<220> FEATURE:
<223> OTHER INFORMATION: synthetic

<400> SEQUENCE: 318

Ile Trp Tyr Asp Glu Phe Asn Lys
1               5

<210> SEQ ID NO 319
<211> LENGTH: 42
<212> TYPE: DNA
<213> ORGANISM: Artificial Sequence
<220> FEATURE:
<223> OTHER INFORMATION: synthetic

<400> SEQUENCE: 319
gcgagagaga gagagagtgg atacagttat ggttttgact ac                      42

<210> SEQ ID NO 320
<211> LENGTH: 14
<212> TYPE: PRT
<213> ORGANISM: Artificial Sequence
<220> FEATURE:
<223> OTHER INFORMATION: synthetic

<400> SEQUENCE: 320

Ala Arg Glu Arg Glu Ser Gly Tyr Ser Tyr Gly Phe Asp Tyr
1               5                   10

<210> SEQ ID NO 321
<211> LENGTH: 318
<212> TYPE: DNA
<213> ORGANISM: Artificial Sequence
<220> FEATURE:
<223> OTHER INFORMATION: synthetic

<400> SEQUENCE: 321
gaaatagtga tgacgcagtc tccagccacc ctgtctgtgt ctccagggga aagagccacc     60
ctctcctgca gggccggtca gagtgttagc agcaacttag cctggtacca gcaaaaacct    120
ggccaggctc ccaggctcct catctatggt gcgtccacca gggccactgg tatcccagcc    180
aggttcagtg gcagtgggtc tgggacagag ttcactctca ccatcagcag cctgcagtct    240
gaagattttg cagtttatta ctgtcagcag tataataact ggtggacgtt cggccaaggg    300
accaaggtgg aaatcaaa                                                  318

<210> SEQ ID NO 322
<211> LENGTH: 106
<212> TYPE: PRT
<213> ORGANISM: Artificial Sequence
<220> FEATURE:
<223> OTHER INFORMATION: synthetic

<400> SEQUENCE: 322

Glu Ile Val Met Thr Gln Ser Pro Ala Thr Leu Ser Val Ser Pro Gly
1               5                   10                  15

Glu Arg Ala Thr Leu Ser Cys Arg Ala Gly Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Trp Thr
                85                  90                  95

Phe Gly Gln Gly Thr Lys Val Glu Ile Lys
            100                 105

<210> SEQ ID NO 323
<211> LENGTH: 18
<212> TYPE: DNA
<213> ORGANISM: Artificial Sequence
<220> FEATURE:
<223> OTHER INFORMATION: synthetic

<400> SEQUENCE: 323
cagagtgtta gcagcaac                                                   18

<210> SEQ ID NO 324
<211> LENGTH: 6
<212> TYPE: PRT
<213> ORGANISM: Artificial Sequence
<220> FEATURE:
<223> OTHER INFORMATION: synthetic

<400> SEQUENCE: 324

Gln Ser Val Ser Ser Asn

<210> SEQ ID NO 325
<211> LENGTH: 9
<212> TYPE: DNA
<213> ORGANISM: Artificial Sequence
<220> FEATURE:
<223> OTHER INFORMATION: synthetic

<400> SEQUENCE: 325 ggtgcgtcc                                                            9

<210> SEQ ID NO 326
<211> LENGTH: 3
<212> TYPE: PRT
<213> ORGANISM: Artificial Sequence
<220> FEATURE:
<223> OTHER INFORMATION: synthetic

<400> SEQUENCE: 326

Gly Ala Ser
 1

<210> SEQ ID NO 327
<211> LENGTH: 24
<212> TYPE: DNA
<213> ORGANISM: Artificial Sequence
<220> FEATURE:
<223> OTHER INFORMATION: synthetic

<400> SEQUENCE: 327
cagcagtata ataactggtg gacg                                          24

<210> SEQ ID NO 328
<211> LENGTH: 8
<212> TYPE: PRT
<213> ORGANISM: Artificial Sequence
<220> FEATURE:
<223> OTHER INFORMATION: synthetic

<400> SEQUENCE: 328

Gln Gln Tyr Asn Asn Trp Trp Thr
 1               5

<210> SEQ ID NO 329
<211> LENGTH: 363
<212> TYPE: DNA
<213> ORGANISM: Artificial Sequence
<220> FEATURE:
<223> OTHER INFORMATION: synthetic

<400> SEQUENCE: 329
caggtgcagc tggtggagtc tgggggaggc gtggtccagc ctggggaggtc cctgagactc      60 tcctgtgcag cgtctggatt caccttcagt agctatggca tgcactgggt ccgccaggct     120
ccaggcaagg ggctggagtg ggtggcagtt atatggtatg atgaatttaa taaatactat     180
gcagactccg tgaagggccg attcaccatc tccagagaca attccaagaa cacgctgtat     240
ctgcaaatga acagcctgag agccgaggac acggctgtgt attactgtgc gagagagaga     300
gagagtggat acagttatgg ttttgactac tggggccagg gaaccctggt caccgtctcc     360
tca                                                                  363

<210> SEQ ID NO 330
<211> LENGTH: 121

```
<212> TYPE: PRT
<213> ORGANISM: Artificial Sequence
<220> FEATURE:
<223> OTHER INFORMATION: synthetic

<400> SEQUENCE: 330
```

| Gln | Val | Gln | Leu | Val | Glu | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Gly | Met | His | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Val | Ile | Trp | Tyr | Asp | Glu | Phe | Asn | Lys | Tyr | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Glu | Arg | Glu | Ser | Gly | Tyr | Ser | Tyr | Gly | Phe | Asp | Tyr | Trp | Gly |
|---|---|---|---|---|---|---|---|---|---|---|---|---|---|---|---|
| | | | 100 | | | | | 105 | | | | | 110 | | |

| Gln | Gly | Thr | Leu | Val | Thr | Val | Ser | Ser |
|---|---|---|---|---|---|---|---|---|
| | | 115 | | | | | 120 | |

```
<210> SEQ ID NO 331
<211> LENGTH: 318
<212> TYPE: DNA
<213> ORGANISM: Artificial Sequence
<220> FEATURE:
<223> OTHER INFORMATION: synthetic
<400> SEQUENCE: 331
gaaatagtga tgacgcagtc tccagccacc ctgtctgtgt ctccagggga aagagccacc    60
ctctcctgca gggccggtca gagtgttagc agcaacttag cctggtacca gcaaaaacct   120
ggccaggctc ccaggctcct catctatggt gcgtccacca gggccactgg tatcccagcc   180
aggttcagtg gcagtgggtc tgggacagag ttcactctca ccatcagcag cctgcagtct   240
gaagattttg cagtttatta ctgtcagcag tataataact ggtggacgtt cggccaaggg   300
accaaggtgg aaatcaaa                                                  318

<210> SEQ ID NO 332
<211> LENGTH: 106
<212> TYPE: PRT
<213> ORGANISM: Artificial Sequence
<220> FEATURE:
<223> OTHER INFORMATION: synthetic

<400> SEQUENCE: 332
```

| Glu | Ile | Val | Met | Thr | Gln | Ser | Pro | Ala | Thr | Leu | Ser | Val | Ser | Pro | Gly |
|---|---|---|---|---|---|---|---|---|---|---|---|---|---|---|---|
| 1 | | | | 5 | | | | | 10 | | | | | 15 | |

| Glu | Arg | Ala | Thr | Leu | Ser | Cys | Arg | Ala | Gly | Gln | Ser | Val | Ser | Ser | Asn |
|---|---|---|---|---|---|---|---|---|---|---|---|---|---|---|---|
| | | | 20 | | | | | 25 | | | | | 30 | | |

| Leu | Ala | Trp | Tyr | Gln | Gln | Lys | Pro | Gly | Gln | Ala | Pro | Arg | Leu | Leu | Ile |
|---|---|---|---|---|---|---|---|---|---|---|---|---|---|---|---|
| | | 35 | | | | | 40 | | | | | 45 | | | |

| Tyr | Gly | Ala | Ser | Thr | Arg | Ala | Thr | Gly | Ile | Pro | Ala | Arg | Phe | Ser | Gly |
|---|---|---|---|---|---|---|---|---|---|---|---|---|---|---|---|
| | 50 | | | | | 55 | | | | | 60 | | | | |

| Ser | Gly | Ser | Gly | Thr | Glu | Phe | Thr | Leu | Thr | Ile | Ser | Ser | Leu | Gln | Ser |
|---|---|---|---|---|---|---|---|---|---|---|---|---|---|---|---|
| 65 | | | | | 70 | | | | | 75 | | | | | 80 |

| Glu | Asp | Phe | Ala | Val | Tyr | Tyr | Cys | Gln | Gln | Tyr | Asn | Asn | Trp | Trp | Thr |
|---|---|---|---|---|---|---|---|---|---|---|---|---|---|---|---|

Phe Gly Gln Gly Thr Lys Val Glu Ile Lys
                85                  90                  95
            100                 105

<210> SEQ ID NO 333
<211> LENGTH: 363
<212> TYPE: DNA
<213> ORGANISM: Artificial Sequence
<220> FEATURE:
<223> OTHER INFORMATION: synthetic

<400> SEQUENCE: 333
caggtgcagc tggtggagtc tgggggaggc gtggtccagc ctggcagagtc cctgagactc     60 tcctgtgcag cgtctggatt caccttcagt agctatggca tgcactgggt ccgccaggct    120
ccaggcaagg gctggagtg gtggcagtt atatggtatg atgaatttaa taaatactat    180
gcagactccg tgaagggccg attcaccatc tccagagaca actccaagaa cacgctgtat    240
ctgcaaatga acagcctgag agccgaggac acggctgtgt attactgtgc gagagagaga    300
gagagtggat acagttatgg ttttgactac tggggccagg gaaccctggt caccgtctcc    360
tca                                                                  363

<210> SEQ ID NO 334
<211> LENGTH: 121
<212> TYPE: PRT
<213> ORGANISM: Artificial Sequence
<220> FEATURE:
<223> OTHER INFORMATION: synthetic

<400> SEQUENCE: 334

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Glu Phe Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Glu Ser Gly Tyr Ser Tyr Gly Phe Asp Tyr Trp Gly
            100                 105                 110

Gln Gly Thr Leu Val Thr Val Ser Ser
        115                 120

<210> SEQ ID NO 335
<211> LENGTH: 319
<212> TYPE: DNA
<213> ORGANISM: Artificial Sequence
<220> FEATURE:
<223> OTHER INFORMATION: synthetic

<400> SEQUENCE: 335
gaaatagtga tgacgcagtc tccagccacc ctgtctgtgt ctccagggga aagagccacc     60
ctctcctgca gggccagtca gagtgttagc agcaacttag cctggtacca gcagaaacct    120
ggccaggctc ccaggctcct catctatggt gcgtccacca gggccactgg tatcccagcc    180

```
aggttcagtg gcagtgggtc tgggacagag ttcactctca ccatcagcag cctgcagtct      240
gaagattttg cagtttatta ctgtcagcag tataataact ggtggacgtt cggccaaggg      300
accaaggtgg aaatcaaac                                                   319
```

<210> SEQ ID NO 336
<211> LENGTH: 106
<212> TYPE: PRT
<213> ORGANISM: Artificial Sequence
<220> FEATURE:
<223> OTHER INFORMATION: synthetic

<400> SEQUENCE: 336

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Trp Thr
                85                  90                  95

Phe Gly Gln Gly Thr Lys Val Glu Ile Lys
            100                 105
```

<210> SEQ ID NO 337
<211> LENGTH: 375
<212> TYPE: DNA
<213> ORGANISM: Artificial Sequence
<220> FEATURE:
<223> OTHER INFORMATION: synthetic

<400> SEQUENCE: 337

```
caggttcagc tggtgcagtc tggacctgag gtgaaggagc ctggggcctc agtgaaggtc      60
tcctgcaagg cttctggtta cacctttacc acctatagta tcacctgggt gcgacaggcc     120
cctggacaag gcttgagtg gatgggatgg atcagcgctt acaattatga cacaaattat     180
gcacagaaga tccagggcag agtcaccatg accacagaca catccacgaa cacagcctac     240
atggaactga ggagcctgag atctgacgac acggccgtgt attactgtgc gagaggcgat     300
ttctggatta ttattcccta ctactactac ggtgtggacg tctggggcca agggaccacg     360
gtcaccgtct cctca                                                      375
```

<210> SEQ ID NO 338
<211> LENGTH: 125
<212> TYPE: PRT
<213> ORGANISM: Artificial Sequence
<220> FEATURE:
<223> OTHER INFORMATION: synthetic

<400> SEQUENCE: 338

```
Gln Val Gln Leu Val Gln Ser Gly Pro Glu Val Lys Glu Pro Gly Ala
1               5                   10                  15

Ser Val Lys Val Ser Cys Lys Ala Ser Gly Tyr Thr Phe Thr Thr Tyr
            20                  25                  30

Ser Ile Thr Trp Val Arg Gln Ala Pro Gly Gln Gly Leu Glu Trp Met
        35                  40                  45
```

```
Gly Trp Ile Ser Ala Tyr Asn Tyr Asp Thr Asn Tyr Ala Gln Lys Ile
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asp Phe Trp Ile Asn Tyr Ser Tyr Tyr Tyr Gly Val
                100                 105                 110

Asp Val Trp Gly Gln Gly Thr Thr Val Thr Val Ser Ser
            115                 120                 125

<210> SEQ ID NO 339
<211> LENGTH: 24
<212> TYPE: DNA
<213> ORGANISM: Artificial Sequence
<220> FEATURE:
<223> OTHER INFORMATION: synthetic

<400> SEQUENCE: 339
ggttacacct ttaccaccta tagt                                            24

<210> SEQ ID NO 340
<211> LENGTH: 8
<212> TYPE: PRT
<213> ORGANISM: Artificial Sequence
<220> FEATURE:
<223> OTHER INFORMATION: synthetic

<400> SEQUENCE: 340

Gly Tyr Thr Phe Thr Thr Tyr Ser
1               5

<210> SEQ ID NO 341
<211> LENGTH: 24
<212> TYPE: DNA
<213> ORGANISM: Artificial Sequence
<220> FEATURE:
<223> OTHER INFORMATION: synthetic

<400> SEQUENCE: 341
atcagcgctt acaattatga caca                                            24

<210> SEQ ID NO 342
<211> LENGTH: 8
<212> TYPE: PRT
<213> ORGANISM: Artificial Sequence
<220> FEATURE:
<223> OTHER INFORMATION: synthetic

<400> SEQUENCE: 342

Ile Ser Ala Tyr Asn Tyr Asp Thr
1               5

<210> SEQ ID NO 343
<211> LENGTH: 54
<212> TYPE: DNA
<213> ORGANISM: Artificial Sequence
<220> FEATURE:
<223> OTHER INFORMATION: synthetic

<400> SEQUENCE: 343
gcgagaggcg atttctggat taattattcc tactactact acggtgtgga cgtc           54
```

```
<210> SEQ ID NO 344
<211> LENGTH: 18
<212> TYPE: PRT
<213> ORGANISM: Artificial Sequence
<220> FEATURE:
<223> OTHER INFORMATION: synthetic

<400> SEQUENCE: 344

Ala Arg Gly Asp Phe Trp Ile Asn Tyr Ser Tyr Tyr Tyr Tyr Gly Val
 1               5                  10                  15

Asp Val

<210> SEQ ID NO 345
<211> LENGTH: 339
<212> TYPE: DNA
<213> ORGANISM: Artificial Sequence
<220> FEATURE:
<223> OTHER INFORMATION: synthetic

<400> SEQUENCE: 345
gacattgtga tgacgcagtc tccactctcc ctgcccgtca tccctggaga gccggcctcc     60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactccc    300
atgtacactt ttggccaggg gaccaagctg gagatcaaa                           339

<210> SEQ ID NO 346
<211> LENGTH: 113
<212> TYPE: PRT
<213> ORGANISM: Artificial Sequence
<220> FEATURE:
<223> OTHER INFORMATION: synthetic

<400> SEQUENCE: 346

Asp Ile Val Met Thr Gln Ser Pro Leu Ser Leu Pro Val Ile Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Met Tyr Thr Phe Gly Gln Gly Thr Lys Leu Glu Ile
            100                 105                 110

Lys

<210> SEQ ID NO 347
<211> LENGTH: 33
<212> TYPE: DNA
<213> ORGANISM: Artificial Sequence
<220> FEATURE:
<223> OTHER INFORMATION: synthetic

<400> SEQUENCE: 347
```

```
cagagcctcc tgcatagtaa tggatacaac tat                                          33
```

<210> SEQ ID NO 348
<211> LENGTH: 11
<212> TYPE: PRT
<213> ORGANISM: Artificial Sequence
<220> FEATURE:
<223> OTHER INFORMATION: synthetic

<400> SEQUENCE: 348

Gln Ser Leu Leu His Ser Asn Gly Tyr Asn Tyr
 1               5                   10

<210> SEQ ID NO 349
<211> LENGTH: 9
<212> TYPE: DNA
<213> ORGANISM: Artificial Sequence
<220> FEATURE:
<223> OTHER INFORMATION: synthetic

<400> SEQUENCE: 349

```
ttgggttct                                                                     9
```

<210> SEQ ID NO 350
<211> LENGTH: 3
<212> TYPE: PRT
<213> ORGANISM: Artificial Sequence
<220> FEATURE:
<223> OTHER INFORMATION: synthetic

<400> SEQUENCE: 350

Leu Gly Ser
 1

<210> SEQ ID NO 351
<211> LENGTH: 30
<212> TYPE: DNA
<213> ORGANISM: Artificial Sequence
<220> FEATURE:
<223> OTHER INFORMATION: synthetic

<400> SEQUENCE: 351

```
atgcaagctc tacaaactcc catgtacact                                              30
```

<210> SEQ ID NO 352
<211> LENGTH: 10
<212> TYPE: PRT
<213> ORGANISM: Artificial Sequence
<220> FEATURE:
<223> OTHER INFORMATION: synthetic

<400> SEQUENCE: 352

Met Gln Ala Leu Gln Thr Pro Met Tyr Thr
 1               5                   10

<210> SEQ ID NO 353
<211> LENGTH: 372
<212> TYPE: DNA
<213> ORGANISM: Artificial Sequence
<220> FEATURE:
<223> OTHER INFORMATION: synthetic

<400> SEQUENCE: 353

```
caggttcagc tggtgcagtc tggacctgag gtgaaggagc ctggggcctc agtgaaggtc             60
tcctgcaagg cttctggtta cacctttacc acctatagta tcacctgggt gcgacaggcc            120
```

```
cctggacaag ggcttgagtg gatgggatgg atcagcgctt acaattatga cacaaattat    180
gcacagaaga tccagggcag agtcaccatg accacagaca catccacgaa cacagcctac    240
atggaactga ggagcctgag atctgacgac acggccgtgt attactgtgc gagaggcgat    300
ttctggatta attattccta ctactactac ggtgtggacg tctggggcca agggaccacg    360
gtcaccgtct cc                                                       372
```

```
<210> SEQ ID NO 354
<211> LENGTH: 124
<212> TYPE: PRT
<213> ORGANISM: Artificial Sequence
<220> FEATURE:
<223> OTHER INFORMATION: synthetic

<400> SEQUENCE: 354
```

Gln Val Gln Leu Val Gln Ser Gly Pro Glu Val Lys Glu Pro Gly Ala
1               5                   10                  15

Ser Val Lys Val Ser Cys Lys Ala Ser Gly Tyr Thr Phe Thr Thr Tyr
            20                  25                  30

Ser Ile Thr Trp Val Arg Gln Ala Pro Gly Gln Gly Leu Glu Trp Met
        35                  40                  45

Gly Trp Ile Ser Ala Tyr Asn Tyr Asp Thr Asn Tyr Ala Gln Lys Ile
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asp Phe Trp Ile Asn Tyr Ser Tyr Tyr Tyr Gly Val
            100                 105                 110

Asp Val Trp Gly Gln Gly Thr Thr Val Thr Val Ser
        115                 120

```
<210> SEQ ID NO 355
<211> LENGTH: 339
<212> TYPE: DNA
<213> ORGANISM: Artificial Sequence
<220> FEATURE:
<223> OTHER INFORMATION: synthetic

<400> SEQUENCE: 355
gatattgtga tgactcagtc tccactctcc ctgcccgtca cccctggaga gccggcctcc    60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactccc    300
atgtacactt ttggccaggg gaccaagctg gagatcaaa                          339
```

```
<210> SEQ ID NO 356
<211> LENGTH: 113
<212> TYPE: PRT
<213> ORGANISM: Artificial Sequence
<220> FEATURE:
<223> OTHER INFORMATION: synthetic

<400> SEQUENCE: 356
```

Asp Ile Val Met Thr Gln Ser Pro Leu Ser Leu Pro Val Ile Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Met Tyr Thr Phe Gly Gln Gly Thr Lys Leu Glu Ile
            100                 105                 110

Lys

<210> SEQ ID NO 357
<211> LENGTH: 373
<212> TYPE: DNA
<213> ORGANISM: Artificial Sequence
<220> FEATURE:
<223> OTHER INFORMATION: synthetic

<400> SEQUENCE: 357
caggttcagc tggtgcagtc tggagctgag gtgaagaagc ctggggcctc agtgaaggtc      60
tcctgcaagg cttctggtta cacctttacc acctatagta tcagctgggt gcgacaggcc     120
cctggacaag ggcttgagtg gatgggatgg atcagcgctt acaattatga cacaaactat     180
gcacagaagc tccagggcag agtcaccatg accacagaca tccacgag cacagcctac       240
atggagctga ggagcctgag atctgacgac acggccgtgt attactgtgc gagaggcgat     300
ttctggatta ttattccta ctactactac ggtgtggacg tctggggcca agggaccacg      360
gtcaccgtct cct                                                        373

<210> SEQ ID NO 358
<211> LENGTH: 124
<212> TYPE: PRT
<213> ORGANISM: Artificial Sequence
<220> FEATURE:
<223> OTHER INFORMATION: synthetic

<400> SEQUENCE: 358

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Ser Ile Ser Trp Val Arg Gln Ala Pro Gly Gln Gly Leu Glu Trp Met
        35                  40                  45

Gly Trp Ile Ser Ala Tyr Asn Tyr Asp Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asp Phe Trp Ile Asn Tyr Ser Tyr Tyr Tyr Gly Val
            100                 105                 110

Asp Val Trp Gly Gln Gly Thr Thr Val Thr Val Ser
            115                 120

<210> SEQ ID NO 359
<211> LENGTH: 340
<212> TYPE: DNA
<213> ORGANISM: Artificial Sequence
<220> FEATURE:
<223> OTHER INFORMATION: synthetic

<400> SEQUENCE: 359

```
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactccc   300
atgtacactt ttggccaggg gaccaagctg gagatcaaac                          340
```

<210> SEQ ID NO 360
<211> LENGTH: 113
<212> TYPE: PRT
<213> ORGANISM: Artificial Sequence
<220> FEATURE:
<223> OTHER INFORMATION: synthetic

<400> SEQUENCE: 360

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Met Tyr Thr Phe Gly Gln Gly Thr Lys Leu Glu Ile
            100                 105                 110

Lys
```

<210> SEQ ID NO 361
<211> LENGTH: 363
<212> TYPE: DNA
<213> ORGANISM: Artificial Sequence
<220> FEATURE:
<223> OTHER INFORMATION: synthetic

<400> SEQUENCE: 361

```
gaggtgcagc tggtggagtc tgggggaggc ttggtccagc ctggggggtc cctgagactc    60
tcctgtgcag cctctggatt cgcctttaga agttattgga tgacctgggt ccgccaggct   120
ccagggaagg gctggagtg gtggccaac atacagcaag atggaaatga taaatactat   180
gtggactctg tgaagggccg attcaccatc tccagagaca acgccaagaa ctcactgtat   240
ctgcaaatga acagcctgag agccgaggac acggctgtgt attactgtgc gagagatacc   300
ggtatagcag aagctggtcc ttttgactac tggggccagg gaaccctggt caccgtctcc   360
tca                                                                  363
```

<210> SEQ ID NO 362
<211> LENGTH: 121
<212> TYPE: PRT
<213> ORGANISM: Artificial Sequence
<220> FEATURE:
<223> OTHER INFORMATION: synthetic

<400> SEQUENCE: 362

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Arg Ser Tyr
            20                  25                  30

Trp Met Thr Trp Val Arg Gln Ala Pro Gly Lys Gly Leu Glu Trp Val
        35                  40                  45

Ala Asn Ile Gln Gln Asp Gly Asn Asp Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Gly Ile Ala Glu Ala Gly Pro Phe Asp Tyr Trp Gly
            100                 105                 110

Gln Gly Thr Leu Val Thr Val Ser Ser
        115                 120

<210> SEQ ID NO 363
<211> LENGTH: 24
<212> TYPE: DNA
<213> ORGANISM: Artificial Sequence
<220> FEATURE:
<223> OTHER INFORMATION: synthetic

<400> SEQUENCE: 363
ggattcgcct ttagaagtta ttgg                                          24

<210> SEQ ID NO 364
<211> LENGTH: 8
<212> TYPE: PRT
<213> ORGANISM: Artificial Sequence
<220> FEATURE:
<223> OTHER INFORMATION: synthetic

<400> SEQUENCE: 364

Gly Phe Ala Phe Arg Ser Tyr Trp
1               5

<210> SEQ ID NO 365
<211> LENGTH: 24
<212> TYPE: DNA
<213> ORGANISM: Artificial Sequence
<220> FEATURE:
<223> OTHER INFORMATION: synthetic

<400> SEQUENCE: 365
atacagcaag atggaaatga taaa                                          24

<210> SEQ ID NO 366
<211> LENGTH: 8
<212> TYPE: PRT
<213> ORGANISM: Artificial Sequence
<220> FEATURE:
<223> OTHER INFORMATION: synthetic

<400> SEQUENCE: 366

Ile Gln Gln Asp Gly Asn Asp Lys
1               5

<210> SEQ ID NO 367
<211> LENGTH: 42
<212> TYPE: DNA
<213> ORGANISM: Artificial Sequence
<220> FEATURE:
<223> OTHER INFORMATION: synthetic

<400> SEQUENCE: 367
gcgagagata ccggtatagc agaagctggt ccttttgact ac                          42

<210> SEQ ID NO 368
<211> LENGTH: 14
<212> TYPE: PRT
<213> ORGANISM: Artificial Sequence
<220> FEATURE:
<223> OTHER INFORMATION: synthetic

<400> SEQUENCE: 368

Ala Arg Asp Thr Gly Ile Ala Glu Ala Gly Pro Phe Asp Tyr
1               5                   10

<210> SEQ ID NO 369
<211> LENGTH: 318
<212> TYPE: DNA
<213> ORGANISM: Artificial Sequence
<220> FEATURE:
<223> OTHER INFORMATION: synthetic

<400> SEQUENCE: 369
gacatccaga tgacccagtc tccttccacc ctgtctgcat ctgtaggaga cagagtctcc        60
atcacttgcc gggccagtca gactattatt agctggttgg cctggtatca gcagaaacca      120
gggaaagccc ctaggctcct gatctataag gcgtctagtt tagaaagtgg ggtcccatca      180
aggttcagcg gcagtggatc tgggacagaa ttcactctca ccatcaacag cctgcagcct      240
gatgattttg caacttatta ctgccaacag tataatcgtt attggacgtt cggccaaggg      300
accaaggtgg aaatcaaa                                                    318

<210> SEQ ID NO 370
<211> LENGTH: 106
<212> TYPE: PRT
<213> ORGANISM: Artificial Sequence
<220> FEATURE:
<223> OTHER INFORMATION: synthetic

<400> SEQUENCE: 370

Asp Ile Gln Met Thr Gln Ser Pro Ser Thr Leu Ser Ala Ser Val Gly
1               5                   10                  15

Asp Arg Val Ser Ile Thr Cys Arg Ala Ser Gln Thr Ile Ile Ser Trp
            20                  25                  30

Leu Ala Trp Tyr Gln Gln Lys Pro Gly Lys Ala Pro Arg Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Gln Tyr Asn Arg Tyr Trp Thr
                85                  90                  95

Phe Gly Gln Gly Thr Lys Val Glu Ile Lys
            100                 105

<210> SEQ ID NO 371
<211> LENGTH: 18
<212> TYPE: DNA
<213> ORGANISM: Artificial Sequence
<220> FEATURE:
<223> OTHER INFORMATION: synthetic

<400> SEQUENCE: 371
cagactatta ttagctgg                                                18

<210> SEQ ID NO 372
<211> LENGTH: 6
<212> TYPE: PRT
<213> ORGANISM: Artificial Sequence
<220> FEATURE:
<223> OTHER INFORMATION: synthetic

<400> SEQUENCE: 372

Gln Thr Ile Ile Ser Trp
 1               5

<210> SEQ ID NO 373
<211> LENGTH: 9
<212> TYPE: DNA
<213> ORGANISM: Artificial Sequence
<220> FEATURE:
<223> OTHER INFORMATION: synthetic

<400> SEQUENCE: 373 aaggcgtct                                                           9

<210> SEQ ID NO 374
<211> LENGTH: 3
<212> TYPE: PRT
<213> ORGANISM: Artificial Sequence
<220> FEATURE:
<223> OTHER INFORMATION: synthetic

<400> SEQUENCE: 374

Lys Ala Ser
 1

<210> SEQ ID NO 375
<211> LENGTH: 24
<212> TYPE: DNA
<213> ORGANISM: Artificial Sequence
<220> FEATURE:
<223> OTHER INFORMATION: synthetic

<400> SEQUENCE: 375
caacagtata atcgttattg gacg                                         24

<210> SEQ ID NO 376
<211> LENGTH: 8
<212> TYPE: PRT
<213> ORGANISM: Artificial Sequence
<220> FEATURE:
<223> OTHER INFORMATION: synthetic

<400> SEQUENCE: 376

Gln Gln Tyr Asn Arg Tyr Trp Thr
 1               5

```
<210> SEQ ID NO 377
<211> LENGTH: 363
<212> TYPE: DNA
<213> ORGANISM: Artificial Sequence
<220> FEATURE:
<223> OTHER INFORMATION: synthetic

<400> SEQUENCE: 377
gaggtgcagc tggtggagtc tgggggaggc ttggtccagc ctggggggtc cctgagactc      60
tcctgtgcag cctctggatt cgcctttaga agttattgga tgacctgggt ccgccaggct     120
ccagggaagg ggctggagtg ggtggccaac atacagcaag atggaaatga taaatactat     180
gtggactctg tgaagggccg attcaccatc tccagagaca acgccaagaa ctcactgtat     240
ctgcaaatga acagcctgag agccgaggac acggctgtgt attactgtgc gagagatacc     300
ggtatagcag aagctggtcc ttttgactac tggggccagg gaaccctggt caccgtctcc     360
tca                                                                   363

<210> SEQ ID NO 378
<211> LENGTH: 121
<212> TYPE: PRT
<213> ORGANISM: Artificial Sequence
<220> FEATURE:
<223> OTHER INFORMATION: synthetic

<400> SEQUENCE: 378

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ala Phe Arg Ser Tyr
            20                  25                  30

Trp Met Thr Trp Val Arg Gln Ala Pro Gly Lys Gly Leu Glu Trp Val
        35                  40                  45

Ala Asn Ile Gln Gln Asp Gly Asn Asp Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Gly Ile Ala Glu Ala Gly Pro Phe Asp Tyr Trp Gly
            100                 105                 110

Gln Gly Thr Leu Val Thr Val Ser Ser
        115                 120

<210> SEQ ID NO 379
<211> LENGTH: 318
<212> TYPE: DNA
<213> ORGANISM: Artificial Sequence
<220> FEATURE:
<223> OTHER INFORMATION: synthetic

<400> SEQUENCE: 379
gacatccaga tgacccagtc tccttccacc ctgtctgcat ctgtaggaga cagagtctcc      60
atcacttgcc gggccagtca gactattatt agctggttgg cctggtatca gcagaaacca     120
gggaaagccc ctaggctcct gatctataag gcgtctagtt tagaaagtgg ggtcccatca     180
aggttcagcg gcagtggatc tgggacagaa ttcactctca ccatcaacag cctgcagcct     240
gatgattttg caacttatta ctgccaacag tataatcgtt attggacgtt cggccaaggg     300
accaaggtgg aaatcaaa                                                   318
```

<210> SEQ ID NO 380
<211> LENGTH: 106
<212> TYPE: PRT
<213> ORGANISM: Artificial Sequence
<220> FEATURE:
<223> OTHER INFORMATION: synthetic

<400> SEQUENCE: 380

```
Asp Ile Gln Met Thr Gln Ser Pro Ser Thr Leu Ser Ala Ser Val Gly
 1               5                  10                  15

Asp Arg Val Ser Ile Thr Cys Arg Ala Ser Gln Thr Ile Ile Ser Trp
             20                  25                  30

Leu Ala Trp Tyr Gln Gln Lys Pro Gly Lys Ala Pro Arg Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Asn Ser Leu Gln Pro
 65                  70                  75                  80

Asp Asp Phe Ala Thr Tyr Tyr Cys Gln Gln Tyr Asn Arg Tyr Trp Thr
             85                  90                  95

Phe Gly Gln Gly Thr Lys Val Glu Ile Lys
            100                 105
```

<210> SEQ ID NO 381
<211> LENGTH: 363
<212> TYPE: DNA
<213> ORGANISM: Artificial Sequence
<220> FEATURE:
<223> OTHER INFORMATION: synthetic

<400> SEQUENCE: 381

```
gaggtgcagc tggtggagtc tgggggaggc ttggtccagc ctggggggtc cctgagactc      60
tcctgtgcag cctctggatt cgcctttaga agttattgga tgagctgggt ccgccaggct     120
ccagggaagg ggctggagtg ggtggccaac atacagcaag atggaaatga taaatactat     180
gtggactctg tgaagggccg attcaccatc tccagagaca cgccaagaa ctcactgtat      240
ctgcaaatga acagcctgag agccgaggac acggctgtgt attactgtgc gagagatacc     300
ggtatagcag aagctggtcc ttttgactac tggggccagg gaaccctggt caccgtctcc     360
tca                                                                    363
```

<210> SEQ ID NO 382
<211> LENGTH: 121
<212> TYPE: PRT
<213> ORGANISM: Artificial Sequence
<220> FEATURE:
<223> OTHER INFORMATION: synthetic

<400> SEQUENCE: 382

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ala Phe Arg Ser Tyr
             20                  25                  30

Trp Met Ser Trp Val Arg Gln Ala Pro Gly Lys Gly Leu Glu Trp Val
         35                  40                  45

Ala Asn Ile Gln Gln Asp Gly Asn Asp Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80
```

```
Leu Gln Met Asn Ser Leu Arg Ala Glu Asp Thr Ala Val Tyr Tyr Cys
                85                  90                  95

Ala Arg Asp Thr Gly Ile Ala Glu Ala Gly Pro Phe Asp Tyr Trp Gly
            100                 105                 110

Gln Gly Thr Leu Val Thr Val Ser Ser
        115                 120

<210> SEQ ID NO 383
<211> LENGTH: 319
<212> TYPE: DNA
<213> ORGANISM: Artificial Sequence
<220> FEATURE:
<223> OTHER INFORMATION: synthetic

<400> SEQUENCE: 383
gacatccaga tgacccagtc tccttccacc ctgtctgcat ctgtaggaga cagagtcacc      60
atcacttgcc gggccagtca gactattatt agctggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatcgtt attggacgtt cggccaaggg     300
accaaggtgg aaatcaaac                                                   319

<210> SEQ ID NO 384
<211> LENGTH: 106
<212> TYPE: PRT
<213> ORGANISM: Artificial Sequence
<220> FEATURE:
<223> OTHER INFORMATION: synthetic

<400> SEQUENCE: 384

Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Thr Ile Ile Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
 65                 70                  75                  80

Asp Asp Phe Ala Thr Tyr Tyr Cys Gln Gln Tyr Asn Arg Tyr Trp Thr
                85                  90                  95

Phe Gly Gln Gly Thr Lys Val Glu Ile Lys
            100                 105

<210> SEQ ID NO 385
<211> LENGTH: 372
<212> TYPE: DNA
<213> ORGANISM: Artificial Sequence
<220> FEATURE:
<223> OTHER INFORMATION: synthetic

<400> SEQUENCE: 385
gacgtgcaac tgttggagtc tgggggagac ttggtacagc ctggggggtc cctgagactc      60
tcctgtgaag cctctggatt cacctttaga aactatgtca tgatctgggt ccgccaggct     120
ccagggaagg ggctggagtg ggtctcaggt attagtaata gtggtggtac tacacactac     180
```

```
acagactccg tgaagggccg gttcaccatt tccagagaca attccaaaaa cacgctgtat    240
ctgcaaatta acagtctgcg agccgaggat acggccgtct attactgtgc gaagggctac    300
ttagacacat ctctgattga ggggaactgg ttcgacccct ggggccaggg aaccctggtc    360
accgtctcct ca                                                       372
```

<210> SEQ ID NO 386
<211> LENGTH: 124
<212> TYPE: PRT
<213> ORGANISM: Artificial Sequence
<220> FEATURE:
<223> OTHER INFORMATION: synthetic

<400> SEQUENCE: 386

```
Asp Val Gln Leu Leu Glu Ser Gly Gly Asp Leu Val Gln Pro Gly Gly
  1               5                  10                  15

Ser Leu Arg Leu Ser Cys Glu Ala Ser Gly Phe Thr Phe Arg Asn Tyr
             20                  25                  30

Val Met Ile Trp Val Arg Gln Ala Pro Gly Lys Gly Leu Glu Trp Val
         35                  40                  45

Ser Gly Ile Ser Asn Ser Gly Gly Thr Thr His Tyr Thr Asp Ser Val
     50                  55                  60

Lys Gly Arg Phe Thr Ile Ser Arg Asp Asn Ser Lys Asn Thr Leu Tyr
 65                  70                  75                  80

Leu Gln Ile Asn Ser Leu Arg Ala Glu Asp Thr Ala Val Tyr Tyr Cys
                 85                  90                  95

Ala Lys Gly Tyr Leu Asp Thr Ser Leu Ile Glu Gly Asn Trp Phe Asp
            100                 105                 110

Pro Trp Gly Gln Gly Thr Leu Val Thr Val Ser Ser
        115                 120
```

<210> SEQ ID NO 387
<211> LENGTH: 24
<212> TYPE: DNA
<213> ORGANISM: Artificial Sequence
<220> FEATURE:
<223> OTHER INFORMATION: synthetic

<400> SEQUENCE: 387

```
ggattcacct ttagaaacta tgtc                                           24
```

<210> SEQ ID NO 388
<211> LENGTH: 8
<212> TYPE: PRT
<213> ORGANISM: Artificial Sequence
<220> FEATURE:
<223> OTHER INFORMATION: synthetic

<400> SEQUENCE: 388

```
Gly Phe Thr Phe Arg Asn Tyr Val
  1               5
```

<210> SEQ ID NO 389
<211> LENGTH: 24
<212> TYPE: DNA
<213> ORGANISM: Artificial Sequence
<220> FEATURE:
<223> OTHER INFORMATION: synthetic

<400> SEQUENCE: 389

```
attagtaata gtggtggtac taca                                           24
```

<210> SEQ ID NO 390
<211> LENGTH: 8
<212> TYPE: PRT
<213> ORGANISM: Artificial Sequence
<220> FEATURE:
<223> OTHER INFORMATION: synthetic

<400> SEQUENCE: 390

Ile Ser Asn Ser Gly Gly Thr Thr
1               5

<210> SEQ ID NO 391
<211> LENGTH: 51
<212> TYPE: DNA
<213> ORGANISM: Artificial Sequence
<220> FEATURE:
<223> OTHER INFORMATION: synthetic

<400> SEQUENCE: 391
gcgaagggct acttagacac atctctgatt gagggaact ggttcgaccc c         51

<210> SEQ ID NO 392
<211> LENGTH: 17
<212> TYPE: PRT
<213> ORGANISM: Artificial Sequence
<220> FEATURE:
<223> OTHER INFORMATION: synthetic

<400> SEQUENCE: 392

Ala Lys Gly Tyr Leu Asp Thr Ser Leu Ile Glu Gly Asn Trp Phe Asp
1               5                   10                  15

Pro

<210> SEQ ID NO 393
<211> LENGTH: 336
<212> TYPE: DNA
<213> ORGANISM: Artificial Sequence
<220> FEATURE:
<223> OTHER INFORMATION: synthetic

<400> SEQUENCE: 393
aatattgtga tgactcagtc tccactctcc ctgcccgtca cccctggaga gccggcctcc    60
atctcctgca ggtctagtca gagcctccta catagtaatg gattcaacta tttgaattgg   120
ttcctgcaga agccagggca gtctccacag ctcctgatct atttgggttc taatcgggcc   180
tccggggtcc ctgacaagtt cagtggcagt ggatcaggca cagattttac actgaacatc   240
aacagagtgg aggctgagga tgttggaatt tatttctgca tgcagactct acaaactccc   300
ctcactttcg gcggagggac caaggtggag atcaaa                             336

<210> SEQ ID NO 394
<211> LENGTH: 112
<212> TYPE: PRT
<213> ORGANISM: Artificial Sequence
<220> FEATURE:
<223> OTHER INFORMATION: synthetic

<400> SEQUENCE: 394

Asn Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Phe Asn Tyr Leu Asn Trp Phe Leu Gln Lys Pro Gly Gln Ser

```
             35                  40                  45
Pro Gln Leu Leu Ile Tyr Leu Gly Ser Asn Arg Ala Ser Gly Val Pro
         50                  55                  60

Asp Lys Phe Ser Gly Ser Gly Ser Gly Thr Asp Phe Thr Leu Asn Ile
 65                  70                  75                  80

Asn Arg Val Glu Ala Glu Asp Val Gly Ile Tyr Phe Cys Met Gln Thr
                 85                  90                  95

Leu Gln Thr Pro Leu Thr Phe Gly Gly Gly Thr Lys Val Glu Ile Lys
            100                 105                 110
```

<210> SEQ ID NO 395
<211> LENGTH: 33
<212> TYPE: DNA
<213> ORGANISM: Artificial Sequence
<220> FEATURE:
<223> OTHER INFORMATION: synthetic

<400> SEQUENCE: 395
cagagcctcc tacatagtaa tggattcaac tat                              33

<210> SEQ ID NO 396
<211> LENGTH: 11
<212> TYPE: PRT
<213> ORGANISM: Artificial Sequence
<220> FEATURE:
<223> OTHER INFORMATION: synthetic

<400> SEQUENCE: 396

```
Gln Ser Leu Leu His Ser Asn Gly Phe Asn Tyr
  1               5                  10
```

<210> SEQ ID NO 397
<211> LENGTH: 9
<212> TYPE: DNA
<213> ORGANISM: Artificial Sequence
<220> FEATURE:
<223> OTHER INFORMATION: synthetic

<400> SEQUENCE: 397 ttgggttct                                                          9

<210> SEQ ID NO 398
<211> LENGTH: 3
<212> TYPE: PRT
<213> ORGANISM: Artificial Sequence
<220> FEATURE:
<223> OTHER INFORMATION: synthetic

<400> SEQUENCE: 398

```
Leu Gly Ser
  1
```

<210> SEQ ID NO 399
<211> LENGTH: 27
<212> TYPE: DNA
<213> ORGANISM: Artificial Sequence
<220> FEATURE:
<223> OTHER INFORMATION: synthetic

<400> SEQUENCE: 399
atgcagactc tacaaactcc cctcact                                     27

<210> SEQ ID NO 400
<211> LENGTH: 9

<212> TYPE: PRT
<213> ORGANISM: Artificial Sequence
<220> FEATURE:
<223> OTHER INFORMATION: synthetic

<400> SEQUENCE: 400

Met Gln Thr Leu Gln Thr Pro Leu Thr
1               5

<210> SEQ ID NO 401
<211> LENGTH: 372
<212> TYPE: DNA
<213> ORGANISM: Artificial Sequence
<220> FEATURE:
<223> OTHER INFORMATION: synthetic

<400> SEQUENCE: 401
gaggtgcagc tgttggagtc tgggggagac ttggtacagc ctgggggtc cctgagactc      60 tcctgtgaag cctctggatt cacctttaga aactatgtca tgatctgggt ccgccaggct    120
ccagggaagg ggctggagtg ggtctcaggt attagtaata gtggtggtac tacacactac    180
acagactccg tgaagggccg gttcaccatt tccagagaca attccaaaaa cacgctgtat    240
ctgcaaatta acagtctgcg agccgaggat acggccgtct attactgtgc gaagggctac    300
ttagacacat ctctgattga ggggaactgg ttcgacccct ggggccaggg aaccctggtc    360
accgtctcct ca                                                        372

<210> SEQ ID NO 402
<211> LENGTH: 124
<212> TYPE: PRT
<213> ORGANISM: Artificial Sequence
<220> FEATURE:
<223> OTHER INFORMATION: synthetic

<400> SEQUENCE: 402

Glu Val Gln Leu Leu Glu Ser Gly Gly Asp Leu Val Gln Pro Gly Gly
1               5                   10                  15

Ser Leu Arg Leu Ser Cys Glu Ala Ser Gly Phe Thr Phe Arg Asn Tyr
            20                  25                  30

Val Met Ile Trp Val Arg Gln Ala Pro Gly Lys Gly Leu Glu Trp Val
        35                  40                  45

Ser Gly Ile Ser Asn Ser Gly Gly Thr Thr His Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Ile Asn Ser Leu Arg Ala Glu Asp Thr Ala Val Tyr Tyr Cys
                85                  90                  95

Ala Lys Gly Tyr Leu Asp Thr Ser Leu Ile Glu Gly Asn Trp Phe Asp
            100                 105                 110

Pro Trp Gly Gln Gly Thr Leu Val Thr Val Ser Ser
        115                 120

<210> SEQ ID NO 403
<211> LENGTH: 336
<212> TYPE: DNA
<213> ORGANISM: Artificial Sequence
<220> FEATURE:
<223> OTHER INFORMATION: synthetic

<400> SEQUENCE: 403
gatattgtga tgactcagtc tccactctcc ctgcccgtca cccctggaga gccggcctcc     60

```
atctcctgca ggtctagtca gagcctccta catagtaatg gattcaacta tttgaattgg    120
ttcctgcaga agccagggca gtctccacag ctcctgatct atttgggttc taatcgggcc    180
tccggggtcc ctgacaagtt cagtggcagt ggatcaggca cagattttac actgaacatc    240
aacagagtgg aggctgagga tgttggaatt tatttctgca tgcagactct acaaactccc    300
ctcactttcg gcggagggac caaggtggag atcaaa                              336
```

<210> SEQ ID NO 404
<211> LENGTH: 112
<212> TYPE: PRT
<213> ORGANISM: Artificial Sequence
<220> FEATURE:
<223> OTHER INFORMATION: synthetic

<400> SEQUENCE: 404

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Phe Asn Tyr Leu Asn Trp Phe Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Lys Phe Ser Gly Ser Gly Ser Gly Thr Asp Phe Thr Leu Asn Ile
65                  70                  75                  80

Asn Arg Val Glu Ala Glu Asp Val Gly Ile Tyr Phe Cys Met Gln Thr
                85                  90                  95

Leu Gln Thr Pro Leu Thr Phe Gly Gly Gly Thr Lys Val Glu Ile Lys
            100                 105                 110

<210> SEQ ID NO 405
<211> LENGTH: 372
<212> TYPE: DNA
<213> ORGANISM: Artificial Sequence
<220> FEATURE:
<223> OTHER INFORMATION: synthetic

<400> SEQUENCE: 405

```
gaggtgcagc tgttggagtc tgggggaggc ttggtacagc ctggggggtc cctgagactc     60
tcctgtgcag cctctggatt cacctttaga aactatgtca tgagctgggt ccgccaggct    120
ccagggaagg ggctggagtg ggtctcagct attagtaata gtggtggtac tacatactac    180
gcagactccg tgaagggccg gttcaccatc tccagagaca attccaagaa cacgctgtat    240
ctgcaaatga acagcctgag agccgaggac acggccgtat attactgtgc gaagggctac    300
ttagacacat ctctgattga ggggaactgg ttcgacccct ggggccaggg aaccctggtc    360
accgtctcct ca                                                        372
```

<210> SEQ ID NO 406
<211> LENGTH: 124
<212> TYPE: PRT
<213> ORGANISM: Artificial Sequence
<220> FEATURE:
<223> OTHER INFORMATION: synthetic

<400> SEQUENCE: 406

Glu Val Gln Leu Leu Glu Ser Gly Gly Gly Leu Val Gln Pro Gly Gly
 1               5                  10                  15

```
Ser Leu Arg Leu Ser Cys Ala Ala Ser Gly Phe Thr Phe Arg Asn Tyr
            20                  25                  30

Val Met Ser Trp Val Arg Gln Ala Pro Gly Lys Gly Leu Glu Trp Val
        35                  40                  45

Ser Ala Ile Ser Asn Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Tyr Leu Asp Thr Ser Leu Ile Glu Gly Asn Trp Phe Asp
            100                 105                 110

Pro Trp Gly Gln Gly Thr Leu Val Thr Val Ser Ser
        115                 120
```

<210> SEQ ID NO 407
<211> LENGTH: 337
<212> TYPE: DNA
<213> ORGANISM: Artificial Sequence
<220> FEATURE:
<223> OTHER INFORMATION: synthetic

<400> SEQUENCE: 407

```
gatattgtga tgactcagtc tccactctcc ctgcccgtca cccctggaga gccggcctcc      60
atctcctgca ggtctagtca gagcctccta catagtaatg gattcaacta tttggattgg     120
tacctgcaga agccagggca gtctccacag ctcctgatct atttgggttc taatcgggcc     180
tccggggtcc ctgacaggtt cagtggcagt ggatcaggca cagattttac actgaaaatc     240
agcagagtgg aggctgagga tgttggggtt tattactgca tgcagactct acaaactccc     300
ctcactttcg gcggagggac caaggtggag atcaaac                              337
```

<210> SEQ ID NO 408
<211> LENGTH: 112
<212> TYPE: PRT
<213> ORGANISM: Artificial Sequence
<220> FEATURE:
<223> OTHER INFORMATION: synthetic

<400> SEQUENCE: 408

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
            20                  25                  30

Asn Gly Phe Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys
            100                 105                 110
```

<210> SEQ ID NO 409
<211> LENGTH: 366
<212> TYPE: DNA
<213> ORGANISM: Artificial Sequence -continued
<220> FEATURE:
<223> OTHER INFORMATION: synthetic

<400> SEQUENCE: 409

```
gaggtgcagc tgttggagtc tggggggaggc ttggtacagc ctgggggggtc cctgagactc    60
tcctgtgcag cctctggatt cacctttagg aagtatgcca tgagctgggt ccgccaggct   120
ccagggaagg gctggagtg gtctcagtt attagtgtta gtggtggtaa cacatactac   180
gcagactccg tgaagggccg gttcaccatc tccagagaca attccaagaa cacgctgtat   240
ctgcaactga acagcctgag agccgaggac acggccgtat attactgtgc gaaggatcta   300
acggatattg tacttatggt gtatgtcgac tactggggcc agggaaccct ggtcaccgtc   360
tcctca                                                              366
```

<210> SEQ ID NO 410
<211> LENGTH: 122
<212> TYPE: PRT
<213> ORGANISM: Artificial Sequence
<220> FEATURE:
<223> OTHER INFORMATION: synthetic

<400> SEQUENCE: 410

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Arg Lys Tyr
            20                  25                  30
Ala Met Ser Trp Val Arg Gln Ala Pro Gly Lys Gly Leu Glu Trp Val
        35                  40                  45
Ser Val Ile Ser Val Ser Gly Gly Asn Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Leu Asn Ser Leu Arg Ala Glu Asp Thr Ala Val Tyr Tyr Cys
                85                  90                  95
Ala Lys Asp Leu Thr Asp Ile Val Leu Met Val Tyr Val Asp Tyr Trp
            100                 105                 110
Gly Gln Gly Thr Leu Val Thr Val Ser Ser
        115                 120

<210> SEQ ID NO 411
<211> LENGTH: 24
<212> TYPE: DNA
<213> ORGANISM: Artificial Sequence
<220> FEATURE:
<223> OTHER INFORMATION: synthetic

<400> SEQUENCE: 411

```
ggattcacct ttaggaagta tgcc                                           24
```

<210> SEQ ID NO 412
<211> LENGTH: 8
<212> TYPE: PRT
<213> ORGANISM: Artificial Sequence
<220> FEATURE:
<223> OTHER INFORMATION: synthetic

<400> SEQUENCE: 412

Gly Phe Thr Phe Arg Lys Tyr Ala
1               5

```
<210> SEQ ID NO 413
<211> LENGTH: 24
<212> TYPE: DNA
<213> ORGANISM: Artificial Sequence
<220> FEATURE:
<223> OTHER INFORMATION: synthetic

<400> SEQUENCE: 413
attagtgtta gtggtggtaa caca                                            24

<210> SEQ ID NO 414
<211> LENGTH: 8
<212> TYPE: PRT
<213> ORGANISM: Artificial Sequence
<220> FEATURE:
<223> OTHER INFORMATION: synthetic

<400> SEQUENCE: 414

Ile Ser Val Ser Gly Gly Asn Thr
 1               5

<210> SEQ ID NO 415
<211> LENGTH: 45
<212> TYPE: DNA
<213> ORGANISM: Artificial Sequence
<220> FEATURE:
<223> OTHER INFORMATION: synthetic

<400> SEQUENCE: 415
gcgaaggatc taacggatat tgtacttatg gtgtatgtcg actac                     45

<210> SEQ ID NO 416
<211> LENGTH: 15
<212> TYPE: PRT
<213> ORGANISM: Artificial Sequence
<220> FEATURE:
<223> OTHER INFORMATION: synthetic

<400> SEQUENCE: 416

Ala Lys Asp Leu Thr Asp Ile Val Leu Met Val Tyr Val Asp Tyr
 1               5                  10                  15

<210> SEQ ID NO 417
<211> LENGTH: 321
<212> TYPE: DNA
<213> ORGANISM: Artificial Sequence
<220> FEATURE:
<223> OTHER INFORMATION: synthetic

<400> SEQUENCE: 417
gacatccaga tgacccagtc tccatcttcc gtgtctgcat ctgtaggaga cagagtcacc     60
atcacttgtc gggcgagtca ggatattgac aggtggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcac cctgcagcct   240
gaagattttg caacttacta ttgtcaacag gctaacagtt tgccgttcac tttcggcgga   300
gggaccaagg tggagatcaa a                                             321

<210> SEQ ID NO 418
<211> LENGTH: 107
<212> TYPE: PRT
<213> ORGANISM: Artificial Sequence
<220> FEATURE:
<223> OTHER INFORMATION: synthetic
```

-continued

<400> SEQUENCE: 418

Asp Ile Gln Met Thr Gln Ser Pro Ser Val Ser Ala Ser Val Gly
1               5                   10                  15

Asp Arg Val Thr Ile Thr Cys Arg Ala Ser Gln Asp Ile Asp Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Thr Leu Gln Pro
65                  70                  75                  80

Glu Asp Phe Ala Thr Tyr Tyr Cys Gln Gln Ala Asn Ser Leu Pro Phe
                85                  90                  95

Thr Phe Gly Gly Gly Thr Lys Val Glu Ile Lys
            100                 105

<210> SEQ ID NO 419
<211> LENGTH: 18
<212> TYPE: DNA
<213> ORGANISM: Artificial Sequence
<220> FEATURE:
<223> OTHER INFORMATION: synthetic

<400> SEQUENCE: 419
caggatattg acaggtgg                                                 18

<210> SEQ ID NO 420
<211> LENGTH: 6
<212> TYPE: PRT
<213> ORGANISM: Artificial Sequence
<220> FEATURE:
<223> OTHER INFORMATION: synthetic

<400> SEQUENCE: 420

Gln Asp Ile Asp Arg Trp
1               5

<210> SEQ ID NO 421
<211> LENGTH: 9
<212> TYPE: DNA
<213> ORGANISM: Artificial Sequence
<220> FEATURE:
<223> OTHER INFORMATION: synthetic

<400> SEQUENCE: 421 gctgcatcc                                                            9

<210> SEQ ID NO 422
<211> LENGTH: 3
<212> TYPE: PRT
<213> ORGANISM: Artificial Sequence
<220> FEATURE:
<223> OTHER INFORMATION: synthetic

<400> SEQUENCE: 422

Ala Ala Ser
1

<210> SEQ ID NO 423
<211> LENGTH: 27
<212> TYPE: DNA
<213> ORGANISM: Artificial Sequence
<220> FEATURE:

<223> OTHER INFORMATION: synthetic

<400> SEQUENCE: 423
caacaggcta acagtttgcc gttcact                                            27

<210> SEQ ID NO 424
<211> LENGTH: 9
<212> TYPE: PRT
<213> ORGANISM: Artificial Sequence
<220> FEATURE:
<223> OTHER INFORMATION: synthetic

<400> SEQUENCE: 424

Gln Gln Ala Asn Ser Leu Pro Phe Thr
 1               5

<210> SEQ ID NO 425
<211> LENGTH: 366
<212> TYPE: DNA
<213> ORGANISM: Artificial Sequence
<220> FEATURE:
<223> OTHER INFORMATION: synthetic

<400> SEQUENCE: 425
gaggtgcagc tgttggagtc tgggggaggc ttggtacagc ctgggggtc cctgagactc         60 tcctgtgcag cctctggatt cacctttagg aagtatgcca tgagctgggt ccgccaggct       120
ccagggaagg ggctggagtg ggtctcagtt attagtgtta gtggtggtaa cacatactac       180
gcagactccg tgaagggccg gttcaccatc tccagagaca attccaagaa cacgctgtat       240
ctgcaactga acagcctgag agccgaggac acggccgtat attactgtgc gaaggatcta       300
acggatattg tacttatggt gtatgtcgac tactggggcc agggaaccct ggtcaccgtc       360
tcctca                                                                 366

<210> SEQ ID NO 426
<211> LENGTH: 122
<212> TYPE: PRT
<213> ORGANISM: Artificial Sequence
<220> FEATURE:
<223> OTHER INFORMATION: synthetic

<400> SEQUENCE: 426

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Lys Tyr
             20                  25                  30

Ala Met Ser Trp Val Arg Gln Ala Pro Gly Lys Gly Leu Glu Trp Val
         35                  40                  45

Ser Val Ile Ser Val Ser Gly Gly Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Leu Asn Ser Leu Arg Ala Glu Asp Thr Ala Val Tyr Tyr Cys
                 85                  90                  95

Ala Lys Asp Leu Thr Asp Ile Val Leu Met Val Tyr Val Asp Tyr Trp
            100                 105                 110

Gly Gln Gly Thr Leu Val Thr Val Ser Ser
        115                 120

<210> SEQ ID NO 427

<211> LENGTH: 321
<212> TYPE: DNA
<213> ORGANISM: Artificial Sequence
<220> FEATURE:
<223> OTHER INFORMATION: synthetic

<400> SEQUENCE: 427

```
gacatccaga tgacccagtc tccatcttcc gtgtctgcat ctgtaggaga cagagtcacc    60
atcacttgtc gggcgagtca ggatattgac aggtggttag cctggtatca gcagaaacca   120
gggaaagccc ctaagctcct gatctatgct gcatccagtt tgcaaagtgg ggtcccatca   180
aggttcagcg gcagtggatc tgggacagat tcactctcac catcagcacc ctgcagcct   240
gaagattttg caacttacta ttgtcaacag gctaacagtt tgccgttcac tttcggcgga   300
gggaccaagg tggagatcaa a                                             321
```

<210> SEQ ID NO 428
<211> LENGTH: 107
<212> TYPE: PRT
<213> ORGANISM: Artificial Sequence
<220> FEATURE:
<223> OTHER INFORMATION: synthetic

<400> SEQUENCE: 428

```
Asp Ile Gln Met Thr Gln Ser Pro Ser Ser Val Ser Ala Ser Val Gly
 1               5                  10                  15
Asp Arg Val Thr Ile Thr Cys Arg Ala Ser Gln Asp Ile Asp Arg Trp
            20                  25                  30
Leu Ala Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Thr Leu Gln Pro
65                  70                  75                  80
Glu Asp Phe Ala Thr Tyr Tyr Cys Gln Gln Ala Asn Ser Leu Pro Phe
                85                  90                  95
Thr Phe Gly Gly Gly Thr Lys Val Glu Ile Lys
            100                 105
```

<210> SEQ ID NO 429
<211> LENGTH: 366
<212> TYPE: DNA
<213> ORGANISM: Artificial Sequence
<220> FEATURE:
<223> OTHER INFORMATION: synthetic

<400> SEQUENCE: 429

```
gaggtgcagc tgttggagtc tgggggaggc ttggtacagc ctgggggtc cctgagactc    60
tcctgtgcag cctctggatt cacctttagg aagtatgcca tgagctgggt ccgccaggct   120
ccagggaagg ggctggagtg ggtctcagct attagtgtta gtggtggtaa cacatactac   180
gcagactccg tgaagggccg gttcaccatc tccagagaca attccaagaa cacgctgtat   240
ctgcaaatga acagcctgag agccgaggac acggccgtat attactgtgc gaaggatcta   300
acggatattt acttatggt gtatgtcgac tactggggcc agggaaccct ggtcaccgtc   360
tcctca                                                              366
```

<210> SEQ ID NO 430
<211> LENGTH: 122
<212> TYPE: PRT

<213> ORGANISM: Artificial Sequence
<220> FEATURE:
<223> OTHER INFORMATION: synthetic

<400> SEQUENCE: 430

```
Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Arg Lys Tyr
             20                  25                  30
Ala Met Ser Trp Val Arg Gln Ala Pro Gly Lys Gly Leu Glu Trp Val
         35                  40                  45
Ser Ala Ile Ser Val Ser Gly Gly Asn Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Leu Thr Asp Ile Val Leu Met Val Tyr Val Asp Tyr Trp
            100                 105                 110
Gly Gln Gly Thr Leu Val Thr Val Ser Ser
        115                 120
```

<210> SEQ ID NO 431
<211> LENGTH: 322
<212> TYPE: DNA
<213> ORGANISM: Artificial Sequence
<220> FEATURE:
<223> OTHER INFORMATION: synthetic

<400> SEQUENCE: 431

```
gacatccaga tgacccagtc tccatcttct gtgtctgcat ctgtaggaga cagagtcacc    60
atcacttgtc gggcgagtca ggatattgac aggtggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ctatcagcag cctgcagcct   240
gaagattttg caacttacta ttgtcaacag gctaacagtt tgccgttcac tttcggcgga   300
gggaccaagg tggagatcaa ac                                             322
```

<210> SEQ ID NO 432
<211> LENGTH: 107
<212> TYPE: PRT
<213> ORGANISM: Artificial Sequence
<220> FEATURE:
<223> OTHER INFORMATION: synthetic

<400> SEQUENCE: 432

```
Asp Ile Gln Met Thr Gln Ser Pro Ser Ser Val Ser Ala Ser Val Gly
  1               5                  10                  15
Asp Arg Val Thr Ile Thr Cys Arg Ala Ser Gln Asp Ile Asp Arg Trp
             20                  25                  30
Leu Ala Trp Tyr Gln Gln Lys Pro Gly Lys Ala Pro Lys Leu Leu Ile
         35                  40                  45
Tyr Ala Ala Ser Ser Leu Gln Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ala Asn Ser Leu Pro Phe
                 85                  90                  95
```

Thr Phe Gly Gly Gly Thr Lys Val Glu Ile Lys
            100                 105

<210> SEQ ID NO 433
<211> LENGTH: 363
<212> TYPE: DNA
<213> ORGANISM: Artificial Sequence
<220> FEATURE:
<223> OTHER INFORMATION: synthetic

<400> SEQUENCE: 433
caggttcaat tggtacagtc tggagttgag gtgaagaagc ctggggcctc agtgaaggtc      60
tcctgcaaga cttctggtta cacttttagc aacaatggtt tcagctgggt gcggcaggcc     120
cctggacaag gcttgagtg gctgggatgg atcagcggtt acaatggaaa cacaaactat     180
gcacagaagt tccagggcag agtcaccatg accacagaca catccacgag tacagcctac     240
atggagttga ggactctgag atctgacgac acggccgtct attactgtgc gagagatcag     300
gactacagta acttccactg gctcgacccc tggggccagg gaaccctggt caccgtcgcc     360
tca                                                                  363

<210> SEQ ID NO 434
<211> LENGTH: 121
<212> TYPE: PRT
<213> ORGANISM: Artificial Sequence
<220> FEATURE:
<223> OTHER INFORMATION: synthetic

<400> SEQUENCE: 434

Gln Val Gln Leu Val Gln Ser Gly Val Glu Val Lys Lys Pro Gly Ala
 1               5                  10                  15

Ser Val Lys Val Ser Cys Lys Thr Ser Gly Tyr Thr Phe Ser Asn Asn
            20                  25                  30

Gly Phe Ser Trp Val Arg Gln Ala Pro Gly Gln Gly Leu Glu Trp Leu
        35                  40                  45

Gly Trp Ile Ser Gly Tyr Asn Gly Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Thr Leu Arg Ser Asp Asp Thr Ala Val Tyr Tyr Cys
                85                  90                  95

Ala Arg Asp Gln Asp Tyr Ser Asn Phe His Trp Leu Asp Pro Trp Gly
            100                 105                 110

Gln Gly Thr Leu Val Thr Val Ala Ser
        115                 120

<210> SEQ ID NO 435
<211> LENGTH: 24
<212> TYPE: DNA
<213> ORGANISM: Artificial Sequence
<220> FEATURE:
<223> OTHER INFORMATION: synthetic

<400> SEQUENCE: 435
ggttacactt ttagcaacaa tggt                                            24

<210> SEQ ID NO 436
<211> LENGTH: 8
<212> TYPE: PRT
<213> ORGANISM: Artificial Sequence
<220> FEATURE:
<223> OTHER INFORMATION: synthetic

<400> SEQUENCE: 436

Gly Tyr Thr Phe Ser Asn Asn Gly
 1               5

<210> SEQ ID NO 437
<211> LENGTH: 24
<212> TYPE: DNA
<213> ORGANISM: Artificial Sequence
<220> FEATURE:
<223> OTHER INFORMATION: synthetic

<400> SEQUENCE: 437
atcagcggtt acaatggaaa caca                                              24

<210> SEQ ID NO 438
<211> LENGTH: 8
<212> TYPE: PRT
<213> ORGANISM: Artificial Sequence
<220> FEATURE:
<223> OTHER INFORMATION: synthetic

<400> SEQUENCE: 438

Ile Ser Gly Tyr Asn Gly Asn Thr
 1               5

<210> SEQ ID NO 439
<211> LENGTH: 42
<212> TYPE: DNA
<213> ORGANISM: Artificial Sequence
<220> FEATURE:
<223> OTHER INFORMATION: synthetic

<400> SEQUENCE: 439
gcgagagatc aggactacag taacttccac tggctcgacc cc                          42

<210> SEQ ID NO 440
<211> LENGTH: 14
<212> TYPE: PRT
<213> ORGANISM: Artificial Sequence
<220> FEATURE:
<223> OTHER INFORMATION: synthetic

<400> SEQUENCE: 440

Ala Arg Asp Gln Asp Tyr Ser Asn Phe His Trp Leu Asp Pro
 1               5                  10

<210> SEQ ID NO 441
<211> LENGTH: 321
<212> TYPE: DNA
<213> ORGANISM: Artificial Sequence
<220> FEATURE:
<223> OTHER INFORMATION: synthetic

<400> SEQUENCE: 441
gacatccaga tgacccagtc tccatcctcc gtgtctgcat ctgtaggaga cagagtcatt        60
atcacttgtc gggcgagtca gggtcttagt agttggctag cctggtatca gcagaaacca      120
gggacagccc ctaagctcct gatccattct gcatccagtt tgcaaactgg ggtcccatca      180
agattcagcg gcagtggatc tgggacagaa ttcgctctca ccatcaacag cctgcagcct      240
gaagattttg gaacttacta ttgtcaacag gctaacagtt tcccgctcac tttcggcggg      300
gggaccaggg tggagatcaa a                                                321

<210> SEQ ID NO 442
<211> LENGTH: 107
<212> TYPE: PRT
<213> ORGANISM: Artificial Sequence
<220> FEATURE:
<223> OTHER INFORMATION: synthetic

<400> SEQUENCE: 442

Asp Ile Gln Met Thr Gln Ser Pro Ser Ser Val Ser Ala Ser Val Gly
 1               5                  10                  15

Asp Arg Val Ile Ile Thr Cys Arg Ala Ser Gln Gly Leu Ser Ser Trp
            20                  25                  30

Leu Ala Trp Tyr Gln Gln Lys Pro Gly Thr Ala Pro Lys Leu Leu Ile
        35                  40                  45

His Ser Ala Ser Ser Leu Gln Thr Gly Val Pro Ser Arg Phe Ser Gly
    50                  55                  60

Ser Gly Ser Gly Thr Glu Phe Ala Leu Thr Ile Asn Ser Leu Gln Pro
65                  70                  75                  80

Glu Asp Phe Gly Thr Tyr Tyr Cys Gln Gln Ala Asn Ser Phe Pro Leu
                85                  90                  95

Thr Phe Gly Gly Gly Thr Arg Val Glu Ile Lys
            100                 105

<210> SEQ ID NO 443
<211> LENGTH: 18
<212> TYPE: DNA
<213> ORGANISM: Artificial Sequence
<220> FEATURE:
<223> OTHER INFORMATION: synthetic

<400> SEQUENCE: 443
cagggtctta gtagttgg                                                 18

<210> SEQ ID NO 444
<211> LENGTH: 6
<212> TYPE: PRT
<213> ORGANISM: Artificial Sequence
<220> FEATURE:
<223> OTHER INFORMATION: synthetic

<400> SEQUENCE: 444

Gln Gly Leu Ser Ser Trp
 1               5

<210> SEQ ID NO 445
<211> LENGTH: 9
<212> TYPE: DNA
<213> ORGANISM: Artificial Sequence
<220> FEATURE:
<223> OTHER INFORMATION: synthetic

<400> SEQUENCE: 445 tctgcatcc                                                            9

<210> SEQ ID NO 446
<211> LENGTH: 3
<212> TYPE: PRT
<213> ORGANISM: Artificial Sequence
<220> FEATURE:
<223> OTHER INFORMATION: synthetic

<400> SEQUENCE: 446

Ser Ala Ser
 1

<210> SEQ ID NO 447
<211> LENGTH: 27
<212> TYPE: DNA
<213> ORGANISM: Artificial Sequence
<220> FEATURE:
<223> OTHER INFORMATION: synthetic

<400> SEQUENCE: 447
caacaggcta acagtttccc gctcact                                          27

<210> SEQ ID NO 448
<211> LENGTH: 9
<212> TYPE: PRT
<213> ORGANISM: Artificial Sequence
<220> FEATURE:
<223> OTHER INFORMATION: synthetic

<400> SEQUENCE: 448

Gln Gln Ala Asn Ser Phe Pro Leu Thr
 1               5

<210> SEQ ID NO 449
<211> LENGTH: 363
<212> TYPE: DNA
<213> ORGANISM: Artificial Sequence
<220> FEATURE:
<223> OTHER INFORMATION: synthetic

<400> SEQUENCE: 449
caggttcagc tggtgcagtc tggagttgag gtgaagaagc ctggggcctc agtgaaggtc      60
tcctgcaaga cttctggtta cactttagc aacaatggtt tcagctgggt gcggcaggcc     120
cctggacaag gcttgagtg gctgggatgg atcagcggtt acaatggaaa cacaaactat     180
gcacagaagt tccagggcag agtcaccatg accacagaca catccacgag tacagcctac     240
atggagttga ggactctgag atctgacgac acggccgtct attactgtgc gagagatcag     300
gactacagta acttccactg gctcgacccc tggggccagg gaaccctggt caccgtctcc     360
tca                                                                  363

<210> SEQ ID NO 450
<211> LENGTH: 121
<212> TYPE: PRT
<213> ORGANISM: Artificial Sequence
<220> FEATURE:
<223> OTHER INFORMATION: synthetic

<400> SEQUENCE: 450

Gln Val Gln Leu Val Gln Ser Gly Val Glu Val Lys Lys Pro Gly Ala
 1               5                  10                  15

Ser Val Lys Val Ser Cys Lys Thr Ser Gly Tyr Thr Phe Ser Asn Asn
                20                  25                  30

Gly Phe Ser Trp Val Arg Gln Ala Pro Gly Gln Gly Leu Glu Trp Leu
            35                  40                  45

Gly Trp Ile Ser Gly Tyr Asn Gly Asn Thr Asn Tyr Ala Gln Lys Phe
        50                  55                  60

Gln Gly Arg Val Thr Met Thr Thr Asp Thr Ser Thr Ser Thr Ala Tyr
 65                  70                  75                  80

Met Glu Leu Arg Thr Leu Arg Ser Asp Asp Thr Ala Val Tyr Tyr Cys
                85                  90                  95

Ala Arg Asp Gln Asp Tyr Ser Asn Phe His Trp Leu Asp Pro Trp Gly
            100                 105                 110

Gln Gly Thr Leu Val Thr Val Ser Ser
        115                 120

<210> SEQ ID NO 451
<211> LENGTH: 321
<212> TYPE: DNA
<213> ORGANISM: Artificial Sequence
<220> FEATURE:
<223> OTHER INFORMATION: synthetic

<400> SEQUENCE: 451
gacatccaga tgacccagtc tccatcctcc gtgtctgcat ctgtaggaga cagagtcatt    60
atcacttgtc gggcgagtca ggtcttagt agttggctag cctggtatca gcagaaacca   120
gggacagccc ctaagctcct gatccattct gcatccagtt tgcaaactgg ggtcccatca   180
agattcagcg gcagtggatc tgggacagaa ttcgctctca ccatcaacag cctgcagcct   240
gaagattttg gaacttacta ttgtcaacag gctaacagtt tcccgctcac tttcggcggg   300
gggaccaagg tggagatcaa a                                             321

<210> SEQ ID NO 452
<211> LENGTH: 107
<212> TYPE: PRT
<213> ORGANISM: Artificial Sequence
<220> FEATURE:
<223> OTHER INFORMATION: synthetic

<400> SEQUENCE: 452

Asp Ile Gln Met Thr Gln Ser Pro Ser Ser Val Ser Ala Ser Val Gly
1               5                   10                  15

Asp Arg Val Ile Ile Thr Cys Arg Ala Ser Gln Gly Leu Ser Ser Trp
            20                  25                  30

Leu Ala Trp Tyr Gln Gln Lys Pro Gly Thr Ala Pro Lys Leu Leu Ile
        35                  40                  45

His Ser Ala Ser Ser Leu Gln Thr Gly Val Pro Ser Arg Phe Ser Gly
    50                  55                  60

Ser Gly Ser Gly Thr Glu Phe Ala Leu Thr Ile Asn Ser Leu Gln Pro
65                  70                  75                  80

Glu Asp Phe Gly Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 453
<211> LENGTH: 363
<212> TYPE: DNA
<213> ORGANISM: Artificial Sequence
<220> FEATURE:
<223> OTHER INFORMATION: synthetic

<400> SEQUENCE: 453
caggttcagc tggtgcagtc tggagctgag gtgaagaagc ctggggcctc agtgaaggtc    60
tcctgcaagg cttctggtta cactttagc aacaatggta tcagctgggt gcgacaggcc   120
cctggacaag gcttgagtg gatgggatgg atcagcggtt acaatggaaa cacaaactat   180
gcacagaagc tccagggcag agtcaccatg accacagaca catccacgag cacagcctac   240
atggagctga ggagcctgag atctgacgac acggccgtgt attactgtgc gagagatcag   300

```
gactacagta acttccactg gctcgacccc tgggccagg gaaccctggt caccgtctcc    360
tca                                                                363
```

<210> SEQ ID NO 454
<211> LENGTH: 121
<212> TYPE: PRT
<213> ORGANISM: Artificial Sequence
<220> FEATURE:
<223> OTHER INFORMATION: synthetic

<400> SEQUENCE: 454

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Asn
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gln Asp Tyr Ser Asn Phe His Trp Leu Asp Pro Trp Gly
            100                 105                 110

Gln Gly Thr Leu Val Thr Val Ser Ser
        115                 120
```

<210> SEQ ID NO 455
<211> LENGTH: 322
<212> TYPE: DNA
<213> ORGANISM: Artificial Sequence
<220> FEATURE:
<223> OTHER INFORMATION: synthetic

<400> SEQUENCE: 455

```
gacatccaga tgacccagtc tccatcttct gtgtctgcat ctgtaggaga cagagtcacc    60
atcacttgtc gggcgagtca gggtcttagt agttggttag cctggtatca gcagaaacca   120
gggaaagccc ctaagctcct gatctattct gcatccagtt tgcaaagtgg ggtcccatca   180
aggttcagcg gcagtggatc tgggacagat ttcactctca ctatcagcag cctgcagcct   240
gaagattttg caacttacta ttgtcaacag gctaacagtt tcccgctcac tttcggcgga   300
gggaccaagg tggagatcaa ac                                            322
```

<210> SEQ ID NO 456
<211> LENGTH: 107
<212> TYPE: PRT
<213> ORGANISM: Artificial Sequence
<220> FEATURE:
<223> OTHER INFORMATION: synthetic

<400> SEQUENCE: 456

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Leu Ser Ser Trp
            20                  25                  30

Leu Ala Trp Tyr Gln Gln Lys Pro Gly Lys Ala Pro Lys Leu Leu Ile
        35                  40                  45
```

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65             70                  75                  80

Glu Asp Phe Ala Thr Tyr Tyr Cys Gln Gln Ala Asn Ser Phe Pro Leu
                 85              90                  95

Thr Phe Gly Gly Gly Thr Lys Val Glu Ile Lys
            100                 105

<210> SEQ ID NO 457
<211> LENGTH: 360
<212> TYPE: DNA
<213> ORGANISM: Artificial Sequence
<220> FEATURE:
<223> OTHER INFORMATION: synthetic

<400> SEQUENCE: 457
caggtgaagt tggtggagtc tgggggaggc gtggtccagc ctggagggtc cctgagagtc      60
tcctgtgcag cgtctggatt caccttcagt agctatggca tgcactgggt ccgccaggct     120
ccaggcaagg ggctggagtg gttggcaatt atatggtatg atggagataa taaatactat     180
tcagactccg tgaagggccg attcaccatc tccagagaca attccaagaa cacgctgtat     240
ctgcaaatga acagcctgag agccgaggac acggctgagt attactgtgt gagagatgcg     300
agtatagcat ctcgtttctt ggactattgg ggccagggaa ccttggtcac cgtctcctca     360

<210> SEQ ID NO 458
<211> LENGTH: 120
<212> TYPE: PRT
<213> ORGANISM: Artificial Sequence
<220> FEATURE:
<223> OTHER INFORMATION: synthetic

<400> SEQUENCE: 458

Gln Val Lys Leu Val Glu Ser Gly Gly Gly Val Gln Pro Gly Arg
 1               5                  10                  15

Ser Leu Arg Val Ser Cys Ala Ala Ser Gly Phe Thr Phe Ser Ser Tyr
            20                  25                  30

Gly Met His Trp Val Arg Gln Ala Pro Gly Lys Gly Leu Glu Trp Leu
        35                  40                  45

Ala Ile Ile Trp Tyr Asp Gly Asp Asn Lys Tyr Tyr Ser Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Glu Tyr Tyr Cys
                 85                  90                  95

Val Arg Asp Ala Ser Ile Ala Ser Arg Phe Leu Asp Tyr Trp Gly Gln
            100                 105                 110

Gly Thr Leu Val Thr Val Ser Ser
        115                 120

<210> SEQ ID NO 459
<211> LENGTH: 24
<212> TYPE: DNA
<213> ORGANISM: Artificial Sequence
<220> FEATURE:
<223> OTHER INFORMATION: synthetic

<400> SEQUENCE: 459

```
ggattcacct tcagtagcta tggc                                              24
```

<210> SEQ ID NO 460
<211> LENGTH: 8
<212> TYPE: PRT
<213> ORGANISM: Artificial Sequence
<220> FEATURE:
<223> OTHER INFORMATION: synthetic

<400> SEQUENCE: 460

Gly Phe Thr Phe Ser Ser Tyr Gly
 1               5

<210> SEQ ID NO 461
<211> LENGTH: 24
<212> TYPE: DNA
<213> ORGANISM: Artificial Sequence
<220> FEATURE:
<223> OTHER INFORMATION: synthetic

<400> SEQUENCE: 461

```
atatggtatg atggagataa taaa                                              24
```

<210> SEQ ID NO 462
<211> LENGTH: 8
<212> TYPE: PRT
<213> ORGANISM: Artificial Sequence
<220> FEATURE:
<223> OTHER INFORMATION: synthetic

<400> SEQUENCE: 462

Ile Trp Tyr Asp Gly Asp Asn Lys
 1               5

<210> SEQ ID NO 463
<211> LENGTH: 39
<212> TYPE: DNA
<213> ORGANISM: Artificial Sequence
<220> FEATURE:
<223> OTHER INFORMATION: synthetic

<400> SEQUENCE: 463

```
gtgagagatg cgagtatagc atctcgtttc ttggactat                              39
```

<210> SEQ ID NO 464
<211> LENGTH: 13
<212> TYPE: PRT
<213> ORGANISM: Artificial Sequence
<220> FEATURE:
<223> OTHER INFORMATION: synthetic

<400> SEQUENCE: 464

Val Arg Asp Ala Ser Ile Ala Ser Arg Phe Leu Asp Tyr
 1               5                  10

<210> SEQ ID NO 465
<211> LENGTH: 321
<212> TYPE: DNA
<213> ORGANISM: Artificial Sequence
<220> FEATURE:
<223> OTHER INFORMATION: synthetic

<400> SEQUENCE: 465

```
gacatccaga tgacccagtc tccatcctca ctgtctgcat ctataggaga cagagtcacc       60
atcacttgtc gggcgactca ggacattaac aattatttag cctggtttca gcagaaacca      120
```

```
gggaaagccc ctaagtccct gatctatgct acatccaatt tgcaaagtgg ggtcccatca    180
aagttcagcg gcagtggatc tgggacagat tacactctca ccatcagcag cctgcagcct    240
gaagattttt caacttatta ctgtcaacag tatcatagtt acccgctcac tttcggcgga    300
gggaccaagg tggagatcaa a                                              321
```

<210> SEQ ID NO 466
<211> LENGTH: 107
<212> TYPE: PRT
<213> ORGANISM: Artificial Sequence
<220> FEATURE:
<223> OTHER INFORMATION: synthetic

<400> SEQUENCE: 466

```
Asp Ile Gln Met Thr Gln Ser Pro Ser Ser Leu Ser Ala Ser Ile Gly
 1               5                  10                  15

Asp Arg Val Thr Ile Thr Cys Arg Ala Thr Gln Asp Ile Asn Asn Tyr
             20                  25                  30

Leu Ala Trp Phe Gln Gln Lys Pro Gly Lys Ala Pro Lys Ser Leu Ile
         35                  40                  45

Tyr Ala Thr Ser Asn Leu Gln Ser Gly Val Pro Ser Lys Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ser Thr Tyr Tyr Cys Gln Gln Tyr His Ser Tyr Pro Leu
                 85                  90                  95

Thr Phe Gly Gly Gly Thr Lys Val Glu Ile Lys
            100                 105
```

<210> SEQ ID NO 467
<211> LENGTH: 18
<212> TYPE: DNA
<213> ORGANISM: Artificial Sequence
<220> FEATURE:
<223> OTHER INFORMATION: synthetic

<400> SEQUENCE: 467

```
caggacatta acaattat                                                   18
```

<210> SEQ ID NO 468
<211> LENGTH: 6
<212> TYPE: PRT
<213> ORGANISM: Artificial Sequence
<220> FEATURE:
<223> OTHER INFORMATION: synthetic

<400> SEQUENCE: 468

```
Gln Asp Ile Asn Asn Tyr
 1               5
```

<210> SEQ ID NO 469
<211> LENGTH: 9
<212> TYPE: DNA
<213> ORGANISM: Artificial Sequence
<220> FEATURE:
<223> OTHER INFORMATION: synthetic

<400> SEQUENCE: 469

```
gctacatcc                                                              9
```

<210> SEQ ID NO 470
<211> LENGTH: 3

<212> TYPE: PRT
<213> ORGANISM: Artificial Sequence
<220> FEATURE:
<223> OTHER INFORMATION: synthetic

<400> SEQUENCE: 470

Ala Thr Ser
 1

<210> SEQ ID NO 471
<211> LENGTH: 27
<212> TYPE: DNA
<213> ORGANISM: Artificial Sequence
<220> FEATURE:
<223> OTHER INFORMATION: synthetic

<400> SEQUENCE: 471
caacagtatc atagttaccc gctcact                                          27

<210> SEQ ID NO 472
<211> LENGTH: 9
<212> TYPE: PRT
<213> ORGANISM: Artificial Sequence
<220> FEATURE:
<223> OTHER INFORMATION: synthetic

<400> SEQUENCE: 472

Gln Gln Tyr His Ser Tyr Pro Leu Thr
 1               5

<210> SEQ ID NO 473
<211> LENGTH: 360
<212> TYPE: DNA
<213> ORGANISM: Artificial Sequence
<220> FEATURE:
<223> OTHER INFORMATION: synthetic

<400> SEQUENCE: 473
caggtgcagc tggtggagtc tgggggaggc gtggtccagc ctggggaggtc cctgagagtc      60 tcctgtgcag cgtctggatt caccttcagt agctatggca tgcactgggt ccgccaggct     120
ccaggcaagg ggctggagtg gttggcaatt atatggtatg atggagataa taaatactat     180
tcagactccg tgaagggccg attcaccatc tccagagaca attccaagaa cacgctgtat     240
ctgcaaatga acagcctgag agccgaggac acggctgagt attactgtgt gagagatgcg     300
agtatagcat ctcgtttctt ggactattgg ggccagggaa ccctggtcac cgtctcctca     360

<210> SEQ ID NO 474
<211> LENGTH: 120
<212> TYPE: PRT
<213> ORGANISM: Artificial Sequence
<220> FEATURE:
<223> OTHER INFORMATION: synthetic

<400> SEQUENCE: 474

Gln Val Gln Leu Val Glu Ser Gly Gly Gly Val Val Gln Pro Gly Arg
 1               5                  10                  15

Ser Leu Arg Val Ser Cys Ala Ala Ser Gly Phe Thr Phe Ser Ser Tyr
             20                  25                  30

Gly Met His Trp Val Arg Gln Ala Pro Gly Lys Gly Leu Glu Trp Leu
         35                  40                  45

Ala Ile Ile Trp Tyr Asp Gly Asp Asn Lys Tyr Tyr Ser Asp Ser Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Glu Tyr Tyr Cys
                85                  90                  95

Val Arg Asp Ala Ser Ile Ala Ser Arg Phe Leu Asp Tyr Trp Gly Gln
            100                 105                 110

Gly Thr Leu Val Thr Val Ser Ser
            115                 120

<210> SEQ ID NO 475
<211> LENGTH: 321
<212> TYPE: DNA
<213> ORGANISM: Artificial Sequence
<220> FEATURE:
<223> OTHER INFORMATION: synthetic

<400> SEQUENCE: 475
gacatccaga tgacccagtc tccatcctca ctgtctgcat ctataggaga cagagtcacc     60
atcacttgtc gggcgactca ggacattaac aattatttag cctggtttca gcagaaacca    120
gggaaagccc ctaagtccct gatctatgct acatccaatt tgcaaagtgg ggtcccatca    180
aagttcagcg gcagtggatc tgggacagat tacactctca ccatcagcag cctgcagcct    240
gaagattttt caacttatta ctgtcaacag tatcatagtt acccgctcac tttcggcgga    300
gggaccaagg tggagatcaa a                                              321

<210> SEQ ID NO 476
<211> LENGTH: 107
<212> TYPE: PRT
<213> ORGANISM: Artificial Sequence
<220> FEATURE:
<223> OTHER INFORMATION: synthetic

<400> SEQUENCE: 476

Asp Ile Gln Met Thr Gln Ser Pro Ser Ser Leu Ser Ala Ser Ile Gly
 1               5                  10                  15

Asp Arg Val Thr Ile Thr Cys Arg Ala Thr Gln Asp Ile Asn Asn Tyr
             20                  25                  30

Leu Ala Trp Phe Gln Gln Lys Pro Gly Lys Ala Pro Lys Ser Leu Ile
         35                  40                  45

Tyr Ala Thr Ser Asn Leu Gln Ser Gly Val Pro Ser Lys Phe Ser Gly
     50                  55                  60

Ser Gly Ser Gly Thr Asp Tyr Thr Leu Thr Ile Ser Ser Leu Gln Pro
65                  70                  75                  80

Glu Asp Phe Ser Thr Tyr Tyr Cys Gln Gln Tyr His Ser Tyr Pro Leu
                85                  90                  95

Thr Phe Gly Gly Gly Thr Lys Val Glu Ile Lys
            100                 105

<210> SEQ ID NO 477
<211> LENGTH: 360
<212> TYPE: DNA
<213> ORGANISM: Artificial Sequence
<220> FEATURE:
<223> OTHER INFORMATION: synthetic

<400> SEQUENCE: 477
caggtgcagc tggtggagtc tgggggaggc gtggtccagc ctgggaggtc cctgagactc     60
tcctgtgcag cgtctggatt caccttcagt agctatggca tgcactgggt ccgccaggct    120

```
ccaggcaagg ggctggagtg ggtggcagtt atatggtatg atggagataa taaatactat    180
gcagactccg tgaagggccg attcaccatc tccagagaca actccaagaa cacgctgtat    240
ctgcaaatga acagcctgag agccgaggac acggctgtgt attactgtgt gagagatgcg    300
agtatagcat ctcgtttctt ggactattgg ggccagggaa ccctggtcac cgtctcctca    360
```

<210> SEQ ID NO 478
<211> LENGTH: 120
<212> TYPE: PRT
<213> ORGANISM: Artificial Sequence
<220> FEATURE:
<223> OTHER INFORMATION: synthetic

<400> SEQUENCE: 478

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Asp Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Ala Ser Ile Ala Ser Arg Phe Leu Asp Tyr Trp Gly Gln
            100                 105                 110

Gly Thr Leu Val Thr Val Ser Ser
        115                 120
```

<210> SEQ ID NO 479
<211> LENGTH: 322
<212> TYPE: DNA
<213> ORGANISM: Artificial Sequence
<220> FEATURE:
<223> OTHER INFORMATION: synthetic

<400> SEQUENCE: 479

```
gacatccaga tgacccagtc tccatcctca ctgtctgcat ctgtaggaga cagagtcacc     60
atcacttgtc gggcgagtca ggacattaac aattatttag cctggtttca gcagaaacca    120
gggaaagccc ctaagtccct gatctatgct acatccagtt tgcaaagtgg ggtcccatca    180
aggttcagcg gcagtggatc tgggacagat ttcactctca ccatcagcag cctgcagcct    240
gaagattttg caacttatta ctgccaacag tatcatagtt acccgctcac tttcggcgga    300
gggaccaagg tggagatcaa ac                                             322
```

<210> SEQ ID NO 480
<211> LENGTH: 107
<212> TYPE: PRT
<213> ORGANISM: Artificial Sequence
<220> FEATURE:
<223> OTHER INFORMATION: synthetic

<400> SEQUENCE: 480

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Asn Asn Tyr
            20                  25                  30
```

```
Leu Ala Trp Phe Gln Gln Lys Pro Gly Lys Ala Pro Lys Ser Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Ser Tyr Pro Leu
                85                  90                  95

Thr Phe Gly Gly Gly Thr Lys Val Glu Ile Lys
            100                 105
```

<210> SEQ ID NO 481
<211> LENGTH: 363
<212> TYPE: DNA
<213> ORGANISM: Artificial Sequence
<220> FEATURE:
<223> OTHER INFORMATION: synthetic

<400> SEQUENCE: 481

```
gaggtgcaac tgttggagtc tgggggagac ttggtacagc ctggggggtc cctgagactc      60
tcctgtgcag cctctgaatt cacctttagc ggctatgcca tgagctgggt ccgccaggct     120
ccagggaagg ggctggagtg ggtctcagtg attcgtggta gtggtgataa cacatactac     180
gcagactccg tgaagggccg gttcagcatc tccagagaca attccaagaa cactctgtat     240
ctgcaaatga acagcctgag agccgaggac acggccgtat attactgtgc gagagtgtat     300
tacgattttt gggaaggggc ttttgatatc tggggccaag ggacaatggt caccgtctct     360
tca                                                                   363
```

<210> SEQ ID NO 482
<211> LENGTH: 121
<212> TYPE: PRT
<213> ORGANISM: Artificial Sequence
<220> FEATURE:
<223> OTHER INFORMATION: synthetic

<400> SEQUENCE: 482

```
Glu Val Gln Leu Leu Glu Ser Gly Gly Asp Leu Val Gln Pro Gly Gly
1               5                   10                  15

Ser Leu Arg Leu Ser Cys Ala Ala Ser Glu Phe Thr Phe Ser Gly Tyr
            20                  25                  30

Ala Met Ser Trp Val Arg Gln Ala Pro Gly Lys Gly Leu Glu Trp Val
        35                  40                  45

Ser Val Ile Arg Gly Ser Gly Asp Asn Thr Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Tyr Asp Phe Trp Glu Gly Ala Phe Asp Ile Trp Gly
            100                 105                 110

Gln Gly Thr Met Val Thr Val Ser Ser
        115                 120
```

<210> SEQ ID NO 483
<211> LENGTH: 24
<212> TYPE: DNA
<213> ORGANISM: Artificial Sequence

```
<220> FEATURE:
<223> OTHER INFORMATION: synthetic

<400> SEQUENCE: 483
gaattcacct ttagcggcta tgcc                                      24

<210> SEQ ID NO 484
<211> LENGTH: 8
<212> TYPE: PRT
<213> ORGANISM: Artificial Sequence
<220> FEATURE:
<223> OTHER INFORMATION: synthetic

<400> SEQUENCE: 484

Glu Phe Thr Phe Ser Gly Tyr Ala
1               5

<210> SEQ ID NO 485
<211> LENGTH: 24
<212> TYPE: DNA
<213> ORGANISM: Artificial Sequence
<220> FEATURE:
<223> OTHER INFORMATION: synthetic

<400> SEQUENCE: 485
attcgtggta gtggtgataa caca                                      24

<210> SEQ ID NO 486
<211> LENGTH: 8
<212> TYPE: PRT
<213> ORGANISM: Artificial Sequence
<220> FEATURE:
<223> OTHER INFORMATION: synthetic

<400> SEQUENCE: 486

Ile Arg Gly Ser Gly Asp Asn Thr
1               5

<210> SEQ ID NO 487
<211> LENGTH: 42
<212> TYPE: DNA
<213> ORGANISM: Artificial Sequence
<220> FEATURE:
<223> OTHER INFORMATION: synthetic

<400> SEQUENCE: 487
gcgagagtgt attacgattt ttgggaaggg gcttttgata tc                  42

<210> SEQ ID NO 488
<211> LENGTH: 14
<212> TYPE: PRT
<213> ORGANISM: Artificial Sequence
<220> FEATURE:
<223> OTHER INFORMATION: synthetic

<400> SEQUENCE: 488

Ala Arg Val Tyr Tyr Asp Phe Trp Glu Gly Ala Phe Asp Ile
1               5                   10

<210> SEQ ID NO 489
<211> LENGTH: 321
<212> TYPE: DNA
<213> ORGANISM: Artificial Sequence
<220> FEATURE:
<223> OTHER INFORMATION: synthetic

<400> SEQUENCE: 489
```

```
gacatccaga tgacccagtc tccatcttcc gtgtctgcat ctgtaggaga cagagtcacc    60
atcacttgtc gggcgagtca gggtattagc acctggttag cctggtatca gcagaaacca   120
gggaaagccc ctaagctcct gatctatgct gcaaccagtt tgcaaagtgg ggtcccatca   180
aggttcagcg gcagtggatc tgggacagat ttcactctcg ccatcagcgg cctgcagcct   240
gaagattttg caacttacta ttgtcaacag gctaacaatt tcccgtacac ttttggccag   300
gggaccaagc tggagatcaa a                                             321
```

<210> SEQ ID NO 490
<211> LENGTH: 107
<212> TYPE: PRT
<213> ORGANISM: Artificial Sequence
<220> FEATURE:
<223> OTHER INFORMATION: synthetic

<400> SEQUENCE: 490

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Thr Trp
            20                  25                  30

Leu Ala Trp Tyr Gln Gln Lys Pro Gly Lys Ala Pro Lys Leu Leu Ile
        35                  40                  45

Tyr Ala Ala Thr Ser Leu Gln Ser Gly Val Pro Ser Arg Phe Ser Gly
    50                  55                  60

Ser Gly Ser Gly Thr Asp Phe Thr Leu Ala Ile Ser Gly Leu Gln Pro
65                  70                  75                  80

Glu Asp Phe Ala Thr Tyr Tyr Cys Gln Gln Ala Asn Asn Phe Pro Tyr
                85                  90                  95

Thr Phe Gly Gln Gly Thr Lys Leu Glu Ile Lys
            100                 105
```

<210> SEQ ID NO 491
<211> LENGTH: 18
<212> TYPE: DNA
<213> ORGANISM: Artificial Sequence
<220> FEATURE:
<223> OTHER INFORMATION: synthetic

<400> SEQUENCE: 491

```
cagggtatta gcacctgg                                                  18
```

<210> SEQ ID NO 492
<211> LENGTH: 6
<212> TYPE: PRT
<213> ORGANISM: Artificial Sequence
<220> FEATURE:
<223> OTHER INFORMATION: synthetic

<400> SEQUENCE: 492

```
Gln Gly Ile Ser Thr Trp
 1               5
```

<210> SEQ ID NO 493
<211> LENGTH: 9
<212> TYPE: DNA
<213> ORGANISM: Artificial Sequence
<220> FEATURE:
<223> OTHER INFORMATION: synthetic

<400> SEQUENCE: 493

-continued gctgcaacc                                                              9

<210> SEQ ID NO 494
<211> LENGTH: 3
<212> TYPE: PRT
<213> ORGANISM: Artificial Sequence
<220> FEATURE:
<223> OTHER INFORMATION: synthetic

<400> SEQUENCE: 494

Ala Ala Thr
 1

<210> SEQ ID NO 495
<211> LENGTH: 27
<212> TYPE: DNA
<213> ORGANISM: Artificial Sequence
<220> FEATURE:
<223> OTHER INFORMATION: synthetic

<400> SEQUENCE: 495
caacaggcta acaatttccc gtacact                                         27

<210> SEQ ID NO 496
<211> LENGTH: 9
<212> TYPE: PRT
<213> ORGANISM: Artificial Sequence
<220> FEATURE:
<223> OTHER INFORMATION: synthetic

<400> SEQUENCE: 496

Gln Gln Ala Asn Asn Phe Pro Tyr Thr
 1               5

<210> SEQ ID NO 497
<211> LENGTH: 363
<212> TYPE: DNA
<213> ORGANISM: Artificial Sequence
<220> FEATURE:
<223> OTHER INFORMATION: synthetic

<400> SEQUENCE: 497
gaggtgcagc tgttggagtc tgggggagac ttggtacagc ctgggggtc cctgagactc        60 tcctgtgcag cctctgaatt caccttagc ggctatgcca tgagctgggt ccgccaggct       120
ccagggaagg ggctggagtg ggtctcagtg attcgtggta gtggtgataa cacatactac      180
gcagactccg tgaagggccg gttcagcatc tccagagaca attccaagaa cacactgtat      240
ctgcaaatga acagcctgag agccgaggac acggccgtat attactgtgc gagagtgtat      300
tacgattttt gggaaggggc ttttgatatc tggggccaag ggacaatggt caccgtctct      360
tca                                                                   363

<210> SEQ ID NO 498
<211> LENGTH: 121
<212> TYPE: PRT
<213> ORGANISM: Artificial Sequence
<220> FEATURE:
<223> OTHER INFORMATION: synthetic

<400> SEQUENCE: 498

Glu Val Gln Leu Leu Glu Ser Gly Gly Asp Leu Val Gln Pro Gly Gly
 1               5                  10                  15

Ser Leu Arg Leu Ser Cys Ala Ala Ser Glu Phe Thr Phe Ser Gly Tyr
            20                  25                  30

Ala Met Ser Trp Val Arg Gln Ala Pro Gly Lys Gly Leu Glu Trp Val
         35                  40                  45

Ser Val Ile Arg Gly Ser Gly Asp Asn Thr Tyr Tyr Ala Asp Ser Val
 50                  55                  60

Lys Gly Arg Phe Ser Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Tyr Tyr Asp Phe Trp Glu Gly Ala Phe Asp Ile Trp Gly
             100                 105                 110

Gln Gly Thr Met Val Thr Val Ser Ser
         115                 120

<210> SEQ ID NO 499
<211> LENGTH: 321
<212> TYPE: DNA
<213> ORGANISM: Artificial Sequence
<220> FEATURE:
<223> OTHER INFORMATION: synthetic

<400> SEQUENCE: 499
gacatccaga tgacccagtc tccatcttcc gtgtctgcat ctgtaggaga cagagtcacc      60
atcacttgtc gggcgagtca gggtattagc acctggttag cctggtatca gcagaaacca     120
gggaaagccc ctaagctcct gatctatgct gcaaccagtt tgcaaagtgg ggtcccatca     180
aggttcagcg gcagtggatc tgggacagat ttcactctcg ccatcagcgg cctgcagcct     240
gaagattttg caacttacta ttgtcaacag gctaacaatt tcccgtacac ttttggccag     300
gggaccaagc tggagatcaa a                                               321

<210> SEQ ID NO 500
<211> LENGTH: 107
<212> TYPE: PRT
<213> ORGANISM: Artificial Sequence
<220> FEATURE:
<223> OTHER INFORMATION: synthetic

<400> SEQUENCE: 500

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Thr Trp
             20                  25                  30

Leu Ala Trp Tyr Gln Gln Lys Pro Gly Lys Ala Pro Lys Leu Leu Ile
         35                  40                  45

Tyr Ala Ala Thr Ser Leu Gln Ser Gly Val Pro Ser Arg Phe Ser Gly
 50                  55                  60

Ser Gly Ser Gly Thr Asp Phe Thr Leu Ala Ile Ser Gly Leu Gln Pro
 65                  70                  75                  80

Glu Asp Phe Ala Thr Tyr Tyr Cys Gln Gln Ala Asn Asn Phe Pro Tyr
                 85                  90                  95

Thr Phe Gly Gln Gly Thr Lys Leu Glu Ile Lys
             100                 105

<210> SEQ ID NO 501
<211> LENGTH: 363
<212> TYPE: DNA
<213> ORGANISM: Artificial Sequence
<220> FEATURE:
<223> OTHER INFORMATION: synthetic

<400> SEQUENCE: 501

```
gaggtgcagc tgttggagtc tgggggaggc ttggtacagc ctggggggtc cctgagactc    60
tcctgtgcag cctctgaatt cacctttagc ggctatgcca tgagctgggt ccgccaggct   120
ccagggaagg gctggagtg gtctcagct attcgtggta gtggtgataa cacatactac    180
gcagactccg tgaagggccg gttcaccatc tccagagaca attccaagaa cacgctgtat   240
ctgcaaatga acagcctgag agccgaggac acggccgtat attactgtgc gagagtgtat   300
tacgattttt gggaaggggc ttttgatatc tggggccaag gacaatggt caccgtctct   360
tca                                                                 363
```

<210> SEQ ID NO 502
<211> LENGTH: 121
<212> TYPE: PRT
<213> ORGANISM: Artificial Sequence
<220> FEATURE:
<223> OTHER INFORMATION: synthetic

<400> SEQUENCE: 502

```
Glu Val Gln Leu Leu Glu Ser Gly Gly Gly Leu Val Gln Pro Gly Gly
  1               5                  10                  15

Ser Leu Arg Leu Ser Cys Ala Ala Ser Glu Phe Thr Phe Ser Gly Tyr
             20                  25                  30

Ala Met Ser Trp Val Arg Gln Ala Pro Gly Lys Gly Leu Glu Trp Val
         35                  40                  45

Ser Ala Ile Arg Gly Ser Gly Asp Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Tyr Tyr Asp Phe Trp Glu Gly Ala Phe Asp Ile Trp Gly
            100                 105                 110

Gln Gly Thr Met Val Thr Val Ser Ser
        115                 120
```

<210> SEQ ID NO 503
<211> LENGTH: 322
<212> TYPE: DNA
<213> ORGANISM: Artificial Sequence
<220> FEATURE:
<223> OTHER INFORMATION: synthetic

<400> SEQUENCE: 503

```
gacatccaga tgacccagtc tccatcttct gtgtctgcat ctgtaggaga cagagtcacc    60
atcacttgtc gggcgagtca gggtattagc acctggttag cctggtatca gcagaaacca   120
gggaaagccc ctaagctcct gatctatgct gcaaccagtt tgcaaagtgg gtcccatca   180
aggttcagcg gcagtggatc tgggacagat ttcactctca ctatcagcag cctgcagcct   240
gaagattttg caacttacta ttgtcaacag gctaacaatt tcccgtacac ttttggccag   300
gggaccaagc tggagatcaa ac                                            322
```

<210> SEQ ID NO 504
<211> LENGTH: 107
<212> TYPE: PRT
<213> ORGANISM: Artificial Sequence
<220> FEATURE:

<223> OTHER INFORMATION: synthetic

<400> SEQUENCE: 504

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Thr Trp
            20                  25                  30

Leu Ala Trp Tyr Gln Gln Lys Pro Gly Lys Ala Pro Lys Leu Leu Ile
        35                  40                  45

Tyr Ala Ala Thr Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Tyr
                85                  90                  95

Thr Phe Gly Gln Gly Thr Lys Leu Glu Ile Lys
            100                 105

<210> SEQ ID NO 505
<211> LENGTH: 357
<212> TYPE: DNA
<213> ORGANISM: Artificial Sequence
<220> FEATURE:
<223> OTHER INFORMATION: synthetic

<400> SEQUENCE: 505
caggtgcagc tggtggagtc tgggggaggc gtggtccagc ctggagggtc cctgagactc      60
tcctgtgcag cgtctggatt caccttcagt gcctatggca tgcactgggt ccgccaggct     120
ccaggcaagg ggctggagtg ggtggcaatt atatggtatg atggaagtaa taaatactac     180
gcagactccg tgaagggccg attcaccatc tccagagaca attccaagaa cacgctgtat     240
ctgcaaatga acagcctgag agccgaggac acggctgtgt attattgtgc gagagaggat     300
acctctatgg ttctctttga ctactggggc cagggaaccc tggtcaccgt ctcctca       357

<210> SEQ ID NO 506
<211> LENGTH: 119
<212> TYPE: PRT
<213> ORGANISM: Artificial Sequence
<220> FEATURE:
<223> OTHER INFORMATION: synthetic

<400> SEQUENCE: 506

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ala Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Thr Ser Met Val Leu Phe Asp Tyr Trp Gly Gln Gly
            100                 105                 110

Thr Leu Val Thr Val Ser Ser

<210> SEQ ID NO 507
<211> LENGTH: 24
<212> TYPE: DNA
<213> ORGANISM: Artificial Sequence
<220> FEATURE:
<223> OTHER INFORMATION: synthetic

<400> SEQUENCE: 507
ggattcacct tcagtgccta tggc                                          24

<210> SEQ ID NO 508
<211> LENGTH: 8
<212> TYPE: PRT
<213> ORGANISM: Artificial Sequence
<220> FEATURE:
<223> OTHER INFORMATION: synthetic

<400> SEQUENCE: 508

Gly Phe Thr Phe Ser Ala Tyr Gly
1               5

<210> SEQ ID NO 509
<211> LENGTH: 24
<212> TYPE: DNA
<213> ORGANISM: Artificial Sequence
<220> FEATURE:
<223> OTHER INFORMATION: synthetic

<400> SEQUENCE: 509
atatggtatg atggaagtaa taaa                                          24

<210> SEQ ID NO 510
<211> LENGTH: 8
<212> TYPE: PRT
<213> ORGANISM: Artificial Sequence
<220> FEATURE:
<223> OTHER INFORMATION: synthetic

<400> SEQUENCE: 510

Ile Trp Tyr Asp Gly Ser Asn Lys
1               5

<210> SEQ ID NO 511
<211> LENGTH: 36
<212> TYPE: DNA
<213> ORGANISM: Artificial Sequence
<220> FEATURE:
<223> OTHER INFORMATION: synthetic

<400> SEQUENCE: 511
gcgagagagg atacctctat ggttctcttt gactac                             36

<210> SEQ ID NO 512
<211> LENGTH: 12
<212> TYPE: PRT
<213> ORGANISM: Artificial Sequence
<220> FEATURE:
<223> OTHER INFORMATION: synthetic

<400> SEQUENCE: 512

Ala Arg Glu Asp Thr Ser Met Val Leu Phe Asp Tyr
1               5                   10

<210> SEQ ID NO 513

<211> LENGTH: 357
<212> TYPE: DNA
<213> ORGANISM: Artificial Sequence
<220> FEATURE:
<223> OTHER INFORMATION: synthetic

<400> SEQUENCE: 513

```
caggtgcagc tggtggagtc tgggggaggc gtggtccagc ctggaggtc cctgagactc      60
tcctgtgcag cgtctggatt caccttcagt gcctatggca tgcactgggt ccgccaggct    120
ccaggcaagg ggctggagtg ggtggcaatt atatggtatg atggaagtaa taaatactac    180
gcagactccg tgaagggccg attcaccatc tccagacaca attccaagaa cacgctgtat    240
ctgcaaatga acagcctgag agccgaggac acggctgtgt attattgtgc gagagaggat    300
acctctatgg ttctctttga ctactggggc cagggaaccc tggtcaccgt ctcctca       357
```

<210> SEQ ID NO 514
<211> LENGTH: 119
<212> TYPE: PRT
<213> ORGANISM: Artificial Sequence
<220> FEATURE:
<223> OTHER INFORMATION: synthetic

<400> SEQUENCE: 514

```
Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Ala Tyr
            20                  25                  30
Gly Met His Trp Val Arg Gln Ala Pro Gly Lys Gly Leu Glu Trp Val
        35                  40                  45
Ala Ile Ile Trp Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Asp Thr Ser Met Val Leu Phe Asp Tyr Trp Gly Gln Gly
            100                 105                 110
Thr Leu Val Thr Val Ser Ser
        115
```

<210> SEQ ID NO 515
<211> LENGTH: 357
<212> TYPE: DNA
<213> ORGANISM: Artificial Sequence
<220> FEATURE:
<223> OTHER INFORMATION: synthetic

<400> SEQUENCE: 515

```
caggtgcagc tggtggagtc tgggggaggc gtggtccagc ctggaggtc cctgagactc      60
tcctgtgcag cgtctggatt caccttcagt gcctatggca tgcactgggt ccgccaggct    120
ccaggcaagg ggctagagtg ggtggcagtt atatggtatg atggaagtaa taaatactat    180
gcagactccg tgaagggccg attcaccatc tccagacaca attccaagaa cacgctgtat    240
ctgcaaatga acagcctgag agccgaggac acggctgtgt attactgtgc gagagaggat    300
acctctatgg ttctctttga ctactggggc cagggaaccc tggtcaccgt ctcctca       357
```

<210> SEQ ID NO 516
<211> LENGTH: 119

<212> TYPE: PRT
<213> ORGANISM: Artificial Sequence
<220> FEATURE:
<223> OTHER INFORMATION: synthetic

<400> SEQUENCE: 516

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ala Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Thr Ser Met Val Leu Phe Asp Tyr Trp Gly Gln Gly
            100                 105                 110

Thr Leu Val Thr Val Ser Ser
        115

<210> SEQ ID NO 517
<211> LENGTH: 1488
<212> TYPE: DNA
<213> ORGANISM: Artificial Sequence
<220> FEATURE:
<223> OTHER INFORMATION: synthetic

<400> SEQUENCE: 517

| | |
|---|---|
| atgtggcaga ttgttttctt tactctgagc tgtgatcttg tcttggccgc agcctataac | 60 |
| aactttcgga agagcatgga cagcatagga agaagcaat atcaggtcca gcatgggtcc | 120 |
| tgcagctaca ctttcctcct gccagagatg gacaactgcc gctcttcctc cagcccctac | 180 |
| gtgtccaatg ctgtgcagag ggacgcgccg ctcgaatacg atgactcggt gcagaggctg | 240 |
| caagtgctgg agaacatcat ggaaaacaac actcagtggc taatgaagct tgagaattat | 300 |
| atccaggaca catgaagaa agaaatggta gagatacagc agaatgcagt acagaaccag | 360 |
| acggctgtga tgatagaaat agggacaaac ctgttgaacc aaacagctga gcaaacgcgg | 420 |
| aagttaactg atgtggaagc ccaagtatta atcagacca cgagacttga acttcagctc | 480 |
| ttggaacact ccctctcgac aaacaaattg gaaaacaga ttttggacca gaccagtgaa | 540 |
| ataaacaaat gcaagataa gaacagtttc ctagaaaaga aggtgctagc tatggaagac | 600 |
| aagcacatca tccaactaca gtcaataaaa gaagagaaag atcagctaca ggtgttagta | 660 |
| tccaagcaaa attccatcat tgaagaacta gaaaaaaaaa tagtgactgc cacggtgaat | 720 |
| aattcagttc ttcaaaagca gcaacatgat ctcatggaga cagttaataa cttactgact | 780 |
| atgatgtcca catcaaactc agctaaggac cccactgttg ctaaagaaga acaaatcagc | 840 |
| ttcagagact gtgctgaagt attcaaatca ggacacacca caaatggcat ctacacgtta | 900 |
| acattcccta ttctacaga agagatcaag gcctactgtg acatgaagc tggaggaggc | 960 |
| gggtggacaa ttattcagcg acgtgaggat ggcagcgttg attttcagag acttggaaaa | 1020 |
| gaatataaag tgggatttgg taacccttca ggagaatatt ggctgggaaa tgagtttgtt | 1080 |
| tcgcaactga ctaatcagca acgctatgtg cttaaaatac ccttaaaga ctgggaaggg | 1140 |

-continued

```
aatgaggctt actcattgta tgaacatttc tatctctcaa gtgaagaact caattatagg    1200 attcaccta aaggacttac agggacagcc ggcaaaataa gcagcatcag ccaaccagga    1260
aatgatttta gcacaaagga tggagacaac gacaaatgta tttgcaaatg ttcacaaatg    1320
ctaacaggag gctggtggtt tgatgcatgt ggtccttcca acttgaacgg aatgtactat    1380
ccacagaggc agaacacaaa taagttcaac ggcattaaat ggtactactg gaaaggctca    1440
ggctattcgc tcaaggccac aaccatgatg atccgaccag cagatttc                1488
```

<210> SEQ ID NO 518
<211> LENGTH: 496
<212> TYPE: PRT
<213> ORGANISM: Artificial Sequence
<220> FEATURE:
<223> OTHER INFORMATION: synthetic

<400> SEQUENCE: 518

```
Met Trp Gln Ile Val Phe Phe Thr Leu Ser Cys Asp Leu Val Leu Ala
 1               5                  10                  15

Ala Ala Tyr Asn Asn Phe Arg Lys Ser Met Asp Ser Ile Gly Lys Lys
             20                  25                  30

Gln Tyr Gln Val Gln His Gly Ser Cys Ser Tyr Thr Phe Leu Leu Pro
         35                  40                  45

Glu Met Asp Asn Cys Arg Ser Ser Ser Pro Tyr Val Ser Asn Ala
     50                  55                  60

Val Gln Arg Asp Ala Pro Leu Glu Tyr Asp Asp Ser Val Gln Arg Leu
 65                  70                  75                  80

Gln Val Leu Glu Asn Ile Met Glu Asn Asn Thr Gln Trp Leu Met Lys
                 85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
    290                 295                 300
```

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ile
                405                 410                 415

Ser Gln Pro Gly Asn Asp Phe Ser Thr Lys Asp Gly Asp Asn Asp Lys
                420                 425                 430

Cys Ile Cys Lys Cys Ser Gln Met Leu Thr Gly Gly Trp Trp Phe Asp
                435                 440                 445

Ala Cys Gly Pro Ser Asn Leu Asn Gly Met Tyr Tyr Pro Gln Arg Gln
450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 519
<211> LENGTH: 215
<212> TYPE: PRT
<213> ORGANISM: Artificial Sequence
<220> FEATURE:
<223> OTHER INFORMATION: synthetic

<400> SEQUENCE: 519

Arg Asp Cys Ala Glu Val Phe Lys Ser Gly His Thr Thr Asn Gly Ile
1               5                   10                  15

Tyr Thr Leu Thr Phe Pro Asn Ser Thr Glu Ile Lys Ala Tyr Cys
            20                  25                  30

Asp Met Glu Ala Gly Gly Gly Gly Trp Thr Ile Ile Gln Arg Arg Glu
            35                  40                  45

Asp Gly Ser Val Asp Phe Gln Arg Thr Trp Lys Glu Tyr Lys Val Gly
        50                  55                  60

Phe Gly Asn Pro Ser Gly Glu Tyr Trp Leu Gly Asn Glu Phe Val Ser
65                  70                  75                  80

Gln Leu Thr Asn Gln Gln Arg Tyr Val Leu Lys Ile His Leu Lys Asp
                85                  90                  95

Trp Glu Gly Asn Glu Ala Tyr Ser Leu Tyr Glu His Phe Tyr Leu Ser
            100                 105                 110

Ser Glu Glu Leu Asn Tyr Arg Ile His Leu Lys Gly Leu Thr Gly Thr
        115                 120                 125

Ala Gly Lys Ile Ser Ser Ile Ser Gln Pro Gly Asn Asp Phe Ser Thr
    130                 135                 140

Lys Asp Gly Asp Asn Asp Lys Cys Ile Cys Lys Cys Ser Gln Met Leu
145                 150                 155                 160

Thr Gly Gly Trp Trp Phe Asp Ala Cys Gly Pro Ser Asn Leu Asn Gly
                165                 170                 175

```
Met Tyr Tyr Pro Gln Arg Gln Asn Thr Asn Lys Phe Asn Gly Ile Lys
            180                 185                 190

Trp Tyr Tyr Trp Lys Gly Ser Gly Tyr Ser Leu Lys Ala Thr Thr Met
        195                 200                 205

Met Ile Arg Pro Ala Asp Phe
        210                 215

<210> SEQ ID NO 520
<211> LENGTH: 215
<212> TYPE: PRT
<213> ORGANISM: Artificial Sequence
<220> FEATURE:
<223> OTHER INFORMATION: synthetic

<400> SEQUENCE: 520

Arg Asp Cys Ala Glu Ile Phe Lys Ser Gly Leu Thr Thr Ser Gly Ile
1               5                   10                  15

Tyr Thr Leu Thr Phe Pro Asn Ser Thr Glu Glu Ile Lys Ala Tyr Cys
            20                  25                  30

Asp Met Asp Val Gly Gly Gly Gly Trp Thr Val Ile Gln His Arg Glu
        35                  40                  45

Asp Gly Ser Val Asp Phe Gln Arg Thr Trp Lys Glu Tyr Lys Glu Gly
    50                  55                  60

Phe Gly Ser Pro Leu Gly Glu Tyr Trp Leu Gly Asn Glu Phe Val Ser
65                  70                  75                  80

Gln Leu Thr Gly Gln His Arg Tyr Val Leu Lys Ile Gln Leu Lys Asp
            85                  90                  95

Trp Glu Gly Asn Glu Ala His Ser Leu Tyr Asp His Phe Tyr Leu Ala
            100                 105                 110

Gly Glu Glu Ser Asn Tyr Arg Ile His Leu Thr Gly Leu Thr Gly Thr
            115                 120                 125

Ala Gly Lys Ile Ser Ser Ile Ser Gln Pro Gly Ser Asp Phe Ser Thr
        130                 135                 140

Lys Asp Ser Asp Asn Asp Lys Cys Ile Cys Lys Cys Ser Gln Met Leu
145                 150                 155                 160

Ser Gly Gly Trp Trp Phe Asp Ala Cys Gly Pro Ser Asn Leu Asn Gly
                165                 170                 175

Gln Tyr Tyr Pro Gln Lys Gln Asn Thr Asn Lys Phe Asn Gly Ile Lys
            180                 185                 190

Trp Tyr Tyr Trp Lys Gly Ser Gly Tyr Ser Leu Lys Ala Thr Thr Met
        195                 200                 205

Met Ile Arg Pro Ala Asp Phe
        210                 215

<210> SEQ ID NO 521
<211> LENGTH: 215
<212> TYPE: PRT
<213> ORGANISM: Artificial Sequence
<220> FEATURE:
<223> OTHER INFORMATION: synthetic

<400> SEQUENCE: 521

Arg Asp Cys Ala Glu Val Phe Lys Ser Gly His Thr Thr Asn Gly Val
1               5                   10                  15

Tyr Thr Leu Thr Leu Pro Asn Ser Thr Glu Glu Val Lys Ala Tyr Cys
            20                  25                  30

Asp Met Glu Ala Gly Gly Gly Gly Trp Thr Ile Ile Gln Arg Arg Glu
        35                  40                  45
```

Asp Gly Ser Val Asp Phe Gln Arg Thr Trp Lys Glu Tyr Lys Val Gly
    50                  55                  60

Phe Gly Asn Pro Ser Gly Glu Tyr Trp Leu Gly Asn Glu Phe Val Ser
65                  70                  75                  80

Gln Leu Thr Asn Gln Gln Arg Tyr Val Leu Lys Ile His Leu Lys Asp
                85                  90                  95

Trp Glu Gly Asn Glu Ala Tyr Ser Leu Tyr Glu His Phe Tyr Leu Ser
            100                 105                 110

Ser Glu Glu Leu Asn Tyr Arg Ile His Leu Lys Gly Leu Thr Gly Thr
        115                 120                 125

Ala Gly Lys Ile Ser Ser Ile Ser Gln Pro Gly Asn Asp Phe Ser Thr
    130                 135                 140

Lys Asp Ala Asp Asn Asp Lys Cys Ile Cys Lys Cys Ser Gln Met Leu
145                 150                 155                 160

Thr Gly Gly Trp Trp Phe Asp Ala Cys Gly Pro Ser Asn Leu Asn Gly
                165                 170                 175

Met Tyr Tyr Pro Gln Arg Gln Asn Thr Asn Lys Phe Asn Gly Ile Lys
            180                 185                 190

Trp Tyr Tyr Trp Lys Gly Ser Gly Tyr Ser Leu Lys Gly Thr Thr Met
        195                 200                 205

Met Ile Arg Pro Ala Asp Phe
    210                 215

<210> SEQ ID NO 522
<211> LENGTH: 674
<212> TYPE: PRT
<213> ORGANISM: Artificial Sequence
<220> FEATURE:
<223> OTHER INFORMATION: synthetic

<400> SEQUENCE: 522

Arg Asp Cys Ala Glu Val Phe Lys Ser Gly His Thr Thr Asn Gly Ile
1               5                   10                  15

Tyr Thr Leu Thr Phe Pro Asn Ser Thr Glu Glu Ile Lys Ala Tyr Cys
            20                  25                  30

Asp Met Glu Ala Gly Gly Gly Gly Trp Thr Ile Ile Gln Arg Arg Glu
        35                  40                  45

Asp Gly Ser Val Asp Phe Gln Arg Thr Trp Lys Glu Tyr Lys Val Gly
    50                  55                  60

Phe Gly Asn Pro Ser Gly Glu Tyr Trp Leu Gly Asn Glu Phe Val Ser
65                  70                  75                  80

Gln Leu Thr Asn Gln Gln Arg Tyr Val Leu Lys Ile His Leu Lys Asp
                85                  90                  95

Trp Glu Gly Asn Glu Ala Tyr Ser Leu Tyr Glu His Phe Tyr Leu Ser
            100                 105                 110

Ser Glu Glu Leu Asn Tyr Arg Ile His Leu Lys Gly Leu Thr Gly Thr
        115                 120                 125

Ala Gly Lys Ile Ser Ser Ile Ser Gln Pro Gly Asn Asp Phe Ser Thr
    130                 135                 140

Lys Asp Gly Asp Asn Asp Lys Cys Ile Cys Lys Cys Ser Gln Met Leu
145                 150                 155                 160

Thr Gly Gly Trp Trp Phe Asp Ala Cys Gly Pro Ser Asn Leu Asn Gly
                165                 170                 175

Met Tyr Tyr Pro Gln Arg Gln Asn Thr Asn Lys Phe Asn Gly Ile Lys
            180                 185                 190

```
Trp Tyr Tyr Trp Lys Gly Ser Gly Tyr Ser Leu Lys Ala Thr Thr Met
            195                 200                 205

Met Ile Arg Pro Ala Asp Phe Gly Gly Pro Gly Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys Gly Gly Gly Ser Gly Ala Pro Arg Asp Cys Ala Glu
            450                 455                 460

Val Phe Lys Ser Gly His Thr Thr Asn Gly Ile Tyr Thr Leu Thr Phe
465                 470                 475                 480

Pro Asn Ser Thr Glu Glu Ile Lys Ala Tyr Cys Asp Met Glu Ala Gly
                485                 490                 495

Gly Gly Gly Trp Thr Ile Ile Gln Arg Arg Glu Asp Gly Ser Val Asp
                500                 505                 510

Phe Gln Arg Thr Trp Lys Glu Tyr Lys Val Gly Phe Gly Asn Pro Ser
            515                 520                 525

Gly Glu Tyr Trp Leu Gly Asn Glu Phe Val Ser Gln Leu Thr Asn Gln
530                 535                 540

Gln Arg Tyr Val Leu Lys Ile His Leu Lys Asp Trp Glu Gly Asn Glu
545                 550                 555                 560

Ala Tyr Ser Leu Tyr Glu His Phe Tyr Leu Ser Ser Glu Glu Leu Asn
                565                 570                 575

Tyr Arg Ile His Leu Lys Gly Leu Thr Gly Thr Ala Gly Lys Ile Ser
                580                 585                 590

Ser Ile Ser Gln Pro Gly Asn Asp Phe Ser Thr Lys Asp Gly Asp Asn
            595                 600                 605
```

```
Asp Lys Cys Ile Cys Lys Cys Ser Gln Met Leu Thr Gly Gly Trp Trp
610                 615                 620

Phe Asp Ala Cys Gly Pro Ser Asn Leu Asn Gly Met Tyr Tyr Pro Gln
625                 630                 635                 640

Arg Gln Asn Thr Asn Lys Phe Asn Gly Ile Lys Trp Tyr Tyr Trp Lys
            645                 650                 655

Gly Ser Gly Tyr Ser Leu Lys Ala Thr Thr Met Met Ile Arg Pro Ala
            660                 665                 670

Asp Phe

<210> SEQ ID NO 523
<211> LENGTH: 663
<212> TYPE: PRT
<213> ORGANISM: Artificial Sequence
<220> FEATURE:
<223> OTHER INFORMATION: synthetic

<400> SEQUENCE: 523

Arg Asp Cys Ala Glu Val Phe Lys Ser Gly His Thr Thr Asn Gly Ile
1               5                   10                  15

Tyr Thr Leu Thr Phe Pro Asn Ser Thr Glu Glu Ile Lys Ala Tyr Cys
            20                  25                  30

Asp Met Glu Ala Gly Gly Gly Gly Trp Thr Ile Ile Gln Arg Arg Glu
        35                  40                  45

Asp Gly Ser Val Asp Phe Gln Arg Thr Trp Lys Glu Tyr Lys Val Gly
    50                  55                  60

Phe Gly Asn Pro Ser Gly Glu Tyr Trp Leu Gly Asn Glu Phe Val Ser
65                  70                  75                  80

Gln Leu Thr Asn Gln Gln Arg Tyr Val Leu Lys Ile His Leu Lys Asp
                85                  90                  95

Trp Glu Gly Asn Glu Ala Tyr Ser Leu Tyr Glu His Phe Tyr Leu Ser
            100                 105                 110

Ser Glu Glu Leu Asn Tyr Arg Ile His Leu Lys Gly Leu Thr Gly Thr
        115                 120                 125

Ala Gly Lys Ile Ser Ser Ile Ser Gln Pro Gly Asn Asp Phe Ser Thr
    130                 135                 140

Lys Asp Gly Asp Asn Asp Lys Cys Ile Cys Lys Cys Ser Gln Met Leu
145                 150                 155                 160

Thr Gly Gly Trp Trp Phe Asp Ala Cys Gly Pro Ser Asn Leu Asn Gly
                165                 170                 175

Met Tyr Tyr Pro Gln Arg Gln Asn Thr Asn Lys Phe Asn Gly Ile Lys
            180                 185                 190

Trp Tyr Tyr Trp Lys Gly Ser Gly Tyr Ser Leu Lys Ala Thr Thr Met
        195                 200                 205

Met Ile Arg Pro Ala Asp Phe Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Asp Pro
            260                 265                 270

Asp Val Gln Ile Ser Trp Phe Val Asn Asn Val Glu Val His Thr Ala
    275                 280                 285

Gln Thr Gln Thr His Arg Glu Asp Tyr Asn Ser Thr Leu Arg Val Val
```

```
            290                 295                 300
Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
        435                 440                 445

Arg Asp Cys Ala Glu Val Phe Lys Ser Gly His Thr Thr Asn Gly Ile
450                 455                 460

Tyr Thr Leu Thr Phe Pro Asn Ser Thr Glu Glu Ile Lys Ala Tyr Cys
465                 470                 475                 480

Asp Met Glu Ala Gly Gly Gly Trp Thr Ile Ile Gln Arg Arg Glu
                485                 490                 495

Asp Gly Ser Val Asp Phe Gln Arg Thr Trp Lys Glu Tyr Lys Val Gly
            500                 505                 510

Phe Gly Asn Pro Ser Gly Glu Tyr Trp Leu Gly Asn Glu Phe Val Ser
        515                 520                 525

Gln Leu Thr Asn Gln Gln Arg Tyr Val Leu Lys Ile His Leu Lys Asp
    530                 535                 540

Trp Glu Gly Asn Glu Ala Tyr Ser Leu Tyr Glu His Phe Tyr Leu Ser
545                 550                 555                 560

Ser Glu Glu Leu Asn Tyr Arg Ile His Leu Lys Gly Leu Thr Gly Thr
                565                 570                 575

Ala Gly Lys Ile Ser Ser Ile Ser Gln Pro Gly Asn Asp Phe Ser Thr
            580                 585                 590

Lys Asp Gly Asp Asn Asp Lys Cys Ile Cys Lys Cys Ser Gln Met Leu
        595                 600                 605

Thr Gly Gly Trp Trp Phe Asp Ala Cys Gly Pro Ser Asn Leu Asn Gly
    610                 615                 620

Met Tyr Tyr Pro Gln Arg Gln Asn Thr Asn Lys Phe Asn Gly Ile Lys
625                 630                 635                 640

Trp Tyr Tyr Trp Lys Gly Ser Gly Tyr Ser Leu Lys Ala Thr Thr Met
                645                 650                 655

Met Ile Arg Pro Ala Asp Phe
            660

<210> SEQ ID NO 524
<211> LENGTH: 448
<212> TYPE: PRT
<213> ORGANISM: Artificial Sequence
<220> FEATURE:
<223> OTHER INFORMATION: synthetic
```

-continued

```
<400> SEQUENCE: 524

Arg Asp Cys Ala Glu Val Phe Lys Ser Gly His Thr Thr Asn Gly Ile
 1               5                  10                  15

Tyr Thr Leu Thr Phe Pro Asn Ser Thr Glu Ile Lys Ala Tyr Cys
             20                  25                  30

Asp Met Glu Ala Gly Gly Gly Trp Thr Ile Ile Gln Arg Arg Glu
         35                  40                  45

Asp Gly Ser Val Asp Phe Gln Arg Thr Trp Lys Glu Tyr Lys Val Gly
 50                  55                  60

Phe Gly Asn Pro Ser Gly Glu Tyr Trp Leu Gly Asn Glu Phe Val Ser
 65                  70                  75                  80

Gln Leu Thr Asn Gln Gln Arg Tyr Val Leu Lys Ile His Leu Lys Asp
                 85                  90                  95

Trp Glu Gly Asn Glu Ala Tyr Ser Leu Tyr His Phe Tyr Leu Ser
             100                 105                 110

Ser Glu Glu Leu Asn Tyr Arg Ile His Leu Lys Gly Leu Thr Gly Thr
             115                 120                 125

Ala Gly Lys Ile Ser Ser Ile Ser Gln Pro Gly Asn Asp Phe Ser Thr
130                 135                 140

Lys Asp Gly Asp Asn Asp Lys Cys Ile Cys Lys Cys Ser Gln Met Leu
145                 150                 155                 160

Thr Gly Gly Trp Trp Phe Asp Ala Cys Gly Pro Ser Asn Leu Asn Gly
                 165                 170                 175

Met Tyr Tyr Pro Gln Arg Gln Asn Thr Asn Lys Phe Asn Gly Ile Lys
             180                 185                 190

Trp Tyr Tyr Trp Lys Gly Ser Gly Tyr Ser Leu Lys Ala Thr Thr Met
             195                 200                 205

Met Ile Arg Pro Ala Asp Phe Glu Pro Arg Gly Pro Thr Ile Lys Pro
210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                 245                 250                 255

Ser Pro Ile Val Thr Cys Val Val Asp Val Ser Glu Asp Asp Pro
             260                 265                 270

Asp Val Gln Ile Ser Trp Phe Val Asn Asn Val Glu Val His Thr Ala
             275                 280                 285

Gln Thr Gln Thr His Arg Glu Asp Tyr Asn Ser Thr Leu Arg Val Val
290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                 325                 330                 335

Ile Ser Lys Pro Lys Gly Ser Val Arg Ala Pro Gln Val Tyr Val Leu
             340                 345                 350

Pro Pro Pro Glu Glu Glu Met Thr Lys Lys Gln Val Thr Leu Thr Cys
             355                 360                 365

Met Val Thr Asp Phe Met Pro Glu Asp Ile Tyr Val Glu Trp Thr Asn
370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
             405                 410                 415
```

Asn Trp Val Glu Arg Asn Ser Tyr Ser Cys Ser Val Val His Glu Gly
                420                 425                 430

Leu His Asn His His Thr Thr Lys Ser Phe Ser Arg Thr Pro Gly Lys
        435                 440                 445

<210> SEQ ID NO 525
<211> LENGTH: 981
<212> TYPE: PRT
<213> ORGANISM: Artificial Sequence
<220> FEATURE:
<223> OTHER INFORMATION: synthetic

<400> SEQUENCE: 525

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

```
Gly Leu Gln Cys Glu Arg Gly Ile Pro Arg Met Thr Pro Lys Ile
            340                 345                 350

Val Asp Leu Pro Asp His Ile Glu Val Asn Ser Gly Lys Phe Asn Pro
            355                 360                 365

Ile Cys Lys Ala Ser Gly Trp Pro Leu Pro Thr Asn Glu Glu Met Thr
370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
            435                 440                 445

Asn Ala Pro Asn Val Ile Asp Thr Gly His Asn Phe Ala Val Ile Asn
            450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
            500                 505                 510

Tyr Glu Leu Cys Val Gln Leu Val Arg Arg Gly Glu Gly Gly Glu Gly
            515                 520                 525

His Pro Gly Pro Val Arg Arg Phe Thr Thr Ala Ser Ile Gly Leu Pro
            530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Asn Ile Lys
            580                 585                 590

Val Pro Gly Asn Leu Thr Ser Val Leu Leu Asn Asn Leu His Pro Arg
            595                 600                 605

Glu Gln Tyr Val Val Arg Ala Arg Val Asn Thr Lys Ala Gln Gly Glu
            610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
                645                 650                 655

Ile Ser Trp Thr Ile Leu Asp Gly Tyr Ser Ile Ser Ile Thr Ile
                660                 665                 670

Arg Tyr Lys Val Gln Gly Lys Asn Glu Asp Gln His Val Asp Val Lys
            675                 680                 685

Ile Lys Asn Ala Thr Ile Ile Gln Tyr Gln Leu Lys Gly Leu Glu Pro
            690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
                725                 730                 735

Ala Pro Ala Asp Leu Gly Gly Gly Lys Gly Pro Gly Glu Pro Arg Gly
            740                 745                 750
```

```
Pro Thr Ile Lys Pro Cys Pro Cys Lys Cys Pro Ala Pro Asn Leu
            755                 760                 765

Leu Gly Gly Pro Ser Val Phe Ile Phe Pro Pro Lys Ile Lys Asp Val
770                 775                 780

Leu Met Ile Ser Leu Ser Pro Ile Val Thr Cys Val Val Val Asp Val
785                 790                 795                 800

Ser Glu Asp Asp Pro Asp Val Gln Ile Ser Trp Phe Val Asn Asn Val
                805                 810                 815

Glu Val His Thr Ala Gln Thr Gln Thr His Arg Glu Asp Tyr Asn Ser
            820                 825                 830

Thr Leu Arg Val Val Ser Ala Leu Pro Ile Gln His Gln Asp Trp Met
            835                 840                 845

Ser Gly Lys Glu Phe Lys Cys Lys Val Asn Asn Lys Asp Leu Pro Ala
        850                 855                 860

Pro Ile Glu Arg Thr Ile Ser Lys Pro Lys Gly Ser Val Arg Ala Pro
865                 870                 875                 880

Gln Val Tyr Val Leu Pro Pro Glu Glu Met Thr Lys Lys Gln
                885                 890                 895

Val Thr Leu Thr Cys Met Val Thr Asp Phe Met Pro Glu Asp Ile Tyr
            900                 905                 910

Val Glu Trp Thr Asn Asn Gly Lys Thr Glu Leu Asn Tyr Lys Asn Thr
            915                 920                 925

Glu Pro Val Leu Asp Ser Asp Gly Ser Tyr Phe Met Tyr Ser Lys Leu
        930                 935                 940

Arg Val Glu Lys Lys Asn Trp Val Glu Arg Asn Ser Tyr Ser Cys Ser
945                 950                 955                 960

Val Val His Glu Gly Leu His Asn His His Thr Thr Lys Ser Phe Ser
                965                 970                 975

Arg Thr Pro Gly Lys
            980

<210> SEQ ID NO 526
<211> LENGTH: 753
<212> TYPE: PRT
<213> ORGANISM: Artificial Sequence
<220> FEATURE:
<223> OTHER INFORMATION: synthetic

<400> SEQUENCE: 526

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125
```

```
Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
    290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Thr Pro Lys Ile
            340                 345                 350

Val Asp Leu Pro Asp His Ile Glu Val Asn Ser Gly Lys Phe Asn Pro
        355                 360                 365

Ile Cys Lys Ala Ser Gly Trp Pro Leu Pro Thr Asn Glu Glu Met Thr
    370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
        435                 440                 445

Asn Ala Pro Asn Val Ile Asp Thr Gly His Asn Phe Ala Val Ile Asn
450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
            500                 505                 510

Tyr Glu Leu Cys Val Gln Leu Val Arg Arg Gly Glu Gly Gly Glu Gly
        515                 520                 525

His Pro Gly Pro Val Arg Arg Phe Thr Thr Ala Ser Ile Gly Leu Pro
    530                 535                 540

Pro Pro Arg Gly Leu Asn Leu Leu Pro Lys Ser Gln Thr Thr Leu Asn
```

```
                  545                 550                 555                 560
Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Asn Ile Lys
            580                 585                 590

Val Pro Gly Asn Leu Thr Ser Val Leu Leu Asn Asn Leu His Pro Arg
            595                 600                 605

Glu Gln Tyr Val Val Arg Ala Arg Val Asn Thr Lys Ala Gln Gly Glu
        610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
                645                 650                 655

Ile Ser Trp Thr Ile Leu Asp Gly Tyr Ser Ile Ser Ser Ile Thr Ile
                660                 665                 670

Arg Tyr Lys Val Gln Gly Lys Asn Glu Asp Gln His Val Asp Val Lys
            675                 680                 685

Ile Lys Asn Ala Thr Ile Ile Gln Tyr Gln Leu Lys Gly Leu Glu Pro
        690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
                725                 730                 735

Ala Pro Ala Asp Leu Gly Gly Gly Lys Ile Asp His His His His
            740                 745                 750

His
```

<210> SEQ ID NO 527
<211> LENGTH: 498
<212> TYPE: PRT
<213> ORGANISM: Artificial Sequence
<220> FEATURE:
<223> OTHER INFORMATION: synthetic

<400> SEQUENCE: 527

```
Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45

Glu His Asp Gly Asn Cys Arg Glu Ser Thr Thr Asp Gln Tyr Asn Thr
    50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160
```

```
Ile Gln Leu Leu Glu Asn Ser Leu Ser Thr Tyr Lys Leu Glu Lys Gln
            165                 170                 175

Leu Leu Gln Gln Thr Asn Glu Ile Leu Lys Ile His Glu Lys Asn Ser
        180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
            260                 265                 270

Lys Gly Gly Lys Arg Glu Glu Lys Pro Phe Arg Asp Cys Ala Asp
        275                 280                 285

Val Tyr Gln Ala Gly Phe Asn Lys Ser Gly Ile Tyr Thr Ile Tyr Ile
    290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
        355                 360                 365

Arg Gln Tyr Met Leu Arg Ile Glu Leu Met Asp Trp Glu Gly Asn Arg
    370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
            420                 425                 430

Asp Asn Cys Met Cys Lys Cys Ala Leu Met Leu Thr Gly Gly Trp Trp
        435                 440                 445

Phe Asp Ala Cys Gly Pro Ser Asn Leu Asn Gly Met Phe Tyr Thr Ala
    450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 528
<211> LENGTH: 330
<212> TYPE: PRT
<213> ORGANISM: Artificial Sequence
<220> FEATURE:
<223> OTHER INFORMATION: synthetic

<400> SEQUENCE: 528

Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 529
<211> LENGTH: 327
<212> TYPE: PRT
<213> ORGANISM: Artificial Sequence
<220> FEATURE:
<223> OTHER INFORMATION: synthetic

<400> SEQUENCE: 529

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 530
<211> LENGTH: 327
<212> TYPE: PRT
<213> ORGANISM: Artificial Sequence
<220> FEATURE:
<223> OTHER INFORMATION: synthetic

<400> SEQUENCE: 530

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

-continued

```
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Leu Gly Gly Pro Ser Val Phe Leu Phe Pro Pro Lys Pro Lys
            115                 120                 125
Asp Thr Leu Met Ile Ser Arg Thr Pro Glu Val Thr Cys Val Val Val
            130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
                180                 185                 190
Trp Leu Asn Gly Lys Glu Tyr Lys Cys Lys Val Ser Asn Lys Gly Leu
            195                 200                 205
Pro Ser Ser Ile Glu Lys Thr Ile Ser Lys Ala Lys Gly Gln Pro Arg
            210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
            275                 280                 285
Arg Leu Thr Val Asp Lys Ser Arg Trp Gln Glu Gly Asn Val Phe Ser
            290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 531
<211> LENGTH: 88
<212> TYPE: PRT
<213> ORGANISM: Homo sapiens

<400> SEQUENCE: 531

Thr Ala Gly Lys Gln Ser Ser Leu Ile Leu His Gly Ala Asp Phe Ser
1               5                   10                  15
Thr Lys Asp Ala Asp Asn Asp Asn Cys Met Cys Lys Cys Ala Leu Met
            20                  25                  30
Leu Thr Gly Gly Trp Trp Phe Asp Ala Cys Gly Pro Ser Asn Leu Asn
            35                  40                  45
Gly Met Phe Tyr Thr Ala Gly Gln Asn His Gly Lys Leu Asn Gly Ile
            50                  55                  60
Lys Trp His Tyr Phe Lys Gly Pro Ser Tyr Ser Leu Arg Ser Thr Thr
65                  70                  75                  80
Met Met Ile Arg Pro Leu Asp Phe
            85
```

METHODS FOR TREATING MALARIA BY ADMINISTERING AN ANTIBODY THAT SPECIFICALLY BINDS ANGIOPOIETIN-2 (ANG-2)

CROSS-REFERENCE TO RELATED APPLICATIONS

This application is a continuation of U.S. application Ser. No. 13/417,372, filed on Mar. 12, 2012, which is a continuation-in-part of U.S. application Ser. No. 12/843,905, filed on Jul. 27, 2010, which claims the benefit under 35 U.S.C. §119 (e) of U.S. Provisional Application No. 61/229,418, filed on Jul. 29, 2009, and U.S. Provisional Application No. 61/295,194, filed on Jan. 15, 2010, the disclosures of which are herein incorporated by reference in their entireties.

REFERENCE TO A SEQUENCE LISTING

This application includes an electronic sequence listing in a file named "440694-Sequence.txt", created on Dec. 18, 2013 and containing 305,089 bytes, which is hereby incorporated by reference in its entirety for all purposes.

FIELD OF THE INVENTION

The present invention relates to antibodies, and antigen-binding fragments thereof, which are specific for angiopoietin-2 (Ang-2), and uses thereof.

BACKGROUND

Angiogenesis is the biological process whereby new blood vessels are formed. Aberrant angiogenesis is associated with several disease conditions including, e.g., proliferative retinopathies, rheumatoid arthritis and psoriasis. In addition, it is well established that angiogenesis is critical for tumor growth and maintenance. Angiopoietin-2 (Ang-2) is a ligand for the Tie-2 receptor (Tie-2) and has been shown to play a role in angiogenesis. Ang-2 is also referred to in the art as Tie-2 ligand. (U.S. Pat. No. 5,643,755; Yancopoulos et al., 2000, Nature 407:242-248).

Antibodies and other peptide inhibitors that bind to Ang-2 are mentioned in, e.g., U.S. Pat. Nos. 6,166,185; 7,521,053; 7,205,275; 2006/0018909 and 2006/0246071. There is a need in the art for novel Ang-2 modulating agents, including Ang-2 antibodies, that can be used to treat diseases and conditions caused by or exacerbated by angiogenesis.

BRIEF SUMMARY OF THE INVENTION

The present invention provides methods for treating or preventing malaria by administering to a patient in need thereof an antibody that specifically binds Ang-2, or an antigen-binding fragment of an antibody that specifically binds Ang-2.

The present inventors, in view of various lines of evidence and investigation, have recognized a need for new Ang-2 inhibitors, including anti-Ang-2 antibodies which do not bind to or antagonize the related molecule Ang-1. For example, previous studies have demonstrated or suggested a beneficial role for Ang-1 in hemostasis (see, e.g., Li et al., 2001, *Thrombosis and Haemostasis* 85:191-374) and in protecting the adult vasculature against plasma leakage (see, e.g., Thurston et al., 2000, *Nature Medicine* 6:460-463; Thurston et al., 1999, *Science* 286:2511-2514). Thus, the present inventors recognized that, in certain anti-angiogenic therapeutic situations, it may be beneficial to preserve Ang-1 activity. Accordingly, the present invention provides antibodies which bind specifically to Ang-2 but do not substantially bind to Ang-1. The present invention also includes antibodies that block the interaction between Ang-2 and its receptor Tie-2 but do not substantially block the interaction between Ang-1 and Tie-2. The antibodies of the invention are useful, inter alia, for inhibiting the angiogenesis-promoting activities of Ang-2 and for treating diseases and disorders caused by or related to the process of angiogenesis.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions.

In one embodiment, the invention comprises an antibody or antigen-binding fragment of an antibody comprising a heavy chain variable region (HCVR) having an amino acid sequence selected from the group consisting of SEQ ID NO: 2, 18, 22, 26, 42, 46, 50, 66, 70, 74, 90, 94, 98, 114, 118, 122, 138, 142, 146, 162, 166, 170, 186, 190, 194, 210, 214, 218, 234, 238, 242, 258, 262, 266, 282, 286, 290, 306, 310, 314, 330, 334, 338, 354, 358, 362, 378, 382, 386, 402, 406, 410, 426, 430, 434, 450, 454, 458, 474, 478, 482, 498, 502, 506, 514, and 516, or a substantially similar sequence thereof having at least 90%, at least 95%, at least 98% or at least 99% sequence identity. In one embodiment, the antibody or antigen-binding portion of an antibody comprises a HCVR having an amino acid sequence selected from the group consisting of SEQ ID NO: 18, 42, 66, 162, 210, 266, and 434.

In one embodiment, the invention comprises an antibody or antigen-binding fragment of an antibody comprising a light chain variable region (LCVR) having an amino acid sequence selected from the group consisting of SEQ ID NO: 10, 20, 24, 34, 44, 48, 58, 68, 72, 82, 92, 96, 106, 116, 120, 130, 140, 144, 154, 164, 168, 178, 188, 192, 202, 212, 216, 226, 236, 240, 250, 260, 264, 274, 284, 288, 298, 308, 312, 322, 332, 336, 346, 356, 360, 370, 380, 384, 394, 404, 408, 418, 428, 432, 442, 452, 456, 466, 476, 480, 490, 500, and 504, or a substantially similar sequence thereof having at least 90%, at least 95%, at least 98% or at least 99% sequence identity. In one embodiment, the antibody or antigen-binding portion of an antibody comprises a LCVR having an amino acid sequence selected from the group consisting of SEQ ID NO: 20, 44, 68, 164, 212, 274, and 442.

In specific embodiments, the antibody or antigen-binding fragment thereof comprises a HCVR and LCVR (HCVR/LCVR) amino acid sequence pair selected from the group consisting of SEQ ID NO: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/466, 474/476, 478/480, 482/490, 498/500, and 502/504. In one embodiment, the antibody or fragment thereof comprises a HCVR and LCVR selected from the amino acid sequence pairs of SEQ ID NO: 18/20, 42/44, 66/68, 162/164, 210/212, 266/274, and 434/442.

In a next aspect, the invention provides an antibody or antigen-binding fragment of an antibody comprising a heavy chain CDR3 (HCDR3) domain having an amino acid sequence selected from the group consisting of SEQ ID NO: 8, 32, 56, 80, 104, 128, 152, 176, 200, 224, 248, 272, 296, 320, 344, 368, 392, 416, 440, 464, 488, and 512, or a substantially similar sequence thereof having at least 90%, at least 95%, at least 98% or at least 99% sequence identity; and a light chain CDR3 (LCDR3) domain selected from the group consisting of SEQ ID NO: 16, 40, 64, 88, 112, 136, 160, 184, 208, 232, 256, 280, 304, 328, 352, 376, 400, 424, 448, 472, and 496, or a substantially similar sequence thereof having at least 90%, at least 95%, at least 98% or at least 99% sequence identity.

In certain embodiments, the antibody or antigen-binding portion of an antibody comprises a HCDR3/LCDR3 amino acid sequence pair selected from the group consisting of SEQ ID NO: 8/16, 32/40, 56/64, 80/88, 104/112, 128/136, 152/160, 176/184, 200/208, 224/232, 248/256, 272/280, 296/304, 320/328, 344/352, 368/376, 392/400, 416/424, 440/448, 464/472, and 488/496. In one embodiment, the antibody or antigen-binding portion of an antibody comprises a HCDR3/LCDR3 amino acid sequence pair selected from the group consisting of SEQ ID NO: 8/16, 32/40, 56/64, 152/160, 200/208, 272/280, and 440/448. Non-limiting examples of anti-Ang-2 antibodies having these HCDR3/LCDR3 pairs are the antibodies designated H1H685, H1H690, H1H691, H1H696, H1H706, H1M724, and H2M744, respectively.

In a further embodiment, the invention comprises an antibody or fragment thereof further comprising a HCDR1 domain having an amino acid sequence selected from the group consisting of SEQ ID NO: 4, 28, 52, 76, 100, 124, 148, 172, 196, 220, 244, 268, 292, 316, 340, 364, 388, 412, 436, 460, 484, and 508, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 30, 54, 78, 102, 126, 150, 174, 198, 222, 246, 270, 294, 318, 342, 366, 390, 414, 438, 462, 486, and 510, or a substantially similar sequence thereof having at least 90%, at least 95%, at least 98% or at least 99% sequence identity; LCDR1 domain having an amino acid sequence selected from the group consisting of SEQ ID NO: 12, 36, 60, 84, 108, 132, 156, 180, 204, 228, 252, 276, 300, 324, 348, 372, 396, 420, 444, 468, and 492, or a substantially similar sequence thereof having at least 90%, at least 95%, at least 98% or at least 99% sequence identity; and a LCDR2 domain having an amino acid sequence selected from the group consisting of SEQ ID NO: 14, 38, 62, 86, 110, 134, 158, 182, 206, 230, 254, 278, 302, 326, 350, 374, 398, 422, 446, 470, and 494, or a substantially similar sequence thereof having at least 90%, at least 95%, at least 98% or at least 99% sequence identity.

Certain non-limiting, exemplary antibodies and antigen-binding fragments of the invention comprise HCDR1, HCDR2, HCDR3, LCDR1, LCDR2 and LCDR3 domains, respectively, selected from the group consisting of: (i) SEQ ID NO: 4, 6, 8, 12, 14 and 16 (e.g., H1H685); (ii) SEQ ID NO: 28, 30, 32, 36, 38 and 40 (e.g., H1H690); (iii) SEQ ID NO: 52, 54, 56, 60, 62 and 64 (e.g., H1H691); (iv) SEQ ID NO: 148, 150, 152, 156, 158 and 160 (e.g., H1H696); (v) SEQ ID NO: 196, 198, 200, 204, 206 and 208 (e.g., H1H706); (vi) SEQ ID NO: 268, 270, 272, 276, 278 and 280 (e.g., H1M724); and (vii) SEQ ID NO: 436, 438, 440, 444, 446 and 448 (e.g., H2M744).

In a related embodiment, the invention comprises an antibody or antigen-binding fragment of an antibody which specifically binds Ang-2, wherein the antibody or fragment comprises the heavy and light chain CDR domains (i.e., CDR1, CDR2 and CDR3) contained within heavy and light chain variable domain sequences selected from the group consisting of SEQ ID NO: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/466, 474/476, 478/480, 482/490, 498/500, and 502/504. In one embodiment, the antibody or fragment thereof comprises the CDR sequences contained within HCVR and LCVR selected from the amino acid sequence pairs of SEQ ID NO: 18/20, 42/44, 66/68, 162/164, 210/212, 266/274, and 434/442.

In another aspect, the invention provides nucleic acid molecules encoding anti-Ang-2 antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 21, 25, 41, 45, 49, 65, 69, 73, 89, 93, 97, 113, 117, 121, 137, 141, 145, 161, 165, 169, 185, 189, 193, 209, 213, 217, 233, 237, 241, 257, 261, 265, 281, 285, 289, 305, 309, 313, 329, 333, 337, 353, 357, 361, 377, 381, 385, 401, 405, 409, 425, 429, 433, 449, 453, 457, 473, 477, 481, 497, 501, 505, 513, and 515, or a substantially identical sequence having at least 90%, at least 95%, at least 98%, or at least 99% identity thereto. In one embodiment, the antibody or fragment thereof comprises a HCVR encoded by a nucleic acid sequence selected from the group consisting of SEQ ID NO: 17, 41, 65, 161, 209, 265, and 433.

In one embodiment, the invention provides an antibody or fragment thereof comprising a LCVR encoded by a nucleic acid sequence selected from the group consisting of SEQ ID NO: 9, 19, 23, 33, 43, 47, 57, 67, 71, 81, 91, 95, 105, 115, 119, 129, 139, 143, 153, 163, 167, 177, 187, 191, 201, 211, 215, 225, 235, 239, 249, 259, 263, 273, 283, 287, 297, 307, 311, 321, 331, 335, 345, 355, 359, 369, 379, 383, 393, 403, 407, 417, 427, 431, 441, 451, 455, 465, 475, 479, 489, 499, and 503, or a substantially identical sequence having at least 90%, at least 95%, at least 98%, or at least 99% identity thereto. In one embodiment, the antibody or fragment thereof comprises a LCVR encoded by a nucleic acid sequence selected from the group consisting of SEQ ID NO: 19, 43, 67, 163, 211, 273, and 441.

In one embodiment, the invention provides an antibody or antigen-binding fragment of an antibody comprising a HCDR3 domain encoded by a nucleotide sequence selected from the group consisting of SEQ ID NO: 7, 31, 55, 79, 103, 127, 151, 175, 199, 223, 247, 271, 295, 319, 343, 367, 391, 415, 439, 463, 487, and 511, or a substantially identical sequence having at least 90%, at least 95%, at least 98%, or at least 99% identity thereto; and a LCDR3 domain encoded by a nucleotide sequence selected from the group consisting of SEQ ID NO: 15, 39, 63, 87, 111, 135, 159, 183, 207, 231, 255, 279, 303, 327, 351, 375, 399, 423, 447, 471, and 495, or a substantially identical sequence having at least 90%, at least 95%, at least 98%, or at least 99% identity thereto. In one embodiment, the antibody or fragment thereof comprises HCDR3 and LCDR3 sequences encoded by the nucleic acid sequence pairs selected from the group consisting of SEQ ID NO: 7/15, 31/39, 55/63, 151/159, 199/207, 271/279, and 439/447.

In a further embodiment, the antibody or fragment thereof further comprises: a HCDR1 domain encoded by a nucleotide sequence selected from the group consisting of SEQ ID NO: 3, 27, 51, 75, 99, 123, 147, 171, 195, 219, 243, 267, 291, 315, 339, 363, 387, 411, 435, 459, 483, and 507, or a substantially identical sequence having at least 90%, at least 95%, at least 98%, or at least 99% identity thereto; a HCDR2 domain encoded by a nucleotide sequence selected from the group consisting of SEQ ID NO: 5, 29, 53, 77, 101, 125, 149, 173, 197, 221, 245, 269, 293, 317, 341, 365, 389, 413, 437, 461, 485, and 509, or a substantially identical sequence having at least 90%, at least 95%, at least 98%, or at least 99% identity thereto; a LCDR1 domain encoded by a nucleotide sequence selected from the group consisting of SEQ ID NO: 11, 35, 59, 83, 107, 131, 155, 179, 203, 227, 251, 275, 299, 323, 347, 371, 395, 419, 443, 467, and 491, or a substantially identical sequence having at least 90%, at least 95%, at least 98%, or at least 99% identity thereto; and a LCDR2 domain encoded by a nucleotide sequence selected from the group consisting of SEQ ID NO: 13, 37, 61, 85, 109, 133, 157, 181, 205, 229, 253, 277, 301, 325, 349, 373, 397, 421, 445, 469, and 493, or a substantially identical sequence having at least 90%, at least 95%, at least 98%, or at least 99% identity thereto.

In one embodiment, the antibody or fragment thereof comprises the heavy and light chain CDR sequences encoded by the nucleic acid sequences of SEQ ID NO: 17 and 19; SEQ ID NO: 41 and 43; SEQ ID NO: 65 and 67; SEQ ID NO: 161 and 163; SEQ ID NO: 209 and 211; SEQ ID NO: 265 and 273; or SEQ ID NO: 433 and 441.

The invention encompasses anti-Ang-2 antibodies having a modified glycosylation pattern. In some applications, modification to remove undesirable glycosylation sites may be useful. For example, the present invention encompasses modified versions of any antibody set forth herein wherein the modified version lacks a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising a recombinant human antibody or fragment thereof which specifically binds Ang-2 and a pharmaceutically acceptable carrier or diluent. In a related aspect, the invention features a composition which is a combination of an Ang-2 inhibitor and a second therapeutic agent. In one embodiment, the Ang-2 inhibitor is an antibody or fragment thereof. In one embodiment, the second therapeutic agent is any agent that is advantageously combined with an Ang-2 inhibitor. Exemplary agents that may be advantageously combined with an Ang-2 inhibitor include, without limitation, any agent that inhibits or reduces angiogenesis, other cancer therapeutic agents, anti-inflammatory agents, cytokine inhibitors, growth factor inhibitors, anti-hematopoietic factors, non-steroidal anti-inflammatory drugs (NSAIDs), antiviral agents, and antibiotics.

In yet another aspect, the invention provides methods for inhibiting Ang-2 activity using the anti-Ang-2 antibody or antigen-binding portion of the antibody of the invention, wherein the therapeutic methods comprise administering a therapeutically effective amount of a pharmaceutical composition comprising an antibody or antigen-binding fragment of an antibody of the invention. The disorder treated is any disease or condition which is improved, ameliorated, inhibited or prevented by removal, inhibition or reduction of Ang-2 activity. Preferably, the anti-Ang-2 antibody or antibody fragment of the invention is useful to treat any disease or condition caused by, associated with, or perpetuated by the process of angiogenesis. In certain embodiments of the invention, the anti-Ang-2 antibodies or antigen-binding portions thereof are useful for the treatment of cancer. In the context of cancer therapies, the anti-Ang-2 antibodies of the invention or antigen-binding portions thereof can be administered alone or in combination with other anti-cancer therapeutic antibodies, chemotherapeutic agents and/or radiation therapy. In other embodiments of the present invention, the anti-Ang-2 antibodies or antigen-binding fragments thereof are useful for the treatment of one or more eye disorders, e.g., age-related macular degeneration, diabetic retinopathy, etc., and/or one or more inflammatory or infectious diseases.

Other embodiments will become apparent from a review of the ensuing detailed description.

BRIEF DESCRIPTION OF THE FIGURES

FIG. 1 is an alignment of the last 88 C-terminal amino acids of human Ang-2 (residues 409 to 496 of SEQ ID NO:518) with the corresponding amino acid sequence of human Ang-1 (SEQ ID NO:531). Residues that differ between hAng-1 and hAng-2 are indicated by white text and black shading. Asterisks (*) indicate the amino acids of hAng-2 which were shown to interact with human Tie-2 by crystal structure analysis. See Barton et al., *Nat. Struct. Mol. Biol.* 13:524-532 (2006). Triangles (▲) indicate the Tie-2-interacting amino acid positions that differ between hAng-2 and hAng-1.

DETAILED DESCRIPTION

Figure 2:
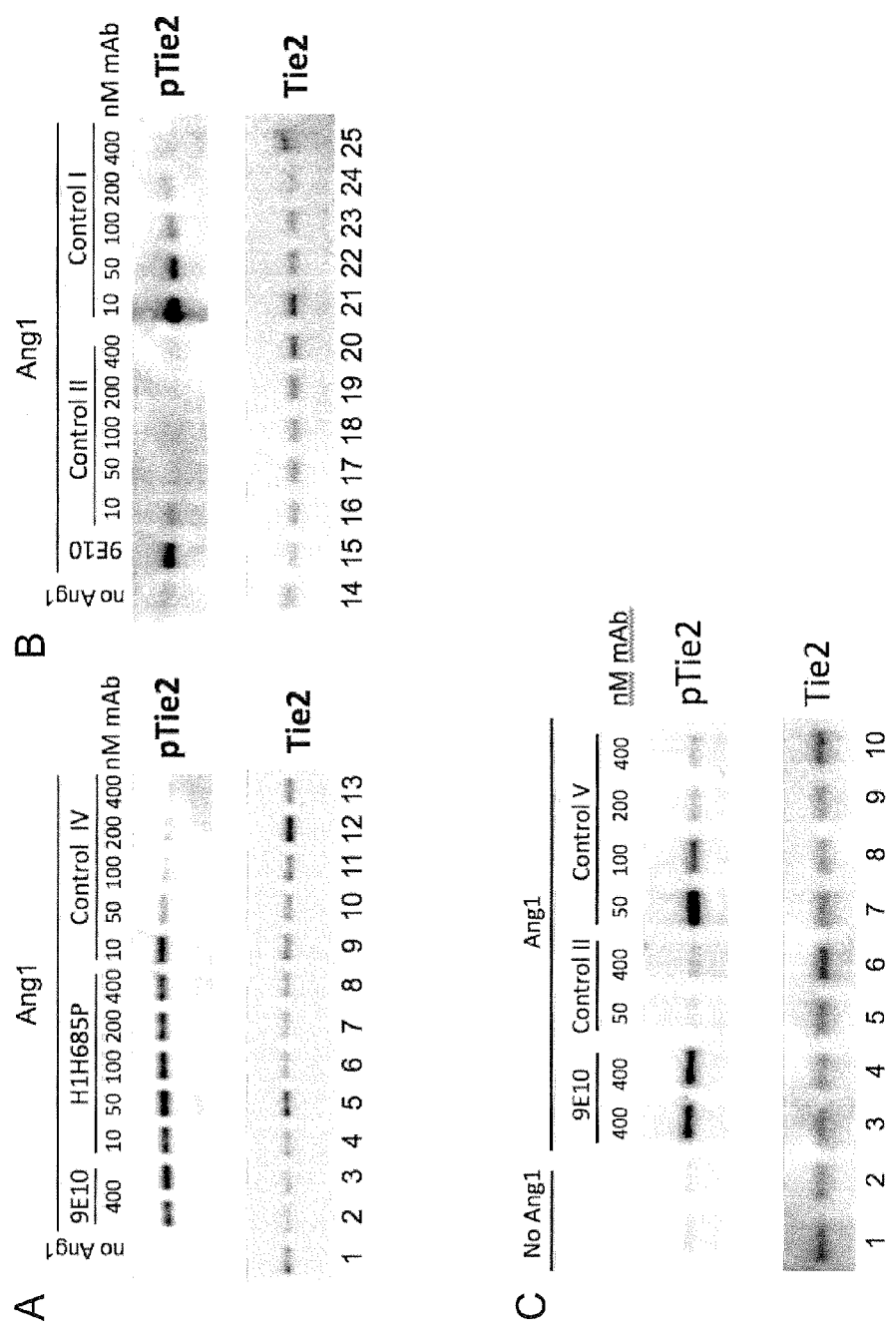
FIG. 2 (Panels A-C) depict the results of Western blots which illustrate the extent to which Ang-2 binding molecules inhibit, or fail to inhibit, Ang-1-induced Tie-2 phosphorylation.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

As used herein, the term "angiopoietin-2" or "Ang-2", unless specified as being from a non-human species (e.g., "mouse Ang-2," "monkey Ang-2," etc.), refers to human Ang-2 or a biologically active fragment thereof (e.g., a fragment of the Ang-2 protein which is capable of inducing angiogenesis in vitro or in vivo). Human Ang-2 is encoded by the nucleic acid sequence shown in SEQ ID NO:517 and has the amino acid sequence of SEQ ID NO:518. The amino acid sequences of mouse and monkey Ang-2 proteins are available from the NCBI protein sequence database under Accession Nos. NP_031452 and BAE89705.1, respectively.

The term "angiopoietin-1" or "Ang-1", unless specified as being from a non-human species (e.g., "mouse Ang-1," "monkey Ang-1," etc.), refers to human Ang-1 or a biologically active fragment thereof. Human Ang-1 has the amino acid sequence as set forth in the NCBI protein sequence database under Accession No. AAB50557. The term "Tie-2" (also referred to in the art as "TEK") unless specified as being from a non-human species (e.g., "mouse Tie-2," "monkey Tie-2," etc.), refers to human Tie-2 or a biologically active fragment thereof. Human Tie-2 has the amino acid sequence as set forth in the NCBI protein sequence database under Accession No. AAA61130.

The term "antibody", as used herein, is intended to refer to immunoglobulin molecules comprising four polypeptide chains, two heavy (H) chains and two light (L) chains interconnected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-Ang-2 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody", as used herein, is intended to refer to an antibody that is substantially free of other antibodies having different antigenic specificities (e.g., an isolated antibody that specifically binds human Ang-2 or a human Ang-2 fragment is substantially free of antibodies that specifically bind antigens other than human Ang-2). The term "specifically binds," or the like, means that an antibody or antigen-binding fragment thereof forms a complex with an antigen that is relatively stable under physiologic conditions. Specific binding can be characterized by a $K_D$ of about $1 \times 10^{-8}$ M or less. Methods for determining whether two molecules specifically bind are well known in the art and include, for example, equilibrium dialysis, surface plasmon resonance, and the like. An isolated antibody that specifically binds human Ang-2 may, however, have cross-reactivity to other antigens, such as Ang-2 molecules from other species. Moreover, an isolated antibody may be substantially free of other cellular material and/or chemicals.

A "neutralizing" or "blocking" antibody, as used herein, is intended to refer to an antibody whose binding to Ang-2 blocks the interaction between Ang-2 and its receptor (Tie-2) and/or results in inhibition of at least one biological function of Ang-2. The inhibition caused by an Ang-2 neutralizing or blocking antibody need not be complete so long as it is detectable using an appropriate assay. Exemplary assays for detecting Ang-2 inhibition are described elsewhere herein.

The fully-human anti-Ang-2 antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are back-mutated to the corresponding germline residue(s) or to a conservative amino acid substitution (natural or non-natural) of the corresponding germline residue(s) (such sequence changes are referred to herein as "germline back-mutations"). A person of ordinary skill in the art, starting with the heavy and light chain variable region sequences disclosed herein, can easily produce numerous antibodies and antigen-binding fragments which comprise one or more individual germline back-mutations or combinations thereof. In certain embodiments, all of the framework and/or CDR residues within the $V_H$ and/or $V_L$ domains are mutated back to the germline sequence. In other embodiments, only certain residues are mutated back to the germline sequence, e.g., only the mutated residues found within the first 8 amino acids of FR1 or within the last 8 amino acids of FR4, or only the mutated residues found within CDR1, CDR2 or CDR3. Furthermore, the antibodies of the present invention may contain any combination of two or more germline back-mutations within the framework and/or CDR regions, i.e., wherein certain individual residues are mutated back to the germline sequence while certain other residues that differ from the germline sequence are maintained. Once obtained, antibodies and antigen-binding fragments that contain one or more germline back-mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-Ang-2 antibodies comprising variants of any of the HCVR, LCVR, and/or CDR amino acid sequences disclosed herein having one or more conservative substitutions. For example, the present invention includes anti-Ang-2 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein. In one embodiment, the antibody comprises an HCVR having the amino acid sequence of SEQ ID NO:18 with 8 or fewer conservative amino acid substitutions. In another embodiment, the antibody comprises an HCVR having the amino acid sequence of SEQ ID NO:18 with 6 or fewer conservative amino acid substitutions. In another embodiment, the antibody comprises an HCVR having the amino acid sequence of SEQ ID NO:18 with 4 or fewer conservative amino acid substitutions. In another embodiment, the antibody comprises an HCVR having the amino acid sequence of SEQ ID NO:18 with 2 or fewer conservative amino acid substitutions. In one embodiment, the antibody comprises an LCVR having the amino acid sequence of SEQ ID NO:20 with 8 or fewer conservative amino acid substitutions. In another embodiment, the antibody comprises an LCVR having the amino acid sequence of SEQ ID NO:20 with 6 or fewer conservative amino acid substitutions. In another embodiment, the antibody comprises an LCVR having the amino acid sequence of SEQ ID NO:20 with 4 or fewer conservative amino acid substitutions. In another embodiment, the antibody comprises an LCVR having the amino acid sequence of SEQ ID NO:20 with 2 or fewer conservative amino acid substitutions.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

Preparation of Human Antibodies

Methods for generating monoclonal antibodies, including fully human monoclonal antibodies are known in the art. Any such known methods can be used in the context of the present invention to make human antibodies that specifically bind to human Ang-2 and which possess one or more of the antigen-binding and/or functional characteristics of any of the exemplary anti-Ang-2 antibodies disclosed herein.

Using VELOCIMMUNE™ technology or any other known method for generating monoclonal antibodies, high affinity chimeric antibodies to Ang-2 are initially isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-Ang-2 antibodies and antibody fragments of the present invention encompass proteins having amino acid sequences that vary from those of the described antibodies, but that retain the ability to bind human Ang-2. Such variant antibodies and antibody fragments comprise one or more additions, deletions, or substitutions of amino acids when compared to parent sequence, but exhibit biological activity that is essentially equivalent to that of the described antibodies. Likewise, the anti-Ang-2 antibody-encoding DNA sequences of the present invention encompass sequences that comprise one or more additions, deletions, or substitutions of nucleotides when compared to the disclosed sequence, but that encode an anti-Ang-2 antibody or antibody fragment that is essentially bioequivalent to an anti-Ang-2 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-Ang-2 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation.

Biological and Therapeutic Characteristics of the Antibodies

In general, the antibodies of the instant invention bind to human Ang-2 with a $K_D$ of less than 100 pM, typically with a $K_D$ of less than 50 pM, and in certain embodiments, with a $K_D$ of less than 40 pM, when measured by binding to antigen either immobilized on solid phase or in solution phase.

In addition, certain exemplary anti-Ang-2 antibodies of the invention may exhibit one or more of the following characteristics: (1) ability to bind to human Ang-2 but not to mouse Ang-2; (2) ability to bind to human Ang-2 and to mouse Ang-2; (3) ability to bind to human Ang-2 but not to human Ang-1, -3 or -4; (4) ability to bind to human Ang-2 but not to mouse Ang-1, -3 or -4; (5) ability to bind to human Ang-2 and to human Ang-1, -3 or -4; (6) ability to bind to human Ang-2 and to mouse Ang-1, -3 or -4; (7) ability to block binding of human Ang-2 to human Tie-2; (8) ability to block binding of human Ang-2 to mouse Tie-2; (9) ability to block binding of mouse Ang-2 to human Tie-2; (10) ability to block binding of mouse Ang-2 to mouse Tie-2; (11) ability to block binding of human Ang-1 to human Tie-2; (12) ability to block binding of human Ang-1 to mouse Tie-2; (13) ability to block binding of mouse Ang-1 to human Tie-2; (14) ability to block binding of mouse Ang-1 to mouse Tie-2; (15) ability to inhibit human Ang-2-induced phosphorylation of human Tie-2; (16) ability to inhibit human Ang-2-induced phosphorylation of mouse Tie-2; (17) ability to inhibit mouse Ang-2-induced phosphorylation of human Tie-2; (18) ability to inhibit mouse Ang-2 induced phosphorylation of mouse Tie-2; (19) ability to inhibit human Ang-1-induced phosphorylation of human Tie-2; (20) ability to inhibit human Ang-1-induced phosphorylation of mouse Tie-2; (21) ability to inhibit mouse Ang-1-induced phosphorylation of human Tie-2; (22) ability to inhibit mouse-Ang-1-induced phosphorylation of mouse Tie-2; (23) ability to inhibit in vivo angiogenesis in an experimental model (e.g., angiogenesis induced by a Matrigel plug containing MCF-7 cells implanted subcutaneously into nude mice); and/or (24) ability to inhibit or decrease tumor volume in a mouse xenograft model.

The present invention also includes antibodies that bind with high affinity to a construct comprising the Ang-2 fibronectin-like domain but lacking the Ang-2 N-terminal coiled-coil domain (such constructs are referred to herein as "Ang-2FD"). Exemplary Ang-2FD constructs include human Ang-2FD (SEQ ID NO:519), mouse Ang-2FD (SEQ ID NO:520), and monkey Ang-2FD (SEQ ID NO:521). The human, mouse and monkey Ang-2FD constructs may be monomeric or dimeric. Ang-2FD constructs may also include other non-Ang-2 amino acid sequences such as a human or mouse Fc domain linked to the Ang-2FD molecules. Another exemplary Ang-2FD construct is referred to herein as "hBA2" (or human "bow-Ang2") which is a tetramer of human Ang-2 fibrinogen-like domains associated with one another via a human or mouse Fc domain to form a bow-tie-like configuration. Typically, hBA2 consists of two Ang-2 dimers, wherein each Ang-2 dimer contains two Ang-2 fibronectin-like domains connected to one another via an Fc domain. Exemplary hBA2 components include the polypeptides designated hBA2-hIgG1 (SEQ ID NO:522) and hBA2-mIgG2a (SEQ ID NO:523). Unexpectedly, certain anti-Ang-2 antibodies of the present invention were found to bind to Ang-2FD constructs with much higher affinities than an known Ang-2 control antibody (see Examples set forth herein).

High affinity binding, in the context of anti-Ang-2 antibody binding to a human or mouse dimeric Ang-2FD construct, means that the anti-Ang-2 antibody binds the human or mouse dimeric Ang-2FD with a $K_D$ of less than 300 pM. For example, anti-Ang-2 antibodies that bind with high affinity to human or mouse dimeric Ang-2FD include antibodies that bind to human or mouse dimeric Ang-2-FD with a $K_D$ of less than 300 pM, less than 250 pM, less than 200 pM, less than 190 pM, less than 180 pM, less than 170 pM, less than 160 pM, less than 150 pM, less than 140 pM, less than 130 pM, less than 120 pM, less than 110 pM, less than 100 pM, less than 90 pM, less than 80 pM, less than 70 pM, less than 60 pM or less than 50 pM, as measured at 25° C. in a surface Plasmon resonance assay.

High affinity binding, in the context of anti-Ang-2 antibody binding to a monkey dimeric Ang-2FD construct, means that the anti-Ang-2 antibody binds the monkey dimeric Ang-2FD with a $K_D$ of less than 500 pM. For example, anti-Ang-2 antibodies that bind with high affinity to monkey dimeric Ang-2FD include antibodies that bind to monkey Ang-2-FD with a $K_D$ of less than 500 pM, less than 450 pM, less than 400 pM, less than 350 pM, less than 300 pM, less than 250 pM, less than 200 pM, less than 190 pM, less than 180 pM, less than 170 pM, less than 160 pM, less than 150 pM, less than 140 pM, less than 130 pM, less than 120 pM, less than 110 pM, less than 100 pM, less than 90 pM, or less than 80 pM, as measured at 25° C. in a surface Plasmon resonance assay.

High affinity binding, in the context of anti-Ang-2 antibody binding to a human monomeric Ang-2FD construct, means that the anti-Ang-2 antibody binds the human monomeric Ang-2FD with a $K_D$ of less than 40 nM. For example, anti-Ang-2 antibodies that bind with high affinity to human monomeric Ang-2FD include antibodies that bind to human monomeric Ang-2-FD with a $K_D$ of less than 40 nM, less than 30 nM, less than 25 nM, less than 20 nM, less than 15 nM, less than 10 nM, less than 9 nM, less than 8 nM, less than 7 nM, less than 6 nM, less than 5 nM, less than 4 nM, less than 3 nM, less than 2 nM, less than 1 nM, less than 0.9 nM, less than 0.8 nM, less than 0.7 nM, or less than 0.6 nM as measured at 25° C. in a surface Plasmon resonance assay.

High affinity binding, in the context of anti-Ang-2 antibody binding to a hBA2 construct, means that the anti-Ang-2 antibody binds the hBA2 with a $K_D$ of less than 80 pM. For example, anti-Ang-2 antibodies that bind with high affinity to hBA2 include antibodies that bind to hBA2 with a $K_D$ of less than 80 pM, less than 75 pM, less than 70 pM, less than 65 pM, less than 60 pM, less than 55 pM, less than 50 pM, less than 45 pM, less than 40 pM, less than 35 pM, less than 30 pM, less than 25 pM, less than 20 pM, less than 18 pM, less than 16 pM, less than 14 pM, or less than 12 pM, as measured at 25° C. in a surface Plasmon resonance assay.

The present invention includes antibodies that bind Ang-2 but do not substantially bind Ang-1. As used herein, an antibody "does not substantially bind Ang-1" if the antibody, when tested for binding to Ang-1 in a surface plasmon resonance assay in which the antibody is captured on a surface and full-length wild-type human Ang-1 at a concentration of about 25 nM is injected over the captured antibody surface at a flowrate of about 60 μl/min for about 3 minutes at 25° C., exhibits a $K_D$ of greater than about 1 nM, e.g., a $K_D$ of greater than about 5 nM, greater than about 10 nM, greater than about 50 nM, greater than about 100 nM, greater than about 150 nM, greater than about 200 nM, greater than about 250 nM, greater than about 300 nM, greater than about 350 nM, greater than about 400 nM, greater than about 450 nM, greater than about 500 nM, or more. (See, e.g., Example 4). In addition, an antibody "does not substantially bind Ang-1" if the antibody fails to exhibit any binding to Ang-1 when tested in such an assay or equivalent thereof.

The present invention also includes antibodies that block the binding of Ang-2 to Tie-2 but do not substantially block the binding of Ang-1 to Tie-2. As used herein, an antibody "does not substantially block the binding of Ang-1 to Tie-2" if, when the antibody is premixed with Ang-1 antigen at a ratio of about 100:1 (antibody:antigen) and allowed to incubate at 25° C. for about 60 minutes and then the equilibrated mixture is tested for binding to Tie-2 by surface plasmon resonance over a Tie-2-coated surface (5 μl/min for 5 min. at 25° C.), the amount of Ang-1 bound to Tie-2 is at least 50% the amount of Ang-1 bound to Tie-2 in the presence of an irrelevant control molecule. (See, e.g., Example 6). For example, if the amount of Ang-1 bound to Tie-2 following preincubation with an antibody is at least about 50%, at least about 55%, at least about 60%, at least about 65%, at least about 70%, at least about 75%, at least about 80%, at least about 85%, at least about 90%, at least about 95%, or about 100% the amount of Ang-1 that binds to Tie-2 following preincubation with an irrelevant control molecule under the above noted experimental conditions, then the antibody is deemed to "not substantially block the binding of Ang-1 to Tie-2."

Moreover, the present invention includes antibodies that block or substantially attenuate a biological activity of Ang-2 (e.g., Ang-2-mediated phosphorylation of Tie-2; Ang-2-induced angiogenesis; etc.) but do not block or substantially attenuate the corresponding biological activity of Ang-1 (e.g., Ang-1-mediated phosphorylation of Tie-2; Ang-1-induced angiogenesis; etc). Assays and tests useful for determining whether an antibody satisfies one or more of the characteristics listed above will be readily known and easily practiced by persons of ordinary skill in the art and/or can be fully ascertained from the present disclosure. For example, the experimental procedures detailed below can be used to determine whether a given antibody binds or does not bind to Ang-2 and/or Ang-1; blocks or does not block binding of Ang-2 and/or Ang-1 to Tie-2; inhibits or does not inhibit Ang-2- and/or Ang-1-mediated phosphorylation of Tie-2; etc.

Epitope Mapping and Related Technologies

To screen for antibodies that bind to a particular epitope (e.g., those which block binding of IgE to its high affinity receptor), a routine cross-blocking assay such as that described "Antibodies," Harlow and Lane (Cold Spring Harbor Press, Cold Spring Harb., NY) can be performed. Other methods include alanine scanning mutants, peptide blots (Reineke (2004) Methods Mol Biol 248:443-63), or peptide cleavage analysis. In addition, methods such as epitope excision, epitope extraction and chemical modification of antigens can be employed (Tomer (2000) Protein Science 9: 487-496).

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the anti-Ang-2 antibodies of the invention into groups of antibodies binding different epitopes.

Anti-Ang-2 antibodies can bind to an epitope within the amino-terminal coiled-coil domain or within the carboxy-terminal fibrinogen-like domain ("FD"). In preferred embodiments of the present invention, the anti-Ang-2 antibodies and antigen binding fragments thereof bind to an epitope within the FD.

The amino acids within the FD of Ang-2 that interact with Tie-2 have been ascertained from crystal structure analysis. See Barton et al., *Nat. Struct. Mol. Biol.* 13:524-532 (May 2006). With regard to antibodies that block the binding of Ang-2 to Tie-2 but do not substantially block binding of Ang-1 to Tie-2 (e.g., H1H685P, see Examples 5 and 6 below), the epitope to which such antibodies bind may include one or more amino acids of Ang-2 that (a) interact with Tie-2 and (b) are non-identical to the corresponding amino acid in Ang-1. (See FIG. 1). Thus, the epitope to which such Ang-2 preferential antibodies bind may include one or more of the following amino acids of hAng-2 (SEQ ID NO:518): S-417; K-432; I-434; N-467; F-469; Y-475; or S-480. For example, the present inventors have discovered that antibodies which interact with amino acids F-469, Y-475, and S-480 of Ang-2 (SEQ ID NO:518) preferentially interact with Ang-2 over Ang-1, and this preferential binding may have therapeutic benefits. Thus, the present invention includes anti-Ang-2 antibodies which specifically bind human angiopoietin-2 (hAng-2) but do not substantially bind hAng-1, wherein the antibodies bind an epitope on hAng-2 (SEQ ID NO:518) comprising amino acids F-469, Y-475, and S-480. Similarly, the present invention includes anti-Ang-2 antibodies which block the binding of hAng-2 to hTie-2 but do not substantially block the binding of hAng-1 to hTie-2, wherein the antibodies bind an epitope on hAng-2 (SEQ ID NO:518) comprising amino acids F-469, Y-475, and S-480.

The present invention includes anti-Ang-2 antibodies that bind to the same epitope as any of the specific exemplary antibodies described herein (e.g., H1H685, H1H690, H1H691, H1H696, H1H706, H1M724 and/or H2M744). Likewise, the present invention also includes anti-Ang-2 antibodies that compete for binding to Ang-2 with any of the specific exemplary antibodies described herein (e.g., H1H685, H1H690, H1H691, H1H696, H1H706, H1M724 and/or H2M744).

One can easily determine whether an antibody binds to the same epitope as, or competes for binding with, a reference anti-Ang-2 antibody by using routine methods known in the art. For example, to determine if a test antibody binds to the same epitope as a reference anti-Ang-2 antibody of the invention, the reference antibody is allowed to bind to an Ang-2 protein or peptide under saturating conditions. Next, the ability of a test antibody to bind to the Ang-2 molecule is assessed. If the test antibody is able to bind to Ang-2 following saturation binding with the reference anti-Ang-2 antibody, it can be concluded that the test antibody binds to a different epitope than the reference anti-Ang-2 antibody. On the other hand, if the test antibody is not able to bind to the Ang-2 molecule following saturation binding with the reference anti-Ang-2 antibody, then the test antibody may bind to the same epitope as the epitope bound by the reference anti-Ang-2 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding with a reference anti-Ang-2 antibody, the above-described binding methodology is performed in two orientations: In a first orientation, the reference antibody is allowed to bind to an Ang-2 molecule under saturating conditions followed by assessment of binding of the test antibody to the Ang-2 molecule. In a second orientation, the test antibody is allowed to bind to an Ang-2 molecule under saturating conditions followed by assessment of binding of the reference antibody to the Ang-2 molecule. If, in both orientations, only the first (saturating) antibody is capable of binding to the Ang-2 molecule, then it is concluded that the test antibody and the reference antibody compete for binding to Ang-2. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Species Selectivity and Species Cross-Reactivity

According to certain embodiments of the invention, the anti-Ang-2 antibodies bind to human Ang-2 but not to Ang-2 from other species. Alternatively, the anti-Ang-2 antibodies of the invention, in certain embodiments, bind to human Ang-2 and to Ang-2 from one or more non-human species. For example, the Ang-2 antibodies of the invention may bind to human Ang-2 and may bind or not bind, as the case may be, to one or more of mouse, rat, guinea pig, hamster, gerbil, pig, cat, dog, rabbit, goat, sheep, cow, horse, camel, cynomolgous, marmoset, rhesus or chimpanzee Ang-2.

Immunoconjugates

The invention encompasses anti-Ang-2 monoclonal antibodies conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, see for example, WO 05/103081).

Multispecific Antibodies

The antibodies of the present invention may be monospecific, bispecific, or multispecific. Multispecific mAbs may be specific for different epitopes of one target polypeptide or may contain antigen-binding domains specific for more than one target polypeptide. See, e.g., Tutt et al. (1991) J. Immunol. 147:60-69. The anti-Ang-2 antibodies of the present invention, or portions thereof, can be linked to or co-expressed with another functional molecule, e.g., another peptide or protein, to form a multispecific molecule. For example, an antibody or fragment thereof can be functionally linked (e.g., by chemical coupling, genetic fusion, noncovalent association or otherwise) to one or more other molecular entities, such as another antibody or antibody fragment, to produce a bispecific or a multispecific antibody with a second binding specificity.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Formulation and Administration

The invention provides therapeutic compositions comprising the anti-Ang-2 antibodies or antigen-binding fragments thereof of the present invention. The therapeutic compositions in of the present invention may further comprise one or more pharmaceutically acceptable carriers, excipients, and other agents that are incorporated into formulations to provide improved transfer, delivery, tolerance, and the like (herein collectively referred to as "pharmaceutically acceptable carriers or diluents"). A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA, 1998, J Pharm Sci Technol 52:238-311.

The dose of antibody may vary depending upon the age and the size of a subject to be administered, target disease, conditions, route of administration, and the like. The preferred dose is typically calculated according to body weight or body surface area. When an antibody of the present invention is used for treating a condition or disease associated with Ang-2 activity in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering Ang-2 antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered, e.g., subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly).

For the treatment of eye disorders, the antibodies and antigen-binding fragments of the invention may be administered, e.g., by eye drops, subconjunctival injection, subconjunctival implant, intravitreal injection, intravitreal implant, sub-Tenon's injection or sub-Tenon's implant.

The pharmaceutical composition can be also delivered in a vesicle, in particular a liposome (see Langer 1990 Science 249:1527-1533; Treat et al. (1989) in Liposomes in the Therapy of Infectious Disease and Cancer, Lopez-Berestein and Fidler (eds.), Liss, New York, pp. 353-365; Lopez-Berestein, ibid., pp. 317-327; see generally ibid.).

In certain situations, the pharmaceutical composition can be delivered in a controlled release system. In one embodiment, a pump may be used (see Langer, supra; Sefton 1987 CRC Crit. Ref. Biomed. Eng. 14:201). In another embodiment, polymeric materials can be used. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The antibodies of the invention are useful, inter alia, for the treatment, prevention and/or amelioration of any disease or disorder associated with Ang-2 activity, including diseases or disorders associated with angiogenesis. The antibodies and antigen-binding fragments of the present invention may be used to treat, e.g., primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the antibodies and antigen-binding fragments of the invention are used to treat one or more of the following cancers: renal cell carcinoma, pancreatic carcinoma, breast cancer, prostate cancer, malignant gliomas, osteosarcoma, colorectal cancer, malignant mesothelioma, multiple myeloma, ovarian cancer, small cell lung cancer, non-small cell lung cancer, synovial sarcoma, thyroid cancer, or melanoma.

The antibodies and antigen-binding fragments of the present invention may also be useful for the treatment of one or more eye disorders. Exemplary eye disorders that can be treated with the antibodies and antigen-binding fragments of the invention include, e.g., age-related macular degeneration, diabetic retinopathy, and other eye disorders associated with choroidal neovascularization, vascular leak, retinal edema and inflammation. Additionally, the anti-Ang-2 antibodies of the invention may be administered as an adjuvant to glaucoma surgery to prevent early hem- and lymphangiogenesis and macrophage recruitment to the filtering bleb after glaucoma surgery, and improve clinical outcome.

In other embodiments of the present invention, the antibodies or antigen-binding fragments are used to treat hypertension, diabetes (including non insulin dependent diabetes mellitus), psoriasis, arthritis (including rheumatoid arthritis), asthma, sepsis, kidney disease and edema associated with injury, stroke or tumor.

Ang-2 expression has been shown to correlate with the severity of various inflammatory and/or infectious diseases (see, e.g., Siner et al., 2009, Shock 31:348-353; Yeo et al., 2008, Proc. Natl. Acad. Sci. (USA):105:17097-17102). Accordingly, the anti-Ang-2 antibodies of the present invention can be used to treat, prevent or ameliorate one or more inflammatory or infectious diseases. Exemplary infectious diseases that can be treated, prevented or ameliorated by administration of the anti-Ang-2 antibodies of the invention include, but are not limited to: viral hemorrhagic fevers (e.g., dengue fever), rickettsial infection, toxic shock syndrome, sepsis, hepatitis C, *Bartonella bacilliformis* infection, leishmaniasis, mycobacterial infection, and Epstein-Barr virus infection.

The present invention, in particular, provides methods for treating or preventing malaria (*Plasmodium falciparum* infection). For example, the methods of the present invention are useful for the treatment or prevention of severe malaria and/or cerebral malaria. The methods according to this aspect of the invention comprise administering to a subject a pharmaceutical composition comprising an anti-Ang-2 antibody of the invention, or an antigen-binding fragment thereof. The methods according to this aspect of the invention can be used to treat a patient who has been infected with a *Plasmodium* species (e.g., *P. falciparum, P. ovale, P. malariae, P. vivax*, etc.) or who has been identified as exhibiting one or more clinical symptoms of malaria, and/or who exhibits one or more biomarkers associated with malaria [see e.g., WO 2012/016333]). The methods of the present invention are also useful for the prevention of malaria. For example, the present invention includes methods comprising administering a pharmaceutical composition comprising an anti-Ang-2 antibody of the invention, or an antigen-binding fragment thereof to a patient who is at risk of being infected or exposed to a parasite associated with malaria.

Combination Therapies

Combination therapies may include an anti-Ang-2 antibody of the invention and, for example, another Ang-2 antagonist (e.g., an anti-Ang-2 antibody, peptibody, or CovXbody such as CVX-060 (see U.S. Pat. No. 7,521,425)). The anti-Ang-2 antibodies of the invention may also be administered together with another anti-angiogenic agent such as, e.g., a VEGF antagonist (e.g., a VEGF-Trap, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib), an anti-DLL4 antibody (e.g., an anti-DLL4 antibody disclosed in US 2009/0142354 such as REGN421), etc.), or with an antagonist of epidermal growth factor receptor (EGFR) (e.g., anti-EGFR antibody or small molecule inhibitor of EGFR activity). Other agents that may be beneficially administered in combination with the anti-Ang-2 antibodies of the invention include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors. The present invention also includes therapeutic combinations comprising any of the anti-Ang-2 antibodies mentioned herein and an inhibitor of one or more of VEGF, DLL4, EGFR, or any of the aforementioned cytokines, wherein the inhibitor is an aptamer, an antisense molecule, a ribozyme, an siRNA, a peptibody, a nanobody or an antibody fragment (e.g., Fab fragment; F(ab')2 fragment; Fd fragment; Fv fragment; scFv; dAb fragment; or other engineered molecules, such as diabodies, triabodies, tetrabodies, minibodies and minimal recognition units). The anti-Ang-2 antibodies of the invention may also be administered in combination with anti-virals, antibiotics, analgesics, corticosteroids and/or NSAIDs. The anti-Ang-2 antibodies of the invention may also be administered as part of a treatment regimen that also includes radiation treatment and/or conventional chemotherapy. When combined with one or more additional agents, the anti-Ang-2 antibodies of the invention may be administered prior to, simultaneous with (e.g., in the same formulation or in separate formulations), or subsequent to the administration of the other agent(s).

Diagnostic Uses of the Antibodies

The anti-Ang-2 antibodies of the present invention may also be used to detect and/or measure Ang-2 in a sample, e.g., for diagnostic purposes. For example, an anti-Ang-2 antibody, or fragment thereof, may be used to diagnose a condition or disease characterized by aberrant expression (e.g., over-expression, under-expression, lack of expression, etc.) of Ang-2. Exemplary diagnostic assays for Ang-2 may comprise, e.g., contacting a sample, obtained from a patient, with an anti-Ang-2 antibody of the invention, wherein the anti-Ang-2 antibody is labeled with a detectable label or reporter molecule. Alternatively, an unlabeled anti-Ang-2 antibody can be used in diagnostic applications in combination with a secondary antibody which is itself detectably labeled. The detectable label or reporter molecule can be a radioisotope, such as $^3H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure Ang-2 in a sample include enzyme-linked immunosorbent assay (ELISA), radioimmunoassay (RIA), and fluorescence-activated cell sorting (FACS).

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Human Ang-2

Human Ang-2 antigen was administered directly, with an adjuvant to stimulate the immune response, to a VELOCIMMUNE® mouse comprising DNA encoding human Immunoglobulin heavy and kappa light chain variable regions. The antibody immune response was monitored by an Ang-2-specific immunoassay. When a desired immune response was achieved splenocytes were harvested and fused with mouse myeloma cells to preserve their viability and form hybridoma cell lines. The hybridoma cell lines were screened and selected to identify cell lines that produce Ang-2-specific antibodies. Using this technique several anti-Ang-2 chimeric antibodies (i.e., antibodies possessing human variable domains and mouse constant domains) were obtained; exemplary antibodies generated in this manner were designated as follows: H1M724, H1M727, H1M728, H2M730, H1M732, H1M737, H2M742, H2M743, H2M744, H1M749, H2M750 and H1M810.

Anti-Ang-2 antibodies were also isolated directly from antigen-positive B cells without fusion to myeloma cells, as described in U.S. 2007/0280945A1. Using this method, several fully human anti-Ang-2 antibodies (i.e., antibodies possessing human variable domains and human constant domains) were obtained; exemplary antibodies generated in this manner were designated as follows: H1H685, H1H690, H1H691, H1H693, H1H694, H1H695, H1H696, H1H704, H1H706 and H1H707.

The biological properties of the exemplary anti-Ang-2 antibodies generated in accordance with the methods of this Example are described in detail in the Examples set forth below.

Example 2

Variable Gene Utilization Analysis

To analyze the structure of antibodies produced, the nucleic acids encoding antibody variable regions were cloned and sequenced. From the nucleic acid sequence and predicted amino acid sequence of the antibodies, gene usage was identified for each heavy chain variable region (HCVR) and light chain variable region (LCVR) (Table 1).

TABLE 1

| Antibody | HCVR | | | LCVR | | Antibody Identifier HCVR/LCVR |
|---|---|---|---|---|---|---|
| | $V_H$ | $D_H$ | $J_H$ | $V_K$ | $J_K$ | SEQ ID NOs |
| H1H685 | 3-13 | 3-16 | 4 | 3-20 | 1 | 2/10 |
| H1H690 | 3-23 | 4-4 | 3 | 3-11 | 4 | 26/34 |
| H1H691 | 3-9 | 4-17 | 6 | 3-20 | 4 | 50/58 |
| H1H693 | 3-23 | 4-4 | 3 | 1-12 | 1 | 74/82 |
| H1H694 | 3-15 | 6-6 | 4 | 1-5 | 1 | 98/106 |
| H1H695 | 3-33 | 5-12 | 6 | 3-15 | 5 | 122/130 |
| H1H696 | 3-11 | 4-17 | 4 | 1-16 | 4 | 146/154 |
| H1H704 | 3-33 | 6-6 | 4 | 1-16 | 5 | 170/178 |
| H1H706 | 3-33 | 3-3 | 3 | 1-16 | 1 | 194/202 |
| H1H707 | 3-33 | 3-3 | 3 | 3-20 | 4 | 218/226 |
| H1M724 | 3-33 | 3-3 | 5 | 1-17 | 4 | 266/274 |
| H1M727 | 1-18 | 3-3 | 6 | 2-28 | 2 | 338/346 |
| H1M728 | 3-7 | 6-19 | 4 | 1-5 | 1 | 290/298 |
| H2M730 | 3-7 | 6-13 | 4 | 1-5 | 1 | 362/370 |
| H1M732 | 3-15 | 1-7 | 4 | 1-17 | 3 | 242/250 |
| H2M742 | 3-23 | 5-5 | 5 | 2-28 | 4 | 386/394 |
| H2M743 | 3-23 | 2-8 | 4 | 1-12 | 4 | 410/418 |
| H2M744 | 1-18 | 4-4 | 5 | 1-12 | 4 | 434/442 |
| H1M749 | 3-33 | 5-5 | 4 | 3-15 | 1 | 314/322 |
| H2M750 | 3-33 | 6-6 | 4 | 1-16 | 4 | 458/466 |
| H1M810 | 3-23 | 3-3 | 3 | 1-12 | 1 | 482/490 |

Table 2 sets forth the heavy and light chain variable region amino acid sequence pairs of selected anti-Ang-2 antibodies and their corresponding antibody identifiers. The N, P and G designations refer to antibodies having heavy and light chains with identical CDR sequences but with sequence variations in regions that fall outside of the CDR sequences (i.e., in the framework regions). Thus, N, P and G variants of a particular antibody have identical CDR sequences within their heavy and light chain variable regions but contain modifications within the framework regions.

TABLE 2

| Name | HCVR/LCVR SEQ ID NOs | Name | HCVR/LCVR SEQ ID NOs | Name | HCVR/LCVR SEQ ID NOs |
|---|---|---|---|---|---|
| H1H685N | 2/10 | H1H685P | 18/20 | H1H685G | 22/24 |
| H1H690N | 26/34 | H1H690P | 42/44 | H1H690G | 46/48 |
| H1H691N | 50/58 | H1H691P | 66/68 | H1H691G | 70/72 |
| H1H693N | 74/82 | H1H693P | 90/92 | H1H693G | 94/96 |
| H1H694N | 98/106 | H1H694P | 114/116 | H1H694G | 118/120 |
| H1H695N | 122/130 | H1H695P | 138/140 | H1H695G | 142/144 |
| H1H696N | 146/154 | H1H696P | 162/164 | H1H696G | 166/168 |
| H1H704N | 170/178 | H1H704P | 186/188 | H1H704G | 190/192 |
| H1H706N | 194/202 | H1H706P | 210/212 | H1H706G | 214/216 |
| H1H707N | 218/226 | H1H707P | 234/236 | H1H707G | 238/240 |
| H1M724N | 266/274 | H1M724P | 282/284 | H1M724G | 286/288 |
| H1M727N | 338/346 | H1M727P | 354/356 | H1M727G | 358/360 |
| H1M728N | 290/298 | H1M728P | 306/308 | H1M728G | 310/312 |
| H2M730N | 362/370 | H2M730P | 378/380 | H2M730G | 382/384 |
| H1M732N | 242/250 | H1M732P | 258/260 | H1M732G | 262/264 |
| H1M737N | 506/X* | H1M737P | 514/X* | H1M737G | 516/X* |
| H2M742N | 386/394 | H2M742P | 402/404 | H2M742G | 406/408 |
| H2M743N | 410/418 | H2M743P | 426/428 | H2M743G | 430/432 |
| H2M744N | 434/442 | H2M744P | 450/452 | H2M744G | 454/456 |
| H1M749N | 314/322 | H1M749P | 330/332 | H1M749G | 334/336 |
| H2M750N | 458/466 | H2M750P | 474/476 | H2M750G | 478/480 |
| H1M810N | 482/490 | H1M810P | 498/500 | H1M810G | 502/504 |

*The amino acid sequence of the LCVR of H1M737 is not shown.

Control Constructs Used in the Following Examples

Various control constructs (anti-Ang-2 antibodies and anti-Ang-2 peptibodies) were included in the following experiments for comparative purposes. The control constructs are designated as follows: Control I: a human anti-Ang-2 antibody with heavy and light chain variable domains having the amino acid sequences of the corresponding domains of "Ab536(THW)," as set forth in US 2006/0018909 (see also Oliner et al., 2004, Cancer Cell 6:507-516); Control II: a peptibody that binds human Ang-2 having the amino acid sequence of "2×Con4(C)," as set forth in U.S. Pat. No. 7,205,275, (see also Oliner et al., 2004, Cancer Cell 6:507-516); Control III: a peptibody that binds human Ang-2 having the amino acid sequence of "L1-7," as set forth in U.S. Pat. No. 7,138,370; Control IV: a human anti-Ang-2 antibody with heavy and light chain variable regions having the amino acid sequences of the corresponding domains of "3.19.3" as set forth in US 2006/0246071; and Control V: a human anti-Ang-2 antibody with heavy and light chain variable regions having the amino acid sequences of the corresponding domains of "MEDI1/5" as set forth in WO 2009/097325. (Not all control constructs were used in every Example). In the tables that follow, the notations "Ab" and "Pb" are included to identify antibody and peptibody controls, respectively (I.a., Control I=Ab; Control II=Pb; Control III=Pb; Control IV=Ab; and Control V=Ab).

Example 3

Antigen Binding Affinity Determination

Equilibrium dissociation constants ($K_D$ values) for the binding of selected purified Ang-2 antibodies to dimeric fibrinogen-like domain of human (SEQ ID NO: 519), mouse (*Mus musculus*; SEQ ID NO: 520) and monkey (*Macca fascicularis*; SEQ ID NO: 521) Ang-2 (Ang-2FD) conjugated to human IgG1 (SEQ ID NO:528) were determined by surface kinetics using a real-time biosensor surface plasmon resonance assay. Antibody was captured on a goat anti-mouse IgG polyclonal antibody surface, a goat anti-human κ polyclonal antibody (Southern Biotech, Birmingham, Ala.) surface or a goat anti-human IgG polyclonal antibody (Jackson Immuno Research Lab, West Grove, Pa.) surface created through direct amine coupling to a BIACORE™ CM5 sensor chip to form a captured antibody surface. Varying concentrations (ranging from 50 nM to 6.25 nM) of protein were injected at 100 μl/min over captured antibody surface for 90 seconds. Antigen-antibody binding and dissociation were monitored in real time at room temperature. Kinetic analysis was performed to calculate $K_D$ and half-life of antigen/antibody complex dissociation. The results are summarized in Table 3 below.

TABLE 3

| Antibody | Dimeric Human Ang-2FD | | Dimeric Mouse Ang-2FD | | Dimeric Monkey Ang-2FD | |
|---|---|---|---|---|---|---|
| | $K_D$ (pM) | $T_{1/2}$ (min) | $K_D$ (pM) | $T_{1/2}$ (min) | $K_D$ (pM) | $T_{1/2}$ (min) |
| H1M724N | 179 | 42.7 | 694 | 16 | 730 | 25.7 |
| H1M728N | 137 | 58.4 | 5650 | 9.9 | 1580 | 69.5 |
| H2M730N | 210 | 47 | — | — | 842 | 36.6 |
| H1M732N | 484 | 35.5 | 1700 | 21.4 | 7330 | 24.1 |
| H1M737N | 251 | 34.5 | 1740 | 6.3 | 3810 | 16 |
| H2M742N | 295 | 38 | 610 | 30.8 | 6170 | 28.5 |
| H2M743N | 154 | 167 | 882 | 195.2 | 234 | 169.2 |
| H2M744N | 98.9 | 109.1 | 143 | 223.1 | 500 | 281.7 |
| H2M749N | 165 | 42.9 | 529 | 25.5 | 1500 | 40.9 |
| H2M750N | 362 | 32.2 | — | — | 1470 | 23 |

The above experiment was repeated using selected purified anti-Ang-2 antibodies cloned onto human IgG1. The results are summarized in Table 4 below.

TABLE 4

| Antibody | Dimeric Human Ang-2FD | | Dimeric Mouse Ang-2FD | | Dimeric Monkey Ang-2FD | |
|---|---|---|---|---|---|---|
| | $K_D$ (pM) | $T_{1/2}$ (min) | $K_D$ (pM) | $T_{1/2}$ (min) | $K_D$ (pM) | $T_{1/2}$ (min) |
| H1H685P | 71.4 | 229.4 | 148 | 128.7 | 99.4 | 177.1 |
| H1H690P | 79 | 126.1 | 91.3 | 105.2 | 55.6 | 195.2 |
| H1H691P | 220 | 38.5 | 220 | 43.8 | 290 | 41 |
| H1H693P | 500 | 37.1 | 446 | 63.7 | 1170 | 17.6 |
| H1H694P | 126 | 265.6 | 237 | 166.5 | 356 | 85.6 |
| H1H695P | 245 | 147 | 347 | 124.2 | 440 | 84.1 |
| H1H696P | 289 | 38.8 | 402 | 37.6 | 354 | 36.6 |
| H1H704P | 331 | 86.1 | 484 | 61.9 | 818 | 33.5 |
| H1H706P | 201 | 50.4 | 357 | 47 | 164 | 53.3 |
| H1H707P | 262 | 26.6 | 328 | 34.4 | 283 | 22.3 |
| H1H724N | 115 | 107 | 185 | 84 | 239 | 173 |
| H1H728N | 162 | 81 | 5760 | 20 | 2000 | 77 |
| H1H730N | 234 | 62 | 97.1 | 90 | 3400 | 87 |
| H1H732N | 386 | 57 | 529 | 51 | 439 | 118 |
| H1H742N | 186 | 65 | 276 | 58 | 683 | 93 |
| H1H743N | 88.2 | 254 | 124 | 233 | 96.5 | 780 |
| H1H744N | 114 | 127 | 158 | 115 | 346 | 164 |
| H1H749N | 118 | 109 | 177 | 96 | 407 | 143 |
| H1H750N | 164 | 127 | 218 | 121 | 199 | 244 |
| Control I (Ab) | 339 | 34.8 | 339 | 47.1 | 537 | 27.1 |

Additional binding experiments were conducted using selected anti-Ang-2 antibodies at two different temperatures to further assess cross-species affinity. Each selected antibody or control construct was captured at a flow rate of 40 μL/min for 1 minute on a goat anti-human kappa polyclonal antibody surface created through direct chemical coupling to a BIACORE™ chip to form a captured antibody surface. Human, monkey and mouse Ang-2FD-Fc at a concentration of 25 nM or 0.78 nM was injected over the captured antibody surface at a flowrate of 60 µL/min for 3 minutes, and antigen-antibody dissociation was monitored in real time for 20 minutes at either 25° C. or 37° C.

Results are summarized in Tables 5 (25° C. binding) and 6 (37° C. binding) below.

TABLE 5

Binding at 25° C.

| Antibody | Dimeric Human Ang-2FD-mFc | | Dimeric Mouse Ang-2FD-hFc | | Dimeric Monkey Ang-2FD-hFc | |
|---|---|---|---|---|---|---|
| | $K_D$ (Molar) | $T_{1/2}$ (min) | $K_D$ (Molar) | $T_{1/2}$ (min) | $K_D$ (Molar) | $T_{1/2}$ (min) |
| H1H685P | 1.17E−11 | 227 | 6.51E−11 | 208 | 2.20E−11 | 275 |
| H1H744N | 1.16E−10 | 23 | 3.85E−10 | 33 | 2.44E−10 | 24 |
| Control I (Ab) | 1.07E−09 | 15 | 1.07E−09 | 15 | 1.03E−09 | 4 |
| Control IV (Ab) | 1.27E−11 | 269 | 4.02E−11 | 289 | 1.55E−11 | 342 |

TABLE 6

Binding at 37° C.

| Antibody | Dimeric Human Ang-2FD-mFc | | Dimeric Mouse Ang-2FD-hFc | | Dimeric Monkey Ang-2FD-hFc | |
|---|---|---|---|---|---|---|
| | $K_D$ (Molar) | $T_{1/2}$ (min) | $K_D$ (Molar) | $T_{1/2}$ (min) | $K_D$ (Molar) | $T_{1/2}$ (min) |
| H1H685P | 2.70E−11 | 60 | 9.39E−11 | 64 | 7.21E−11 | 65 |
| H1H744N | 1.05E−10 | 18 | 2.15E−10 | 26 | 3.20E−10 | 11 |
| Control I (Ab) | — | — | 3.90E−10 | 12 | — | — |
| Control IV (Ab) | 9.91E−12 | 184 | 5.40E−11 | 119 | 4.74E−11 | 107 |

In another experiment, $K_D$ values for selected purified antibodies that bind to a human "bow-Ang-2" tetrameric construct ("hBA2") were determined (using the methods described above). hBA2 consists of two dimers, each dimer containing two Ang-2 fibronectin-like domains connected to one another by a human Fc domain. The amino acid sequence of the dimer constituents of hBA2 is represented by SEQ ID NO:522. The results are summarized in Table 7 below.

TABLE 7

| | hBA2 | |
|---|---|---|
| Antibody | $K_D$ (pM) | $T_{1/2}$ (min) |
| H1H685P | 11.9 | 587.2 |
| H1H690P | 17.9 | 299.3 |
| H1H691P | 106 | 50.6 |
| H1H693P | 299 | 28.7 |
| H1H694P | 68.4 | 111.3 |
| H1H695P | 40.1 | 254.3 |
| H1H696P | 111 | 51.5 |
| H1H704P | 93.9 | 117.7 |
| H1H706P | 79.1 | 63.9 |
| H1H707P | 75.2 | 51.4 |
| H1H724N | 23.3 | 323 |
| H1H728N | 41.8 | 185 |
| H1H730N | 55.9 | 152 |
| H1H732N | 132 | 73 |
| H1H742N | 72.1 | 87 |
| H1H743N | 9.71 | 1118 |

TABLE 7-continued

| | hBA2 | |
|---|---|---|
| Antibody | $K_D$ (pM) | $T_{1/2}$ (min) |
| H1H744N | 17.2 | 442 |
| H1H749N | 32.5 | 235 |
| H1H750N | 36.9 | 284 |
| Control I (Ab) | 83 | 57.5 |

In yet another experiment, $K_D$ values for selected purified antibodies that bind to wild-type human Ang-2 (hAng-2-WT; SEQ ID NO: 518) and the fibrinogen-like domain of human Ang2 (hAng-2FD) were determined (as described above). The results are summarized in Table 8 below.

TABLE 8

| | Monomeric hAng-2FD | | hAng-2-WT | |
|---|---|---|---|---|
| Antibody | $K_D$ (nM) | $T_{1/2}$ (min) | $K_D$ (pM) | $T_{1/2}$ (min) |
| H1M724N | 1.75 | 17.4 | 33.1 | 568 |
| H1M728N | 1.17 | 33.9 | 33.8 | 725 |
| H2M730N | 2.06 | 24.4 | 49.2 | 519 |
| H1M732N | 6.13 | 18.7 | 131 | 333 |
| H1M737N | 2.82 | 13.1 | 59.3 | 282 |
| H2M742N | 4.81 | 18.0 | 67.9 | 437 |
| H2M743N | 0.399 | 156.7 | 14.3 | 2366 |
| H2M744N | 0.475 | 89.3 | 28.9 | 846 |
| H2M749N | 1.38 | 27.9 | 49 | 479 |
| H2M750N | 4.42 | 21.5 | 40.8 | 991 |
| H1H685P | 0.578 | 55 | 47.6 | 1000 |
| H1H691P | 11 | 0.57 | 19.1 | 684.6 |
| H1H690P | 0.594 | 25.16 | 12.4 | 1568 |
| H1H693P | 44.8 | 0.61 | 425 | 100 |
| H1H694P | 7.89 | 9.85 | 158 | 209.7 |
| H1H695P | 1.12 | 50.59 | 31.1 | 1770.7 |
| H1H696P | 38.4 | 0.20 | 40.3 | 642.7 |
| H1H704P | 0.39 | 3.31 | 36.2 | 747.6 |
| H1H706P | 11 | 1.02 | 27.4 | 661.9 |
| H1H707P | 145 | — | 77.1 | 217.4 |
| H1H724N | 2.4 | 13.34 | 22.6 | 895 |
| H1H728N | 1.18 | 5.86 | 43 | 566 |
| H1H730N | 2.84 | 3.44 | 47.5 | 534 |
| H1H732N | 264 | 0.22 | 202 | 264 |
| H1H742N | 486 | 2.29 | 44.9 | 666 |
| H1H743N | 2.35 | 33.03 | 9.48 | 3927 |
| H1H744N | 1.02 | 42.14 | 30.8 | 837 |
| H1H749N | 1.13 | 33.48 | 12.5 | 1833 |
| H1H750N | 0.787 | 30.20 | 9.5 | 4442 |
| Control I (Ab) | 44.5 | 0.03 | 47.6 | 512 |
| Control II (Pb) | 90 | — | 44.7 | 334.8 |

Additional experiments were conducted to measure the binding properties of selected anti-Ang-2 antibodies to monomeric hAng-2FD at 25° C. and 37° C. Each selected antibody or control construct was captured at a flow rate of 40 µL/min for 1 minute on a goat anti-human IgG polyclonal antibody surface created through direct chemical coupling to a BIACORE™ chip to form a captured antibody surface. Human Ang-2FD at a concentration of 500 nM or 7.8 nM was injected over the captured antibody surface at a flowrate of 60 µL/min for 3 minutes, and antigen-antibody dissociation was monitored in real time for 20 minutes at either 25° C. or 37° C.

Results are summarized in Tables 9 (25° C.) and 10 (37° C.) below. N/D=not determined.

TABLE 9

Binding to monomeric hAng-2FD at 25° C.

| | ka (Ms$^{-1}$) | kd (s$^{-1}$) | K$_D$ (Molar) | T½ |
|---|---|---|---|---|
| H1H685P | 2.44E+05 | 7.96E-05 | 3.36E-10 | 145 minutes |
| H1H744N | 2.92E+05 | 1.24E-04 | 4.24E-10 | 93 minutes |
| Control I (Ab) | 4.00E+05 | 5.10E-02 | 1.28E-07 | 14 seconds |
| Control II (Pb) | steady-state | steady-state | 9.00E-08 | steady-state |
| Control III (Pb) | 5.40E+05 | 6.30E-02 | 1.17E-07 | 11 seconds |
| Control IV (Ab) | 2.84E+05 | 3.56E-02 | 1.25E-07 | 19 seconds |

TABLE 10

Binding to monomeric hAng-2FD at 37° C.

| | ka (Ms$^{-1}$) | kd (s$^{-1}$) | K$_D$ (Molar) | T½ |
|---|---|---|---|---|
| H1H685P | 4.06E+05 | 1.39E-04 | 3.42E-10 | 83 minutes |
| H1H744N | 3.86E+05 | 5.48E-04 | 1.42E-09 | 21 minutes |
| Control I (Ab) | steady-state | steady-state | 1.51E-07 | steady-state |
| Control II (Pb) | N/D | N/D | N/D | N/D |
| Control III (Pb) | steady-state | steady-state | 2.94E-07 | steady-state |
| Control IV (Ab) | steady-state | steady-state | 9.40E-08 | steady-state |

As shown in this Example, several of the anti-Ang-2 antibodies generated in accordance with the methods of Example 1 bound to Ang-2 constructs with equivalent or higher affinities than the controls. For example, antibodies H1H685, H1H690, H1H724 and H1H744 bound to dimeric human Ang-2-FD with K$_D$'s of 71.4, 79, 115, and 114 pM, respectively, whereas Control I antibody bound to dimeric human Ang-2-FD with a K$_D$ of 339 pM (see Table 4). Similarly, antibodies H1H685, H1H690, H1H724 and H1H744 bound to human BA2 (a tetrameric Ang-2 fibrinogen-like domain construct) with K$_D$'s of 11.9, 17.9, 23.3 and 17.2 pM, respectively, whereas Control I antibody bound to hBA2 with a K$_D$ of 83 pM (see Table 7). Thus, as compared to the control constructs, many of the antibodies of the invention exhibit enhanced binding to Ang-2. Antibody H1H685P showed especially robust binding properties to Ang-2 as compared to the control constructs.

Example 4

Preferential Binding to Ang-2 Over Ang-1

Binding experiments (plasmon resonance assays) were conducted to ascertain whether selected antibodies bound to both Ang-2 and Ang-1 or if they preferentially bound to Ang-2 only. Each selected antibody or control construct was captured at a flow rate of 40 μL/min for 1 minute on a goat anti-human IgG polyclonal antibody surface created through direct chemical coupling to a BIACORE™ chip to form a captured antibody surface. Full-length wild-type human Ang-1 or Ang-2 at a concentration of 25 nM or 0.78 nM were injected over the captured antibody surface at a flowrate of 60 μL/min for 3 minutes, and antigen-antibody dissociation was monitored in real time for 20 minutes at either 25° C. or 37° C.

The results of these experiments are summarized in Tables 11-14 below. N/D=not determined. "No binding" means that no detectable binding was observed under the particular experimental conditions used in these experiments.

TABLE 11a

Binding to hAng-2-WT at 25° C.

| | ka (Ms$^{-1}$) | kd (s$^{-1}$) | K$_D$ (Molar) | T½ (minutes) |
|---|---|---|---|---|
| H1H685P | 6.59E+05 | 1.60E-05 | 2.42E-11 | 722 |
| H1H744N | 7.65E+05 | 2.57E-05 | 3.35E-11 | 450 |
| Control I (Ab) | 4.74E+05 | 2.26E-05 | 4.76E-11 | 512 |
| Control II (Pb) | 7.73E+05 | 3.45E-05 | 4.47E-11 | 335 |
| Control III (Pb) | 3.29E+05 | 1.98E-05 | 6.01E-11 | 584 |
| Control IV (Ab) | 3.80E+06 | 2.74E-04 | 7.22E-11 | 42 |

TABLE 11b

Binding to hAng-2-WT at 25° C.

| | ka (Ms$^{-1}$) | kd (s$^{-1}$) | K$_D$ (Molar) | T½ (minutes) |
|---|---|---|---|---|
| H1H685P | 1.15E+05 | 8.50E-06 | 7.39E-11 | 1359 |
| Control II (Pb) | 8.30E+04 | 5.41E-05 | 6.52E-10 | 213 |
| Control V (Ab) | 1.12E+05 | 2.66E-05 | 2.73E-10 | 434 |

TABLE 12a

Binding to hAng-1-WT at 25° C.

| | ka (Ms$^{-1}$) | kd (s$^{-1}$) | K$_D$ (Molar) | T½ (minutes) |
|---|---|---|---|---|
| H1H685P | No binding | No binding | No binding | No binding |
| H1H744N | 4.10E+05 | 3.81E-05 | 9.30E-11 | 303 |
| Control I (Ab) | 4.55E+05 | 2.49E-05 | 5.47E-11 | 464 |
| Control II (Pb) | 4.53E+05 | 3.54E-05 | 7.82E-11 | 326 |
| Control III (Pb) | No binding | No binding | No binding | No binding |
| Control IV (Ab) | 6.60E+05 | 1.11E-04 | 1.68E-10 | 105 |

TABLE 12b

Binding to hAng-1-WT at 25° C.

| | ka (Ms$^{-1}$) | kd (s$^{-1}$) | K$_D$ (Molar) | T½ (minutes) |
|---|---|---|---|---|
| H1H685P | No binding | No binding | No binding | No binding |
| Control II (Pb) | 3.04E+05 | 2.51E-05 | 8.26E-11 | 460 |
| Control V (Ab) | 2.75E+05 | 6.68E-05 | 2.43E-10 | 173 |

TABLE 13a

Binding to hAng-2-WT at 37° C.

| | ka (Ms$^{-1}$) | kd (s$^{-1}$) | K$_D$ (Molar) | T½ (minutes) |
|---|---|---|---|---|
| H1H685P | 8.54E+05 | 3.76E-05 | 4.40E-11 | 707 |
| H1H744N | 7.01E+05 | 2.43E-04 | 3.47E-10 | 48 |

TABLE 13b

Binding to hAng-2-WT at 37° C.

| | ka (Ms$^{-1}$) | kd (s$^{-1}$) | K$_D$ (Molar) | T½ (minutes) |
|---|---|---|---|---|
| H1H685P | 1.36E+05 | 2.16E-05 | 1.59E-10 | 535 |
| Control II (Pb) | 3.79E+04 | 1.17E-04 | 3.09E-09 | 99 |
| Control V (Ab) | 9.42E+04 | 7.92E-05 | 8.41E-10 | 146 |

TABLE 14a

Binding to hAng-1-WT at 37° C.

| | ka (Ms$^{-1}$) | kd (s$^{-1}$) | K$_D$ (Molar) | T½ (minutes) |
|---|---|---|---|---|
| H1H685P | No binding | No binding | No binding | No binding |
| H1H744N | 1.47E+06 | 5.20E-05 | 3.12E-11 | 222 |
| Control III (Pb) | No binding | No binding | No binding | No binding |

TABLE 14b

Binding to hAng-1-WT at 37° C.

| | ka (Ms$^{-1}$) | kd (s$^{-1}$) | K$_D$ (Molar) | T½ (minutes) |
|---|---|---|---|---|
| H1H685P | No binding | No binding | No binding | No binding |
| Control II (Pb) | 2.81E+05 | 4.35E-05 | 1.55E-10 | 266 |
| Control V (Ab) | 4.42E+05 | 5.47E-05 | 1.24E-10 | 211 |

These results show that H1H685P is unique among the antibodies tested in this experiment in that it binds with high affinity to Ang-2 but does not bind to Ang-1. The only other construct that exhibits binding to Ang-2 but not to Ang-1 is Control III. It should be emphasized, however, that Control III is a peptibody and that all of the other antibodies tested in this experiment bound to both Ang-2 and Ang-1. The selectivity for Ang-2 binding may confer therapeutic benefits on H1H685P that are not possessed by antibodies that bind to both Ang-2 and Ang-1.

Example 5

Inhibition of Ang-2 Binding to Human Tie-2

Tie-2 is a natural receptor for Ang-2. Anti-Ang-2 antibodies were tested for their ability to block Ang-2 binding to human Tie-2 (hTie-2). hTie-2-mFc (a chimeric construct consisting of human Tie-2 conjugated to mouse IgG; SEQ ID NO:525) was coated onto 96-well plates at a concentration of 2 µg/ml and incubated overnight followed by washing four times in wash buffer (PBS with 0.05% Tween-20). The plate was then blocked with PBS (Irvine Scientific, Santa Ana, Calif.) containing 0.5% BSA (Sigma-Aldrich Corp., St. Louis, Mo.) for one hour at room temperature. In a separate plate, purified anti-Ang-2 antibodies, at a starting concentration of 50 nM, were serially diluted by a factor of three across the plate. Human, mouse or monkey Ang-2FD protein conjugated to human IgG (Ang-2FD-hFc) were added to final concentrations of 2 nM, 8 nM, or 2 nM respectively and incubated for one hour at room temperature. The antibody/Ang-2FD-Fc mixture was then added to the plate containing hTie-2-mFc and incubated for one hour at room temperature. Detection of Ang-2FD-hFc bound to hTie-2-mFc protein was determined with Horse-Radish Peroxidase (HRP) conjugated to a-human IgG antibody (Jackson Immuno Research Lab, West Grove, Pa.) and developed by standard colorimetric response using tetramethylbenzidine (TMB) substrate (BD Biosciences, San Jose, Calif.). Absorbance was read at OD$_{450}$ for 0.1 sec. Percent blocking of Ang-2FD-hFc binding to hTie-2-mFc by 16.67 nM of selected anti-Ang-2 antibodies is shown in Table 15.

TABLE 15

| | Percent Blocking of Ang-2FD Binding to Tie-2 | | |
|---|---|---|---|
| Antibody | Human Ang-2FD-hFc | Mouse Ang-2FD-hFc | Monkey Ang-2FD-hFc |
| H1M724N | 99.5 | 96.6 | 95.2 |
| H1M728N | 98.5 | 83.9 | 97.1 |
| H2M730N | 98.9 | 55.0 | 97.3 |
| H1M732N | 97.7 | 90.9 | 95.8 |
| H1M737N | 99.1 | 95.4 | 90.5 |
| H2M742N | 99.6 | 98.6 | 94.1 |
| H2M743N | 99.6 | 98.4 | 95.1 |
| H2M744N | 99.5 | 98.4 | 95.5 |
| H2M749N | 99.5 | 97.3 | 97.4 |
| H2M750N | 99.4 | 53.7 | 97.4 |
| Control I (Ab) | 94.5 | 90.2 | 96.9 |

In a similar experiment, selected purified anti-Ang-2 antibodies cloned onto human IgG1 were tested for their ability to block Ang-2FD binding to hTie-2 (as described above). Percent blocking of Ang-2FD-hFc binding to hTie-2-mFc by 16.67 nM of selected anti-Ang-2 antibodies is shown in Table 16. NT: not tested.

TABLE 16

| | Percent Blocking of Ang-2FD Binding to Tie-2 | | |
|---|---|---|---|
| Antibody | Human Ang-2FD-hFc | Mouse Ang-2FD-hFc | Monkey Ang-2FD-hFc |
| H1H685P | 93.8 | 97.1 | 62.2 |
| H1H690P | 97.2 | 98.0 | 99.6 |
| H1H691P | 97.4 | 96.7 | 99.8 |
| H1H693P | 73.9 | 63.6 | NT |
| H1H694P | 79.8 | 36.0 | NT |
| H1H695P | 98.4 | 97.6 | NT |
| H1H696P | 98.2 | 94.9 | 99.2 |
| H1H704P | 97.0 | 41.8 | NT |
| H1H706P | 97.1 | 95.9 | 99.8 |
| H1H707P | 95.1 | 93.8 | NT |
| H1H724N | 96.6 | 97.1 | 96.6 |
| H1H744N | 97.9 | 97.6 | 96.2 |
| Control I (Ab) | 97.3 | 82.2 | 98.5 |

In another experiment, selected purified anti-Ang-2 antibodies were tested for their ability to block binding of 20pM biotinylated hBA2 to hTie-2 (as described above). For this experiment, human Tie-2 conjugated to a histidine tag (hTie-2-His; SEQ ID NO:526) was used in a similar fashion to the hTie-2-mFc described above. Antibody concentrations from 5 nM were serially diluted three-fold. An IC$_{50}$ (Inhibitory Concentration) value was generated by calculating the amount of antibody required to block 50% of the signal from the binding of biotin-hBA2 to Tie-2. An average IC$_{50}$ value for each antibody was calculated based on two separate experiments. The results are summarized in Table 17. NB: no blocking observed at 5 nM concentration.

TABLE 17

| Antibody | Biotin - hBA2 Average IC$_{50}$ (pM) |
|---|---|
| H1M724N | 9.72 |
| H1M728N | 14.05 |
| H2M730N | 14.60 |
| H1M732N | 82.17 |
| H1M737N | 13.01 |
| H2M742N | 9.65 |
| H2M743N | 11.01 |
| H2M744N | 11.43 |

TABLE 17-continued

| Antibody | Biotin - hBA2 Average $IC_{50}$ (pM) |
|---|---|
| H2M749N | 6.43 |
| H2M750N | 8.83 |
| Control I (Ab) | 30.23 |
| Control II (Pb) | 7.75 |
| Control III (Pb) | 16.49 |

In a similar experiment, selected purified anti-Ang-2 antibodies cloned onto human IgG1 were tested for their ability to block binding of biotinylated hBA2 to hTie-2 (as described above). The results are shown in Table 18. NB: no blocking observed at 5 nM concentration.

TABLE 18

| Antibody | Biotin - hBA2 $IC_{50}$ (pM) |
|---|---|
| H1H685P | 20 |
| H1H690P | 17 |
| H1H691P | 13 |
| H1H693P | NB |
| H1H694P | NB |
| H1H695P | 59 |
| H1H696P | 22 |
| H1H704P | 56 |
| H1H706P | 8 |
| H1H707P | 22 |
| H1H724N | 4 |
| H1H744N | 25 |

This Example illustrates that several of the anti-Ang-2 antibodies generated in accordance with the methods of Example 1 blocked the interaction between the Ang-2 fibrinogen-like domain and its receptor (TIE-2) to an equivalent or greater extent than the control antibody. For example, antibodies H1H690, H1H691, H1H695, H1H696, H1H704, H1H706, H1H707, H1H724 and H1H744 each caused greater than 95% blocking of human, mouse and monkey Ang-2FD constructs to the TIE-2 receptor, similar to the results observed with the control constructs (see Table 16).

Example 6

Inhibition of Full-Length Ang-2 and Ang-1 Binding to Human Tie-2

Tie-2 is a receptor for Ang-1 as well as Ang-2. Therefore, in the present Example, the ability of certain anti-Ang-2 antibodies to block binding of Ang-2 or Ang-1 to human Tie-2 was measured and compared.

The ELISA experiments shown in this Example were conducted in a similar manner to the experiments of Example 5. Briefly, hTie-2-mFc (a chimeric construct consisting of human Tie-2 conjugated to mouse IgG; SEQ ID NO:525) was coated onto 96-well plates at a concentration of 2 µg/ml and incubated overnight followed by washing four times in wash buffer (PBS with 0.05% Tween-20). The plate was then blocked with PBS (Irvine Scientific, Santa Ana, Calif.) containing 0.5% BSA (Sigma-Aldrich Corp., St. Louis, Mo.) for one hour at room temperature. In a separate plate, purified anti-Ang-2 antibodies and control constructs, at a starting concentration of 300 nM, were serially diluted by a factor of three across the plate. Full-length human Ang-2 or Ang-1 protein conjugated to 6×histidine tag (R&D Systems, Minneapolis, Minn.) were added to a final concentration of 0.6 nM and incubated for one hour at room temperature. The antibody/antigen mixture was then added to the plate containing hTie-2-mFc and incubated for one hour at room temperature. Detection of Ang-2-His or Ang-1-His bound to hTie-2-mFc protein was determined with Horse-Radish Peroxidase (HRP) conjugated to a-Penta-His antibody (Qiagen, Valencia, Calif.) and developed by standard colorimetric response using tetramethylbenzidine (TMB) substrate (BD Biosciences, San Jose, Calif.). Absorbance was read at $OD_{450}$ for 0.1 sec. An $IC_{50}$ (Inhibitory Concentration) value was generated by calculating the amount of antibody required to block 50% of the signal from the binding of human Ang-2 or Ang-1 to Tie-2. The results, expressed in terms of $IC_{50}$ are shown in Table 19, columns (1) and (2). The extent to which the antibodies or control constructs block the hAng-2/Tie-2 interaction relative to the hAng-1/Tie-2 interaction is reflected in the fold difference in $IC_{50}$ shown in column (3); that is, a higher number in column (3) indicates a greater capacity to block the hAng-2/Tie-2 interaction than the hAng-1/Tie-2 interaction.

TABLE 19

| Antibody | (1) Blocking hAng-2 WT to Tie-2 $IC_{50}$ (M) | (2) Blocking hAng-1 WT to Tie-2 $IC_{50}$ (M) | (3) Fold Difference in hAng-1 Blocking $IC_{50}$ Compared to h-Ang-2 Blocking $IC_{50}$* |
|---|---|---|---|
| H1H685P | 1.294E-10 | >3.000E-07 | >2318 |
| H1H744N | 7.871E-11 | 1.872E-07 | 2378 |
| Control I (Ab) | 9.372E-11 | 6.171E-08 | 658 |
| Control II (Pb) | 3.096E-11 | 5.509E-11 | 1.8 |
| Control III (Pb) | 1.626E-10 | >1.000E-06 | >6150 |
| Control IV (Ab) | 1.476E-10 | 4.252E-09 | 28.8 |

*Calculated by dividing the hAng-1 blocking $IC_{50}$ (column 2) by the hAng-2 blocking $IC_{50}$ (column 1).

In an effort to further assess the ability of selected anti-hAng-2 antibodies to block the binding of Ang-1 to Tie-2, a biosensor surface plasmon resonance experiment was conducted. In this experiment, a human Tie-2 full-length extracellular domain construct (hTie-2-mFc-ecto) was amine-coupled on a BIACORE™ chip to create a receptor coated surface. Selected anti-hAng-2 antibodies and control constructs, at 1 µM (100-fold excess over antigen), were pre-mixed with 10 nM of hAng-1-WT, followed by 60 minutes incubation at 25° C. to allow antibody-antigen binding to reach equilibrium to form equilibrated solutions. The equilibrated solutions were injected over the receptor surfaces at 5 µL/min for 5 minutes at 25° C. Changes in resonance units (RU) due to the binding of the hAng-1-WT to hTie-2-mFc were determined. An irrelevant peptibody construct with no binding to hAng-1 was included in this experiment to establish the 0% blocking baseline, and a human Tie-2-mFc construct was used as a positive control for blocking. The amount of Ang-1 bound to Tie-2 following antibody preincubation, expressed as a percentage of the amount of Ang-1 bound to Tie-2 following negative control preincubation, is shown in Table 20. (A greater amount of Ang-1 binding to Tie-2 signifies a lower degree of antibody blocking).

TABLE 20

| Antibody | RU (average) | Percent of Negative Control Binding |
|---|---|---|
| Negative Control (irrelevant peptibody) | 169 | 100 |

TABLE 20-continued

| Antibody | RU (average) | Percent of Negative Control Binding |
|---|---|---|
| hTie-2-mFc | 71 | 42 |
| H1H685P | 137 | 81 |
| H1H744N | 57 | 34 |
| H1H691P | 117 | 69 |
| H1H706P | 140 | 83 |
| H1H724N | 57 | 34 |
| Control I (Ab) | 48 | 28 |
| Control II (Pb) | 48 | 28 |
| Control III (Pb) | 160 | 95 |

The foregoing experiment was repeated using different amounts of Ang-2 blockers and controls. In particular, a human Tie-2 full-length extracellular domain construct (hTie-2-mFc-ecto) was amine-coupled on a BIACORE™ chip to create a receptor-coated surface. Selected anti-hAng-2 antibodies and control constructs (50 or 150 nM) were mixed with hAng-2-WT (25 nM) followed by 60 minutes incubation at 25° C. to allow antibody-antigen binding to reach equilibrium. The equilibrated solutions were injected over the receptor surfaces at 10 μL/min for 5 minutes at 25° C. To evaluate the ability of the selected anti-hAng-2 antibodies to block Ang-1-WT binding to hTie-2, a similar procedure was followed except the antibodies were tested at three concentrations (50, 100 or 1000 nM) and incubated with 10 nM of hAng-1-WT. Changes in resonance units (RU) due to the binding of the Ang-2-WT or hAng-1-WT to hTie-2-mFc were determined. An irrelevant antibody with no binding to either angiopoietin was included in these experiments to establish the 0% blocking baseline, and a human Tie-2-mFc construct was used as a positive control for blocking. Results are summarized in Tables 21 (hAng-1 applied to a hTie-2 surface) and 22 (hAng-2 applied to a hTie-2 surface).

TABLE 21

(hAng-1 WT)

| | Amount of Antibody or Control | | | | | |
|---|---|---|---|---|---|---|
| | 50 nM | | 100 nM | | 1000 nM | |
| Antibody | Specific Bound RU | Percent of Neg. Ctrl Binding | Specific Bound RU | Percent of Neg. Ctrl Binding | Specific Bound RU | Percent of Neg. Ctrl Binding |
| Negative Control (irrelevant antibody) | 316 | 100 | 307 | 100 | 276 | 100 |
| hTie-2-mFc | 70 | 22 | 39 | 13 | −47 | 0 |
| H1H685P | 299 | 95 | 291 | 95 | 289 | 105 |
| Control II (Pb) | 8 | 2.5 | 4 | 1.3 | −1 | 0 |
| Control V (Ab) | 150 | 48 | 114 | 37 | 29 | 11 |

TABLE 22

(hAng-2 WT)

| | Amount of Antibody or Control | | | |
|---|---|---|---|---|
| | 50 nM | | 150 nM | |
| Antibody | Specific Bound RU | Percent of Neg. Ctrl Binding | Specific Bound RU | Percent of Neg. Ctrl Binding |
| Negative Control (irrelevant antibody) | 281 | 100 | 278 | 100 |
| hTie-2-mFc | 97 | 35 | 82 | 30 |
| H1H685P | 12 | 4.3 | 12 | 4.3 |
| Control II (Pb) | 10 | 3.6 | 10 | 3.6 |
| Control V (Ab) | 12 | 4.3 | 12 | 4.3 |

The results obtained from these experiments are in agreement with previous results which showed that H1H685P preferentially binds to Ang-2 over Ang-1 (see Example 4). In particular, the results from this Example show that several anti-Ang-2 antibodies (e.g., H1H685P and H1H706P) do not significantly block the binding of human Ang-1 to human Tie-2, even though, in other experiments, it was demonstrated that these antibodies potently blocked the interaction between Ang-2 and Tie-2 (see Example 5, Table 16). Moreover, in these experiments none of the control constructs, except for the Control III peptibody, exhibited the same degree of preferential binding/blocking of Ang-2 over Ang-1 as the exemplary anti-Ang-2 antibodies of the present invention, such as H1H685P.

Example 7

Inhibition of Ang-2-Mediated Tie-2 Phosphorylation by Anti-Ang-2 Antibodies

The inventors of the present invention have demonstrated that Ang-2 expression can be induced in human umbilical vein endothelial cells (HUVECs) by the transcription factor FOXO1 (Daly et al. 2006 PNAS 103:15491). Further, the inventors have shown that infection of HUVECs with an adenovirus encoding FOXO1 results in expression and secretion of Ang-2, followed by activation of Tie-2 phosphorylation (Daly et al. 2006 PNAS 103:15491).

Anti-Ang-2 antibodies were tested for their ability to inhibit Tie-2 phosphorylation. Briefly, $7 \times 10^5$ HUVECs (Vec Technologies, Rensselaer, N.Y.) were plated in 6 cm cell culture dishes in 3.5 ml of MCDB131 Complete medium (Vec Technologies, Rensselaer, N.Y.). The following day, the cells were washed with Opti-MEM (Invitrogen Corp., Carlsbad, Calif.) and fed with 2 ml of Opti-MEM. Recombinant adenoviruses encoding either green fluorescent protein (GFP; control) or human FOXO1 (Daly et al. 2004 Genes Dev. 18:1060) were added to the cells at a concentration of 10 pfu/cell and incubated for four hours. Cells were then washed with MCDB131 and fed with 2 ml of MCDB131 containing anti-Ang-2 antibodies at a concentration of 0.5 μg/ml. At twenty hours post infection, cells were lysed and subjected to Tie-2 immunoprecipitation as described by Daly et al., *Proc. Natl. Acad. Sci. USA* 103:15491-15496 (2006). Immunoglobulin was collected on protein A/G beads (Santa Cruz Biotechnology, Santa Cruz, Calif.) for one hour. Beads were washed with cold lysis buffer and resuspended in SDS sample buffer for analysis by western blot with antibodies specific for phosphotyrosine (Millipore, Billerica, Mass.) or Tie-2. Signals were detected using HRP-conjugated secondary antibodies and ECL reagents (GE Healthcare, Piscataway, N.J.). X-Ray films were scanned and the phospho-Tie-2 and Tie-2 signals were quantified using ImageJ software. The phospho-Tie-2/Tie-2 ratios were used to determine the % inhibition for each anti-Ang-2 antibody (i.e. Percent inhibition=Reduction in phospho-Tie-2/Tie-2 as compared to control). For example, a reduction in Tie-2 phosphorylation to the level observed in the control sample is considered to be 100% inhibition. Relative inhibition (+, ++, +++) for each anti-Ang-2 antibody tested according to the percent inhibition observed (25-50%, 50-75%, 75-100%, respectively) is shown in Table 23.

TABLE 23

| Antibody | Inhibition of Tie-2 phosphorylation |
|---|---|
| H1H685P | +++ |
| H1H690P | +++ |
| H1H691P | +++ |
| H1H693P | +++ |
| H1H694P | ++ |
| H1H695P | +++ |
| H1H696P | +++ |
| H1H704P | +++ |
| H1H706P | +++ |
| H1H707P | +++ |
| H1M724N | +++ |
| H1M728N | ++ |
| H1M732N | ++ |
| H1M742N | ++ |
| H1M743N | +++ |
| H1M744N | +++ |
| H1M749N | ++ |
| H1M750N | +++ |
| Control I (Ab) | + |
| Control II (Pb) | +++ |

As demonstrated in this Example, the anti-Ang-2 antibodies generated in accordance with the methods of Example 1 inhibited Tie-2 phosphorylation to a greater extent than the Control I antibody. Especially robust inhibition was observed with antibodies H1H685, H1H690, H1H691, H1H693, H1H695, H1H696, H1H704, H1H706, H1H707, H1M724, H1M744 and H1M750.

Example 8

Inhibition of Ang-1-Mediated Tie-2 Phosphorylation

As shown in the previous Example, Ang-2 can mediate the phosphorylation of Tie-2. Ang-1 is also capable of promoting Tie-2 phosphorylation. In the present Example, the ability of selected anti-Ang-2 antibodies to block Ang-1-mediated phosphorylation of Tie-2 was assessed.

EA.hy926 cells (Edgell et al., *Proc. Natl. Acad. Sci. USA* 80:3734-3737 (1983)) were plated at 5×10$^6$ cells per 10 cm dish in 10 ml DMEM with 10% FBS, HAT, L-glutamine and penicillin/streptomycin. After 24 hours, cells were serum-starved for 1 hour in 10 ml DMEM+1 mg/ml BSA. Cells were then stimulated for 10 minutes with 500 ng/ml of recombinant human Ang-1 (R&D Systems) in the presence of either an irrelevant isotype control antibody ("9E10") at 400 nM or the anti-Ang-2 antibody H1H685P, or control agents (Control I, Control II, Control IV, or Control V) at concentrations ranging from 10 to 400 nM.

Following incubation, cells were lysed and Tie-2 was immunoprecipitated as described by Daly et al., *Proc. Natl. Acad. Sci. USA* 103:15491-15496 (2006). Immune complexes were collected by incubation with protein A/G beads (Santa Cruz Biotechnology, Santa Cruz, Calif.) for 60 min. Beads were washed with cold lysis buffer and bound proteins were eluted by heating in SDS sample buffer. Samples were then subjected to Western blot analysis with monoclonal antibodies against Tie-2 or phosphotyrosine (clone 4G10, Millipore, Billerica, Mass.). Results are shown in FIG. 2.

Signals were detected using HRP-conjugated secondary antibodies and ECL reagents (GE Healthcare, Piscataway, N.J.). X-ray films were scanned and the phospho-Tie-2 and Tie-2 signals were quantified using ImageJ software. The phospho-Tie-2/Tie-2 ratios were used to determine the % inhibition for each antibody or peptibody. Percent inhibition=reduction in phospho-Tie-2/Tie-2 as compared to the control sample (400 nM isotype control antibody).

In the presence of the control antibody 9E10, Ang-1 strongly activated Tie-2 phosphorylation (FIG. 2, panel A—compare lanes 2 and 3 vs lane 1). All of the control agents that were tested significantly inhibited Tie-2 phosphorylation, with complete inhibition occurring at 50 nM for Control II (FIG. 2, panel B—lane 17), 100 nM for Control IV (FIG. 2, panel A—lane 11) and 200 nM for Control I (FIG. 2, panel B—lane 24) and Control V (FIG. 2, panel C—lane 9). By contrast, H1H685P had no significant inhibitory effect even at 400 nM (FIG. 2, panel A—lanes 4-8), These results provide additional confirmation of the specificity of H1H685P for Ang-2 over Ang-1.

Example 9

Inhibition of Tumor Growth by Anti-Ang-2 Antibodies

The effect of selected purified anti-Ang-2 antibodies on tumor growth was determined using two tumor cell lines.

PC3 (Human prostate cancer cell line) Briefly, 5×10$^6$ PC3 cells in 100 µl of growth factor-reduced Matrigel (BD Biosciences) were injected subcutaneously into the flanks of 6-8 week old male NCr nude mice (Taconic, Hudson, N.Y.). After tumor volumes reached an average of about 200 mm$^3$, mice were randomized into groups for treatment. Mice in each treatment group were administered an anti-Ang-2 antibody, Fc protein, or control construct, at a concentration of 10 mg/kg via intraperitoneal injection twice per week for approximately three weeks (Table 24) or at concentrations of 2.5, 12.5, or 25 mg/kg via subcuataneous injection twice per week for approximately three weeks (Table 25). Tumor volumes were measured twice per week over the course of the experiment and tumor weights were measured upon excision of tumors at the conclusion of the experiment. Averages (mean+/−standard deviation) of tumor weight and growth were calculated for each treatment group. Percent decrease of tumor weight and growth were calculated from comparison to Fc protein measurements. Results are summarized in Tables 24 and 25.

TABLE 24

| Antibody | Avg Tumor Weight (g) | % Decrease in Tumor Weight | Avg Tumor Growth (mm$^3$) | % Decrease in Tumor Growth |
|---|---|---|---|---|
| Fc protein | 0.66 ± 0.26 | — | 509 ± 213 | — |
| Control I (Ab) | 0.47 ± 0.23 | 29 | 300 ± 242 | 41 |
| H1H724N | 0.55 ± 0.07 | 17 | 392 ± 169 | 23 |
| H1H744N | 0.43 ± 0.20 | 35 | 259 ± 212 | 49 |
| H1H685P | 0.44 ± 0.12 | 33 | 305 ± 143 | 40 |
| H1H691P | 0.59 ± 0.07 | 11 | 485 ± 141 | 5 |
| H1H706P | 0.52 ± 0.14 | 21 | 329 ± 125 | 35 |

TABLE 25

| Antibody | Avg Tumor Growth (mm³) | % Decrease in Tumor Growth |
| --- | --- | --- |
| Fc protein | 1031 ± 485 | — |
| Control II (Pb) (2.5 mg/kg) | 356 ± 196 | 65 |
| Control II (Pb) (12.5 mg/kg) | 360 ± 162 | 65 |
| Control II (Pb) (25 mg/kg) | 527 ± 218 | 49 |
| H1H685P (2.5 mg/kg) | 308 ± 274 | 70 |
| H1H685P (12.5 mg/kg) | 550 ± 150 | 47 |
| H1H685P (25 mg/kg) | 413 ± 208 | 60 |

As shown above, antibodies H1H744N and H1H685P demonstrated especially marked anti-tumor activity in the PC3 mouse tumor model as compared to the control constructs.

The results of similar experiments using the PC3 mouse tumor model and different experimental antibodies (dosed at 2 mg/kg, twice per week) are shown in Tables 26 and 27.

TABLE 26

| Antibody | Avg Tumor Weight (g) | % Decrease in Tumor Weight | Avg Tumor Growth (mm³) | % Decrease in Tumor Growth |
| --- | --- | --- | --- | --- |
| Fc protein | 0.626 ± 0.156 | — | 356 ± 93 | — |
| Control I (Ab) | 0.347 ± 0.093 | 45 | 250 ± 145 | 30 |
| H2M742N | 0.407 ± 0.076 | 35 | 220 ± 102 | 38 |
| H2M743N | 0.372 ± 0.122 | 41 | 179 ± 169 | 50 |

TABLE 27

| Antibody | Avg Tumor Weight (g) | % Decrease in Tumor Weight | Avg Tumor Growth (mm³) | % Decrease in Tumor Growth |
| --- | --- | --- | --- | --- |
| Fc protein | 0.552 ± 0.211 | — | 473 ± 202 | — |
| H1M749N | 0.383 ± 0.275 | 31 | 220 ± 261 | 54 |
| H1M750N | 0.348 ± 0.128 | 37 | 227 ± 195 | 52 |

COLO 205 (Human Colorectal Adenocarcinoma Cell Line)

Briefly, 2×10⁶ COLO 205 cells in 100 µl of serum-free medium were injected subcutaneously into the flank of 6-8 week old male NCr nude mice (Taconic, Hudson, N.Y.). After tumor volumes reached an average of about 150 mm³, mice were randomized into groups for treatment with antibody or Fc protein. Mice in each treatment group were administered an anti-Ang-2 antibody or Fc protein at a concentration of 4 mg/kg via intraperitoneal injection twice per week for approximately two weeks. Tumor volumes were measured twice per week over the course of the experiment and tumor weights were measured upon excision of tumors at the conclusion of the experiment. Averages (mean+/−standard deviation) of tumor weight and growth were calculated for each treatment group. "Avg. Tumor Growth" represents the average growth from the time of treatment initiation (when tumors were approximately 150 mm³). Percent decrease of tumor weight and growth are calculated from comparison to Fc protein measurements. Results are summarized in Table 28.

TABLE 28

| Antibody | Avg Tumor Weight (g) | % Decrease in Tumor Weight | Avg Tumor Growth (mm³) | % Decrease in Tumor Growth |
| --- | --- | --- | --- | --- |
| Fc protein | 0.847 ± 0.180 | — | 731 ± 249 | — |
| Control I (Ab) | 0.503 ± 0.090 | 41 | 367 ± 121 | 50 |
| Control II (Pb) | 0.608 ± 0.085 | 28 | 492 ± 82 | 33 |
| H1M724N | 0.531 ± 0.103 | 37 | 336 ± 125 | 54 |
| H2M742N | 0.576 ± 0.057 | 32 | 427 ± 92 | 42 |
| H2M744N | 0.491 ± 0.051 | 42 | 409 ± 162 | 44 |
| H1M749N | 0.603 ± 0.142 | 29 | 449 ± 169 | 39 |

A similar experiment was carried out to assess the effect of H1H685P, in particular, on COLO 205 tumor growth. Briefly, 2×10⁶ COLO 205 cells in 100 µl of serum-free medium were implanted subcutaneously into the right hind flank of 9-11 week-old male SCID CB17 mice. When the tumors reached ~125 mm³, mice were randomized into 5 groups (n=7-8 mice/group) and treated twice per week with Fc protein (15 mg/kg), H1H685P (5 or 25 mg/kg) or Control II (5 or 25 mg/kg) for a period of 19 days. Tumor volumes were measured twice per week over the course of the experiment and tumor weights were measured upon excision of tumors at the end of the experiment. Averages of tumor weight and growth from the beginning of treatment were calculated for each group. Percent decrease of tumor weight and growth are calculated from comparison to the Fc control group. The results are shown in Table 29.

TABLE 29

| Antibody | Antibody Concentration | Avg Tumor Weight (g) | % Decrease in Tumor Weight | Avg Tumor Growth (mm³) | % Decrease in Tumor Growth |
| --- | --- | --- | --- | --- | --- |
| Fc protein | 25 mg/kg | 0.800 ± 0.108 | — | 675 ± 93 | — |
| Control II (Pb) | 5 mg/kg | 0.481 ± 0.091 | 40 | 288 ± 85 | 57 |
| Control II (Pb) | 25 mg/kg | 0.393 ± 0.136 | 51 | 267 ± 155 | 60 |
| H1H685P | 5 mg/kg | 0.458 ± 0.125 | 43 | 370 ± 114 | 45 |
| H1H685P | 25 mg/kg | 0.430 ± 0.139 | 46 | 295 ± 160 | 56 |

As with the PC3 mouse tumor model, several of the antibodies of the invention, including H1H685P, exhibited substantial anti-tumor activities in the COLO 205 mouse model that were at least equivalent to the anti-tumor activities exhibited by the control molecules.

Example 10

Inhibition of Tumor Growth and Perfusion by a Combination of an Anti-Ang-2 Antibody and a VEGF Inhibitor To determine the effect of combining an anti-Ang-2 antibody with a VEGF inhibitor on the growth of COLO 205 xenografts, $2 \times 10^6$ cells were implanted subcutaneously into the right hind flank of 6-8 week-old female SCID mice. When the tumors reached an average volume of ~350 mm$^3$, mice were randomized into 4 groups (n=6 mice/group) and treated with: human Fc protein (7.5 mg/kg), H1H685P (5 mg/kg), VEGF Trap (see U.S. Pat. No. 7,087,411) (2.5 mg/kg) or the combination of H1H685P+VEGF Trap. Mice were given a total of 3 doses over 10 days of treatment. Tumor volumes were measured twice per week over the course of the experiment. Averages of tumor growth from the start of treatment (mean+/−standard deviation) were calculated for each treatment group. Percent decrease of tumor growth was calculated from comparison to the Fc control group. The results are shown in Table 30. Note that in the VEGF Trap and in the H1H685P+VEGF Trap groups the average tumor size was smaller at the end of treatment than at the beginning, i.e., tumor regression was observed.

TABLE 30

| Antibody | Avg Tumor Growth (mm$^3$) | % Decrease in Tumor Growth |
|---|---|---|
| Fc protein | 366 ± 65 | — |
| H1H685P | 74 ± 77 | 80 |
| VEGF Trap | −62 ± 44 | 117 |
| H1H685P + VEGF Trap | −221 ± 131 | 160 |

The results of this experiment demonstrate that the combination of H1H685P+VEGF Trap causes a decrease in tumor growth that is greater than the percent decrease in tumor growth caused by either component alone.

To provide additional evidence of combination efficacy, the effect of the H1H685P+VEGF Trap combination on the growth of MMT tumors was assessed. $0.5 \times 10^6$ MMT cells were implanted subcutaneously into the right hind flank of 6-8 week-old female SCID mice. When the tumors reached an average volume of ~400 mm$^3$, mice were randomized into 4 groups (n=11 mice/group) and treated with: human Fc protein (17.5 mg/kg), H1H685P (12.5 mg/kg), VEGF Trap (5 mg/kg) or the combination of H1H685P+VEGF Trap. The Fc and H1H685P groups were given 3 doses over 9 days. The VEGF Trap and combination groups were given 4 doses over 12 days. Tumor volumes were measured twice per week over the course of the experiment and tumor weights were measured upon excision of tumors at the end of the experiment (due to their large size, tumors from the Fc and H1H685P groups were collected 3 days before tumors from the VEGF Trap and combination groups). Averages (mean+/−standard deviation) of tumor growth from the beginning of treatment and of tumor weight were calculated for each group. Percent decrease of tumor weight and growth are calculated from comparison to the Fc control group. The results are shown in Table 31.

TABLE 31

| Antibody | Avg Tumor Weight (g) | % Decrease in Tumor Weight | Avg Tumor Growth (mm$^3$) | % Decrease in Tumor Growth |
|---|---|---|---|---|
| Fc protein | 1.591 ± 0.265 | — | 1337 ± 273 | — |
| H1H685P | 1.409 ± 0.314 | 11 | 1135 ± 306 | 15 |
| VEGF Trap | 0.889 ± 0.141 | 44 | 536 ± 179 | 60 |
| H1H685P + VEGF Trap | 0.599 ± 0.066 | 62 | 215 ± 92 | 84 |

These results confirm the enhanced tumor inhibiting effect of H1H685P+VEGF Trap relative to the single agent treatments.

To determine whether the combination of H1H685P+VEGF Trap has a greater effect on tumor vessel function than the single agents, a micro-ultrasound (VisualSonics' Vevo 770 imaging system) was used to assess changes in tumor perfusion. COLO 205 tumors were grown to ~125 mm$^3$ and mice were then treated for 24 hrs with H1H685P, VEGF Trap or the combination of both agents. Following treatment, tumor vessel perfusion was determined based on contrast-enhanced micro-ultrasound 2D image acquisition and analysis of a "wash-in" curve, which represents the amount of contrast agent entering the tumor. Average (mean+/−standard deviation) tumor perfusion was calculated for each group. Percent decrease was calculated from comparison to the Fc control group. The results are shown in Table 32.

TABLE 32

| Antibody | Relative Tumor Perfusion | % Decrease in Tumor Perfusion |
|---|---|---|
| Fc protein | 8.09 ± 2.16 | — |
| H1H685P | 6.32 ± 2.81 | 22 |
| VEGF Trap | 6.99 ± 1.36 | 14 |
| H1H685P + VEGF Trap | 2.46 ± 0.34 | 70 |

Consistent with the enhanced effect of the combination treatment on perfusion, anti-CD31 staining of tumor sections demonstrated a more potent effect of the combination on tumor blood vessel density (data not shown). The increased effect of the H1H685P+VEGF Trap combination on the function of the tumor vasculature provides a potential explanation for the enhanced effects of the combination therapy on tumor growth.

Example 11

Inhibition of Tumor Growth by a Combination of an Anti-Ang-2 Antibody and a Chemotherapeutic Agent To test the effect of H1H685P in combination with a chemotherapeutic agent on tumor growth, $2.5 \times 10^6$ COLO 205 tumor cells were implanted subcutaneously into the right hind flank of 8-9 week-old male SCID mice. When the tumors reached an average volume of ~150 mm$^3$ (day 17 after implantation), mice were randomized into 4 groups (n=5 mice/group) and treated as follows: the first group was treated sc with 15 mg/kg hFc and intraperitoneally (ip) with 5-FU vehicle; the second group was treated sc with 15 mg/kg of H1H685P; the third group was treated ip with 75 mg/kg of 5-FU; the fourth group was treated with the combination of 15 mg/kg H1H685P sc plus 75 mg/kg 5-FU ip. Mice received a total of three treatments, administered every 3-4 days. Tumor volumes were measured twice per week over the course of the experiment. Average (mean+/−standard deviation) tumor growth from the beginning of treatment until day 38 was calculated for each group. Percent decrease of tumor growth was calculated from comparison to the control group. The results are shown in Table 33.

TABLE 33

| Treatment | Avg Tumor Growth (mm$^3$) | % Decrease in Tumor Growth |
|---|---|---|
| Fc protein + 5-FU vehicle | 574 ± 110 | — |
| H1H685P | 405 ± 80 | 29 |
| 5-FU | 313 ± 60 | 45 |
| H1H685P + 5-FU | 175 ± 78 | 70 |

The results of this experiment show that the combination of H1H685P and 5-FU caused a greater decrease in tumor growth than either agent administered separately.

Example 12

Anti-Ang-2 Antibodies Attenuate Ocular Angiogenesis In Vivo

In this Example, the effects of selected anti-Ang-2 antibodies on retinal vascularization in a mouse model was assessed.

In one set of experiments wild-type mice were used. In another set, mice expressing a human Ang-2 in place of the wild-type mouse Ang-2 (designated "hu-Ang-2 mice") were used. The mice at two days of age (P2) were injected subcutaneously with either control Fc or with selected anti-Ang-2 antibodies at a dose of 12.5 mg/kg. Three days later (at P5), pups were euthanized, and eyeballs were enucleated and fixed in 4% PFA for 30 minutes. Retinas were dissected, stained with *Griffonia simplicifolia* lectin-1 for 3 hours or overnight at 4° C. to visualize the vasculature, and flat-mounted on microscope slides. Images were taken using a Nikon Eclipse 80i microscope camera and analyzed using Adobe Photoshop CS3, Fovea 4.0, and Scion 1.63 software.

Areas of the retina covered with superficial vasculature were measured and used as a readout of antibody activity. The reduction in the size of the vascular areas in mice treated with antibody compared to Fc-treated controls is presented in Table 34. The percent reduction in vascular area reflects the anti-angiogenic potency of the antibody. (N/D=not determined)

TABLE 34

| | % Reduction in Vascular Area Relative to Fc Control | |
|---|---|---|
| Antibody | Wild-Type Mice | hAng-2 Mice |
| H1H685P | 39.7 | N/D |
| H1H690P | 30.7 | 41.5 |
| H1H691P | 30.4 | N/D |
| H1H696P | 31.1 | N/D |
| H1H724N | 32.2 | 33.2 |
| H1H744N | 35.8 | 50.5 |
| Control I (Ab) | 26.9 | 35.6 |

As shown in this Example, the selected anti-Ang-2 antibodies of the present invention substantially inhibited ocular angiogenesis in vivo, thus reflecting the likely anti-angiogenic potential of these antibodies in other therapeutic contexts.

Example 13

Amino Acids of Ang-2 Important for Antibody Binding

To further characterize binding between hAng2 and anti-hAng2 mAbs of the invention, seven variant hAng2-FD-mFc proteins were generated, each containing a single point mutation. Amino acids selected for mutation were based on the difference in sequence between hAng-2 and hAng-1 in the region that interacts with hTie-2 (FIG. 1). In particular, amino acids within the fibrinogen-like domain (FD) of Ang-2 which are believed to interact with Tie-2 based on crystal structure analysis, but which differ from the corresponding amino acid in Ang-1, were individually mutated to the corresponding hAng-1 residue. The results of this example indicate the amino acid residues of hAng-2 with which the Ang-2 preferential binding antibodies interact. That is, if a particular residue (or residues) of hAng-2 is/are changed to the corresponding residue of hAng-1, and the binding of an Ang-2 preferential binding antibody is substantially reduced, then it can be concluded that the antibody interacts with that particular residue(s) of hAng-2.

Figure 3:
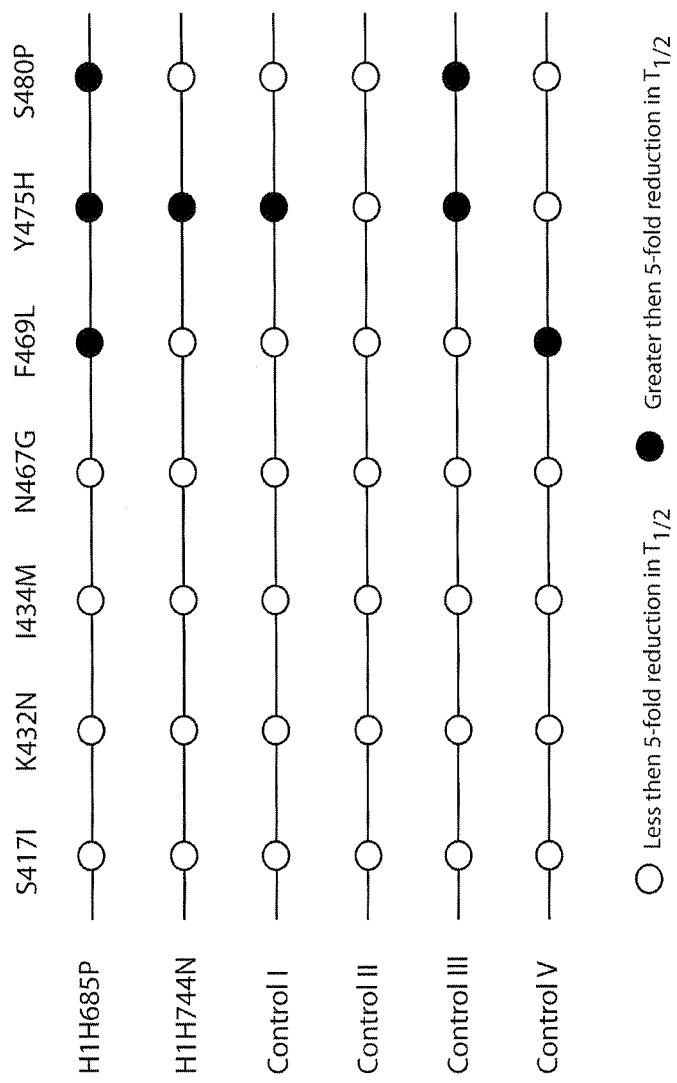
FIG. 3 is a summary of the Ang-2FD-mFc point mutant binding experiment of Example 13, showing the amino acid changes which resulted in greater than a five-fold reduction in T½ of dissociation (depicted by solid circles ●) relative to wild-type for the various antibodies and peptibodies tested.

In this experiment, each of the seven hAng-2FD-mFc mutant proteins were captured (~147-283 RU) on an anti-mouse-Fc surface created through direct chemical coupling to a BIACORE™ chip. Then each Ang-2 antibody (or peptibody, as the case may be) at 100 nM was injected over the captured mFc-tagged hAng-2FD protein surface at a flowrate of 50 µl/min for 180 sec, and the dissociation of variant hAng2-FD-mFc and antibody was monitored in real time for 20 min at 25° C. Results are summarized in Tables 35a-35d and FIG. 3.

TABLE 35a

| Mutated hAng-2 | H1H685P | | | H1H744N | | |
|---|---|---|---|---|---|---|
| Amino Acid(s)[1] | RU | $K_D$ (M) | T ½ (min) | RU | $K_D$ (M) | T ½ (min) |
| WT[2] | 210.70 | 2.23E−11 | 1988 | 213 | 3.98E−11 | 904 |
| S-417-I | 127.65 | 3.05E−11 | 1809 | 127 | 5.12E−11 | 1590 |
| K-432-N | 152.68 | 1.40E−11 | 4468 | 137 | 4.87E−11 | 1690 |
| I-434-M | 235.95 | 1.79E−11 | 3600 | 213 | 3.18E−11 | 2589 |
| N-467-G | 152.25 | 9.38E−12 | 6762 | 139 | 7.72E−11 | 1011 |
| F-469-L | 101.16 | 1.38E−08 | 4 | 180 | 1.95E−10 | 237 |
| Y-475-H | 181.53 | 1.96E−10 | 289 | 247 | 3.06E−10 | 136 |
| S-480-P | 161.13 | 2.05E−10 | 289 | 228 | 2.25E−11 | 2129 |

TABLE 35b

| Mutated hAng-2 | Control I (Ab) | | | Control II (Pb) | | |
|---|---|---|---|---|---|---|
| Amino Acid(s)[1] | RU | $K_D$ (M) | T ½ (min) | RU | $K_D$ (M) | T ½ (min) |
| WT[2] | 195.25 | 4.69E−10 | 54.33 | 67.44 | 4.29E−10 | 39.86 |
| S-417-I | 142.96 | 5.79E−10 | 32.81 | 49.99 | 1.88E−10 | 36.38 |
| K-432-N | 189.69 | 3.49E−10 | 51.75 | 63.21 | 1.39E−10 | 42.34 |
| I-434-M | 282.10 | 4.64E−10 | 48.80 | 89.15 | 1.36E−10 | 57.09 |
| N-467-G | 180.90 | 4.61E−10 | 44.66 | 60.94 | 1.54E−10 | 46.97 |
| F-469-L | 173.01 | 1.05E−09 | 25.13 | 46.73 | 2.40E−10 | 36.20 |
| Y-475-H | 170.05 | 1.15E−08 | 1.85 | 74.79 | 1.40E−10 | 54.12 |
| S-480-P | 181.32 | 2.98E−09 | 13.36 | 71.90 | 1.79E−10 | 45.45 |

TABLE 35c

| Mutated hAng-2 | Control III (Pb) | | | Control V (Ab) | | |
|---|---|---|---|---|---|---|
| Amino Acid(s)[1] | RU | $K_D$ (M) | T ½ (min) | RU | $K_D$ (M) | T ½ (min) |
| WT[2] | 80.33 | 2.07E−11 | 170.03 | 214.48 | 7.97E−10 | 48.43 |
| S-417-I | 57.13 | 5.31E−11 | 114.81 | 126.45 | 2.40E−09 | 29.17 |
| K-432-N | 79.22 | 2.88E−11 | 200.94 | 149.14 | 8.48E−10 | 75.59 |
| I-434-M | 116.22 | 2.15E−10 | 62.77 | 214.75 | 2.23E−09 | 31.76 |
| N-467-G | 74.64 | 8.90E−11 | 109.07 | 146.77 | 1.11E−09 | 55.66 |
| F-469-L | 72.66 | 2.74E−10 | 66.11 | 131.96 | 1.37E−08 | 1.46 |
| Y-475-H | 76.21 | 6.87E−09 | 4.11 | 260.93 | 2.66E−10 | 93.22 |
| S-480-P | 77.93 | 2.78E−09 | 11.69 | 177.10 | 3.47E−09 | 10.33 |

TABLE 35d

| Mutated hAng-2 | Negative Control (irrelevant antibody) | | |
|---|---|---|---|
| Amino Acid(s)[1] | RU | $K_D$ (M) | T ½ (min) |
| WT[2] | 0.81 | N/B | N/B |
| S-417-I | −1.21 | N/B | N/B |
| K-432-N | −0.38 | N/B | N/B |
| I-434-M | −1.31 | N/B | N/B |
| N-467-G | −1.09 | N/B | N/B |
| F-469-L | 0.32 | N/B | N/B |
| Y-475-H | −0.20 | N/B | N/B |
| S-480-P | −0.52 | N/B | N/B |

[1] Amino acid numbering is based on the amino acid numbering of SEQ ID NO: 518.
[2] WT = wild-type Ang-2FD-mFc construct.
N/B = no binding observed.

For purposes of the present invention, an anti-Ang-2 antibody is deemed to interact with a particular Ang-2 amino acid residue if, when the residue is mutated to the corresponding residue of Ang-1, the T½ of dissociation is at least 5-fold less than the T1/2 of dissociation observed for the wild-type construct under the experimental conditions used in this Example. In view of this definition, antibody H1H685P appears to be unique among the antibodies tested in that it interacts with F469, Y475 and S480. Since H1H685P is also unique because of its strong preferential binding to Ang-2 over Ang-1, it can be concluded that F469, Y475 and S480 comprise an epitope that enables the immunological distinction of Ang-2 from Ang-1. The other antibodies/peptibodies tested in this experiment appear to interact with at most one or two of these residues; i.e., H1H744N and Control I interact with Y475; Control III interacts with Y475 and S480; and Control V interacts with F469. Interestingly, Control II, which was shown to block both Ang-1 and Ang-2 binding to Tie-2 with equal potency, does not interact with any of the Ang-2-specific amino acids identified in this experiment.

Example 14

Methods for Treating or Preventing Malaria

A. Model of Cerebral Malaria In Vivo

Experiments are performed to assess the ability of anti-Ang-2 antibodies of the present invention to treat malaria in a mouse model system.

Six-week-old female C57BL/6 mice (approximately 20 g) are used in all experiments. After a 7-day rest period, groups of mice are treated with a monoclonal antibody (mAb) at 15 mg/kg on day −1 and then days 1, 4, 7 and 10 post-infection (p.i.) for prophylactic models, or on days 1, 4, 7 and 10 p.i. for therapeutic models. Experimental groups are administered an anti-angiopoietin 2 (Ang-2) mAb that possesses a human IgG1 Fc domain (H1H685P) subcutaneously (s.c.). Control mice receive an isotype-matched control mAb. Mice are injected intraperitoneally (i.p.) on day 0 with $1 \times 10^6$ *Plasmodium berghei* ANKA (BEI Resources, Manassas, Va.) parasites from an infected donor mouse. Mice are monitored daily for up to 14 days from thin blood smears. In addition, weight and hematocrit are monitored every other day and mice are euthanized once moribund. Experiments are repeated three times to ensure statistical significance. It is expected that mice treated with H1H685P both prophylactically and therapeutically will have higher rates of survival than those treated with a control mAb, but the percent parasitemia of the groups are not expected to differ.

B. Monitoring of Disease Parameters

Blood is collected via the saphenous vein using heparin and stored as plasma at −80° C. Levels of IFNγ, TNFα, MCP-1, Ang-1, sICAM-1 and vWF are assessed using standardized ELISAs and bead arrays. Tissues (including brain, spleen, liver and/or lung) are collected for histology or mRNA transcript analysis by qPCR for the same markers. In addition, vascular permeability is assessed by the injection of 30 mg/kg Evans blue, via lateral tail vein. Approximately 2 h post injection, mice are euthanized, perfused with PBS and the brains collected and placed in formamide for 48 h for Evans blue extraction. For each sample, Evans blue is quantified using a spectrophotometer at 605 nm. It is expected that mice treated with H1H685P both prophylactically and therapeutically will have reduced systemic inflammation and endothelial activation, as evidenced by reduced levels of IFNγ, TNFα, MCP-1, Ang-1, sICAM-1 and vWF compared to those treated with a control mAb. In addition, those animals treated with control mAb both prophylactically and therapeutically will show a loss of blood-brain barrier vascular integrity compared with H1H685P.

C. Visualization and Quantification of Parasite Distribution In Vivo.

Mice are treated and infected as before, except that the animals are infected with a luciferase-expressing strain of *P. berghei* ANKA (PbGFP-LUC$_{CON}$; see Franke-Fayard et al. 2005 *Proc. Natl. Acad. Sci USA* 102: 11468). Animals are injected with D-luciferin (100 mg/kg) intradermally, and luciferase activity visualized in live mice using the Xenogen IVIS Spectrum imager. Whole-body, live images are taken on days 3 to 10 and specific organs imaged after euthanasia. Experiments are repeated three times to ensure statistical significance. It is expected that mice treated with H1H685P both prophylactically and therapeutically will have reduced parasite accumulation in the brain compared to those treated with a control mAb.

D. Statistical Analysis

Survival data is assessed by log-rank test, while all other comparisons are analyzed using a one-way ANOVA with Tukey's Multiple Comparison post-hoc test. A p value of less than 0.05 is considered significant. Analysis is completed using GraphPad Prism (LaJolla, Calif.).

The present invention is not to be limited in scope by the specific embodiments describe herein. Indeed, various modifications of the invention in addition to those described herein will become apparent to those skilled in the art from the foregoing description. Such modifications are intended to fall within the scope of the appended claims.

What is claimed is:

1. A method for treating a symptom of cerebral malaria, the method comprising administering to a patient in need thereof a pharmaceutical composition comprising a therapeutically effective amount of an isolated antibody or antigen-binding fragment thereof that specifically binds human angiopoietin-2 (hAng-2) but does not substantially bind hAng-1, and a pharmaceutically acceptable carrier, wherein the antibody or antigen-binding fragment thereof comprises a heavy chain CDR-1 (HCDR1) having the amino acid sequence of SEQ ID NO:4, an HCDR-2 having the amino acid sequence of SEQ ID NO:6, an HCDR-3 having the amino acid sequence of SEQ ID NO:8, a light chain CDR-1 (LCDR-1) having the amino acid sequence of SEQ ID NO:12, an LCDR-2 having the amino acid sequence of SEQ ID NO:14, and an LCDR-3 having the amino acid sequence of SEQ ID NO:16.

2. The method of claim 1, wherein the antibody or antigen-binding fragment thereof binds an epitope on hAng-2 (SEQ ID NO:518) comprising an amino acid selected from the group consisting of F-469, Y-475, and S-480.

3. The method of claim 2, wherein the antibody or antigen-binding fragment thereof binds an epitope on hAng-2 comprising amino acids F-469, Y-475, and S-480.

4. The method of claim 1, wherein the antibody or antigen-binding fragment thereof comprises a heavy chain variable region (HCVR) having the amino acid sequence of SEQ ID NO: 18 and a light chain variable region (LCVR) having the amino acid sequence of SEQ ID NO:20.

5. The method of claim 1, wherein the symptom of cerebral malaria is a level of sICAM-1 or vWF, and treating the symptom comprises reducing the level of sICAM-1 or vWF as compared to an untreated patient in need thereof.

6. The method of claim 1, wherein the symptom of cerebral malaria is loss of blood-brain barrier vascular integrity, and treating the symptom comprises reducing the loss of blood-brain barrier vascular integrity as compared to an untreated patient in need thereof.

7. The method of claim 1, wherein the symptom of cerebral malaria is parasite accumulation in the brain, and treating the symptom comprises reducing parasite accumulation in the brain as compared to an untreated patient in need thereof.

8. The method of claim 1, wherein the symptom of cerebral malaria is duration of survival, and treating the symptom comprises increasing duration of survival as compared to an untreated patient in need thereof.

* * * * *